US011832513B2

(12) United States Patent
Wirges et al.

(10) Patent No.: US 11,832,513 B2
(45) Date of Patent: Nov. 28, 2023

(54) MATERIALS FOR ELECTRONIC DEVICES

(71) Applicant: Merck Patent GmbH, Darmstadt (DE)

(72) Inventors: Christian Wirges, Weiterstadt (DE); Teresa Mujica-Fernaud, Darmstadt (DE); Elvira Montenegro, Weinheim (DE); Frank Voges, Bad Duerkheim (DE); Florian Maier-Flaig, Weinheim (DE); Thomas Eberle, Landau (DE)

(73) Assignee: MERCK PATENT GMBH, Darmstadt (DE)

( * ) Notice: Subject to any disclaimer, the term of this patent is extended or adjusted under 35 U.S.C. 154(b) by 356 days.

(21) Appl. No.: 16/766,778

(22) PCT Filed: Nov. 20, 2018

(86) PCT No.: PCT/EP2018/081873
§ 371 (c)(1),
(2) Date: May 26, 2020

(87) PCT Pub. No.: WO2019/101719
PCT Pub. Date: May 31, 2019

(65) Prior Publication Data
US 2020/0303654 A1 Sep. 24, 2020

(30) Foreign Application Priority Data

Nov. 23, 2017 (EP) ..................................... 17203293

(51) Int. Cl.
H01L 51/00 (2006.01)
C07D 209/88 (2006.01)
C09K 11/06 (2006.01)
C07D 209/86 (2006.01)
C07D 405/12 (2006.01)
C07D 409/12 (2006.01)
H10K 85/60 (2023.01)
H10K 50/11 (2023.01)
H10K 50/15 (2023.01)
H10K 50/18 (2023.01)
H10K 101/10 (2023.01)

(52) U.S. Cl.
CPC ......... H10K 85/636 (2023.02); C07D 209/86 (2013.01); C07D 209/88 (2013.01); C07D 405/12 (2013.01); C07D 409/12 (2013.01); C09K 11/06 (2013.01); H10K 85/633 (2023.02); C09K 2211/1018 (2013.01); H10K 50/11 (2023.02); H10K 50/15 (2023.02); H10K 50/18 (2023.02); H10K 85/615 (2023.02); H10K 85/624 (2023.02); H10K 85/626 (2023.02); H10K 85/6572 (2023.02); H10K 85/6574 (2023.02); H10K 85/6576 (2023.02); H10K 2101/10 (2023.02)

(58) Field of Classification Search
None
See application file for complete search history.

(56) References Cited

U.S. PATENT DOCUMENTS

| 2011/0198581 | A1* | 8/2011 | Yabunouchi ........... C09K 11/06 548/440 |
| 2015/0318484 | A1 | 11/2015 | Buesing et al. |
| 2015/0322198 | A1* | 11/2015 | Hayer ................. H01L 51/0036 558/290 |
| 2016/0111653 | A1 | 4/2016 | Hiroaki |
| 2016/0163993 | A1* | 6/2016 | Nakano ............... H01L 51/0073 257/40 |
| 2016/0329492 | A1 | 11/2016 | Funahashi et al. |
| 2016/0365517 | A1 | 12/2016 | Mun et al. |
| 2018/0277767 | A1 | 9/2018 | Cha et al. |
| 2020/0243771 | A1 | 7/2020 | Mun et al. |

FOREIGN PATENT DOCUMENTS

| CN | 105175313 A | 12/2015 |
| CN | 105175314 A | 12/2015 |
| CN | 106167463 A | 11/2016 |
| CN | 106478611 A | 3/2017 |
| CN | 106699573 A | 5/2017 |
| CN | 107056626 A | 8/2017 |
| EP | 2348017 A1 | 7/2011 |
| EP | 2772483 A1 | 9/2014 |
| EP | 3010066 A1 | 4/2016 |
| JP | 2014-534161 A | 12/2014 |
| JP | 2015-531002 A | 10/2015 |
| JP | 2015-227316 A | 12/2015 |
| JP | 2016-082158 A | 5/2016 |
| JP | 2016-108290 A | 6/2016 |
| KR | 10-2011-0069077 A | 6/2011 |
| KR | 2014-0103697 | 8/2014 |
| KR | 10-2015-0051662 A | 5/2015 |
| KR | 10-2015-0101933 A | 9/2015 |
| KR | 10-2016-0034832 A | 3/2016 |
| KR | 10-2016-0047379 A | 5/2016 |
| KR | 10-2016-0070662 A | 6/2016 |
| KR | 10-2016-0087755 A | 7/2016 |
| KR | 10-2016-0114526 A | 10/2016 |
| KR | 10-2016-0131887 A | 11/2016 |
| KR | 10-2017-0031073 A | 3/2017 |
| KR | 10-2017-0036602 A | 4/2017 |
| KR | 10-2017-0047801 A | 5/2017 |
| KR | 2017-0084917 A | 7/2017 |
| KR | 2017-0087691 A | 7/2017 |
| KR | 10-2017-0088313 A | 8/2017 |
| KR | 10-2017-0096767 A | 8/2017 |
| TW | 201329046 A | 7/2013 |

(Continued)

OTHER PUBLICATIONS

International Search Report for PCT/EP2018/081873 dated Jan. 29, 2019.

(Continued)

Primary Examiner — Jay Yang
(74) Attorney, Agent, or Firm — Faegre Drinker Biddle & Reath LLP

(57) ABSTRACT

The present application relates to triarylamine compounds of a defined formula. The present application further relates to processes for preparing the compounds, to the use of the compounds in electronic devices, and to electronic devices comprising the compounds.

20 Claims, No Drawings

(56) References Cited

FOREIGN PATENT DOCUMENTS

| WO | 2010/044130 A1 | 4/2010 |
|---|---|---|
| WO | 2011/085185 A1 | 7/2011 |
| WO | WO-2014129764 A1 | 8/2014 |
| WO | 2015/072729 A1 | 5/2015 |
| WO | 2015/072730 A1 | 5/2015 |
| WO | 2015/076523 A1 | 5/2015 |
| WO | 2015/130069 A1 | 9/2015 |
| WO | WO-2015129896 A1 | 9/2015 |
| WO | WO-2017043917 A1 | 3/2017 |
| WO | WO-2017052212 A1 | 3/2017 |
| WO | 2017/090918 A1 | 6/2017 |
| WO | 2017/116167 A1 | 7/2017 |

OTHER PUBLICATIONS

Written Opinion of the International Searching Authority for PCT/EP2018/081873 dated Jan. 29, 2019.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2018/081873, filed Nov. 20, 2018, which claims benefit of European Application No. 17203293.0, filed Nov. 23, 2017, both of which are incorporated herein by reference in their entirety.

The present application relates to triarylamine compounds of a formula (I) defined further down. These compounds are suitable for use in electronic devices. The present application further relates to processes for preparing the compounds mentioned, and to electronic devices comprising the compounds mentioned.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by emission layers and layers having a hole-transporting function. Novel compounds are also being sought for use in these layers, especially hole-transporting compounds and compounds that can serve as matrix material, especially for phosphorescent emitters, in an emitting layer.

In the prior art, various triarylamine compounds are known as hole transport materials for electronic devices. Likewise known is the use of particular triarylamine compounds as matrix materials in emitting layers.

However, there is still a need for alternative compounds suitable for use in electronic devices.

There is also a need for improvement with regard to the performance data in use in electronic devices, especially with regard to operating voltage, lifetime and efficiency. There is a further need for improvement with regard to the processability of the materials, their glass transition temperature, their solubility, their stability in solution, and their refractive index.

It has now been found that particular triarylamine compounds are of excellent suitability for use in electronic devices, especially for use in OLEDs, even more especially for use therein as hole transport materials and for use as matrix materials for phosphorescent emitters.

The present application thus provides compounds of a formula (I)

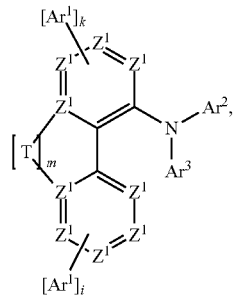

Formula (I)

where the variables that occur are as follows:

$Z^1$ is the same or different at each instance and is selected from $CR^1$ and N, where $Z^1$ is C when an $Ar^1$ or T group is bonded thereto;

$Ar^1$ is the same or different at each instance and is an aromatic ring system which has 6 to 30 aromatic ring atoms and may be substituted by one or more $R^2$ radicals;

$Ar^2$ corresponds to a formula (A) or (B)

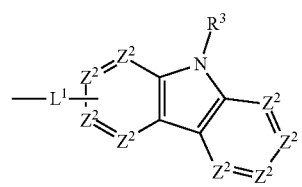

Formula (A)

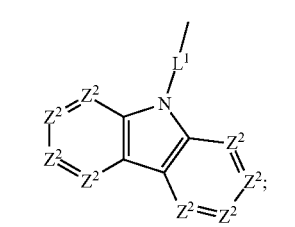

Formula (B)

$Z^2$ is the same or different at each instance and is $CR^3$ or N, where $Z^2$ is C when an $L^1$ group is bonded thereto;

$L^1$ is a single bond, or an aromatic ring system which has 6 to 30 aromatic ring atoms and may be substituted by one or more $R^3$ radicals, or a heteroaromatic ring system which has 5 to 30 aromatic ring atoms and may be substituted by one or more $R^3$ radicals;

$Ar^3$ corresponds to a formula (A), a formula (B), or is an aromatic ring system which has 6 to 30 aromatic ring atoms and may be substituted by one or more $R^4$ radicals, or a heteroaromatic ring system which has 5 to 30 aromatic ring atoms and may be substituted by one or more $R^4$ radicals;

T is selected from $C(R^1)_2$, $Si(R^1)_2$, $NR^1$, O and S;

$R^1$, $R^2$, $R^3$, $R^4$ are the same or different at each instance and are selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —$R^5C$=$CR^5$—, —C≡C—, $Si(R^5)_2$, C=O, C=$NR^5$, —C(=O)O—, —C(=O)$NR^5$—, $NR^5$, P(=O)($R^5$), —O—, —S—, SO or $SO_2$;

$R^5$ is the same or different at each instance and is selected from H, D, F, C(=O)$R^6$, CN, $Si(R^6)_3$, $N(R^6)_2$, P(=O)($R^6)_2$, $OR^6$, S(=O)$R^6$, $S(=O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by —$R^6C$=$CR^6$—, —C≡C—, $Si(R^6)_2$, C=O, C=$NR^6$, —C(=O)O—, —C(=O)$NR^6$—, $NR^6$, P(=O)($R^6$), —O—, —S—, SO or $SO_2$;

$R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

m is 0 or 1;
i is 0, 1, 2, 3, 4 or 5;
k is 0, 1, 2, 3 or 4;
where the sum of k and i is at least 1; and
where $Ar^1$ groups may each be connected via a divalent Y group to the six-membered ring to which they are bonded, and
Y is the same or different at each instance and is selected from $C(R^1)_2$, $Si(R^1)_2$, $NR^1$, O and S.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the definition stated above for an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, $Z^1$ is $CR^1$, where $Z^1$ is C when an $Ar^1$ or T group is bonded thereto.

Preferably, $Ar^1$ at each instance is the same or different and is an aryl group having 6 to 16 aromatic ring atoms. More preferably, $Ar^1$ is the same or different at each instance and is selected from phenyl, biphenyl, terphenyl, quaterphenyl, naphthyl, anthracenyl, fluorenyl, indenofluorenyl and phenanthrenyl, where the groups mentioned may each be substituted by one or more $R^2$ radicals.

There are preferably respectively exactly one or exactly two $Ar^1$ groups in the compound of the formula (I). This means that there are at most two $Ar^1$ groups in the compound of the formula (I). If there is exactly one $Ar^1$ group in the compound of the formula (I), it is preferable for this group to be connected via a divalent Y group to the six-membered ring to which it is bonded. Preferably, the $Ar^1$ group in this case is a phenyl group which may be substituted by one or more $R^2$ radicals. Preferably, in this case, the $Ar^1$ group, the Y bridge and the six-membered ring to which the Y bridge and the $Ar^1$ group bond form a five-membered ring which is inserted between the six-membered ring and the $Ar^1$ group and which with the six-membered ring and the $Ar^1$ group forms a fused unit. This fused unit is preferably selected from fluorene, spirobifluorene, carbazole, dibenzofuran and dibenzothiophene.

Preferred embodiments of the formula (A) are the formulae (A-1) to (A-10)

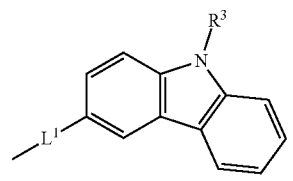

Formula (A-1)

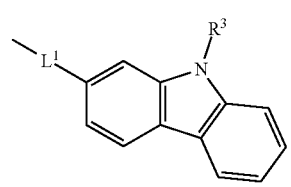

Formula (A-2)

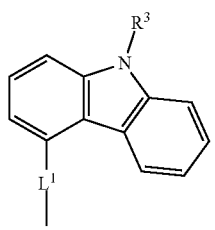

Formula (A-3)

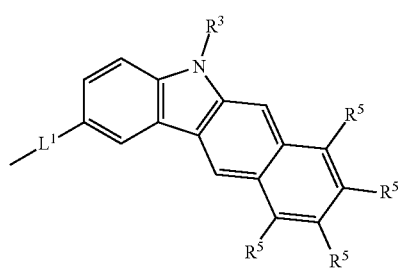

Formula (A-4)

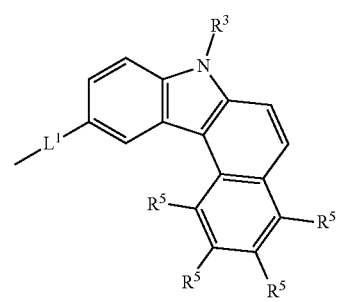

Formula (A-5)

Formula (A-6)
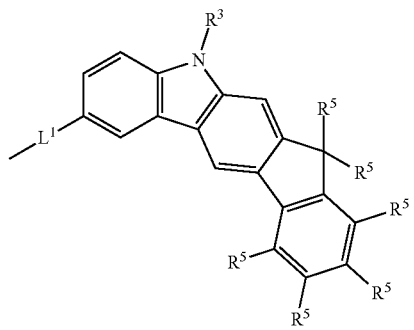
Formula (A-7)
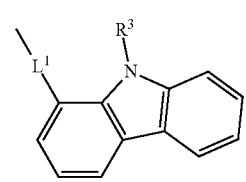
Formula (A-8)
Formula (A-9)
Formula (A-10)
where the variables which appear are defined as above and where the carbazole units may each, at the free positions of their two benzene rings, be substituted by one or more R³ radicals.
Preferred embodiments of the formula (B) are the formulae (B-1) to (B-7)
Formula (B-1)
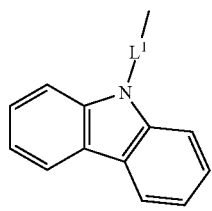
Formula (B-2)
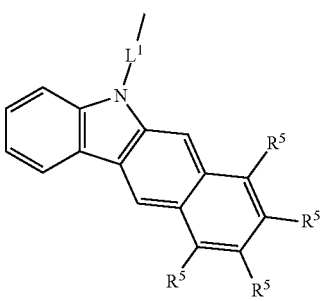
Formula (B-3)
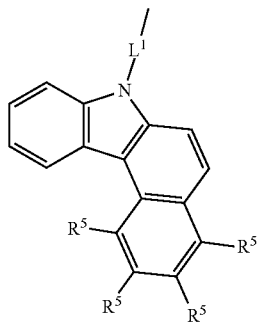
Formula (B-4)
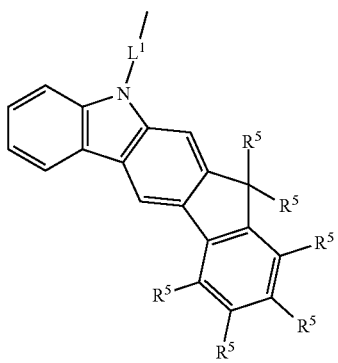
Formula (B-5)
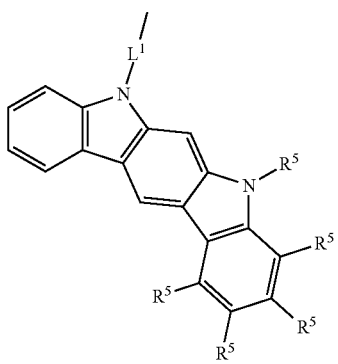

Formula (B-5)

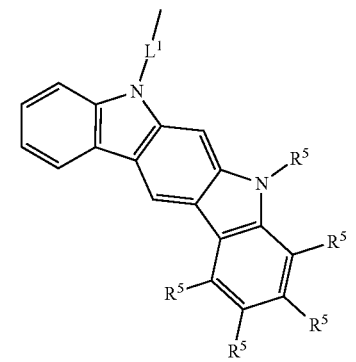

Formula (B-6)

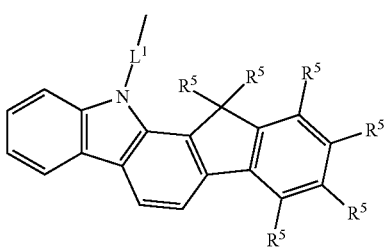

Formula (B-7)

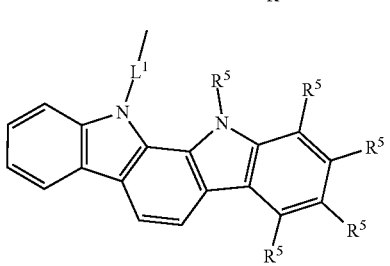

where the variables which appear are defined as above and where the carbazole units may each, at the free positions of their two benzene rings, be substituted by one or more $R^3$ radicals.

$Ar^2$ corresponds preferably to the above-stated formula (A), more preferably to one of the formulae (A-1) to (A-3).

Preferred embodiments of the $Ar^2$ groups are depicted in the following table:

Ar²-1

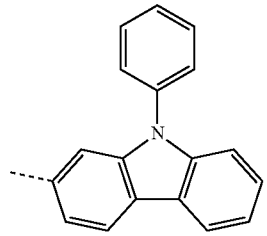

Ar²-2

Ar²-3

Ar²-4

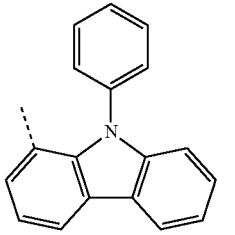

Ar²-5

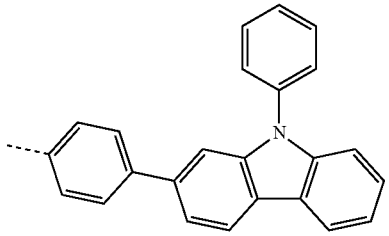

Ar²-6

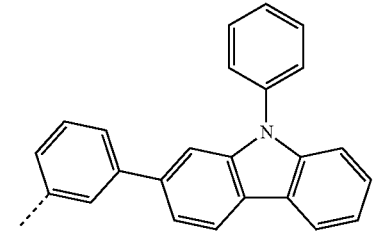

Ar²-7

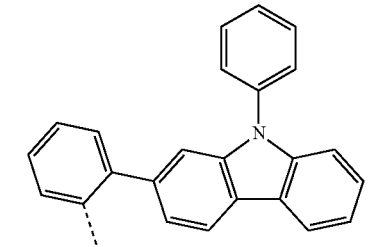

Ar²-8

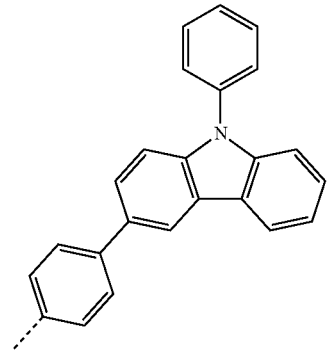

-continued
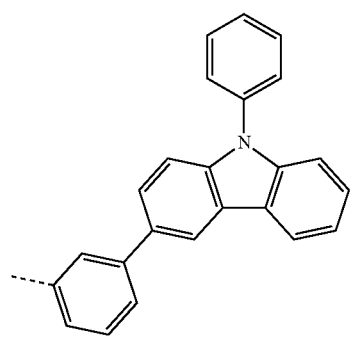
Ar²-9
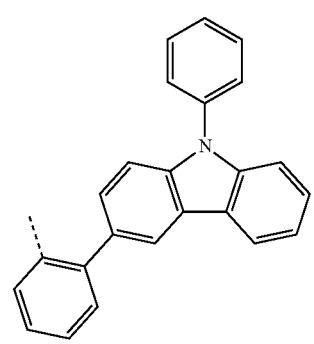
Ar²-10
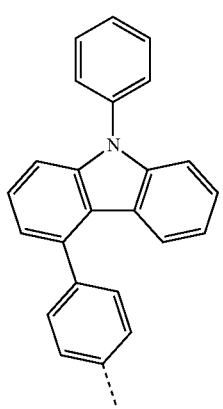
Ar²-11
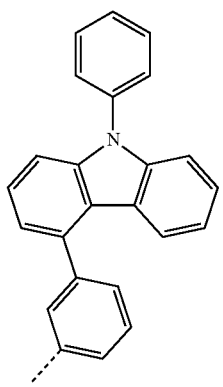
Ar²-12
-continued
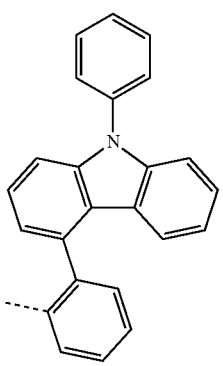
Ar²-13
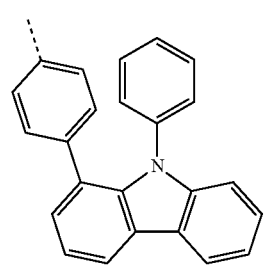
Ar²-14
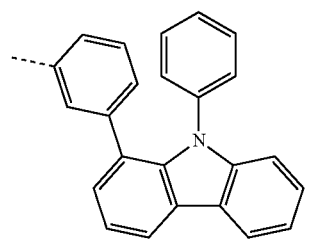
Ar²-15
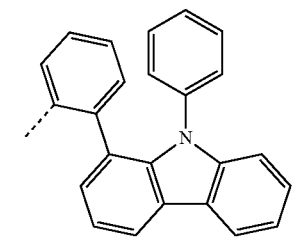
Ar²-16
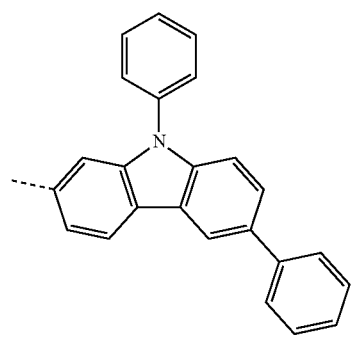
Ar²-17

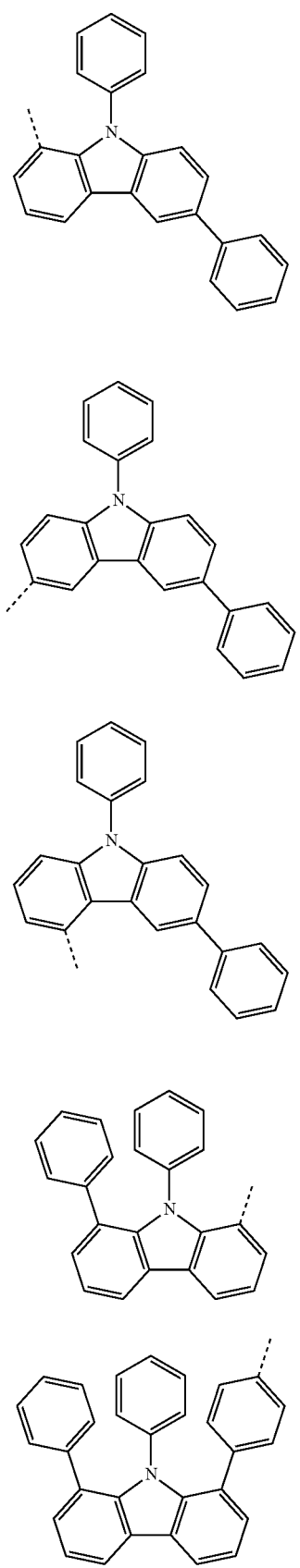
Ar²-18
Ar²-19
Ar²-20
Ar²-21
Ar²-22
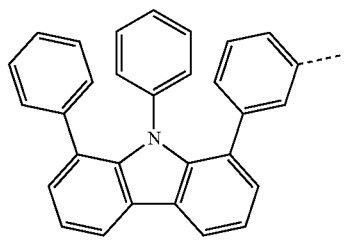
Ar²-23
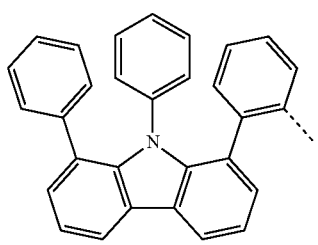
Ar²-24
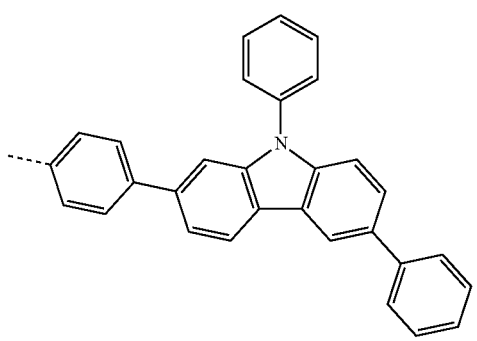
Ar²-25
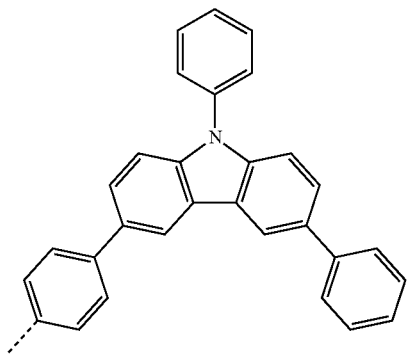
Ar²-26
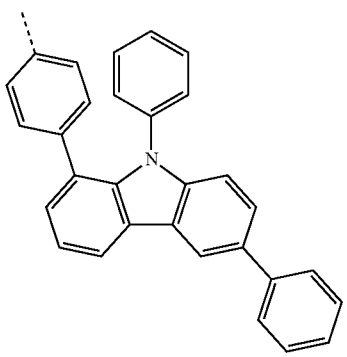
Ar²-27

Ar²-28 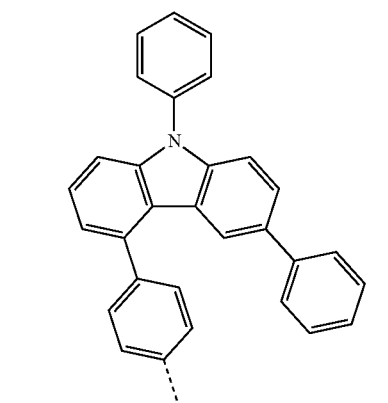
Ar²-29 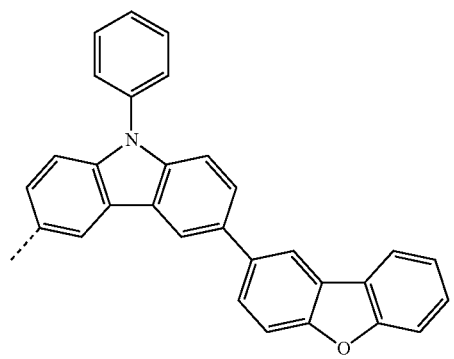
Ar²-30 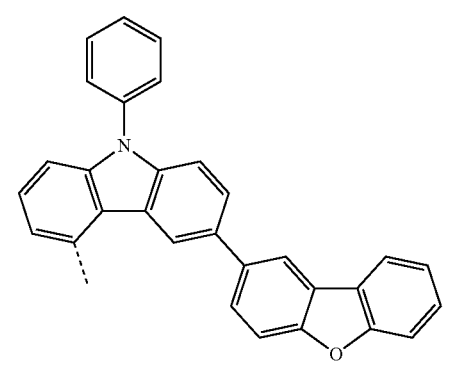
Ar²-31 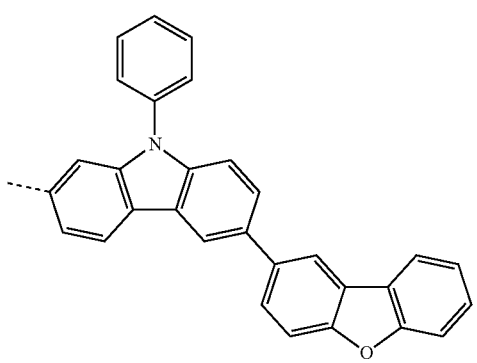
Ar²-32 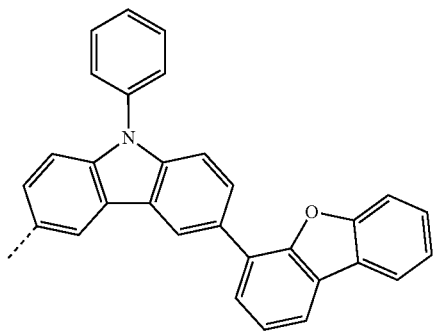
Ar²-33 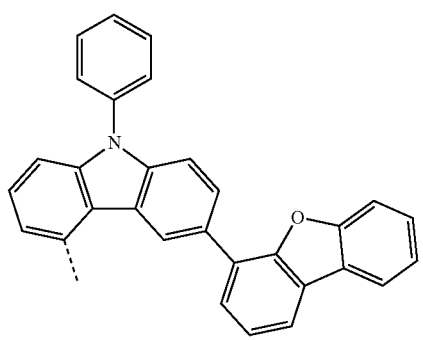
Ar²-34 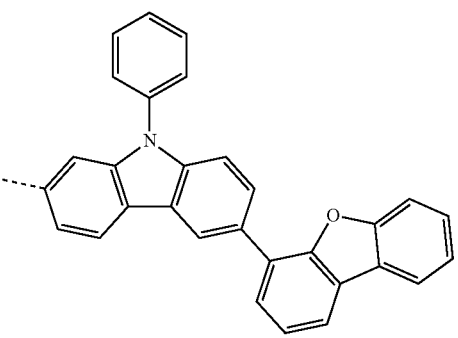
Ar²-35 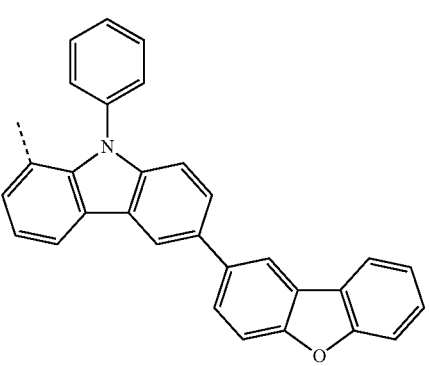

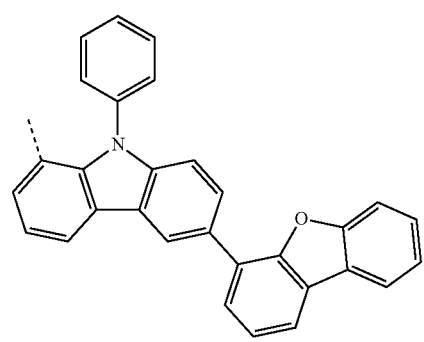
Ar²-36
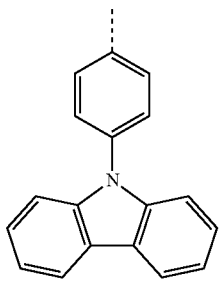
Ar²-40
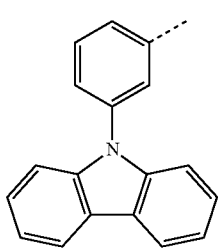
Ar²-41
Ar²-37
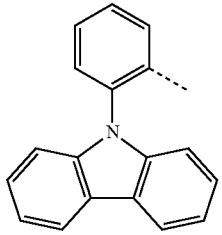
Ar²-42
Ar²-38
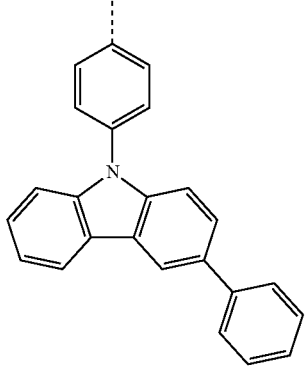
Ar²-43
Ar²-39
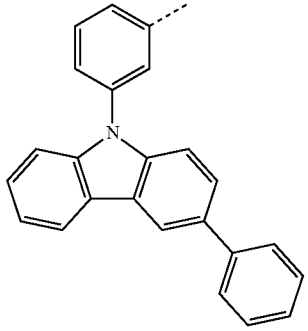
Ar²-44

Ar²-45
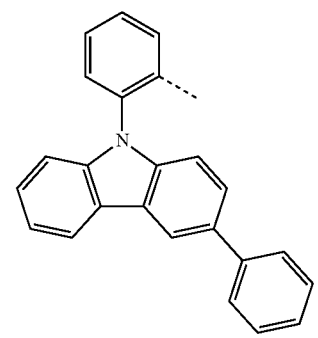
Ar²-49
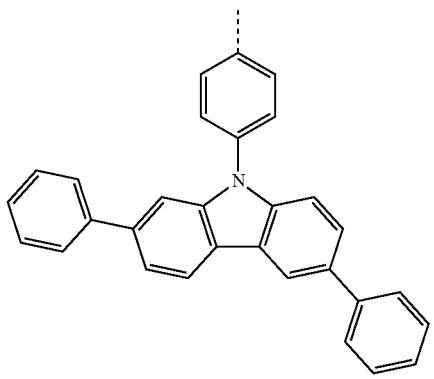
Ar²-46
Ar²-50
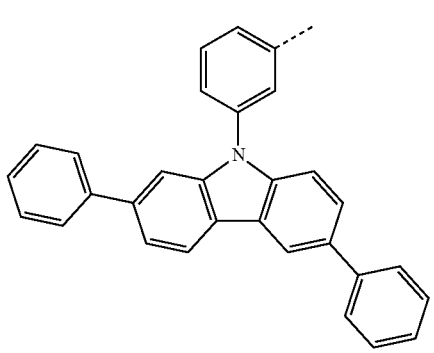
Ar²-47
Ar²-51
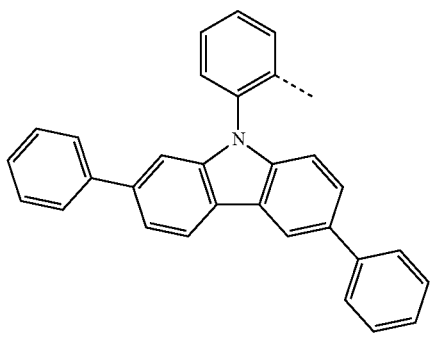
Ar²-48
Ar²-52
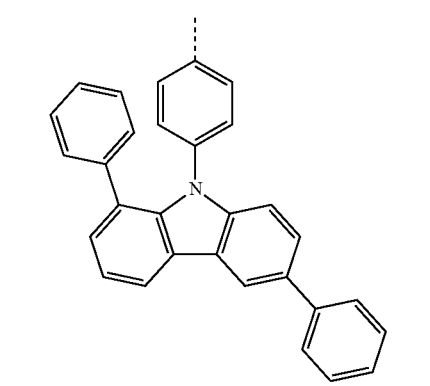

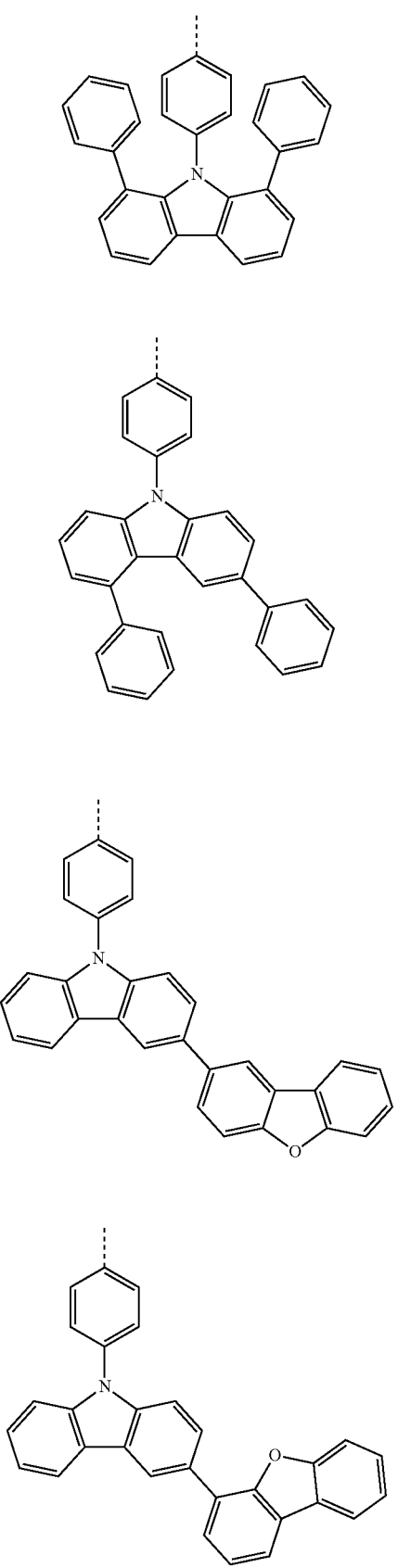
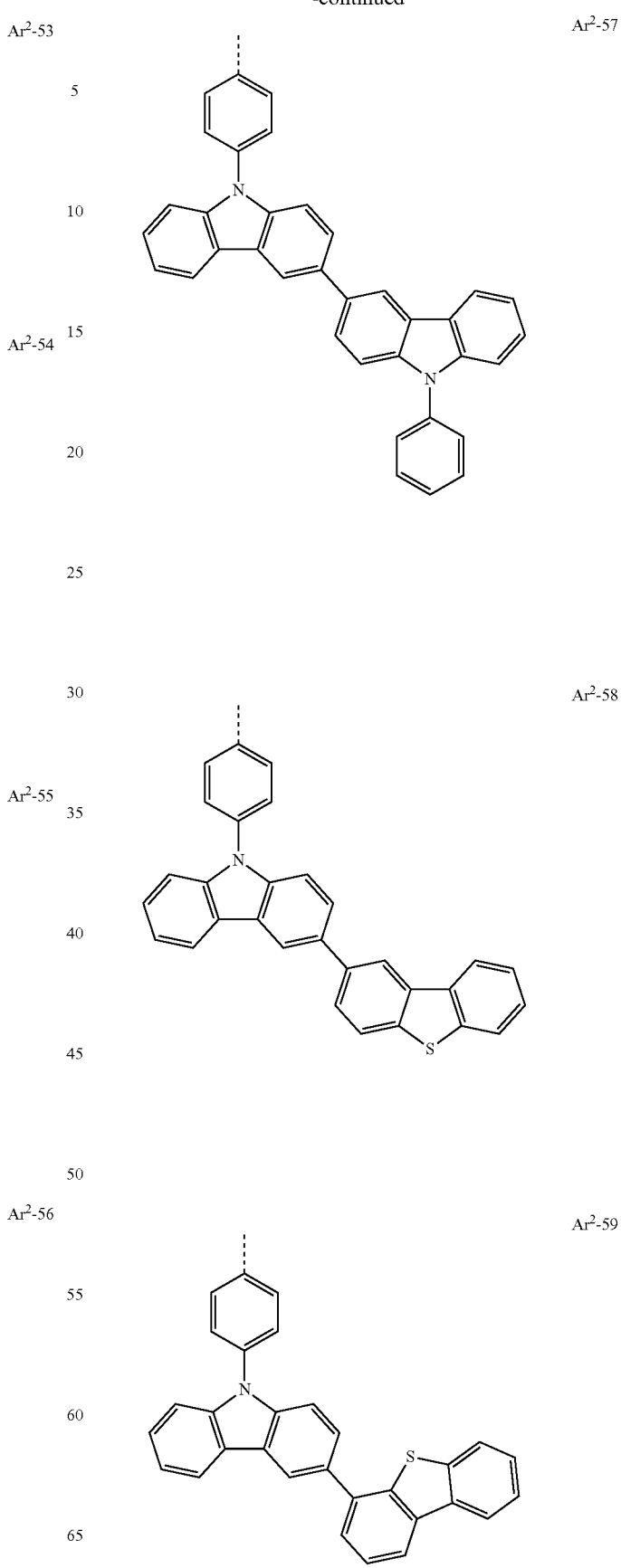

Ar²-60
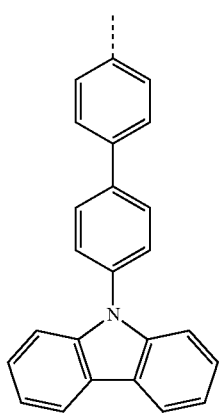
Ar²-61
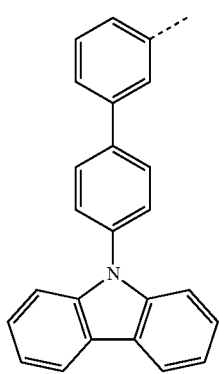
Ar²-62
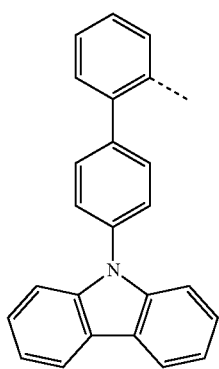
Ar²-63
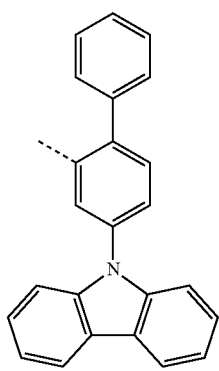
Ar²-64
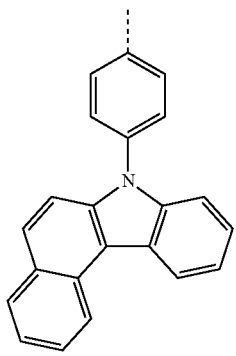
Ar²-65
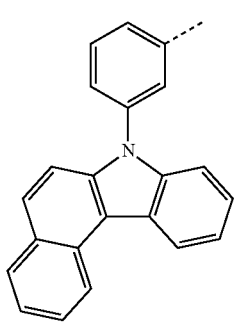
Ar²-66
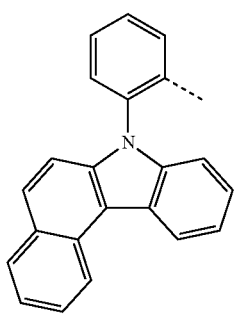
Ar²-67
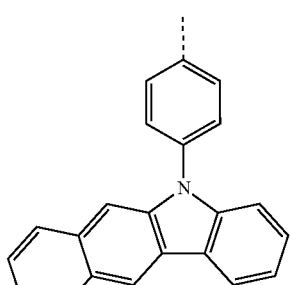
Ar²-68
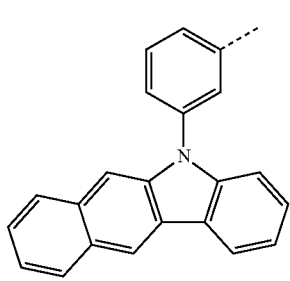

Ar²-69 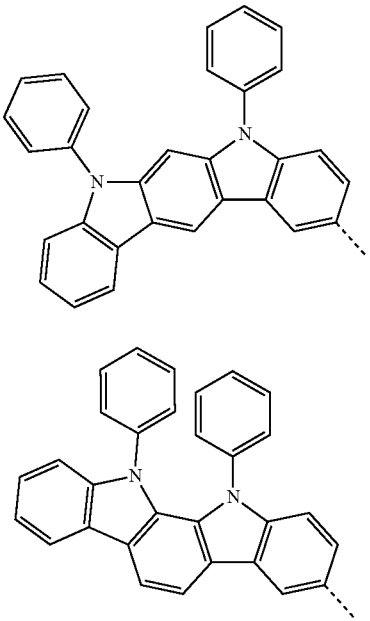

Ar²-70 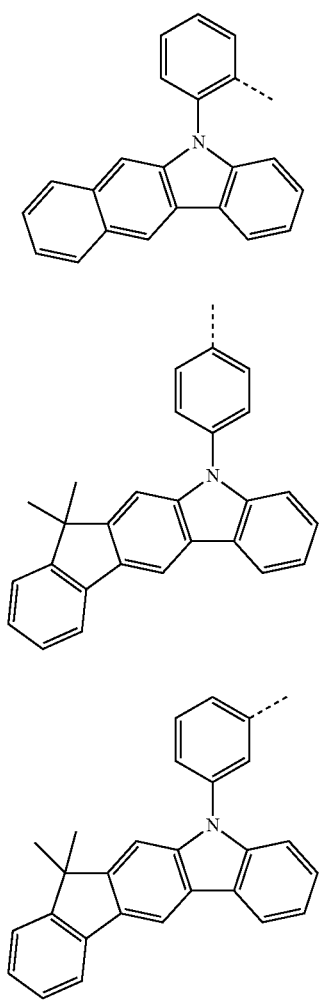

Ar²-74 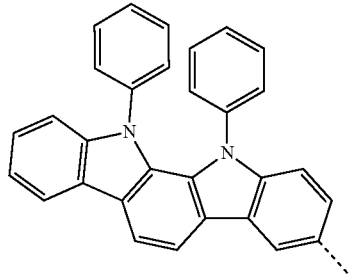

Ar²-75 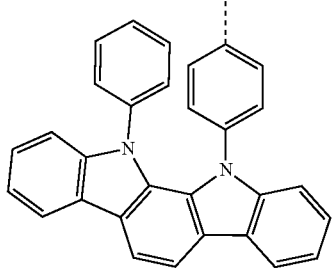

Ar²-71

Ar²-76

Ar²-72

Ar²-73 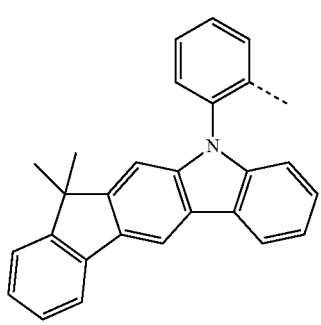

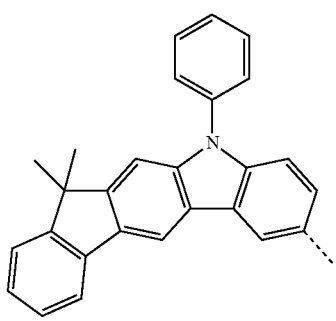

$Z^2$ is preferably the same at each instance and is $CR^3$, where $Z^2$ is C when an $L^1$ group is bonded thereto.

$L^1$ is preferably selected from the aromatic ring systems having 6 to 30 aromatic ring atoms. $L^1$ is more preferably selected from single bond, benzene, naphthalene, para-biphenyl, meta-biphenyl, ortho-biphenyl, terphenyl, dibenzofuran, carbazole, dibenzothiophene, pyridine, pyrimidine, pyrazine, pyridazine, triazine and fluorene, very preferably selected from single bond and phenyl, where the stated groups may each be substituted by one or more $R^3$ radicals.

Preferred $L^1$ groups are depicted in the following table:

(L¹-1) 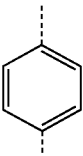

(L¹-2) 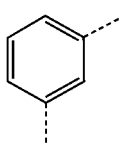

-continued
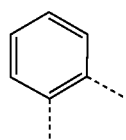 (L¹-3)
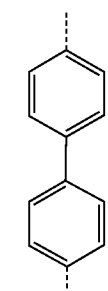 (L¹-4)
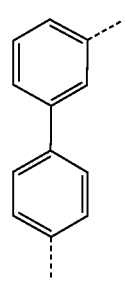 (L¹-5)
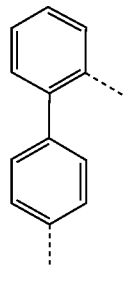 (L¹-6)
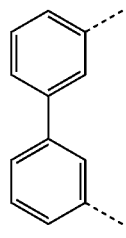 (L¹-7)
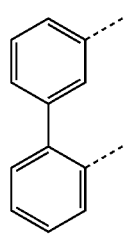 (L¹-8)
-continued
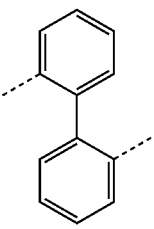 (L¹-9)
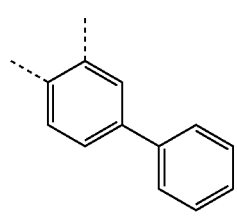 (L¹-10)
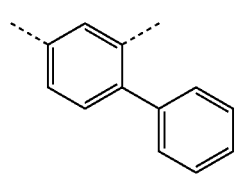 (L¹-11)
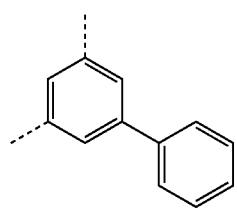 (L¹-12)
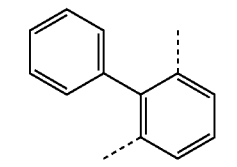 (L¹-13)
(L¹-14)
(L¹-15)
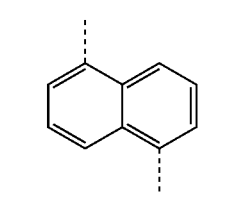 (L¹-16)

-continued
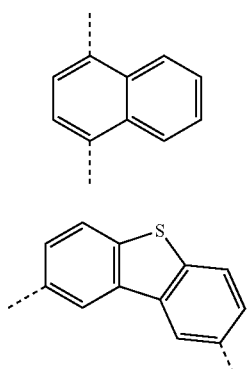
(L¹-17)
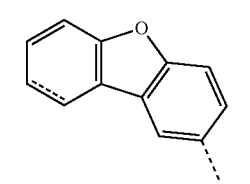
(L¹-18)
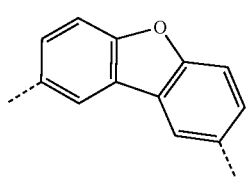
(L¹-19)
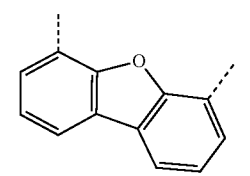
(L¹-19)

(L¹-20)
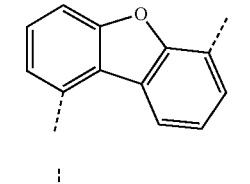
(L¹-21)
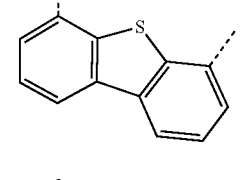
(L¹-22)
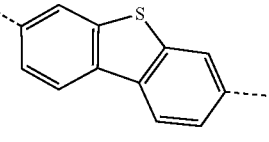
(L¹-23)
-continued
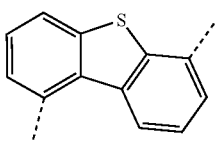
(L¹-24)
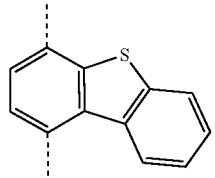
(L¹-25)
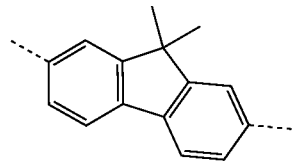
(L¹-26)
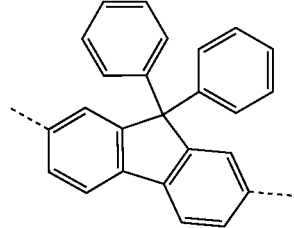
(L¹-27)
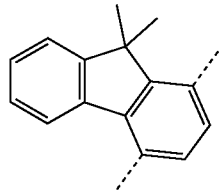
(L¹-28)
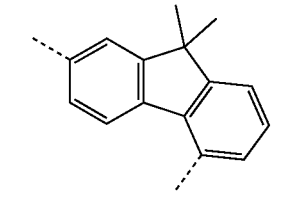
(L¹-29)
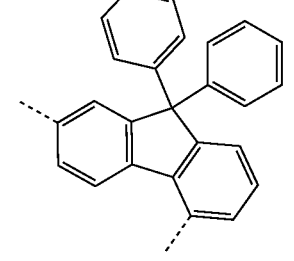
(L¹-30)
(L¹-31)

-continued

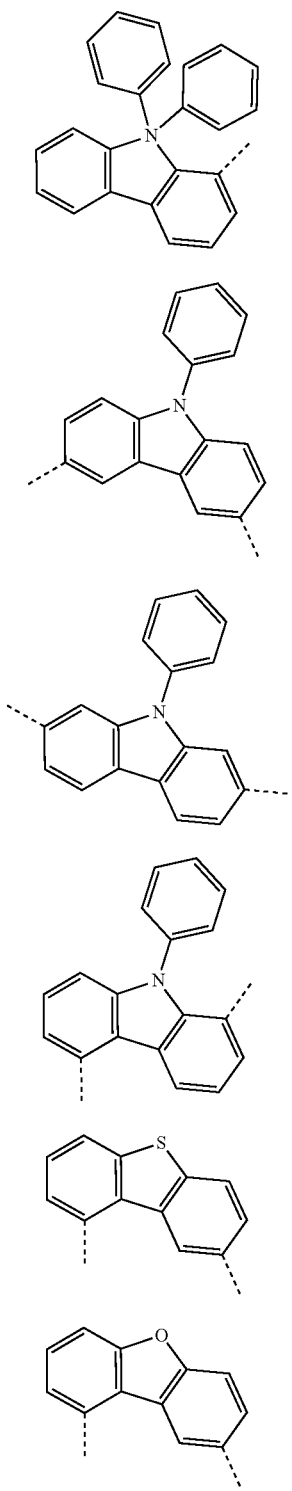

(L¹-32)

(L¹-33)

(L¹-34)

(L¹-35)

(L¹-36)

(L¹-37)

Ar³ is preferably an aromatic ring system which has 6 to 30 aromatic ring atoms and may be substituted by one or more R⁴ radicals. Ar³ is more preferably selected from phenyl, biphenyl, terphenyl, fluorenyl, fluorenyl-phenyl, naphthyl, naphthyl-phenyl, spirobifluorenyl, spirobifluorenyl-phenyl, pyridyl, pyrimidyl, triazinyl, dibenzofuranyl, dibenzofuranyl-phenyl, benzofused dibenzofuranyl, dibenzothiophenyl, dibenzothiophenyl-phenyl, benzofused dibenzothiophenyl, carbazolyl, carbazolyl-phenyl and benzofused carbazolyl, and combinations of two, three or four of these groups, where the groups mentioned may each be substituted by one or more R⁴ radicals.

The Ar³ group preferably does not correspond to one of the formulae (A) and (B).

Preferred embodiments of Ar³ are depicted below:

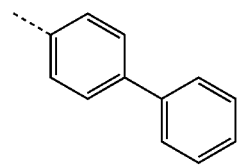

Ar³-1

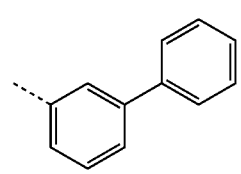

Ar³-2

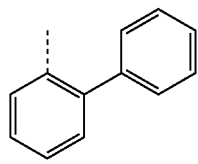

Ar³-3

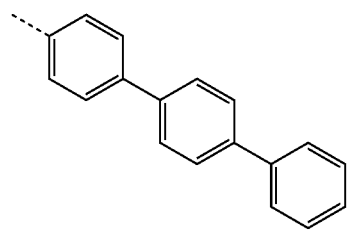

Ar³-4

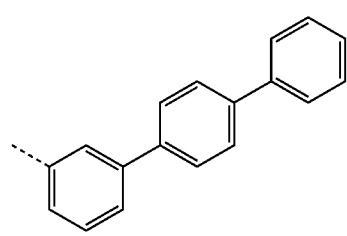

Ar³-5

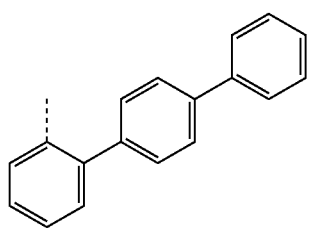

Ar³-6

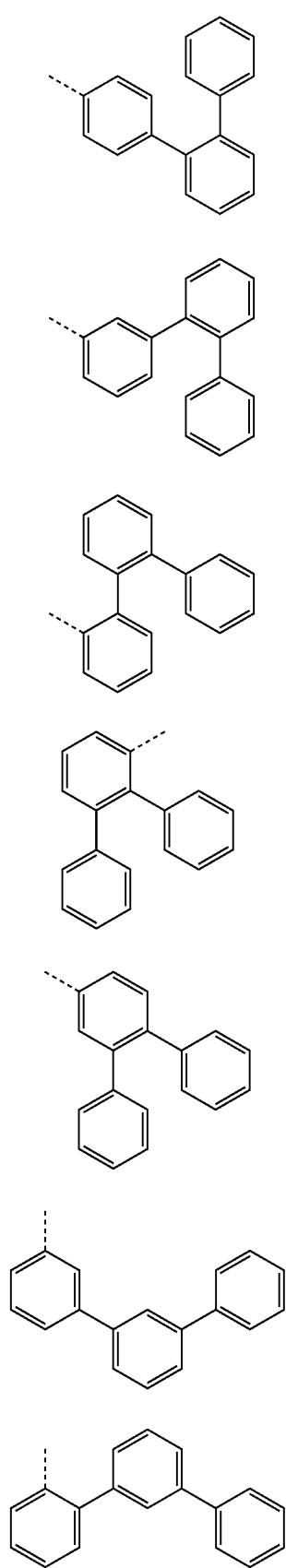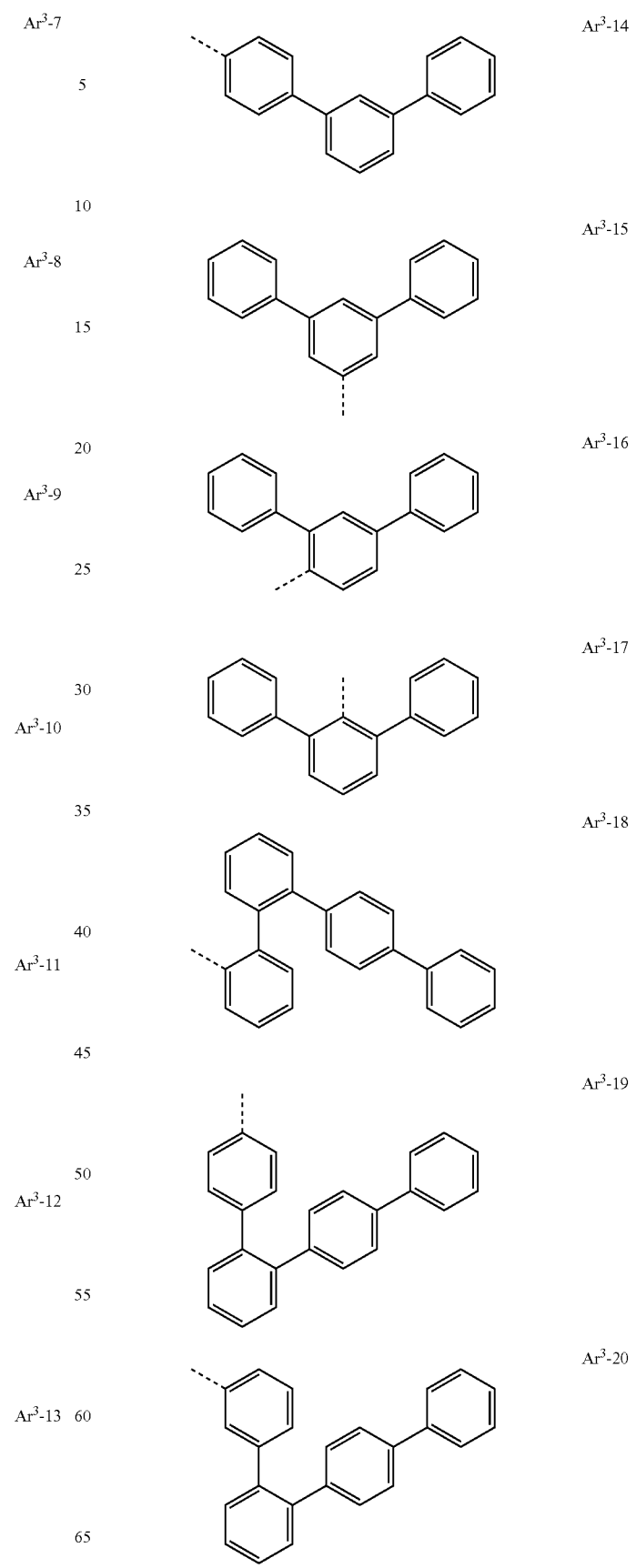

Ar³-21
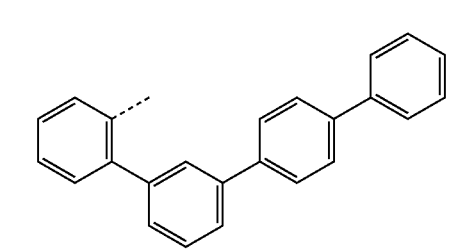
Ar³-22
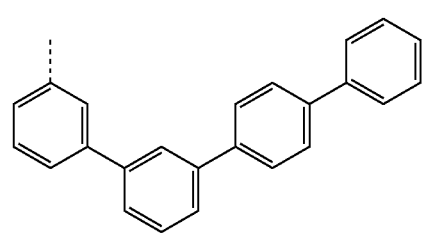
Ar³-23
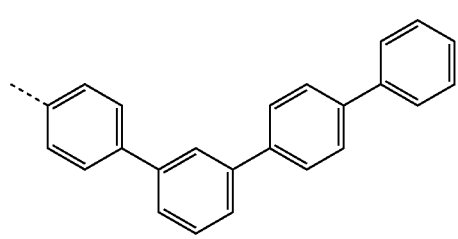
Ar³-24
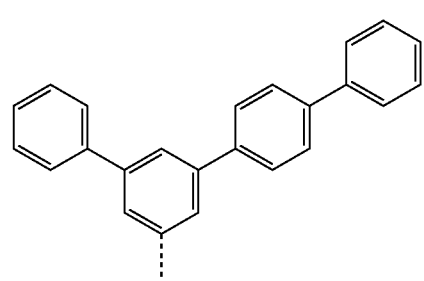
Ar³-25
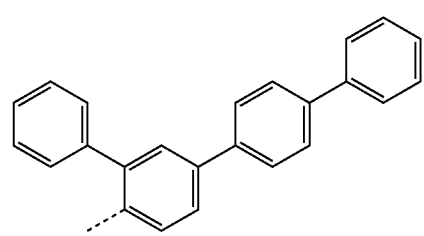
Ar³-26
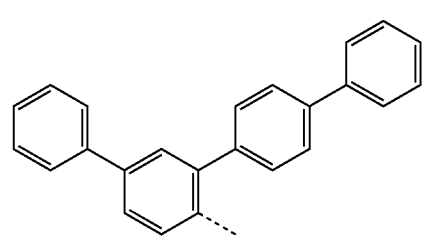
Ar³-27
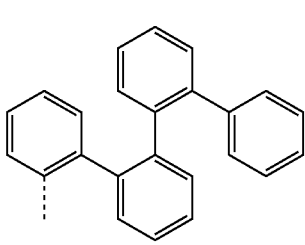
Ar³-28
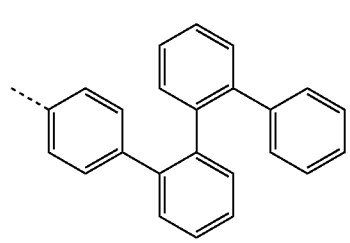
Ar³-29
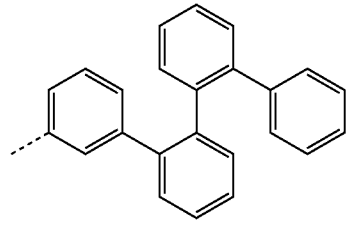
Ar³-30
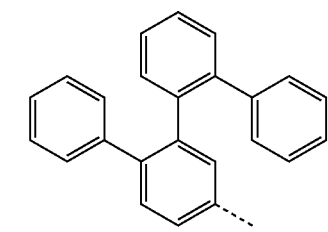
Ar³-31
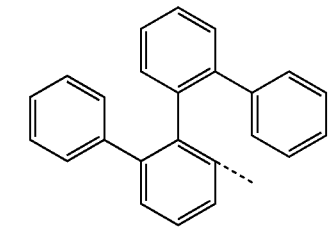
Ar³-32
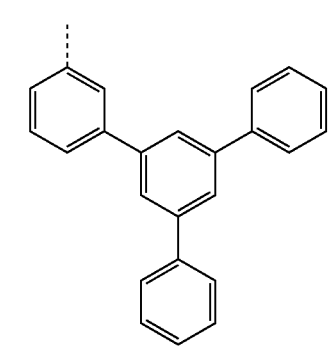

Ar³-33 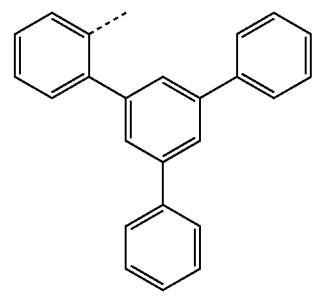
Ar³-34 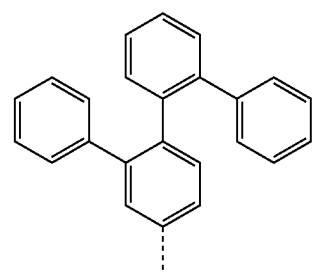
Ar³-35 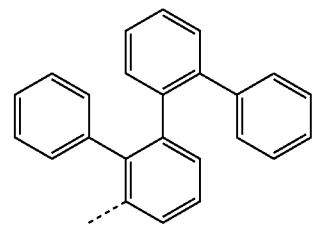
Ar³-36 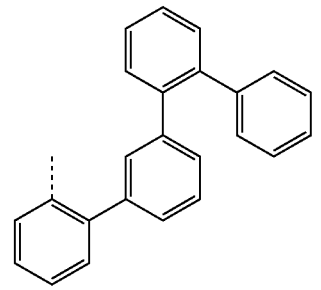
Ar³-37 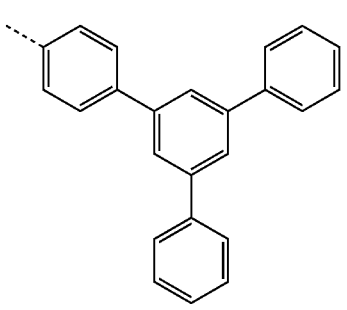
Ar³-38 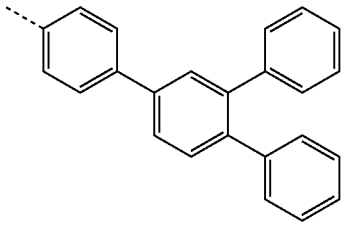
Ar³-39 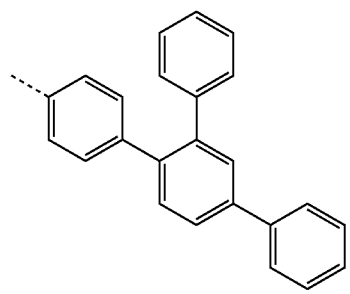
Ar³-40 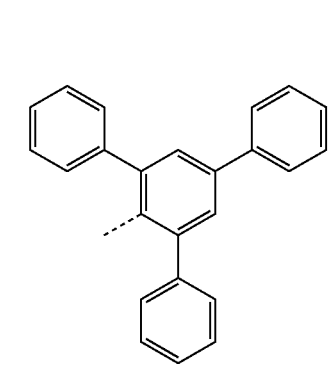
Ar³-41 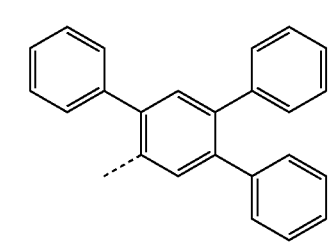
Ar³-42 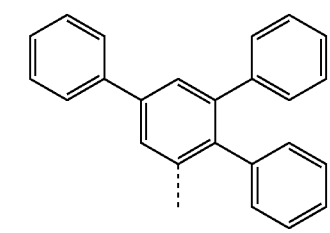
Ar³-43 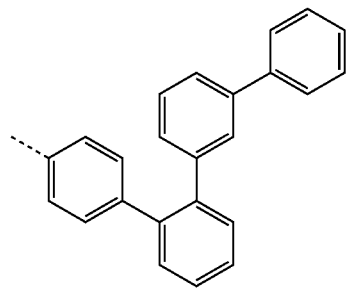

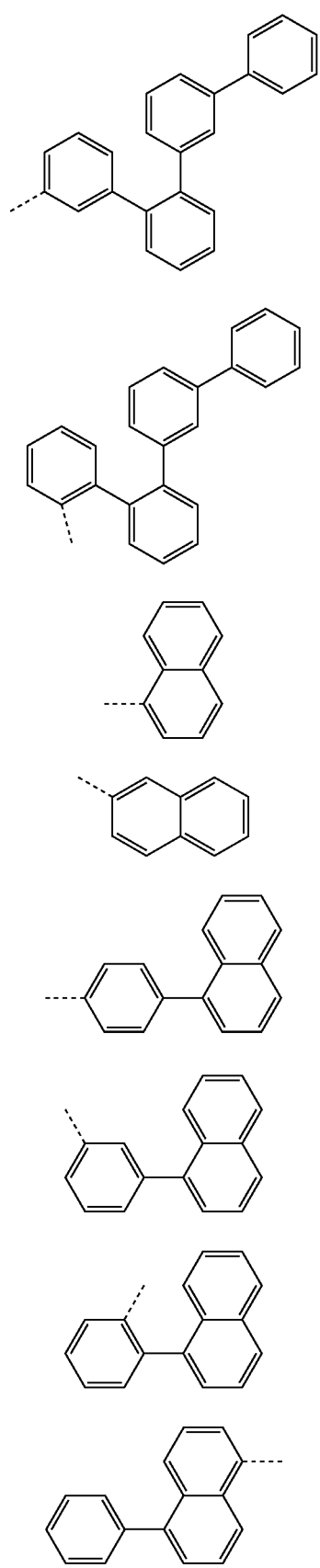
Ar³-44
Ar³-45
Ar³-46
Ar³-47
Ar³-48
Ar³-49
Ar³-50
Ar³-51
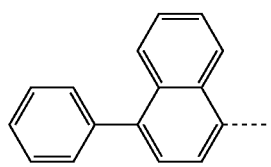
Ar³-52
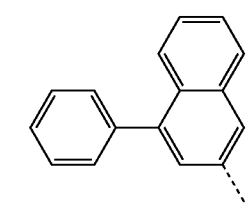
Ar³-53
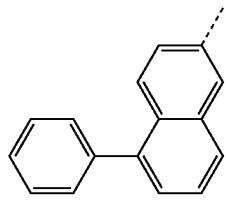
Ar³-54
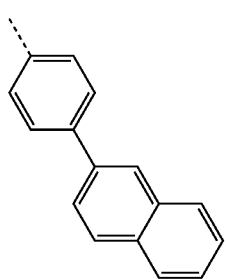
Ar³-55
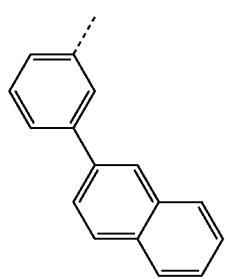
Ar³-56
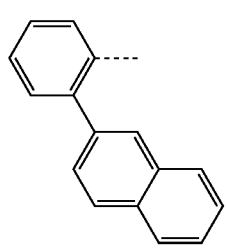
Ar³-57

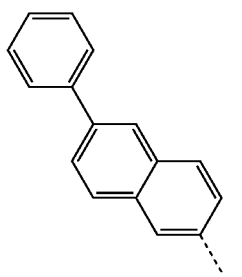
Ar3-58
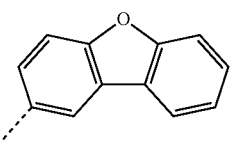
Ar3-59
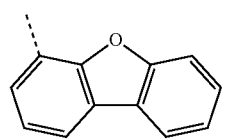
Ar3-60
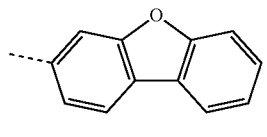
Ar3-61
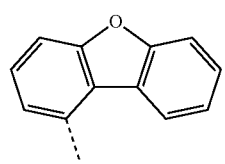
Ar3-62
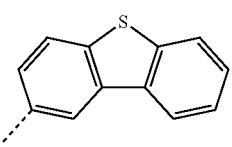
Ar3-63
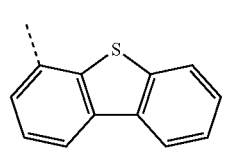
Ar3-64
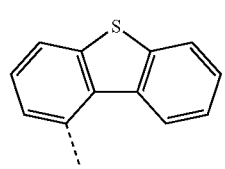
Ar3-65
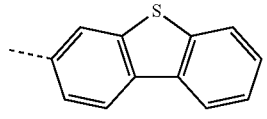
Ar3-66
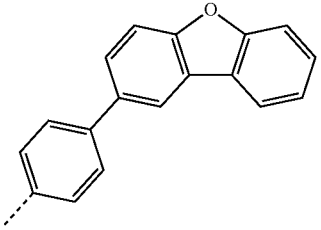
Ar3-67
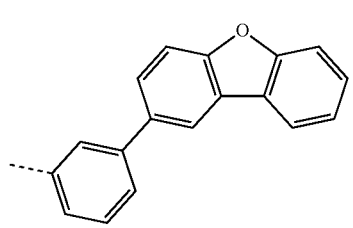
Ar3-68
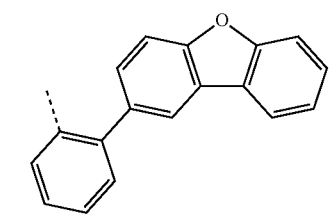
Ar3-69
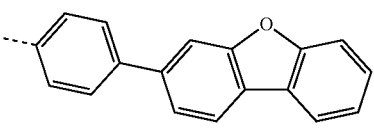
Ar3-70
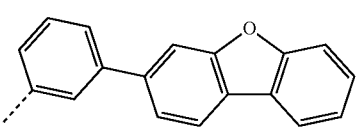
Ar3-71
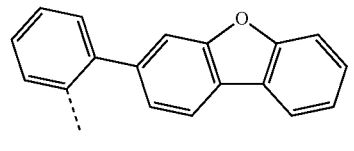
Ar3-72
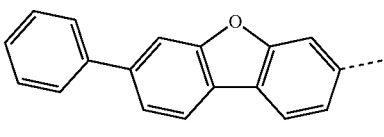
Ar3-73
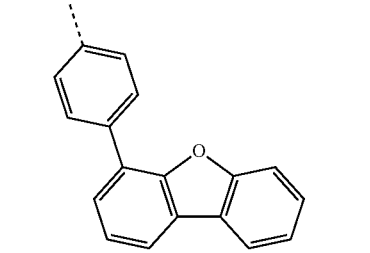
Ar3-74

Ar³-75 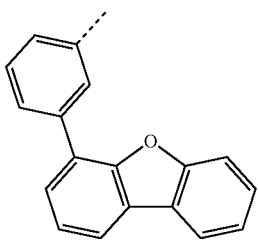
Ar³-76 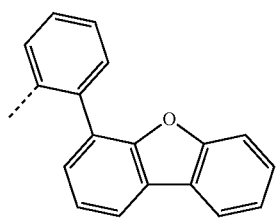
Ar³-77 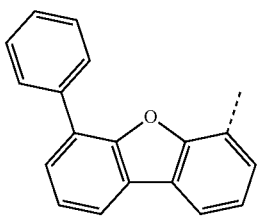
Ar³-78 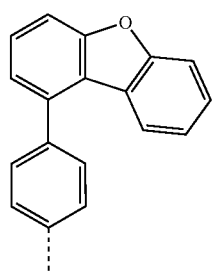
Ar³-79 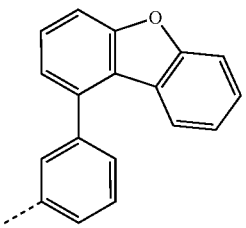
Ar³-80 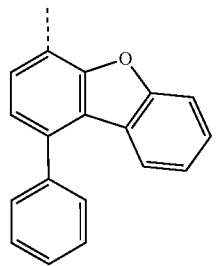
Ar³-81 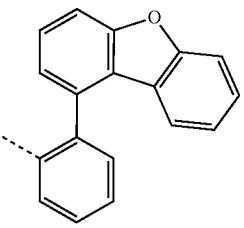
Ar³-82 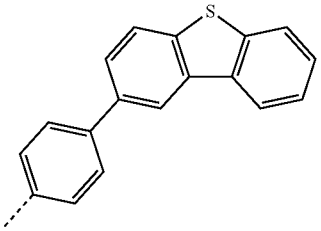
Ar³-83 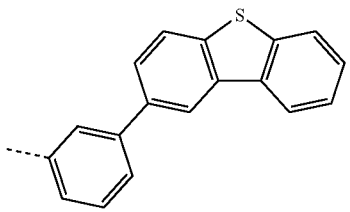
Ar³-84 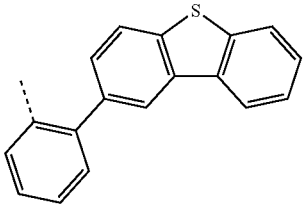
Ar³-85 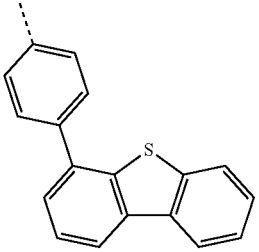
Ar³-86 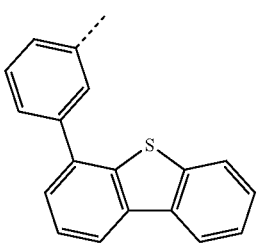

-continued
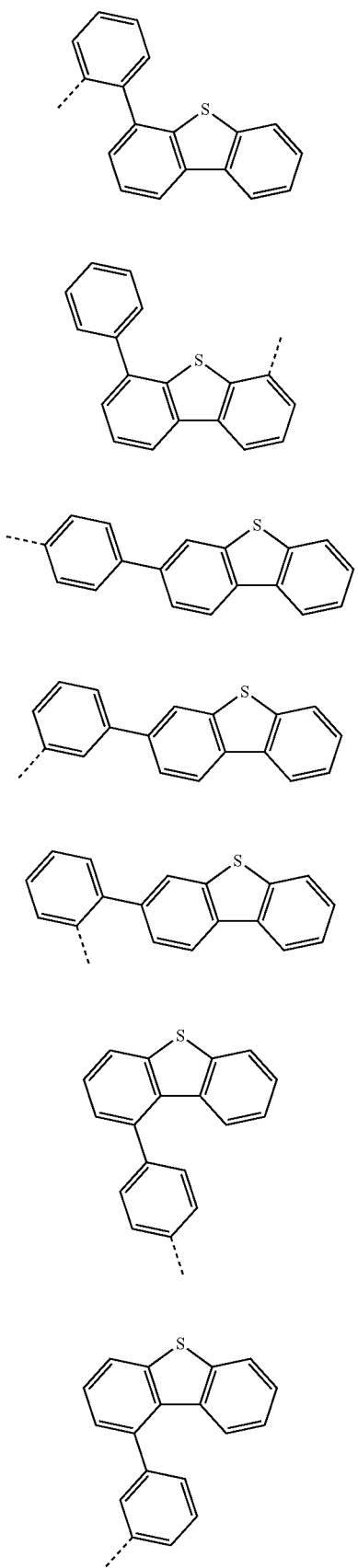
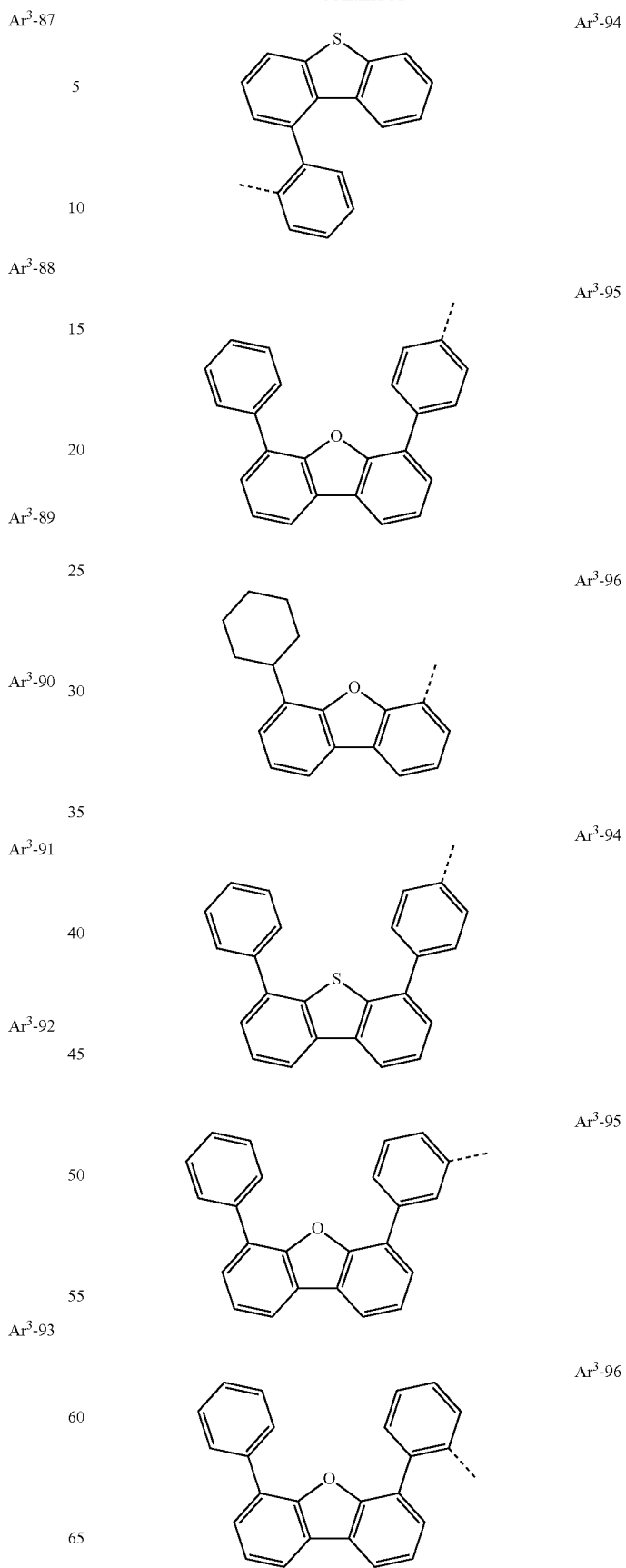

-continued
Ar³-97
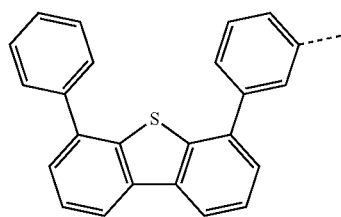
Ar³-98
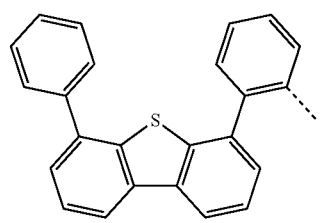
Ar³-99
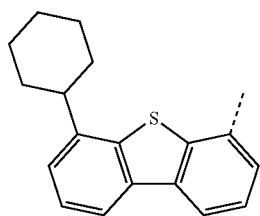
Ar³-100
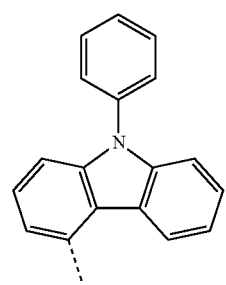
Ar³-101
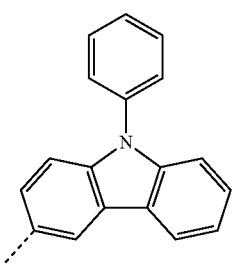
Ar³-102
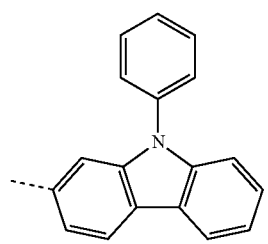
-continued
Ar³-103
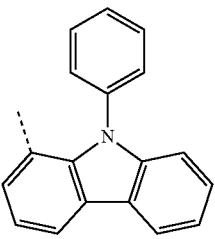
Ar³-104
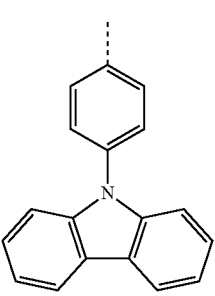
Ar3-105
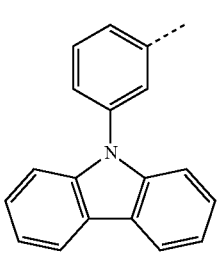
Ar3-106
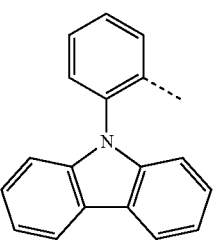
Ar3-107
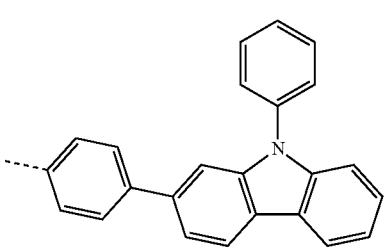
Ar3-108
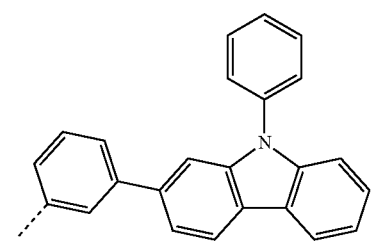

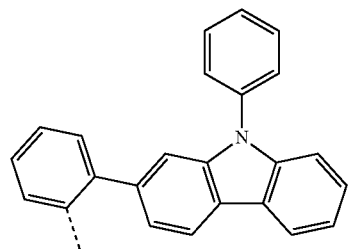 Ar3-109
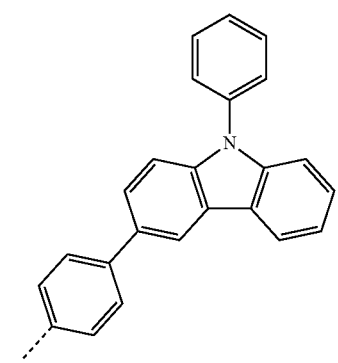 Ar3-110
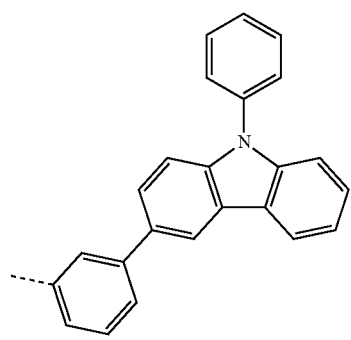 Ar3-111
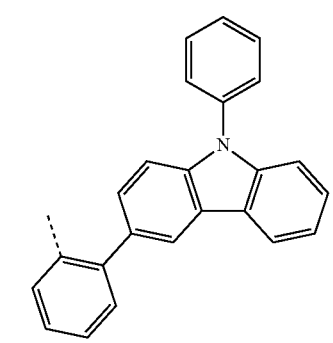 Ar3-112
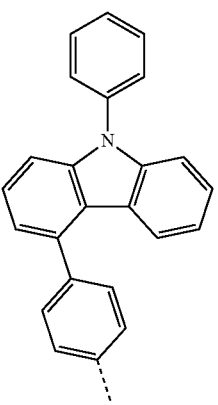 Ar³-113
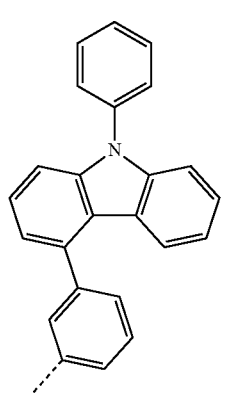 Ar³-114
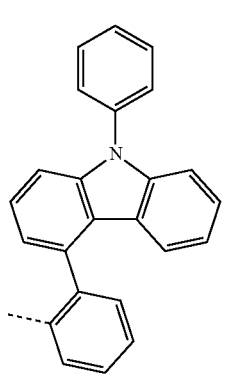 Ar³-115
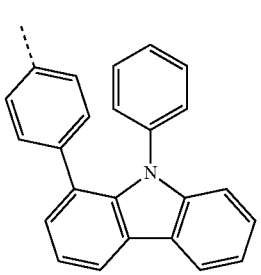 Ar³-116

-continued
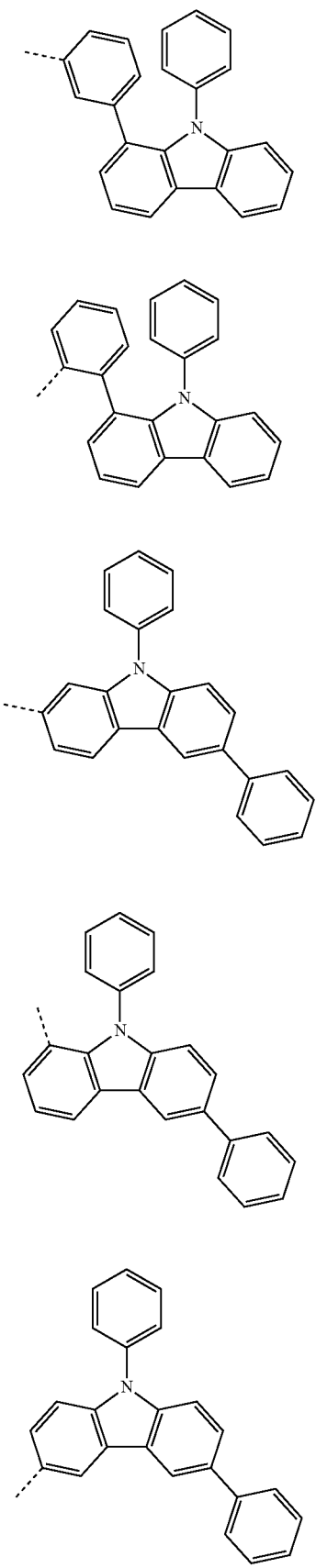
Ar³-117
Ar³-118
Ar³-119
Ar³-120
Ar³-121
-continued
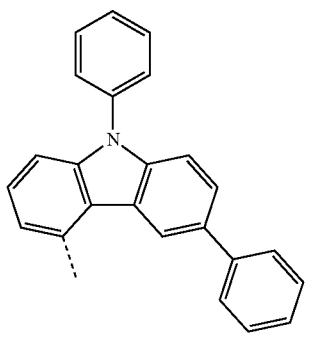
Ar³-122
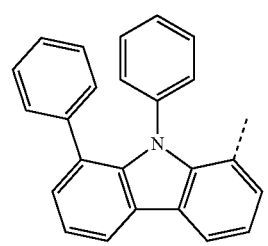
Ar³-123
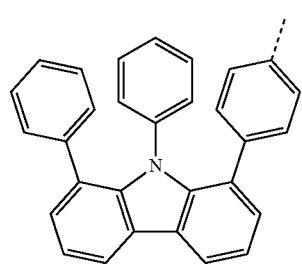
Ar³-124
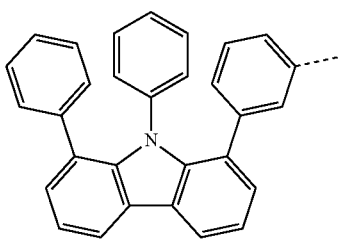
Ar³-125
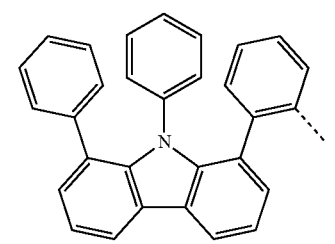
Ar³-126

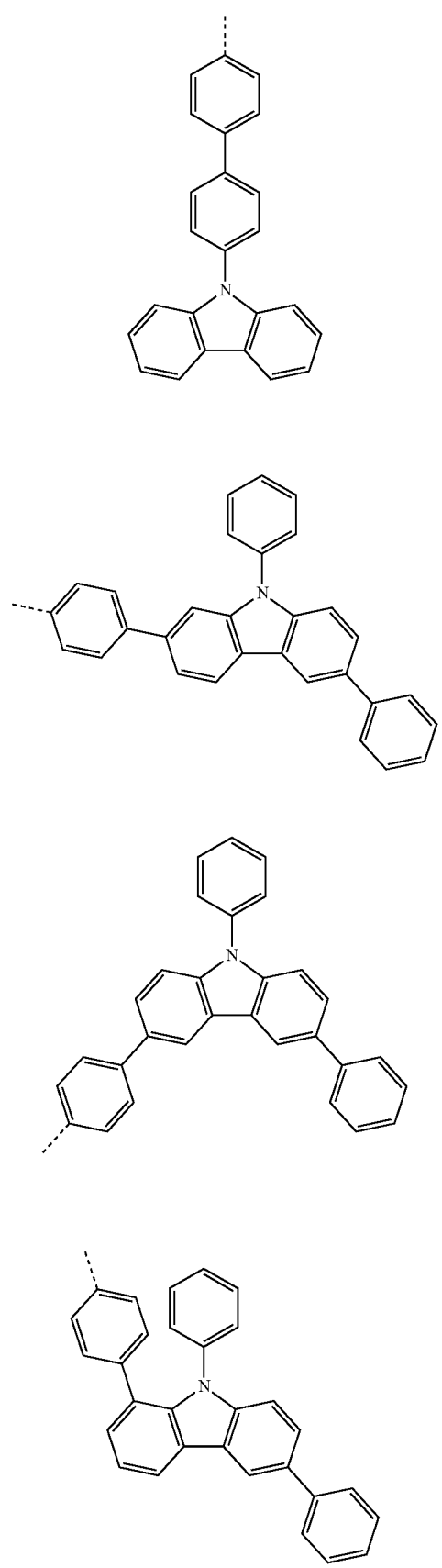
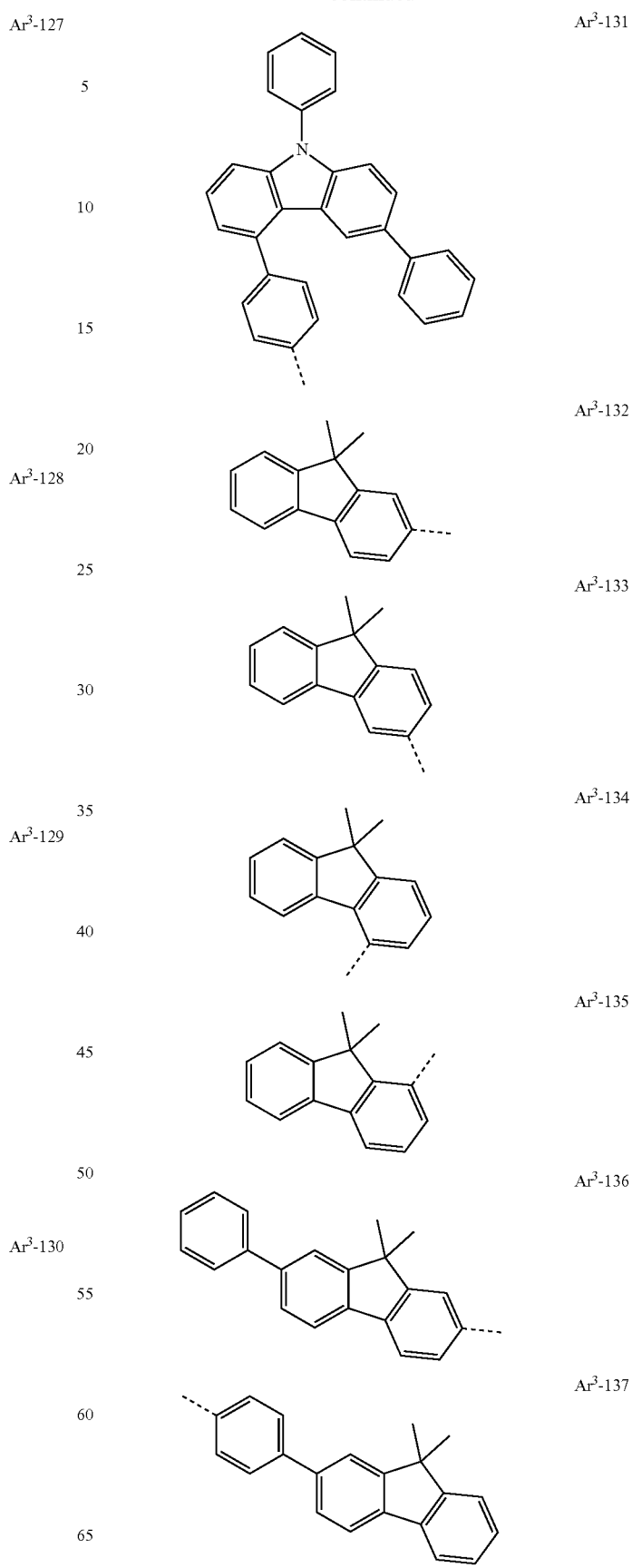

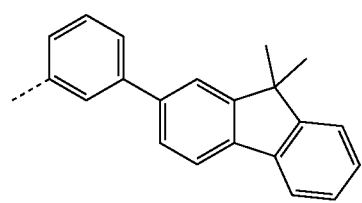 Ar³-138
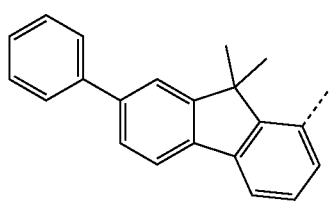 Ar³-139
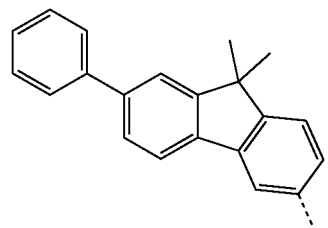 Ar³-140
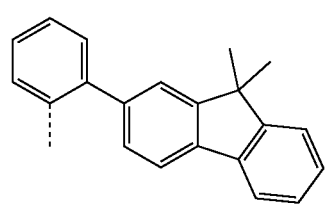 Ar³-141
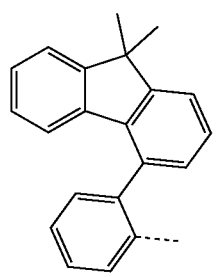 Ar³-142
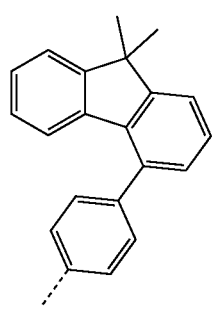 Ar³-143
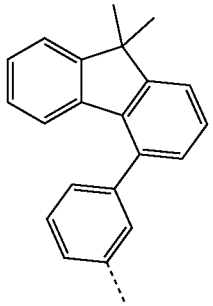 Ar³-144
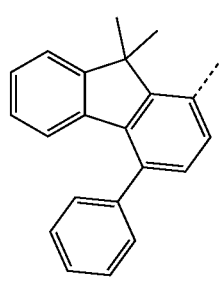 Ar³-145
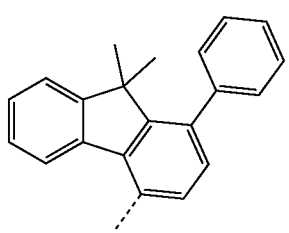 Ar³-146
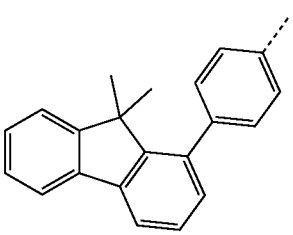 Ar³-147
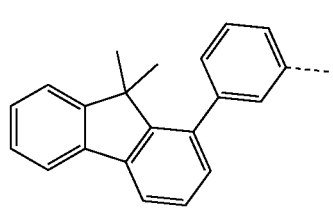 Ar³-148
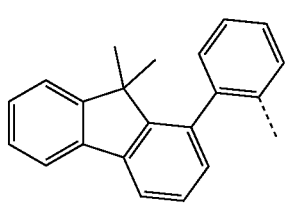 Ar³-149

-continued
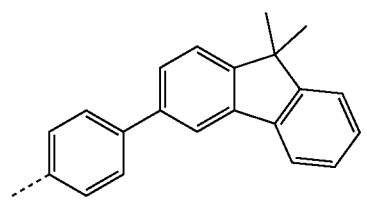 Ar³-150
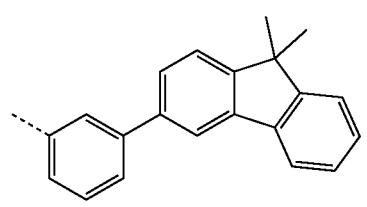 Ar³-151
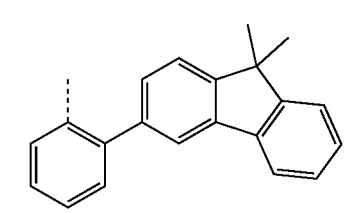 Ar³-152
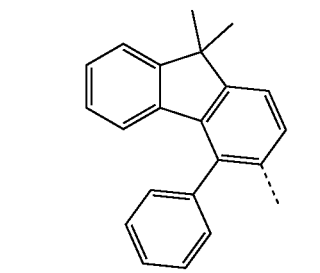 Ar³-153
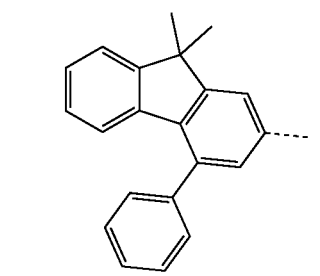 Ar³-154
Ar³-155
Ar³-156
-continued
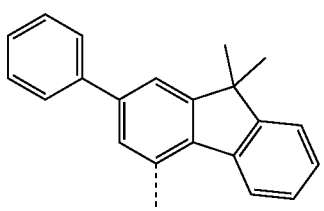 Ar³-157
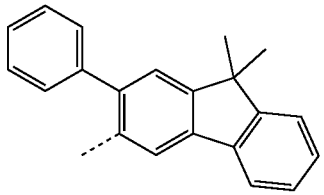 Ar³-158
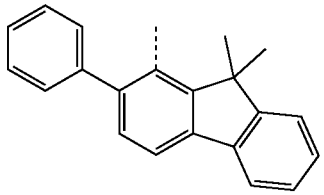 Ar³-159
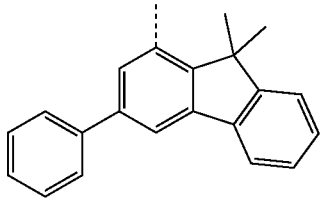 Ar³-160
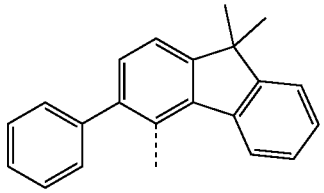 Ar³-161
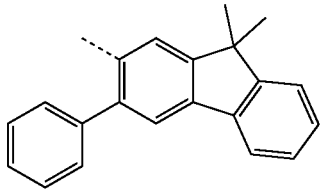 Ar³-162
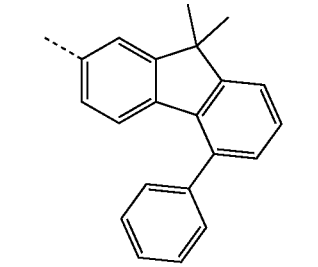 Ar³-163

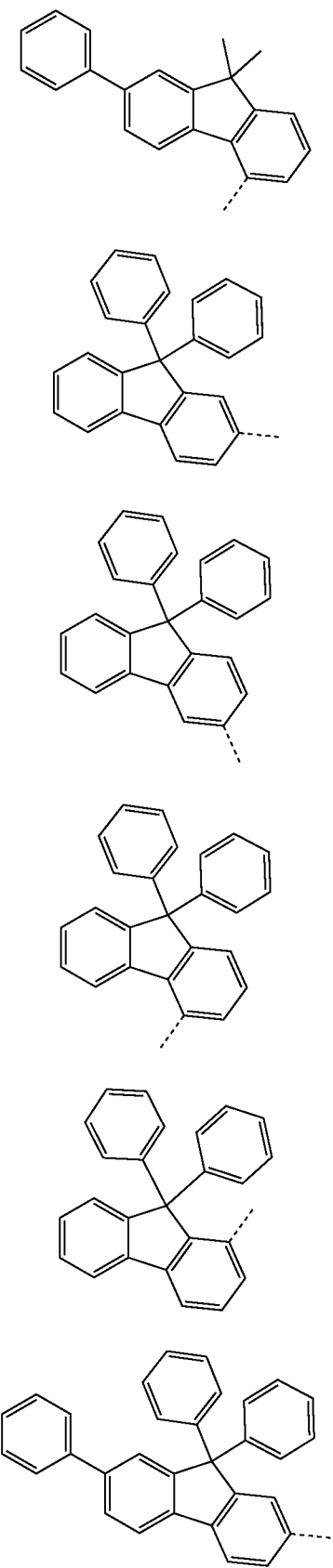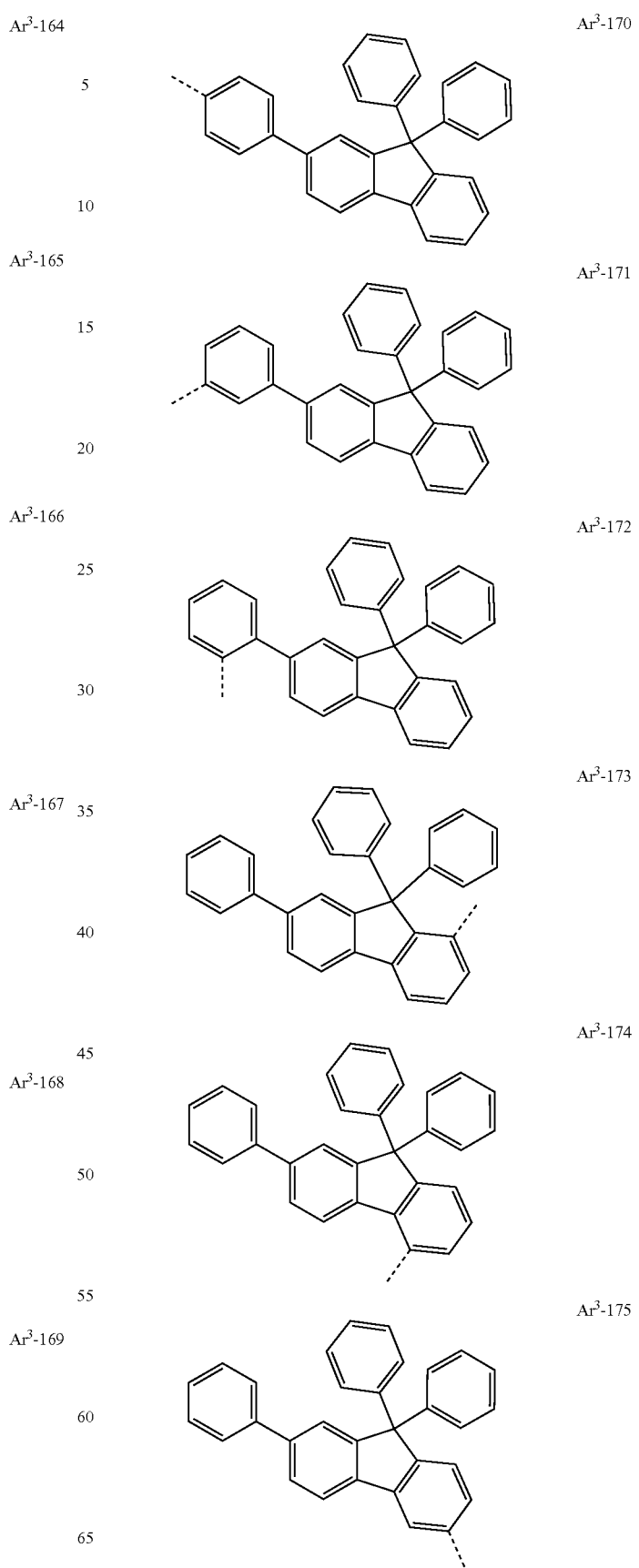

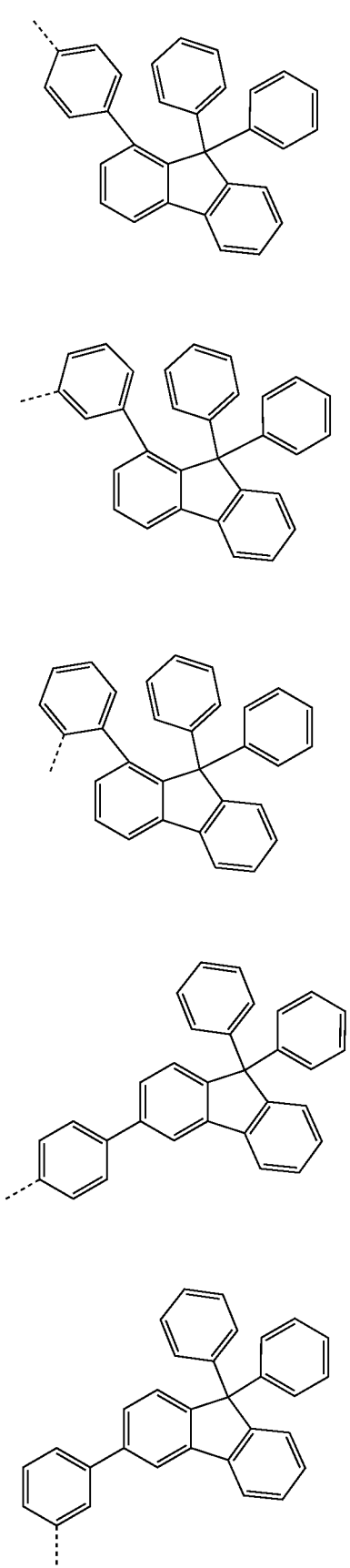
Ar³-176
Ar³-177
Ar³-178
Ar³-179
Ar³-180
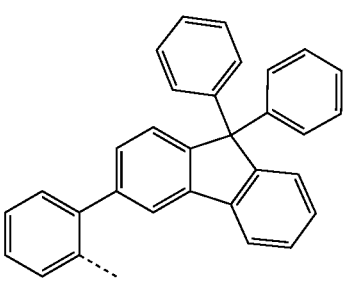
Ar³-181
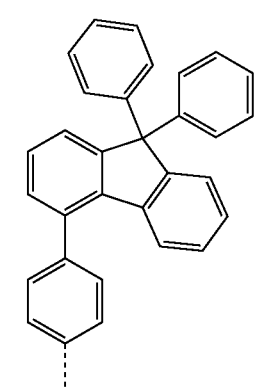
Ar³-182
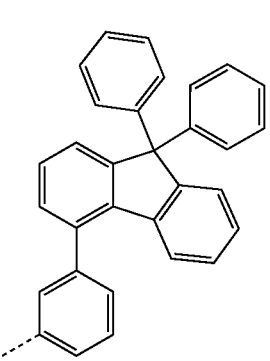
Ar³-183
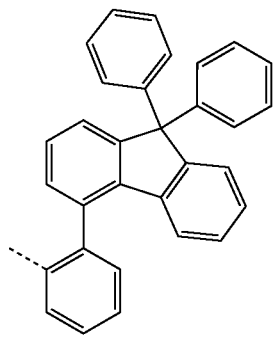
Ar³-184
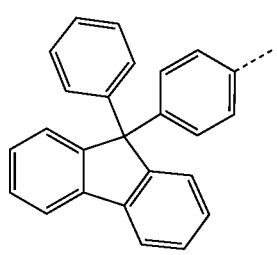
Ar³-185

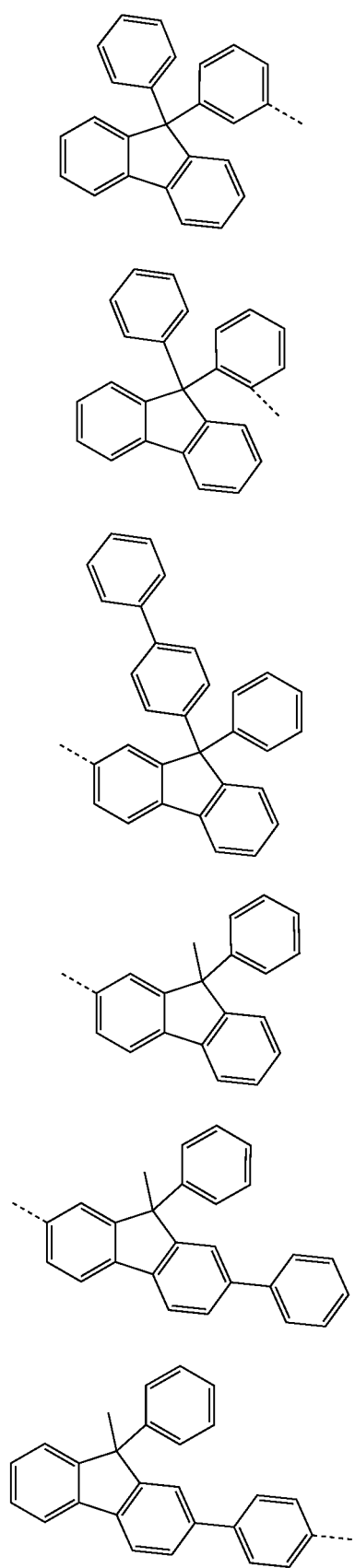
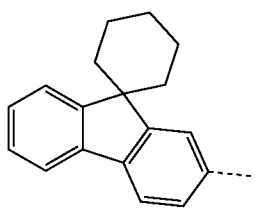

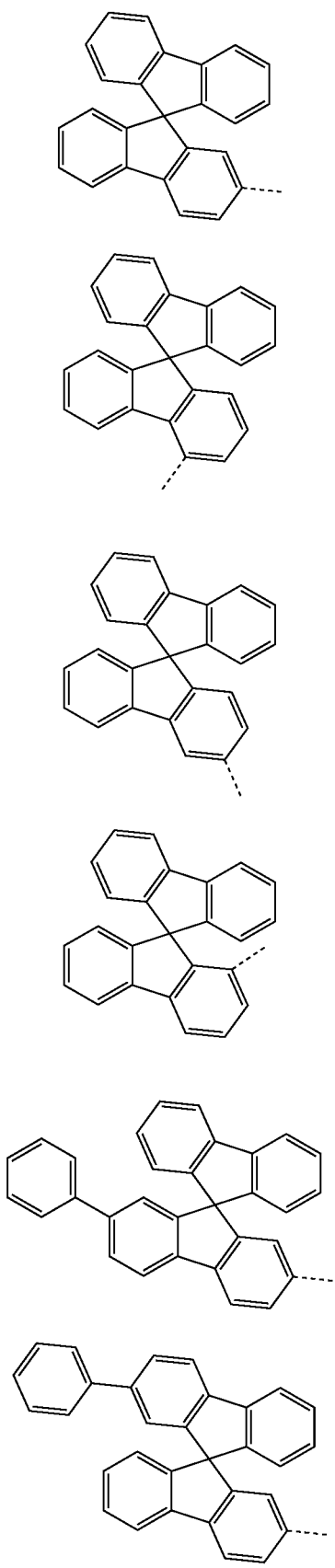
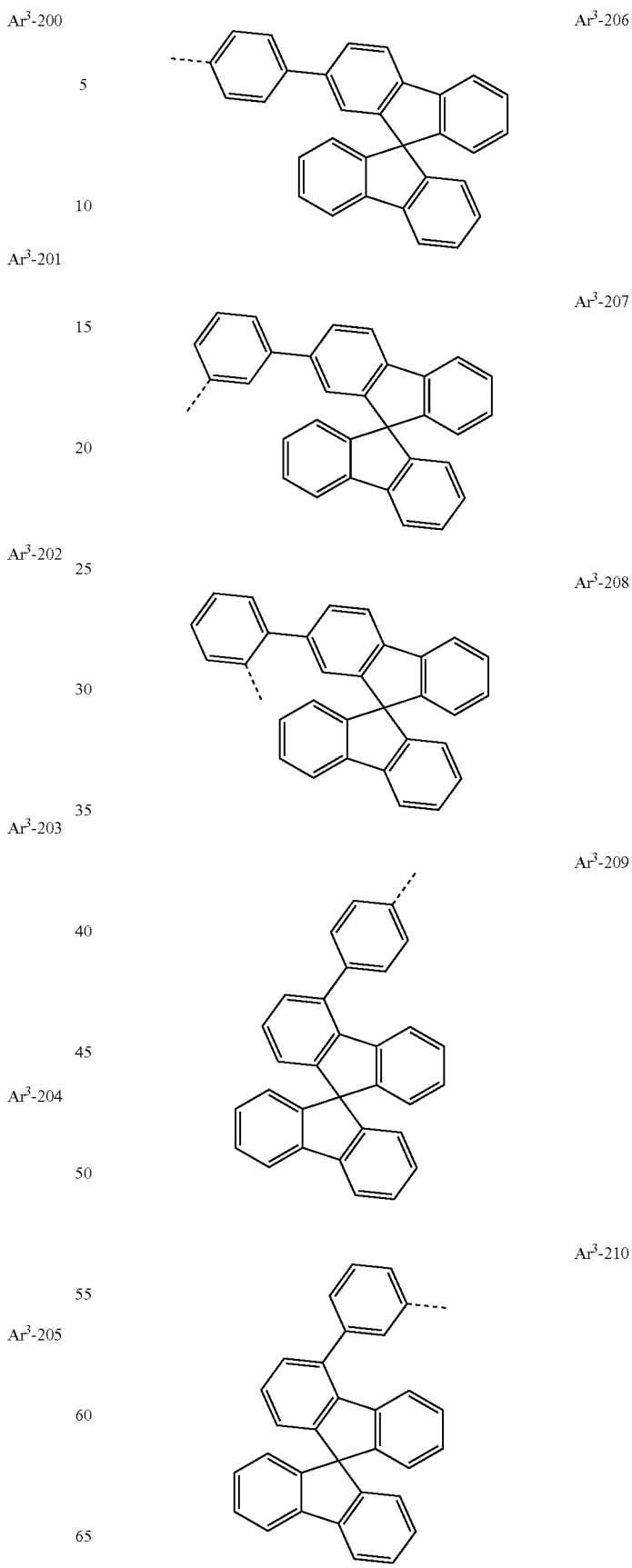

-continued
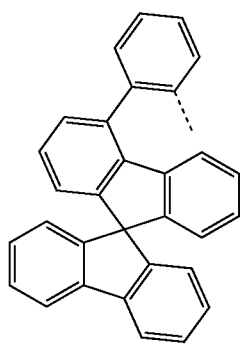
Ar³-211
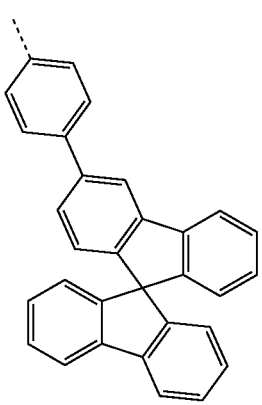
Ar³-212
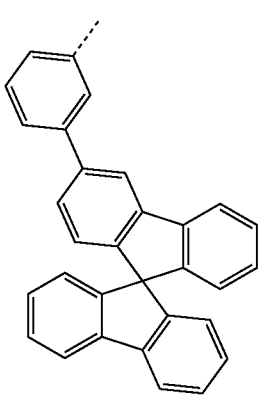
Ar³-213
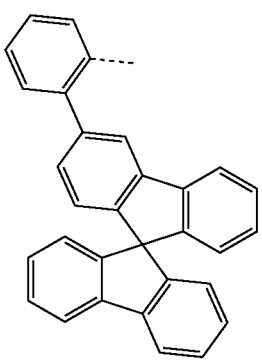
Ar³-214
-continued
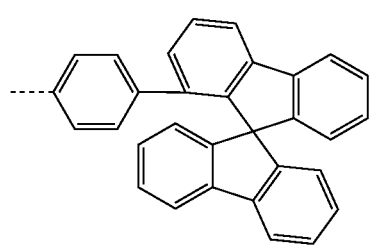
Ar³-215
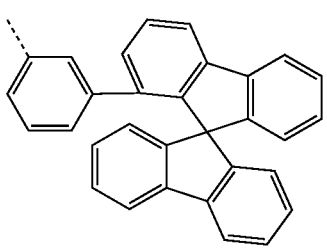
Ar³-216
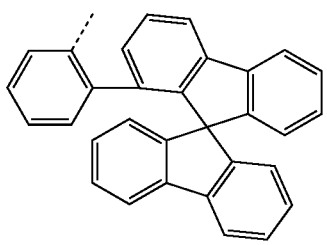
Ar³-217
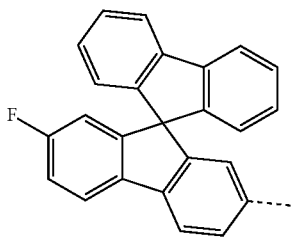
Ar³-218
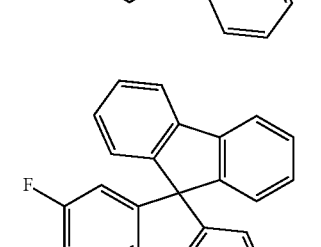
Ar³-219
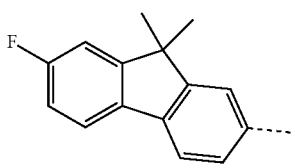
Ar³-220
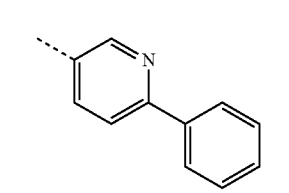
Ar³-221

Ar³-222 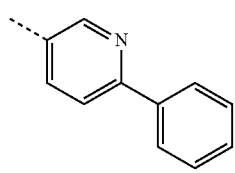
Ar³-223 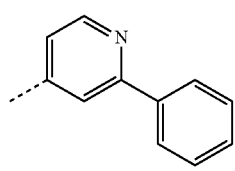
Ar³-224 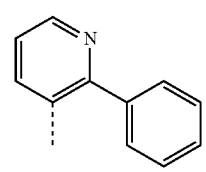
Ar³-225 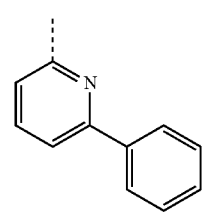
Ar³-226 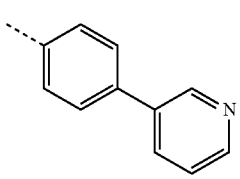
Ar³-227 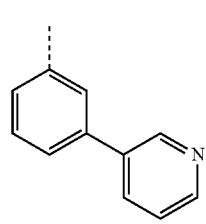
Ar³-228 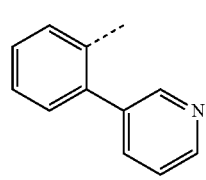
Ar³-229 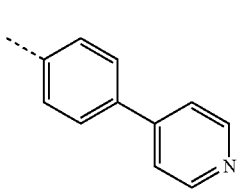
Ar³-230 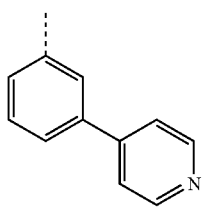
Ar³-231 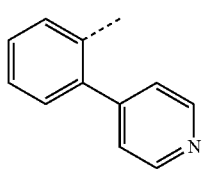
Ar³-232 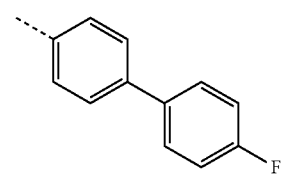
Ar³-233 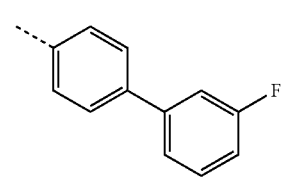
Ar³-234 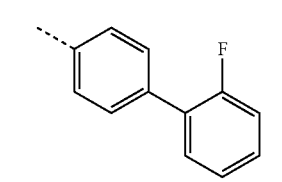
Ar³-235 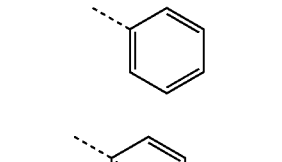
Ar³-236 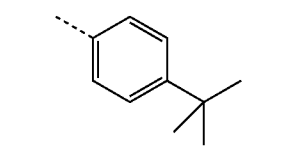
Ar³-237 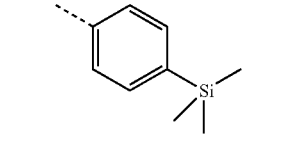
Ar³-238 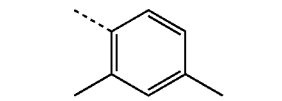
Ar³-239

-continued

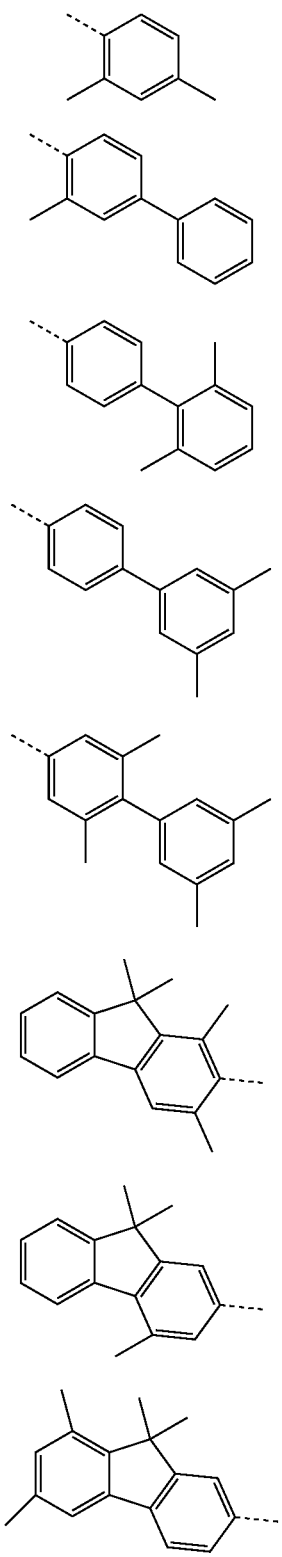

Ar³-240
Ar³-241
Ar³-242
Ar³-243
Ar³-244
Ar³-245
Ar³-246
Ar³-247 which may each be substituted by one or more R⁴ radicals at the free positions.

$R^1$, $R^2$, $R^3$ and $R^4$ are preferably the same or different at each instance and are selected from H, D, F, CN, $Si(R^5)_3$, $N(R^5)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned may each be substituted by one or more $R^5$ radicals; and where one or more $CH_2$ groups in the alkyl groups mentioned may be replaced by —C≡C—, —$R^5$C=C$R^5$—, Si($R^5$)$_2$, C=O, C=N$R^5$, —N$R^5$—, —O—, —S—, —C(=O)O— or —C(=O)N$R^5$—.

More preferably, $R^1$ is H, with the exception of $R^1$ groups bonded to a T group which is $C(R^1)_2$ or $NR^1$. In this case, $R^1$ is preferably selected from alkyl groups having 1 to 20 carbon atoms and aromatic ring systems having 5 to 40 aromatic ring atoms, where the alkyl groups mentioned and the aromatic ring systems mentioned may each be substituted by one or more $R^5$ radicals. More preferably $R^2$ is H. More preferably $R^3$ is H. More preferably $R^4$ is H.

$R^5$ is preferably the same or different at each instance and is selected from H, D, F, ON, $Si(R^6)_3$, $N(R^6)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned may each be substituted by one or more $R^6$ radicals; and where one or more $CH_2$ groups in the alkyl groups mentioned may be replaced by —C≡C—, —$R^6$C=C$R^6$—, Si($R^6$)$_2$, C=O, C=N$R^6$, —N$R^6$—, —O—, —S—, —C(=O)O— or —C(=O)N$R^6$—. More preferably, $R^5$ is H.

$R^6$ is preferably the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl groups, aromatic ring systems and heteroaromatic ring systems mentioned may be substituted by F or CN.

Preferably, m is 0.
Preferably, i is 0 or 1.
Preferably, k is 0 or 1.
Preferably, the sum of i and k is 1 or 2, more preferably 1.

Preferred sub-units of the formula (I) in accordance with the formula (I-A)

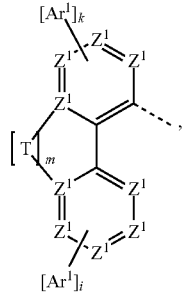

Formula (I-A)

where the dashed line represents the bond to the rest of the formula, are selected from the following structures Formula (I-A-1)
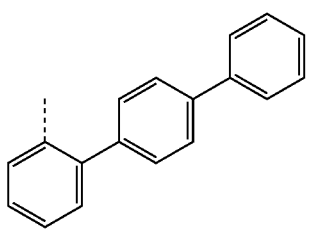
Formula (I-A-2)
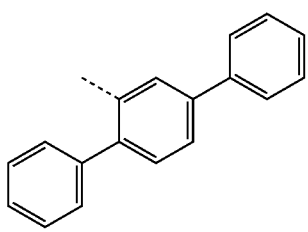
Formula (I-A-3)
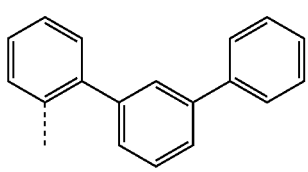
Formula (I-A-4)
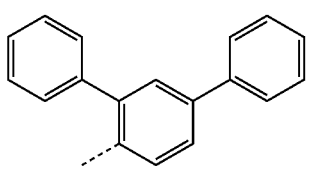
Formula (I-A-5)
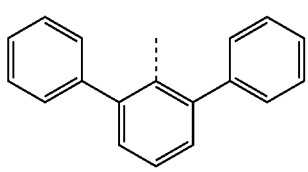
Formula (I-A-6)
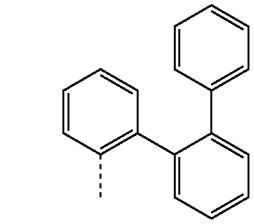
Formula (I-A-7)
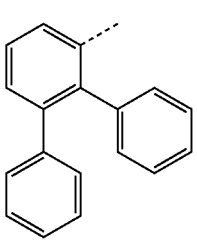
Formula (I-A-8)
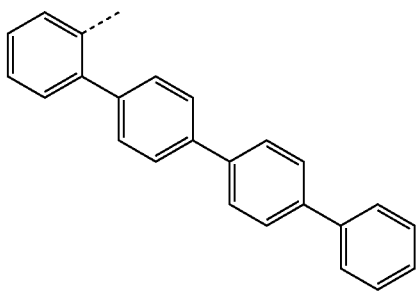
Formula (I-A-9)
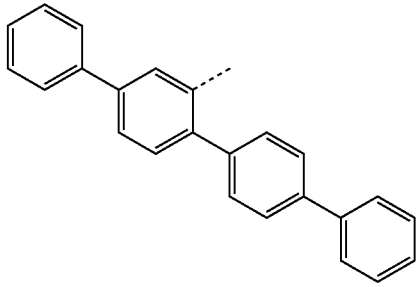
Formula (I-A-10)
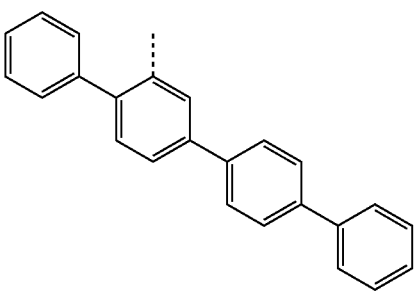
Formula (I-A-11)
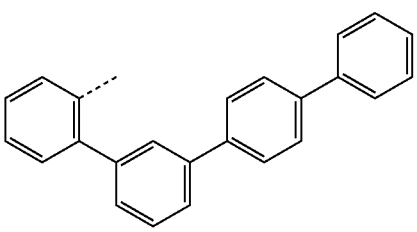
Formula (I-A-12)
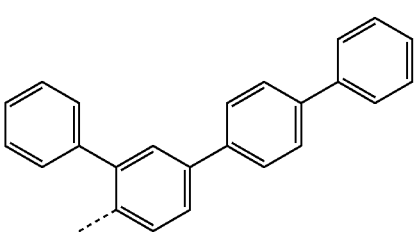

Formula (I-A-13)
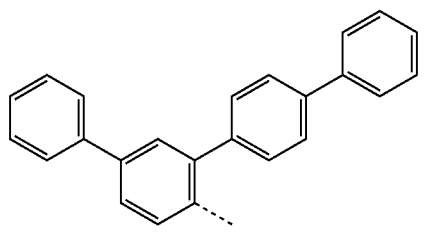
Formula (I-A-14)
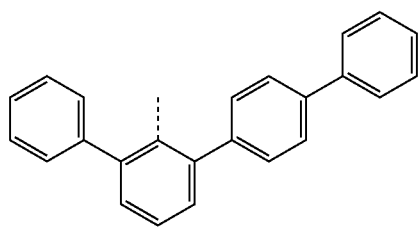
Formula (I-A-15)
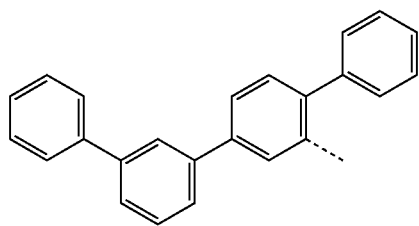
Formula (I-A-16)
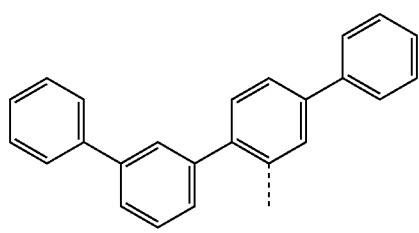
Formula (I-A-17)
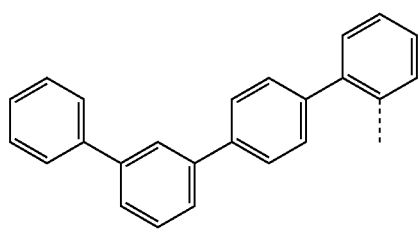
Formula (I-A-18)
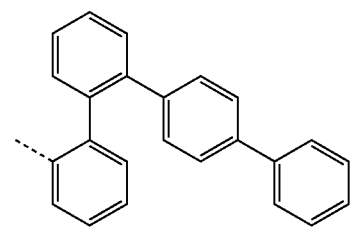
Formula (I-A-19)
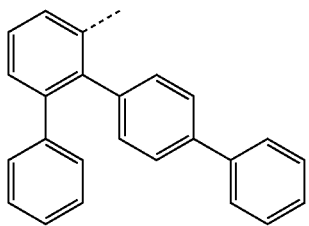
Formula (I-A-20)
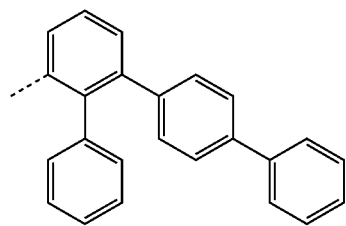
Formula (I-A-21)
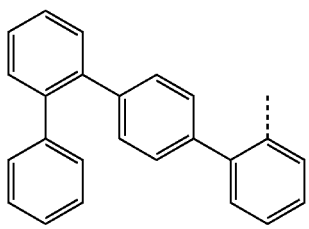
Formula (I-A-22)
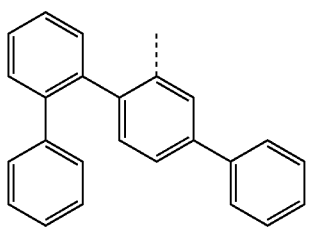
Formula (I-A-23)
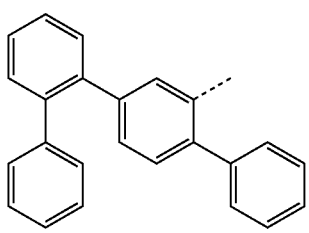
Formula (I-A-24)
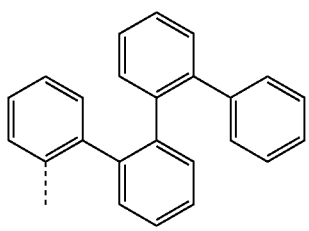

Formula (I-A-25)
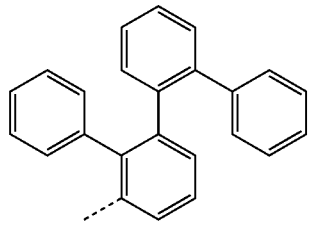
Formula (I-A-26)
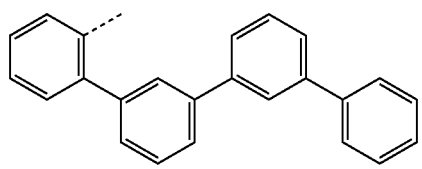
Formula (I-A-27)
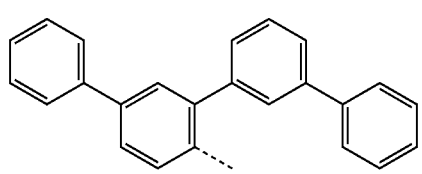
Formula (I-A-28)
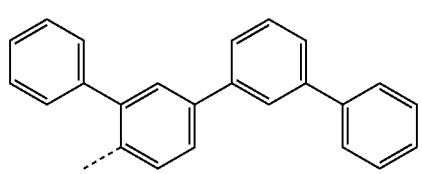
Formula (I-A-29)
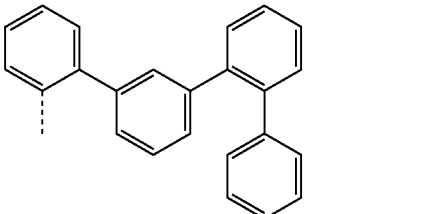
Formula (I-A-30)
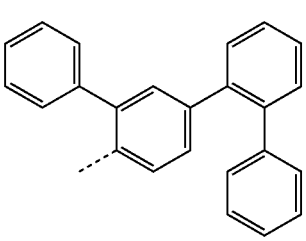
Formula (I-A-31)
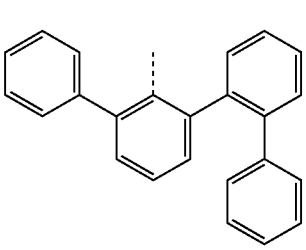
Formula (I-A-32)
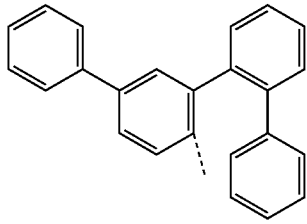
Formula (I-A-33)
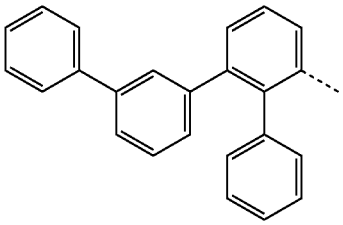
Formula (I-A-34)
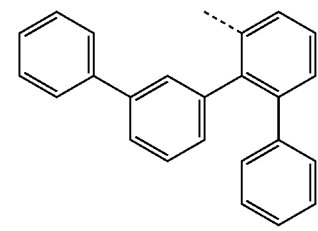
Formula (I-A-35)
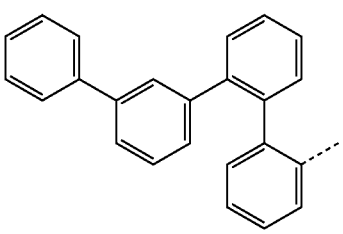
Formula (I-A-36)
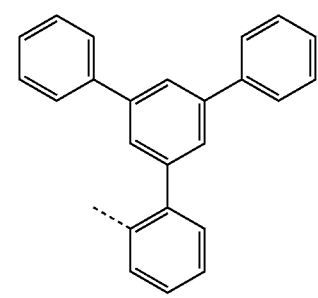
Formula (I-A-37)
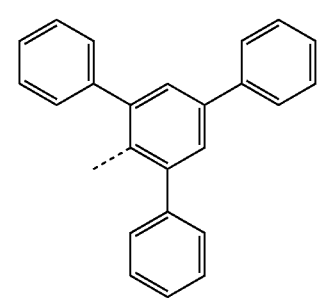

Formula (I-A-38)
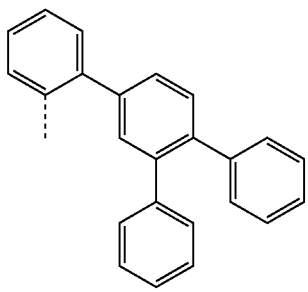
Formula (I-A-39)
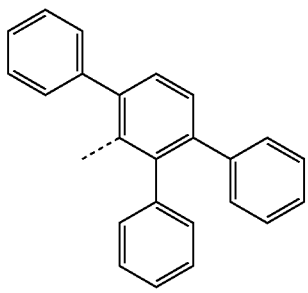
Formula (I-A-40)
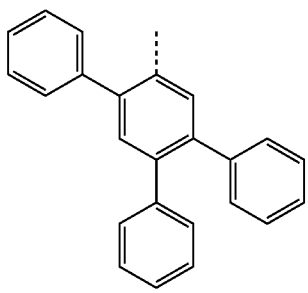
Formula (I-A-41)
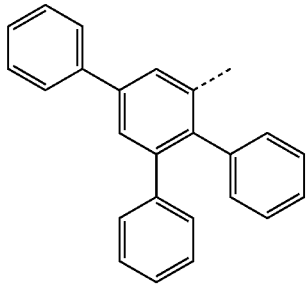
Formula (I-A-42)
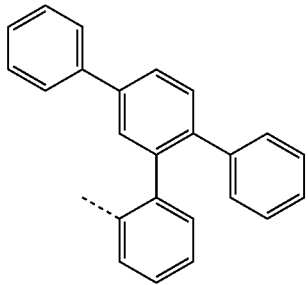
Formula (I-A-43)
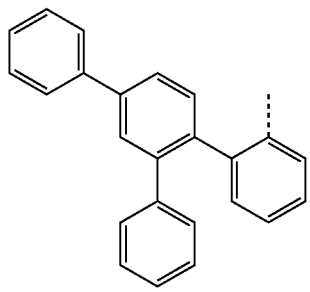
Formula (I-A-44)
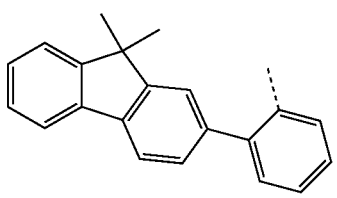
Formula (I-A-45)
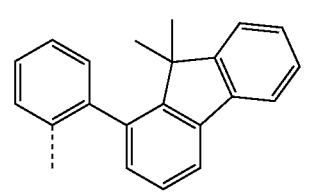
Formula (I-A-46)
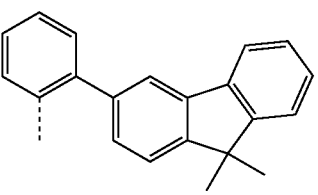
Formula (I-A-47)
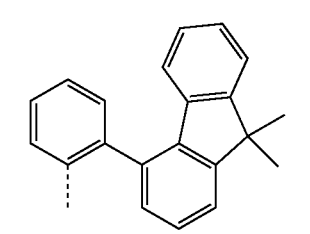
Formula (I-A-48)
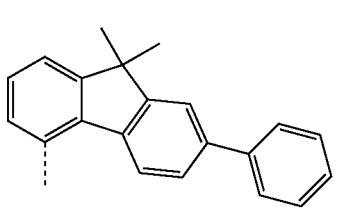
Formula (I-A-49)
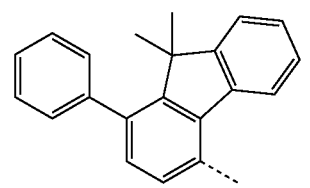

Formula (I-A-50)
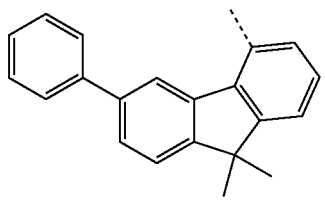
Formula (I-A-51)
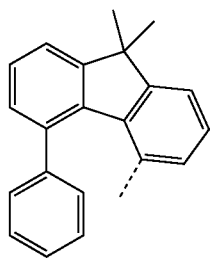
Formula (I-A-52)
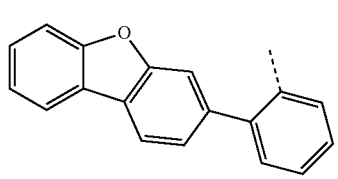
Formula (I-A-53)
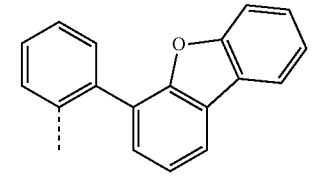
Formula (I-A-54)
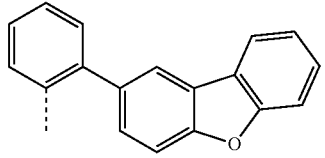
Formula (I-A-55)
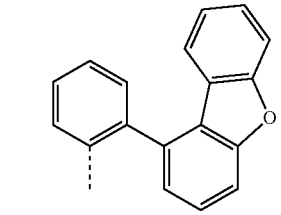
Formula (I-A-56)
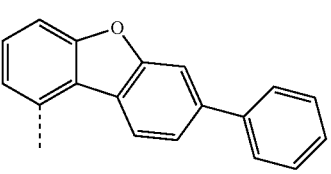
Formula (I-A-57)
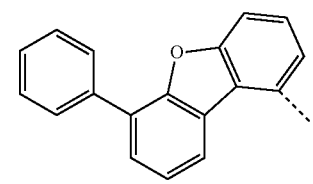
Formula (I-A-58)
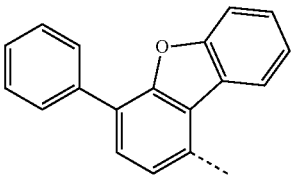
Formula (I-A-59)
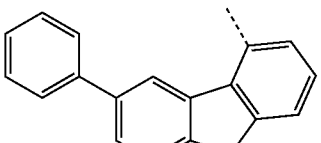
Formula (I-A-60)
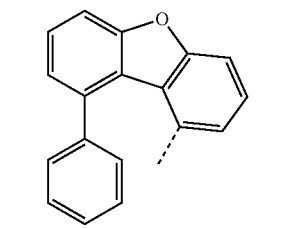
Formula (I-A-61)
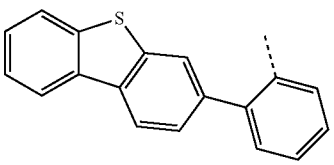
Formula (I-A-62)
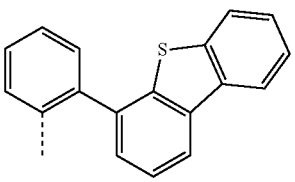
Formula (I-A-63)
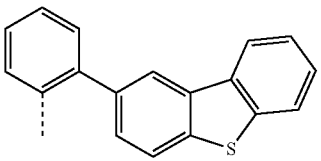
Formula (I-A-64)
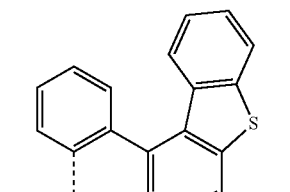
Formula (I-A-65)
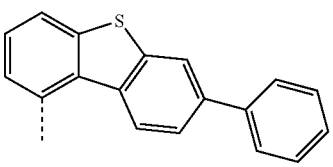

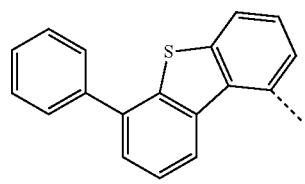
Formula (I-A-66)
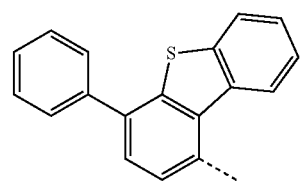
Formula (I-A-67)
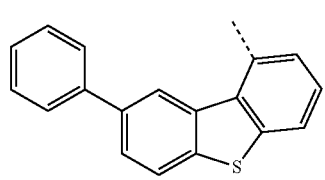
Formula (I-A-68)
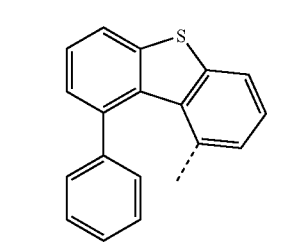
Formula (I-A-69)
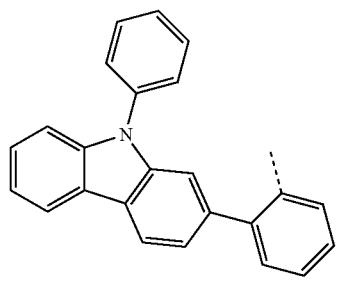
Formula (I-A-70)
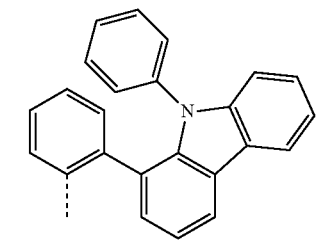
Formula (I-A-71)
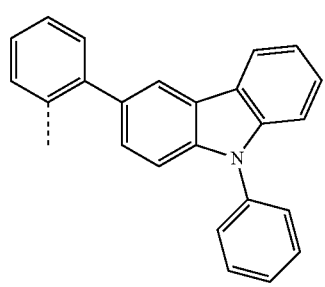
Formula (I-A-72)
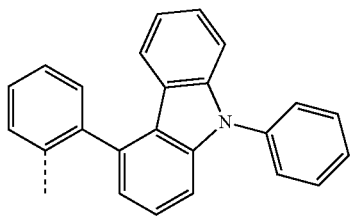
Formula (I-A-73)
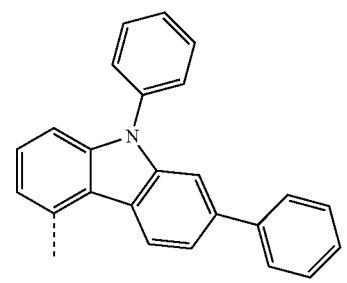
Formula (I-A-74)
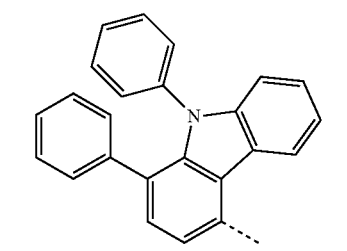
Formula (I-A-75)
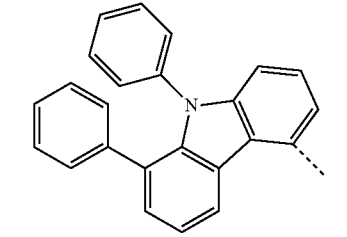
Formula (I-A-76)
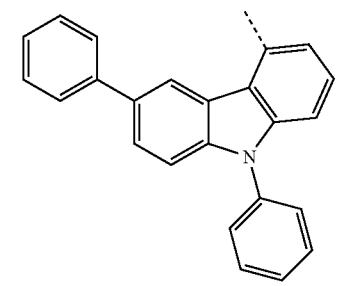
Formula (I-A-77)
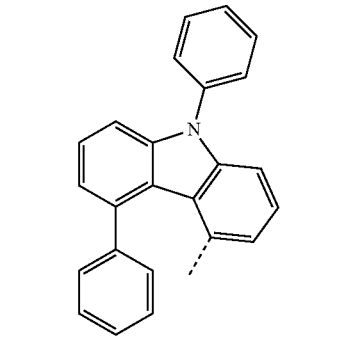
Formula (I-A-78)

Formula (I-A-79)
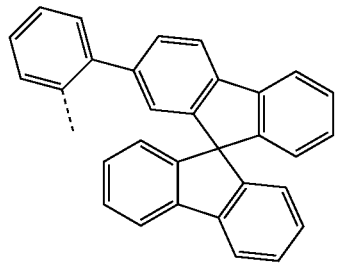
Formula (I-A-80)
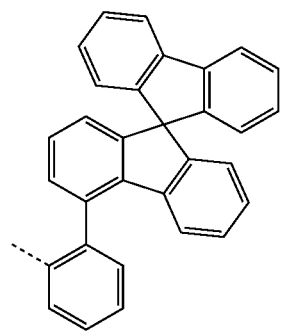
Formula (I-A-81)
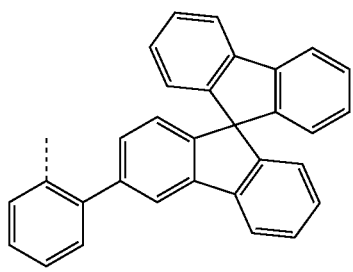
Formula (I-A-82)
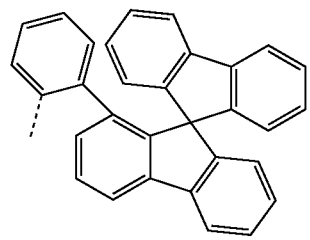
Formula (I-A-83)
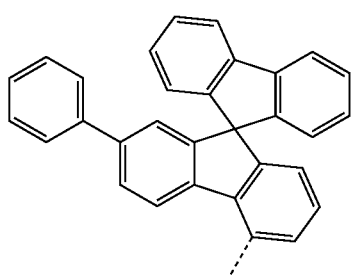
Formula (I-A-84)
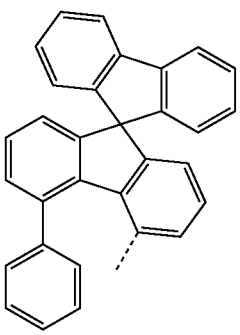
Formula (I-A-85)
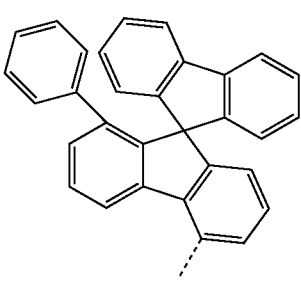
Formula (I-A-86)
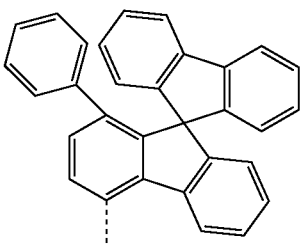
Formula (I-A-87)
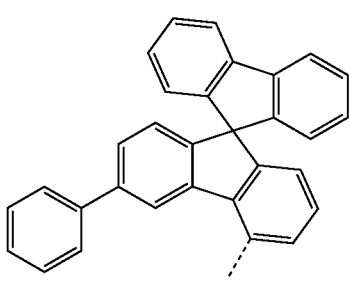
Formula (I-A-88)
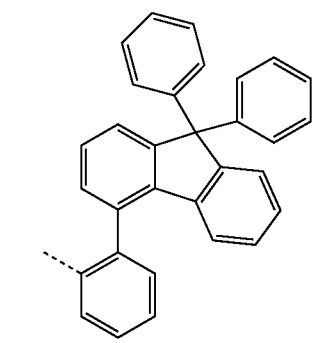

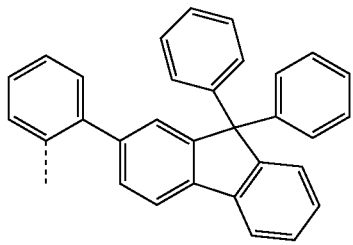
Formula (I-A-89)
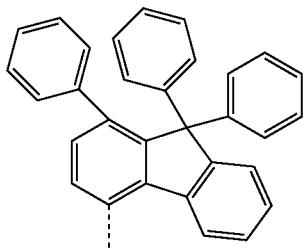
Formula (I-A-94)
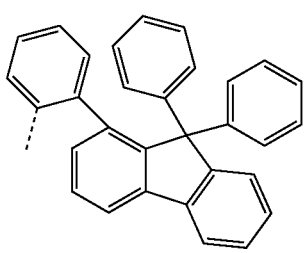
Formula (I-A-90)
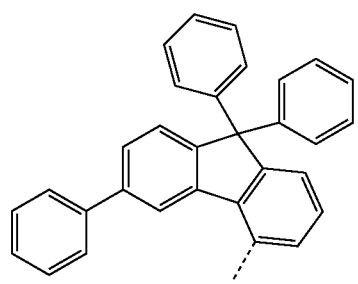
Formula (I-A-95)
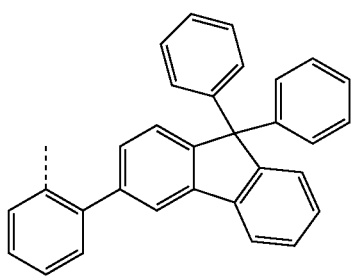
Formula (I-A-91)
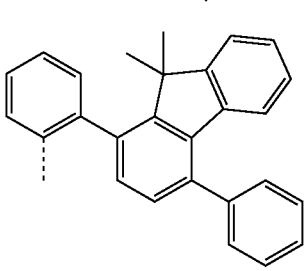
Formula (I-A-96)
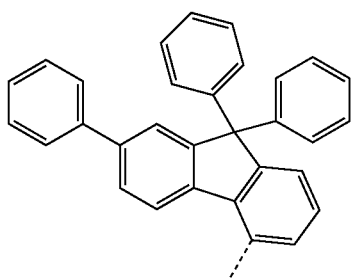
Formula (I-A-92)
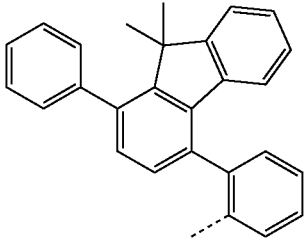
Formula (I-A-97)
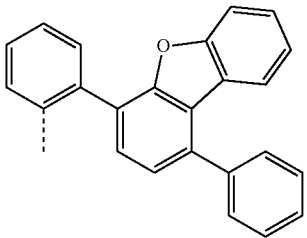
Formula (I-A-98)
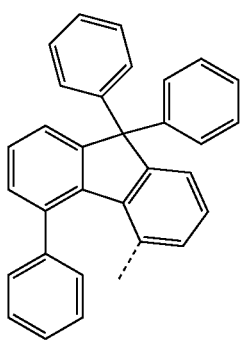
Formula (I-A-93)
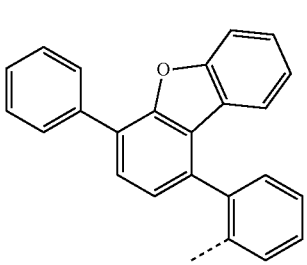
Formula (I-A-99)

-continued
Formula (I-A-100)
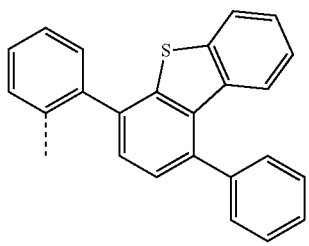
Formula (I-A-101)
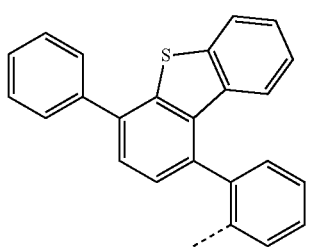
Formula (I-A-102)
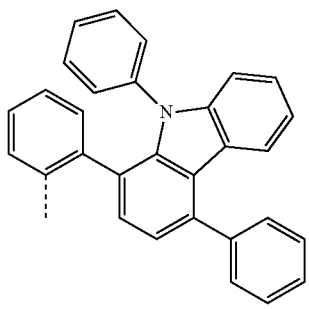
Formula (I-A-103)
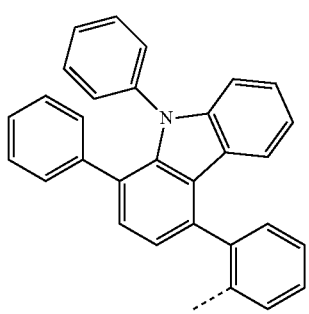
Formula (I-A-104)
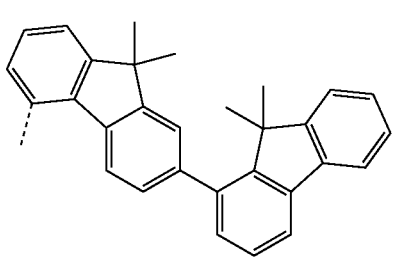
-continued
Formula (I-A-105)
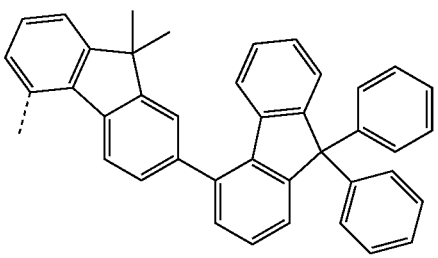
Formula (I-A-106)
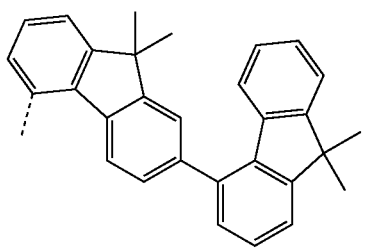
Formula (I-A-107)
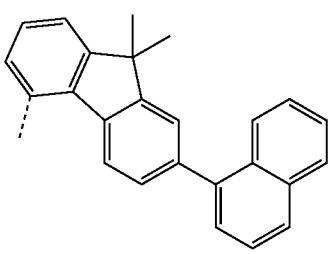
Formula (I-A-108)
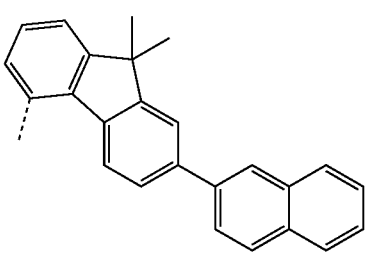
Formula (I-A-109)
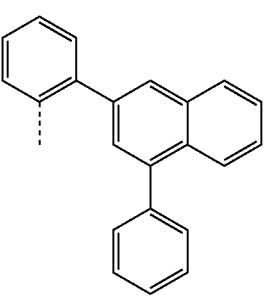
Formula (I-A-110)
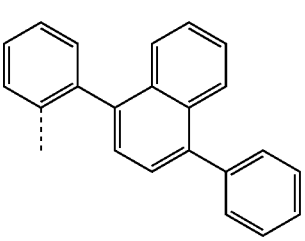

Formula (I-A-111)
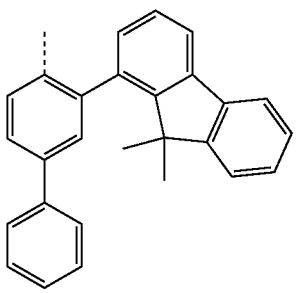
Formula (I-A-112)
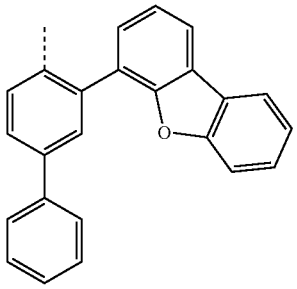
Formula (I-A-113)
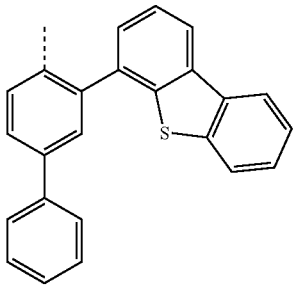
Formula (I-A-114)
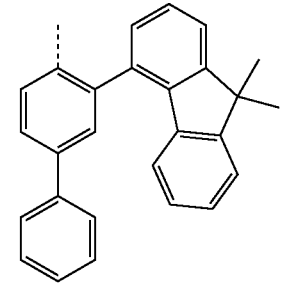
Formula (I-A-115)
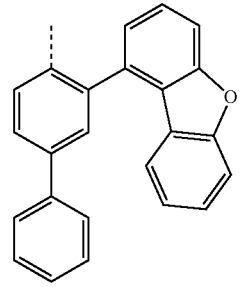
Formula (I-A-116)
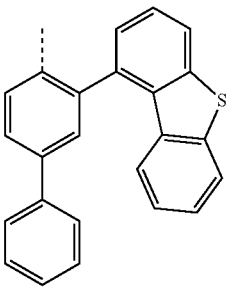
Formula (I-A-117)
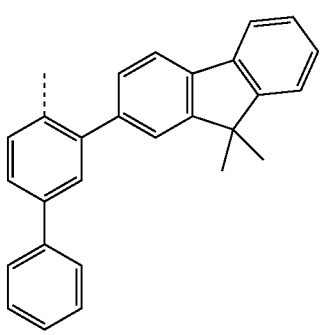
Formula (I-A-118)
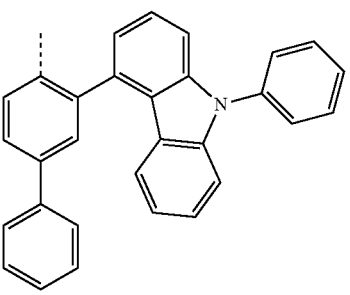
Formula (I-A-119)
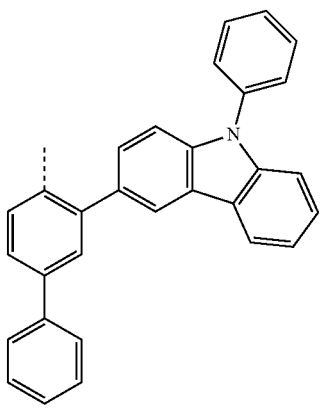
Formula (I-A-120)
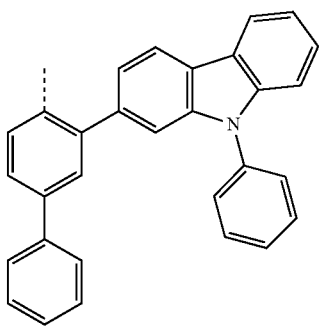

-continued

Formula (I-A-121)
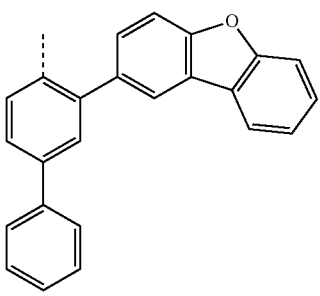

Formula (I-A-122)
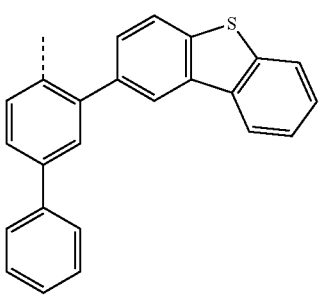

Formula (I-A-123)
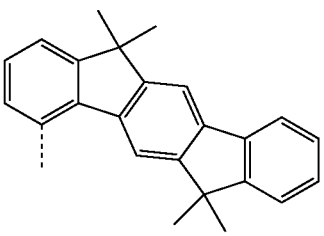

Formula (I-A-124)
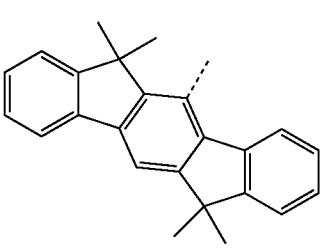

Formula (I-A-125)
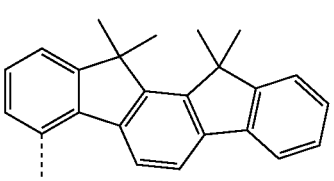

where the dashed line represents the bond to the nitrogen atom in formula (I).

Preferred embodiments of the formula (I) correspond to the following formula (I-1)

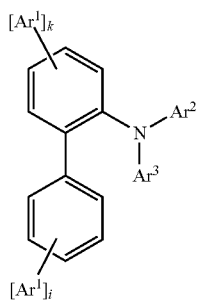

Formula (I-1)

where the variables that occur are as follows:

i is 0 or 1, k is 0 or 1, where the sum of k and i is 1 or 2, preferably 1, the free positions on the benzene rings may each be substituted by an $R^1$ radical, the $Ar^1$ to $Ar^3$ groups are defined as above, and preferably correspond to their preferred embodiments as indicated above, $Ar^1$ is preferably the same or different at each instance and is selected from phenyl and naphthyl, each of which may be substituted by one or more $R^2$ radicals, there being no divalent Y group present.

Alternative embodiments, likewise preferred, of the formula (I) correspond to the following formula (I-2)

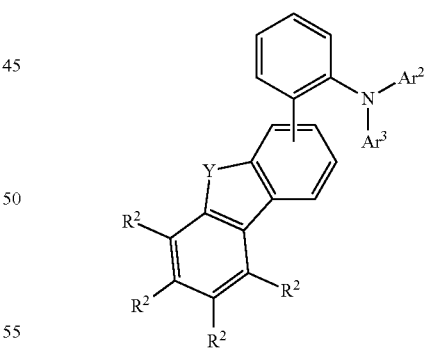

Formula (I-2)

where the variables that occur are as follows:

Y is selected from $C(R^1)_2$, $Si(R^1)_2$, $NR^1$, O and S, preferably from $C(R^1)_2$, $NR^1$, O and S;

the free positions on the benzene rings may each be substituted by an $R^1$ radical, and the other variables that occur are defined as above and preferably correspond to their preferred embodiments as indicated above.

A preferred embodiment of the formula (I-2) corresponds to the following formula (I-2A)

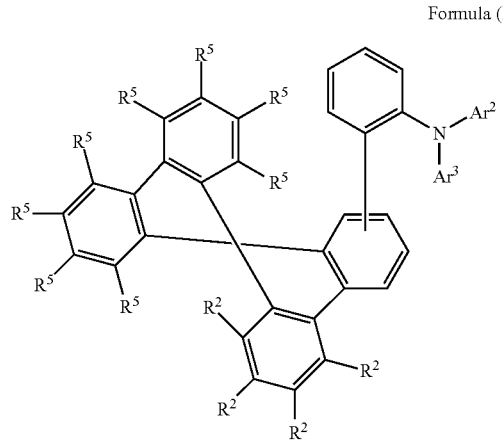

Formula (I-2A)

where the variables that occur are as follows:

the free positions on the benzene rings may each be substituted by an $R^1$ radical, and the other variables that occur are defined as above and preferably correspond to their preferred embodiments as indicated above.

Preferred embodiments of the formula (I-1) correspond to the following formulae (I-1-1) to formula (I-13)

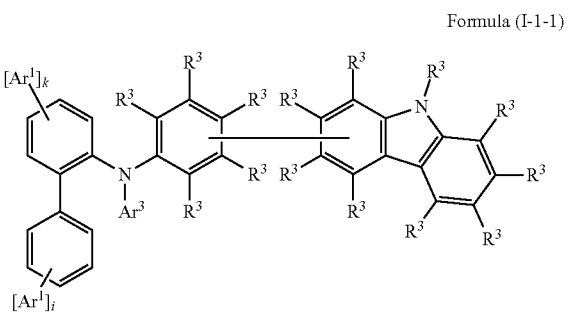

Formula (I-1-1)

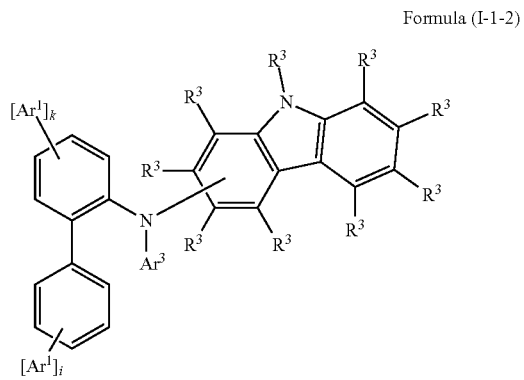

Formula (I-1-2)

-continued

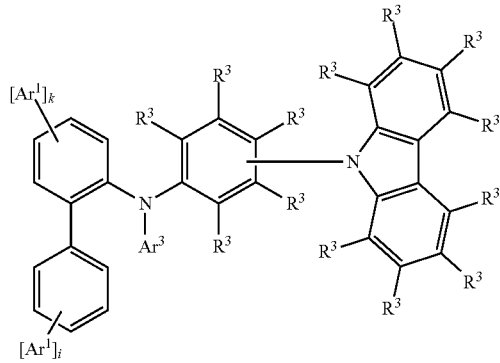

Formula (I-1-3)

where the variables that occur are as follows:
i is 0 or 1,
k is 0 or 1,
where the sum of k and i is 1 or 2, preferably 1,
the free positions on the benzene rings may each be substituted by an $R^1$ radical,
the $Ar^1$ and $Ar^3$ groups are defined as above, and preferably correspond to their preferred embodiments as indicated above,
$Ar^1$ is preferably the same or different at each instance and is selected from phenyl and naphthyl, each of which may be substituted by one or more $R^2$ radicals, there being no divalent group Y present.

Preferred embodiments of the formula (I-2) correspond to the following formulae (I-2-1) to (I-2-3)

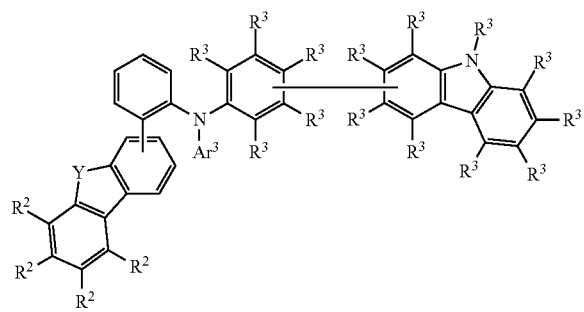

Formula (I-2-1)

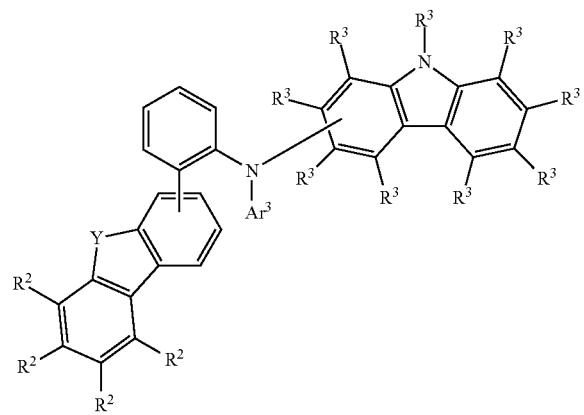

Formula (I-2-2)

-continued

Formula (I-2-3)

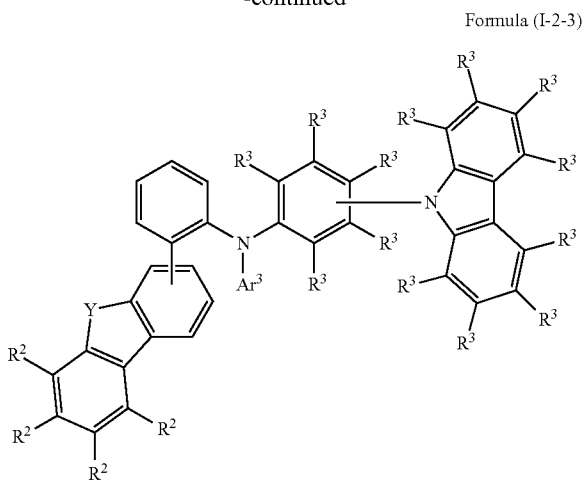

where the variable that occur are as follows:
Y is selected from $C(R^1)_2$, $Si(R^1)_2$, $NR^1$, O and S, preferably from $C(R^1)_2$, $NR^1$, O and S;
the free positions on the benzene rings may each be substituted by an $R^1$ radical, and the other variables that occur are defined as above and preferably correspond to their preferred embodiments as indicated above.

Preferred embodiments of the formula (I-2A) correspond to the following formulae (I-2A-1) to (I-2A-3):

where the variables that occur are as follows:
the free positions on the benzene rings may each be substituted by an $R^1$ radical,
and the other variables that occur are defined as above and preferably correspond to their preferred embodiments as indicated above.

Preferred specific compounds of formula (I) are depicted in the following table:

1

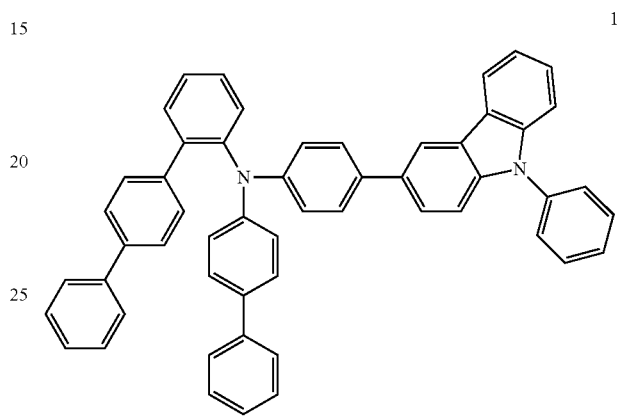

Formula (I-2A-1)

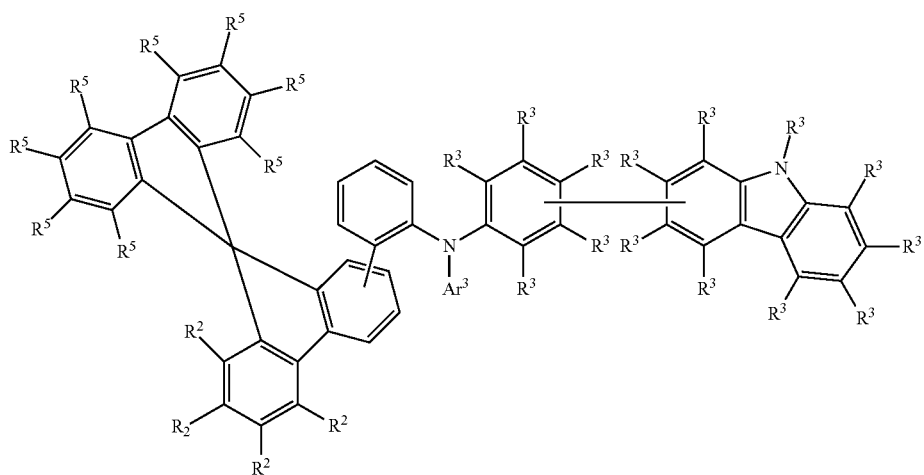

Formula (I-2A-2)

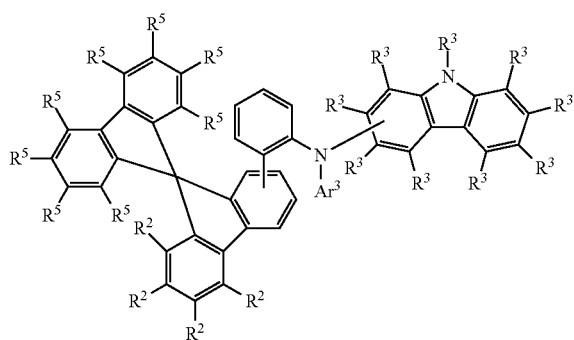

Formula (I-2A-3)

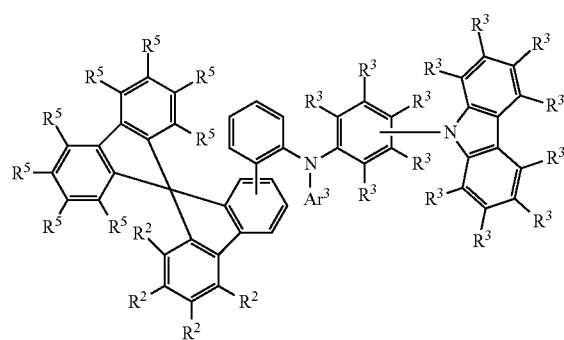

| 2 | 6 |
|---|---|
| 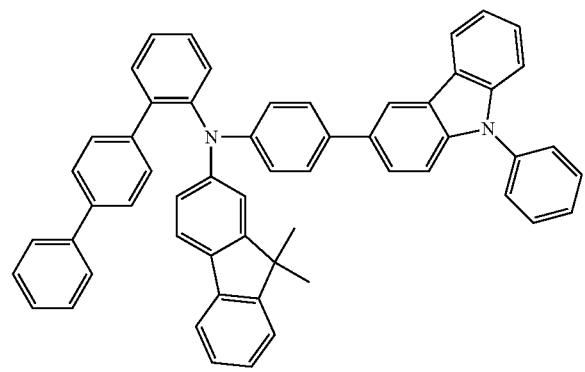 | 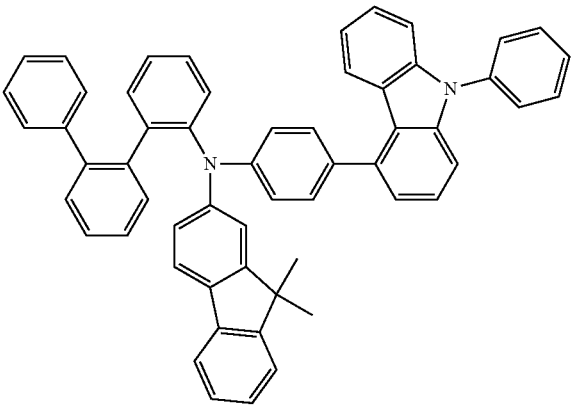 |
| 3 | 7 |
| 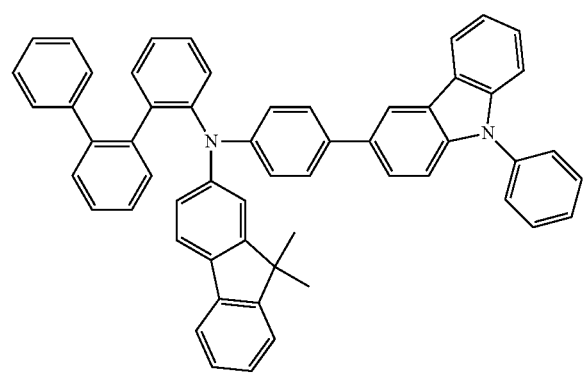 | 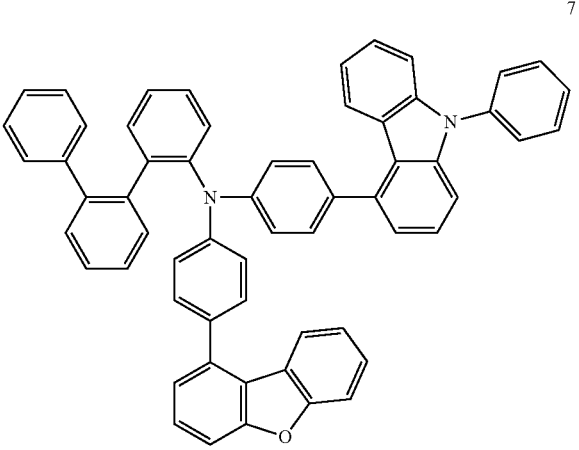 |
| 4 | 8 |
| 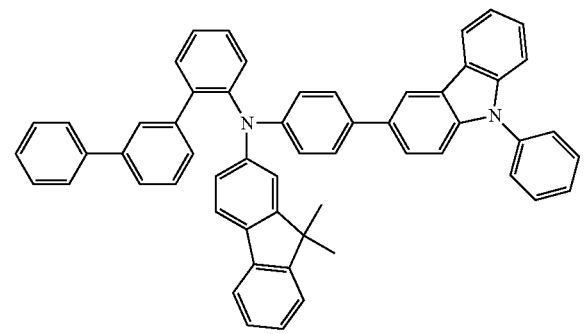 | 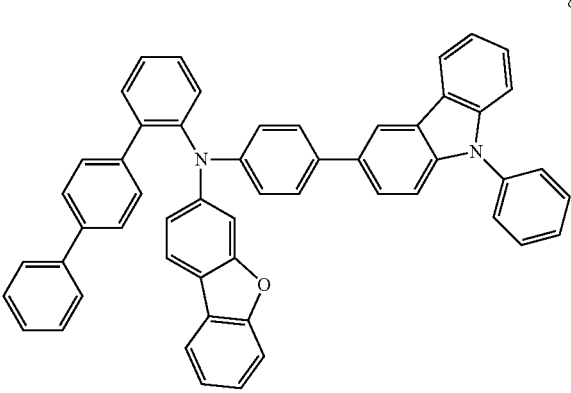 |
| 5 | 9 |
| 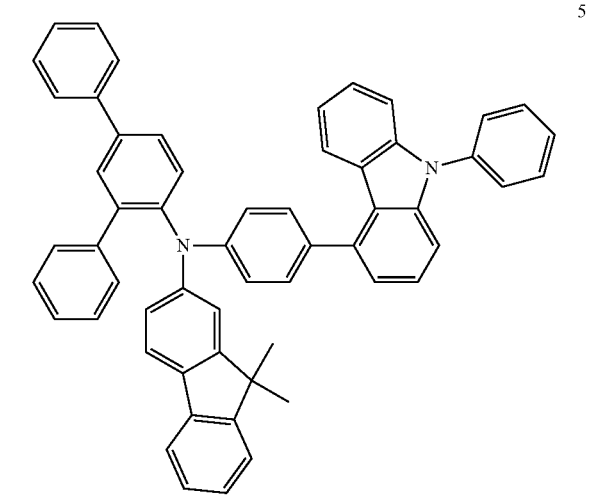 | 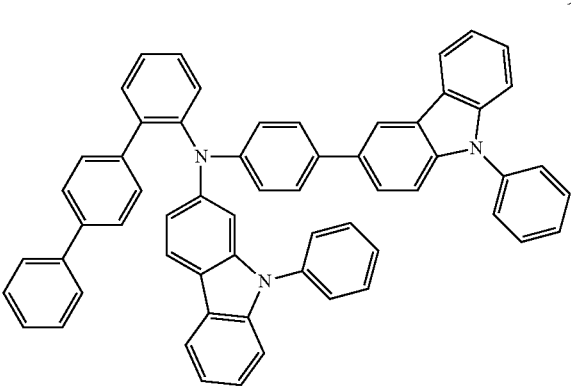 |

101
-continued
10
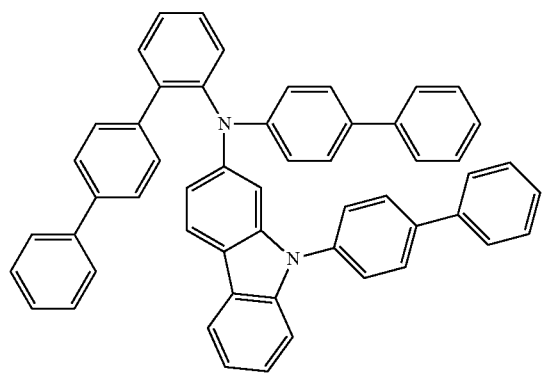
11
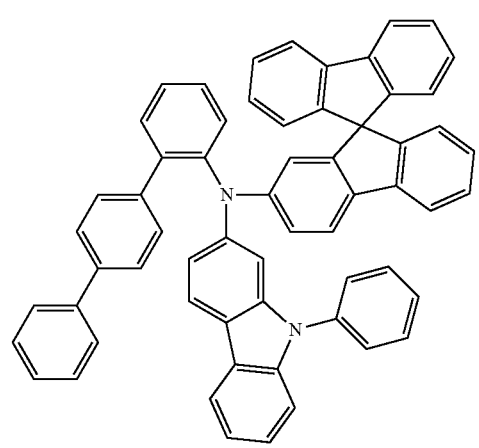
12
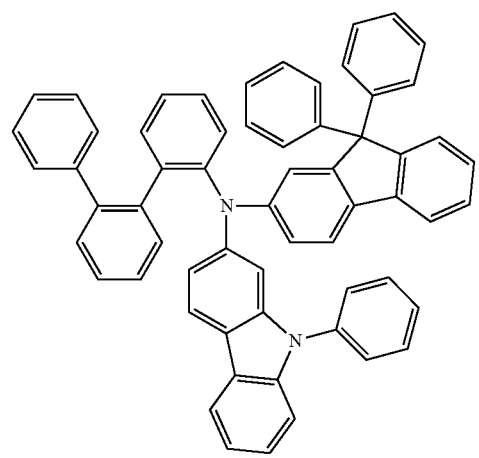
13
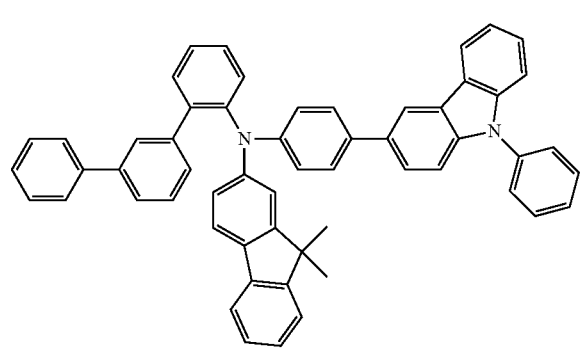
102
-continued
14
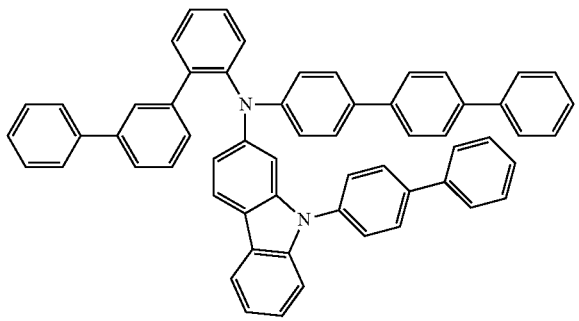
15
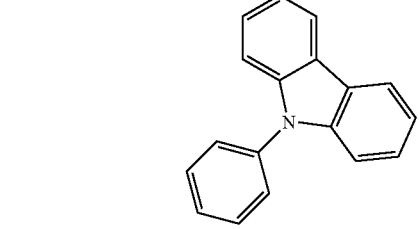
16

17
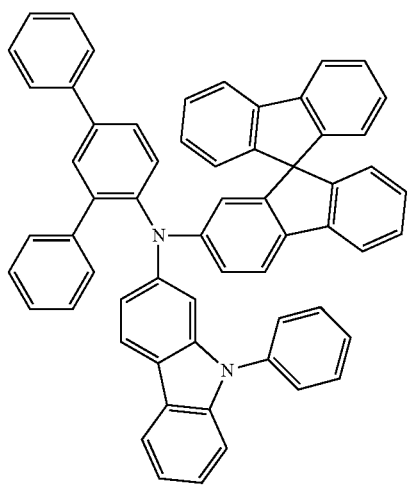
18
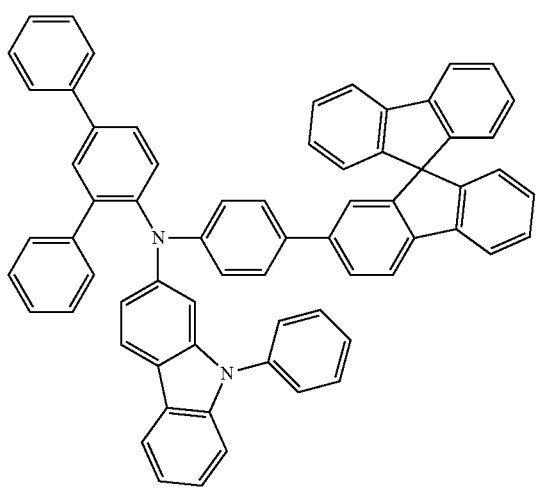
19
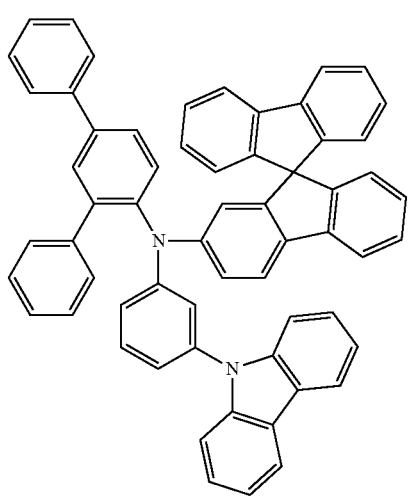
20
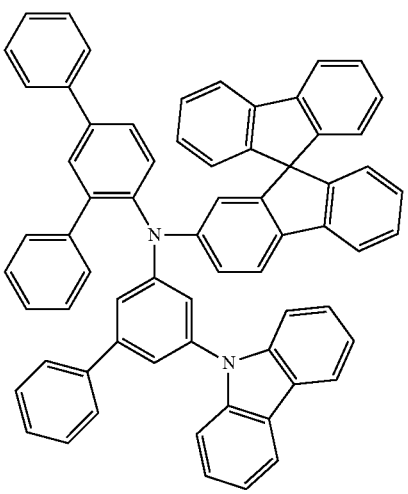
21
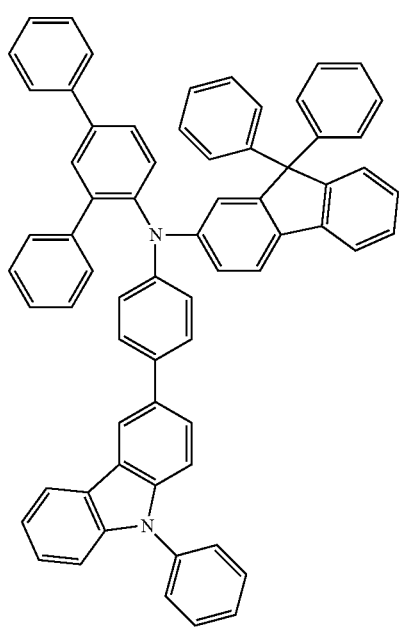

105
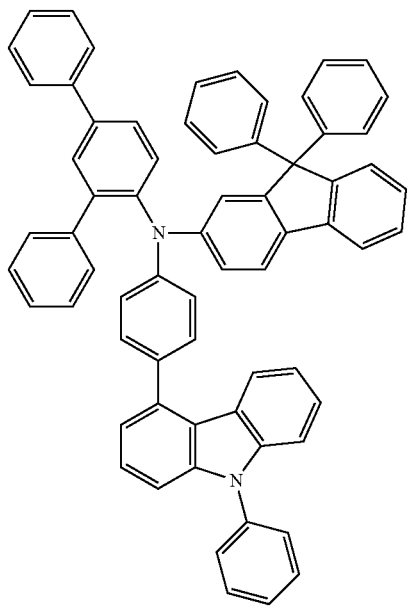
106
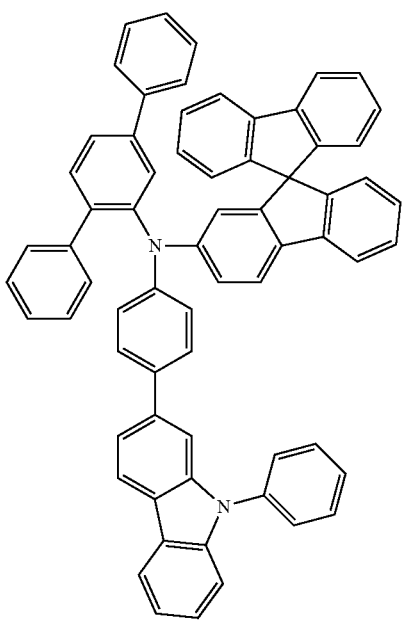
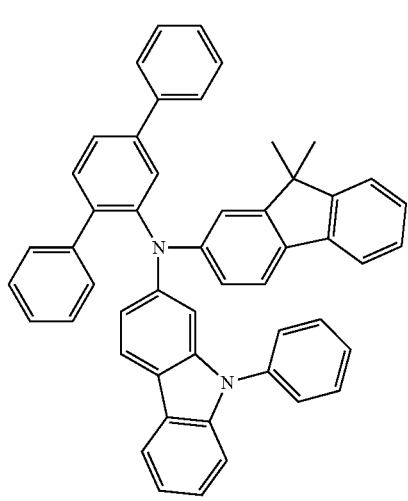
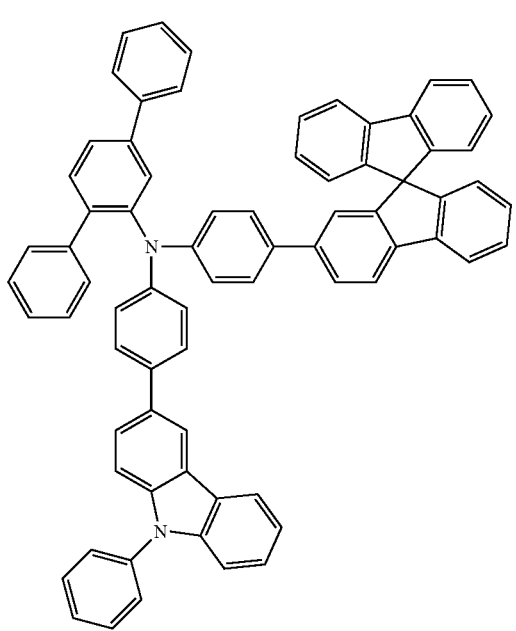

26
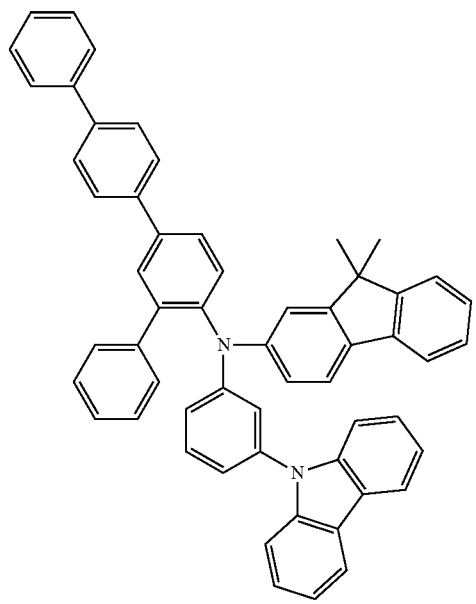
27
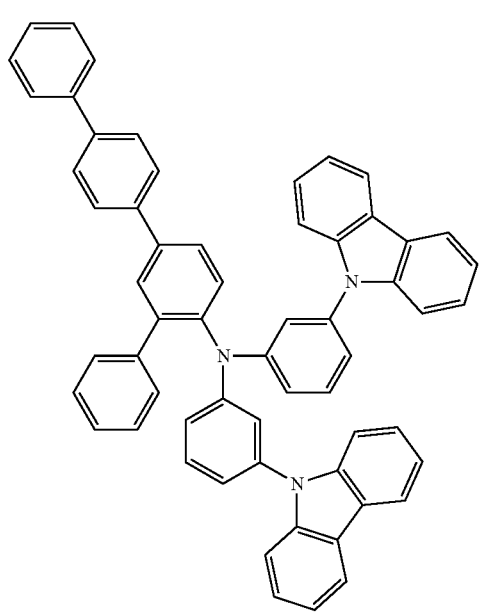
28
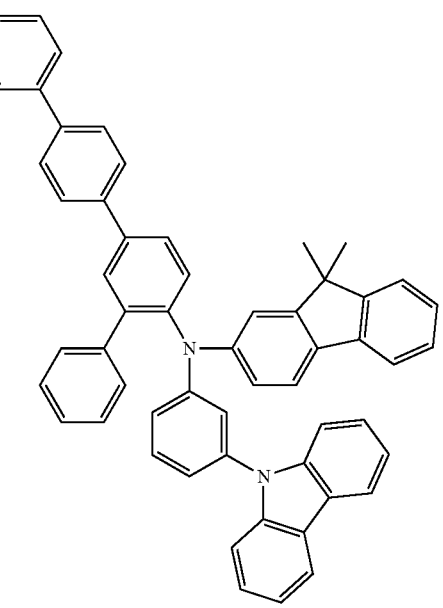
29
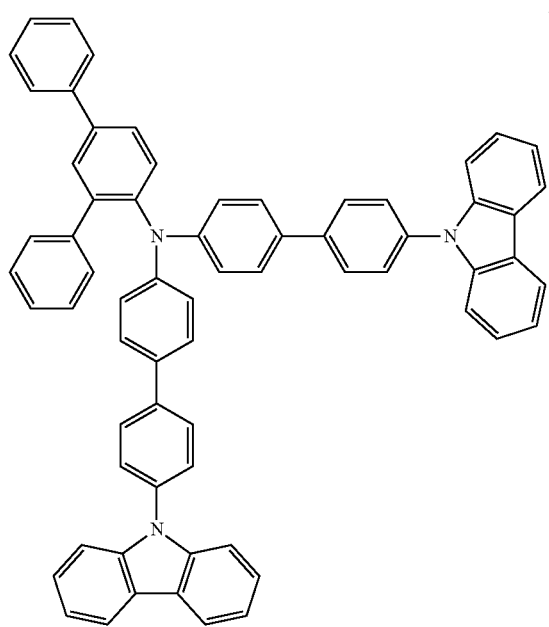

109
-continued
30
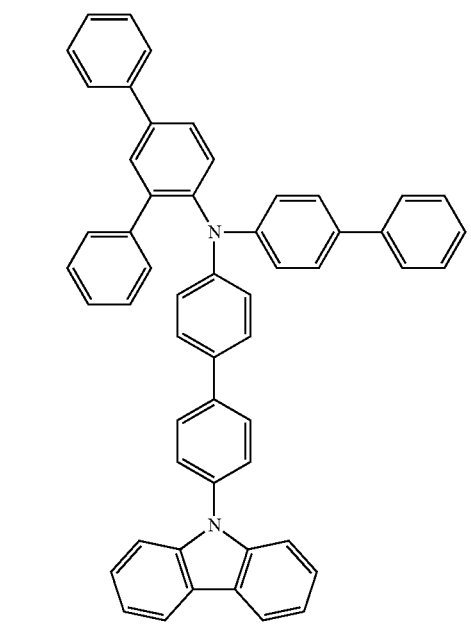
31
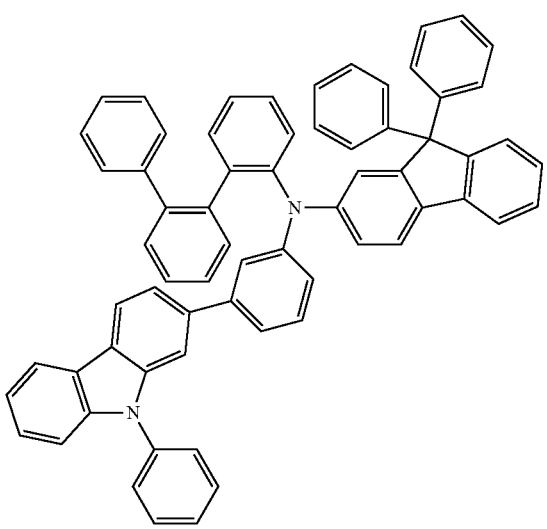
110
-continued
32
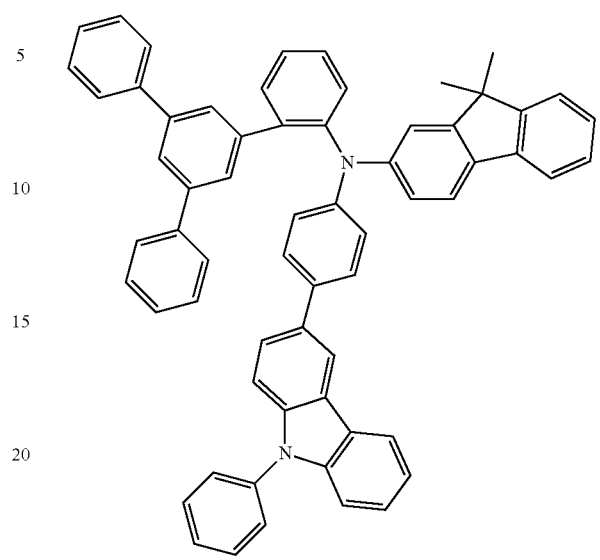
33
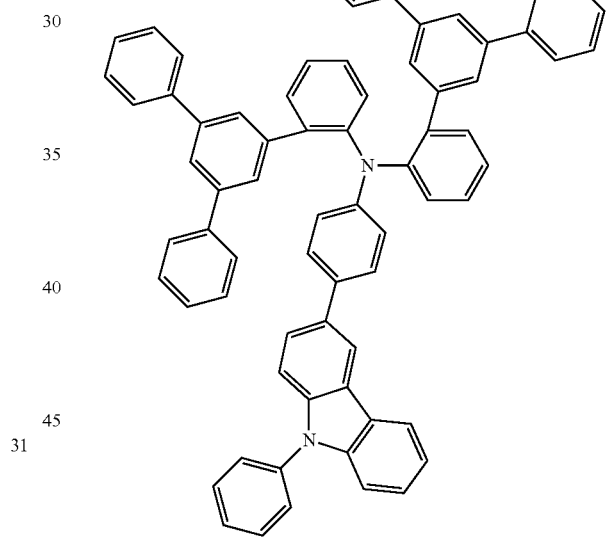
34

111
-continued
35 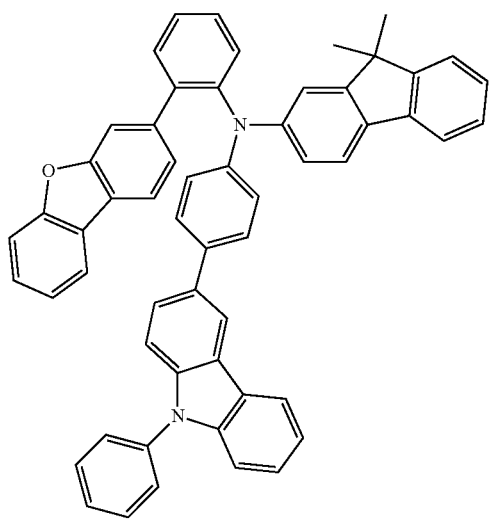
36 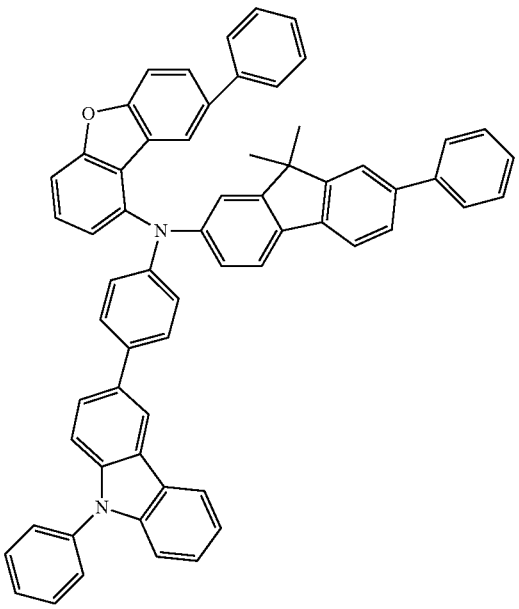
37 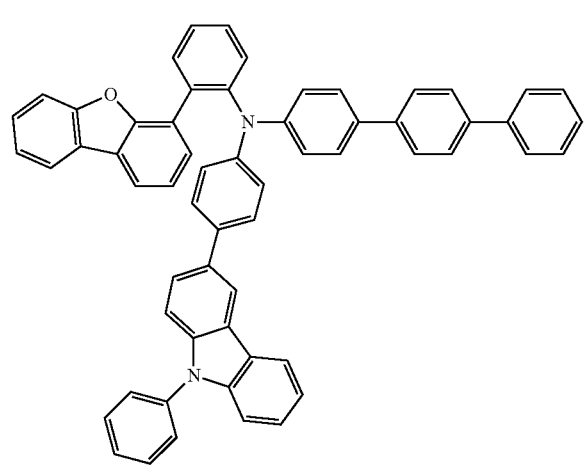
112
-continued
38 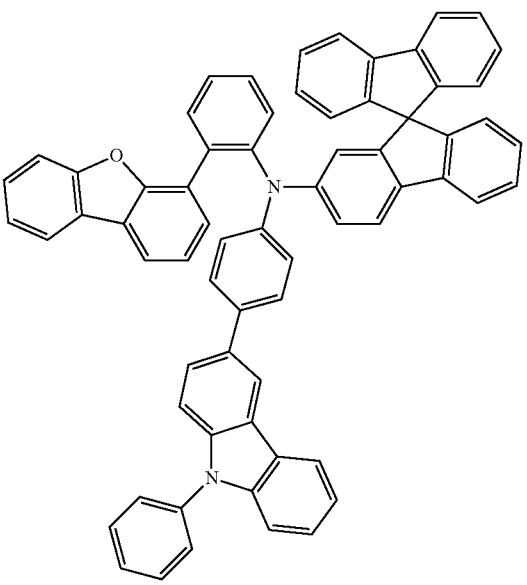
39 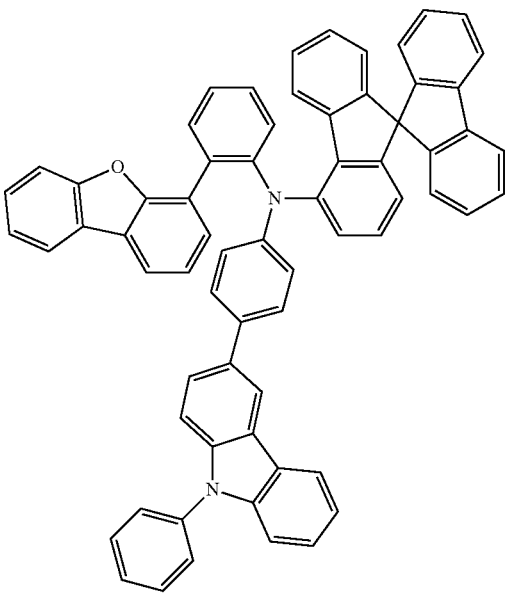

113
40
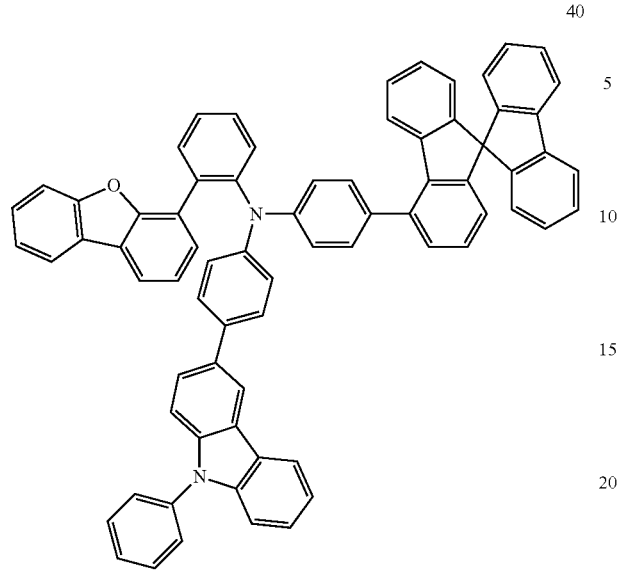
41
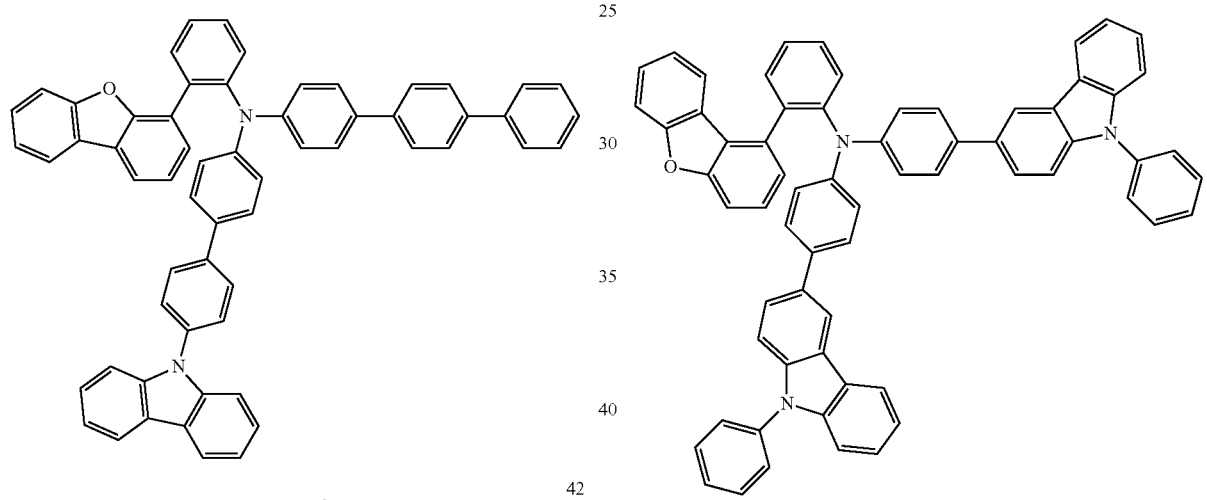
42
114
43
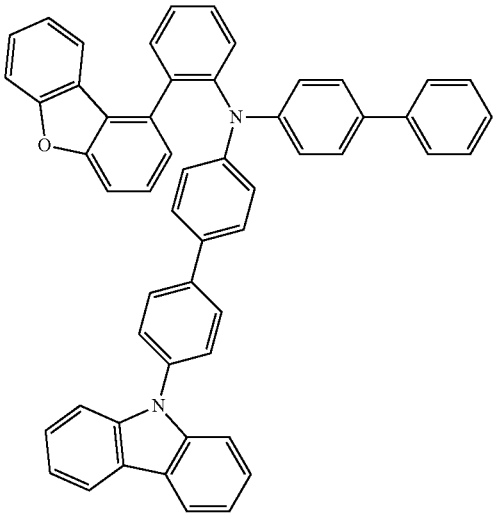
44
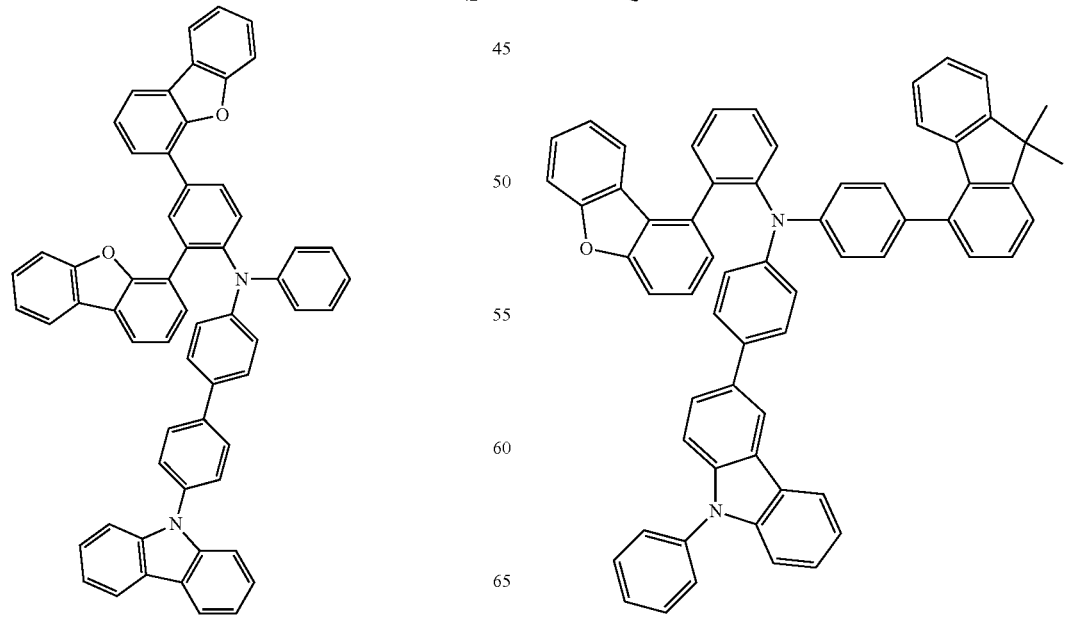
45

-continued
46
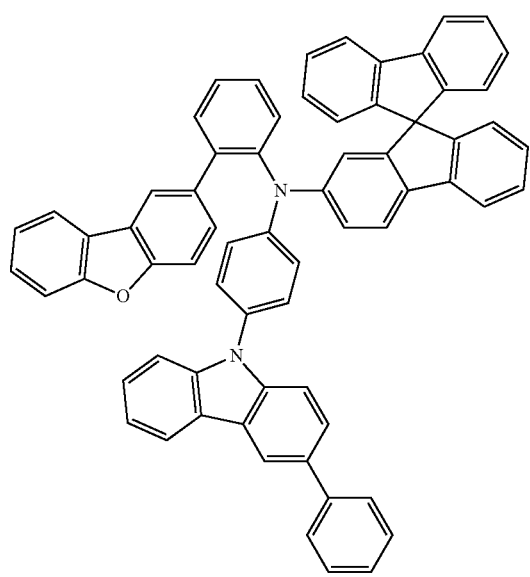
47
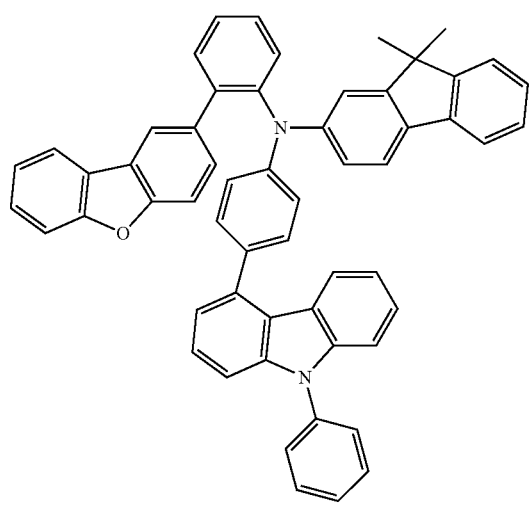
48
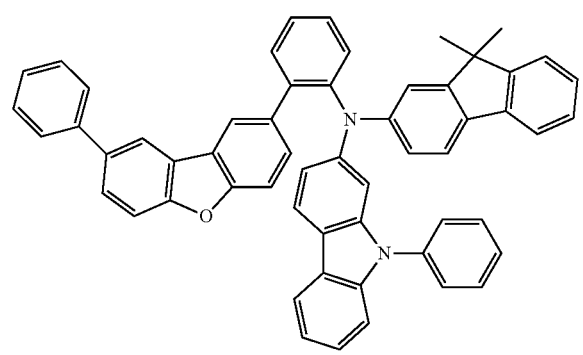
-continued
49
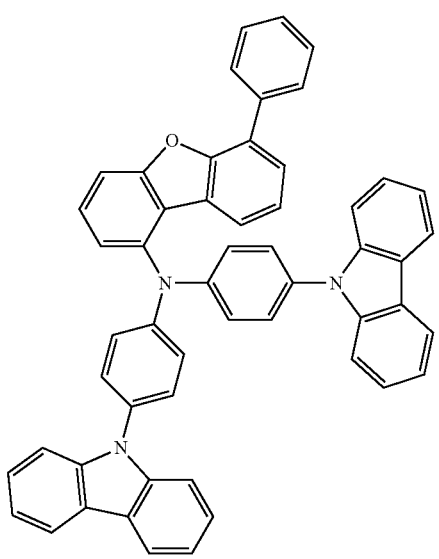
50
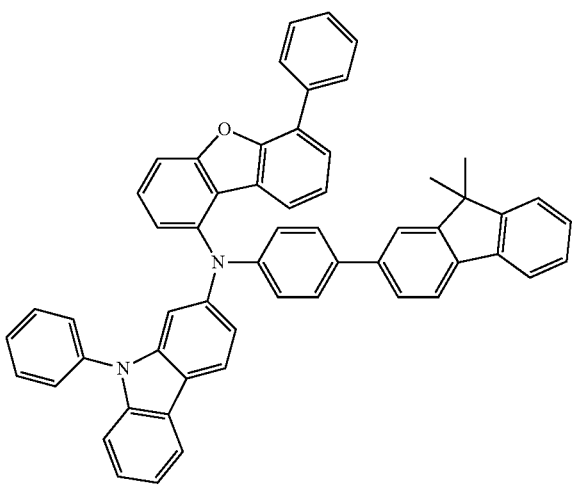
51
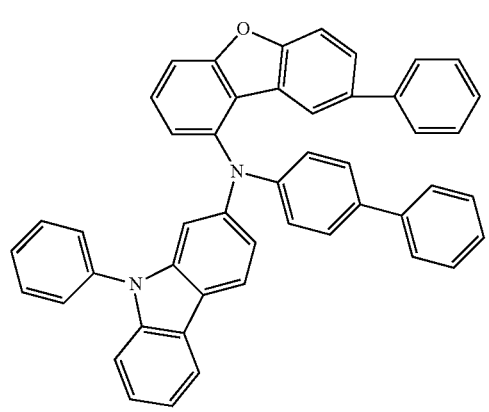

52
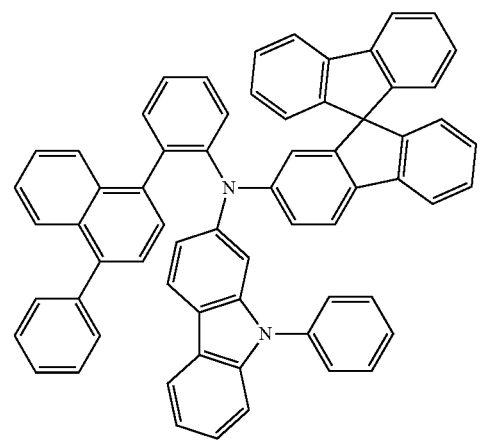
53
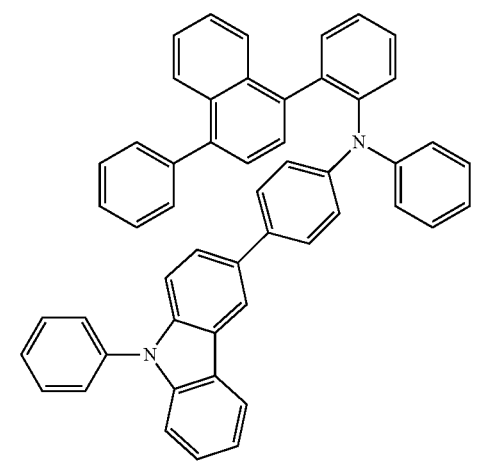
54
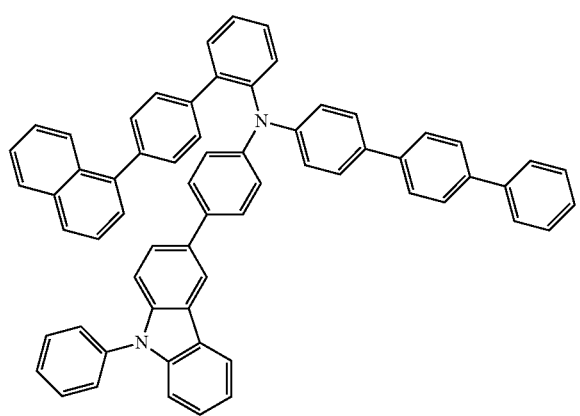
55
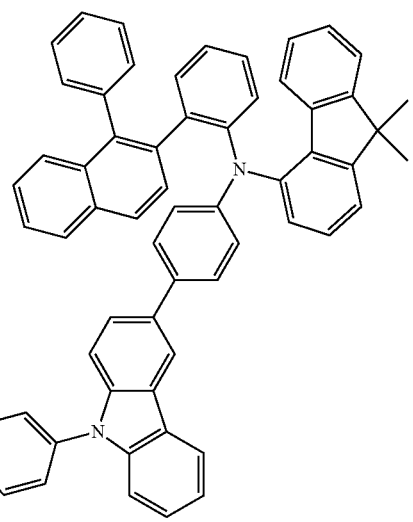
56
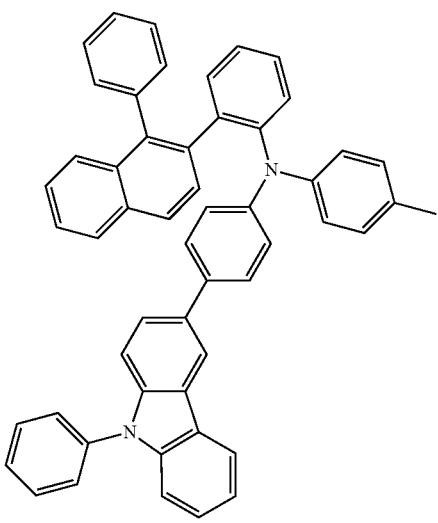
57
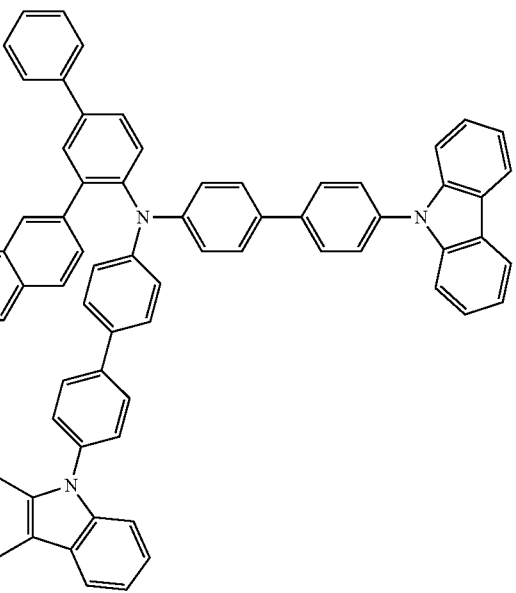

58
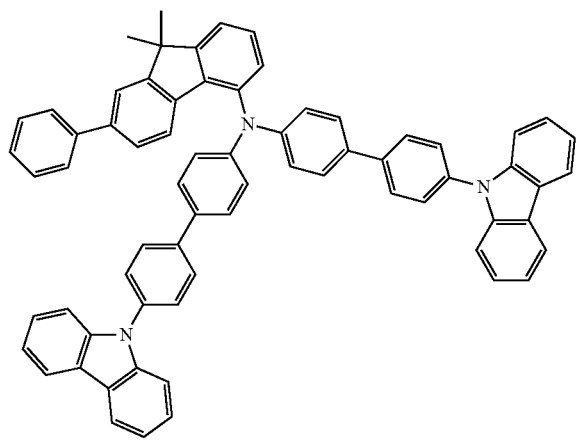
59
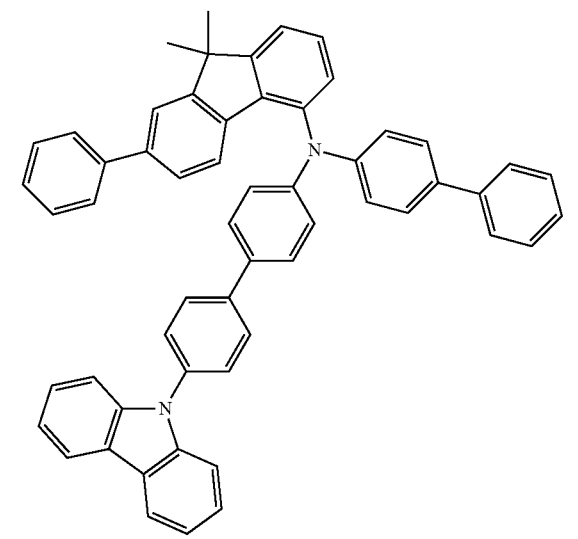
60
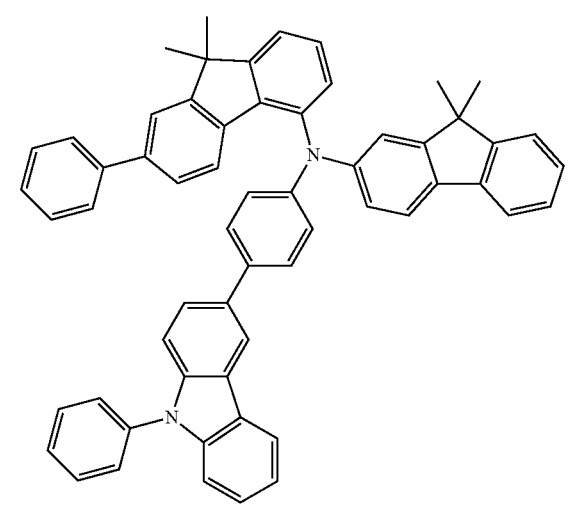
61
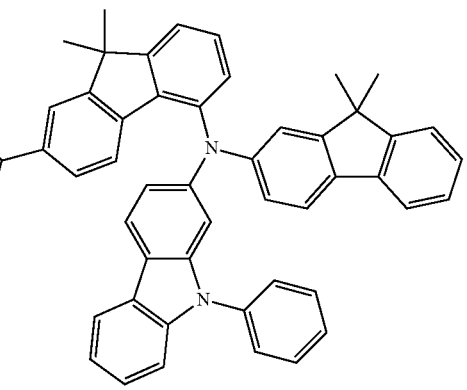
62
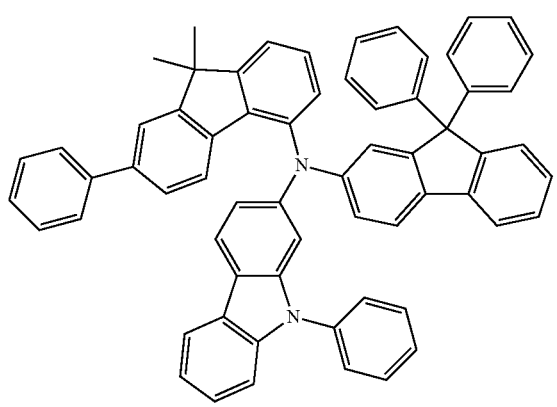
63

-continued
64
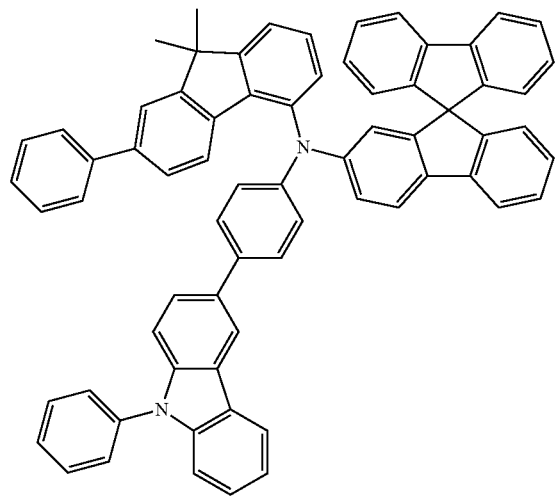
65
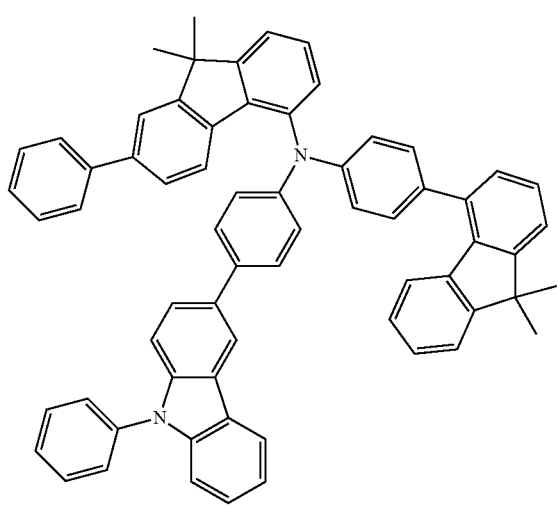
66
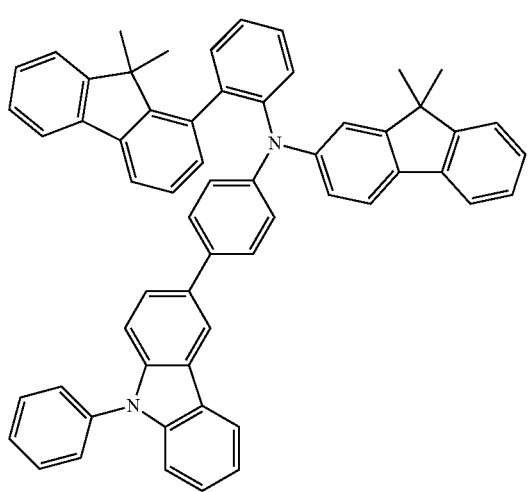
-continued
67
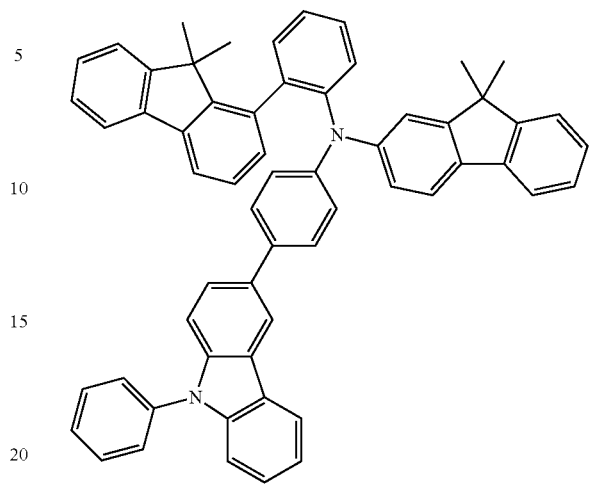
68
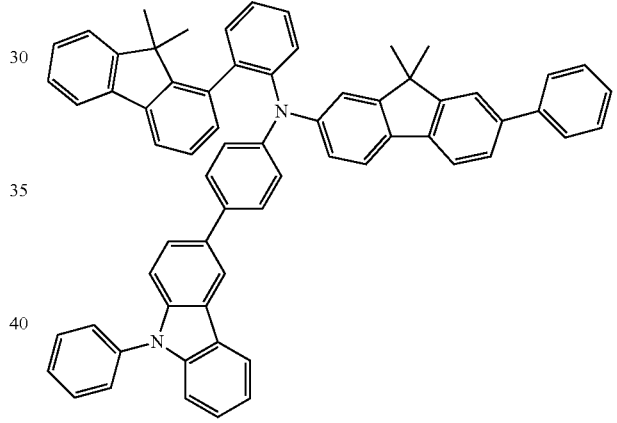
69
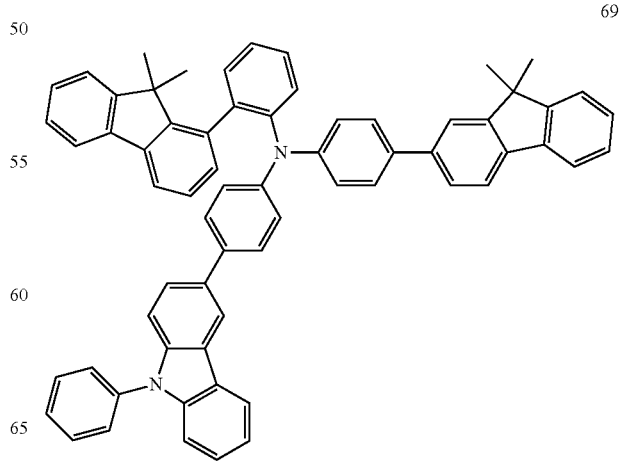

70
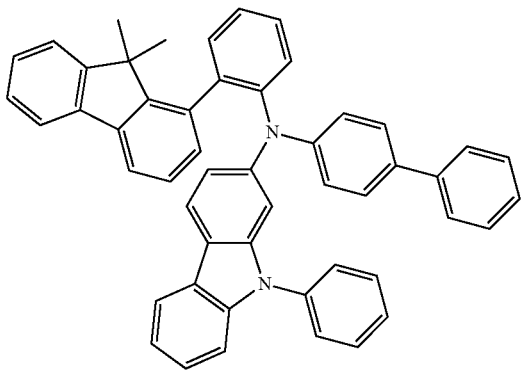
71
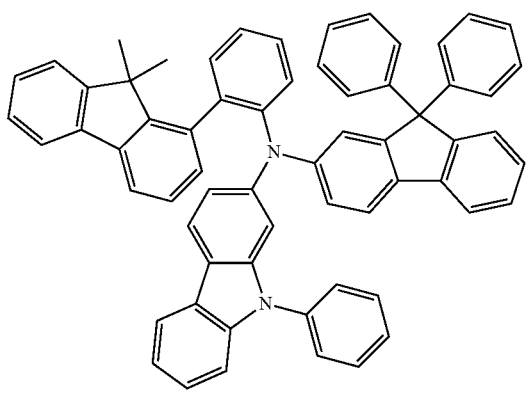
72
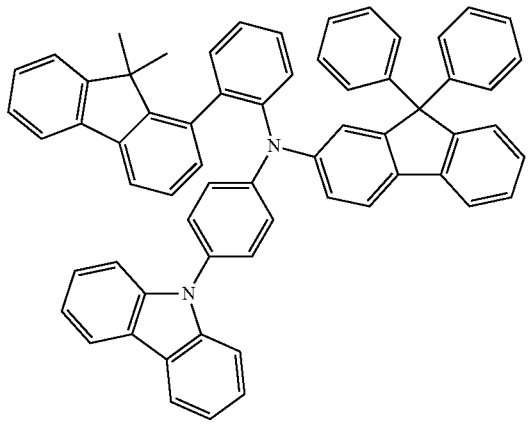
73
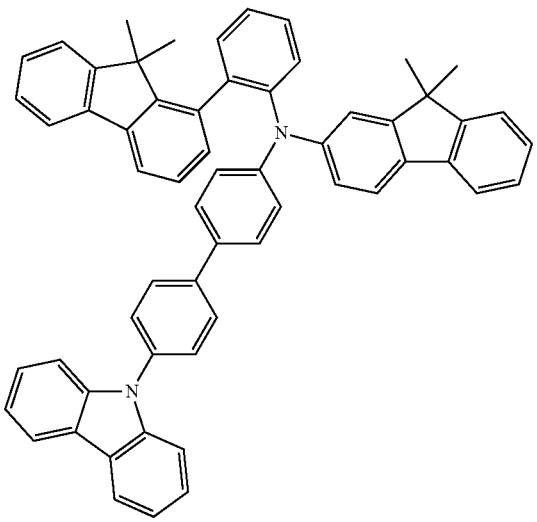
74
75

-continued
76
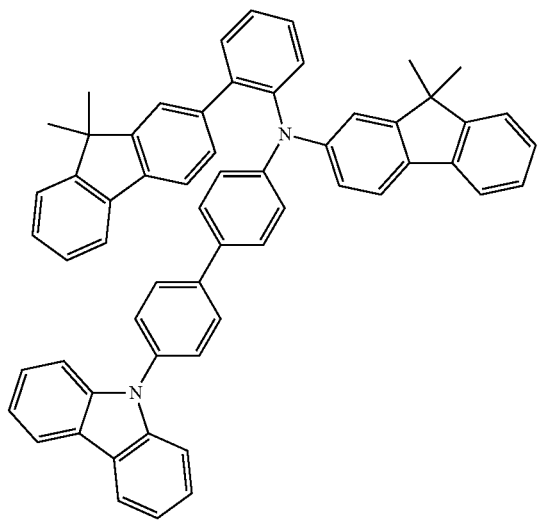
77
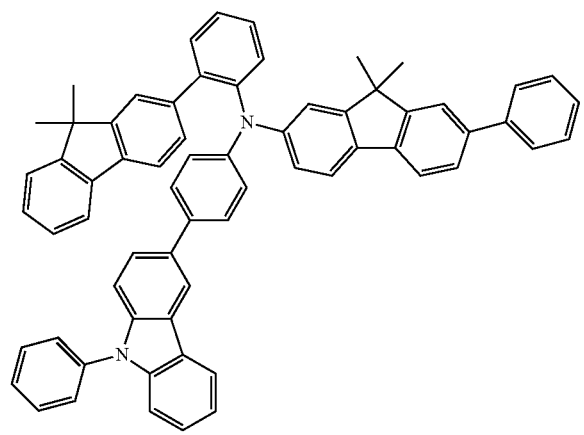
78
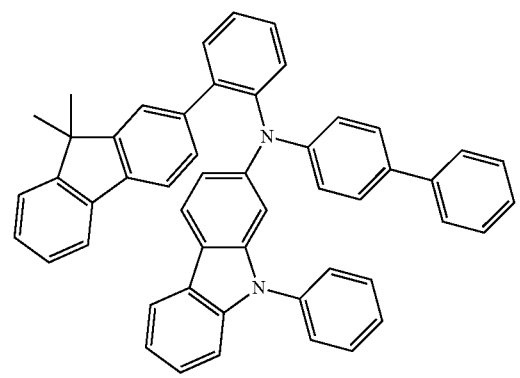
-continued
79
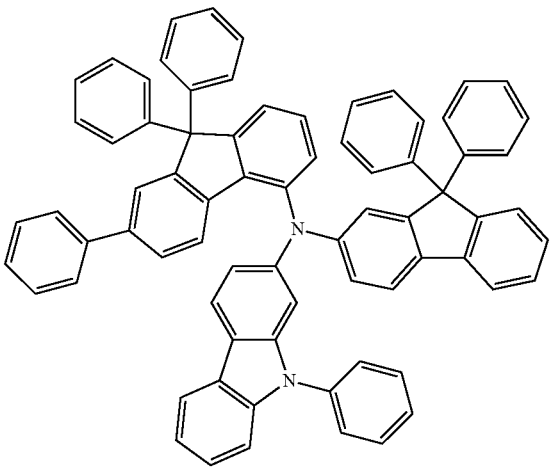
80
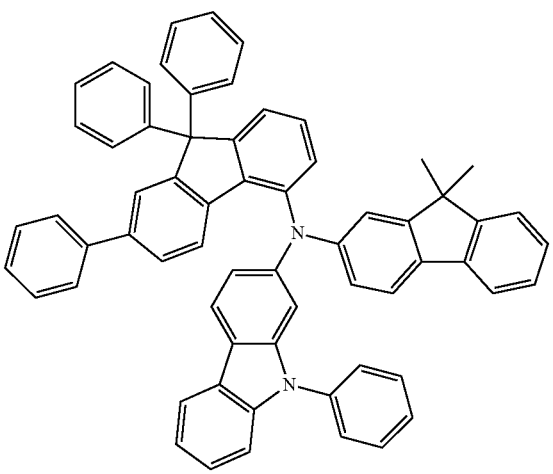
81
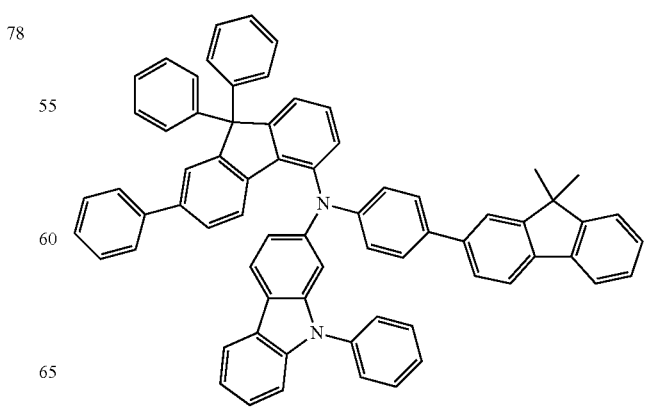

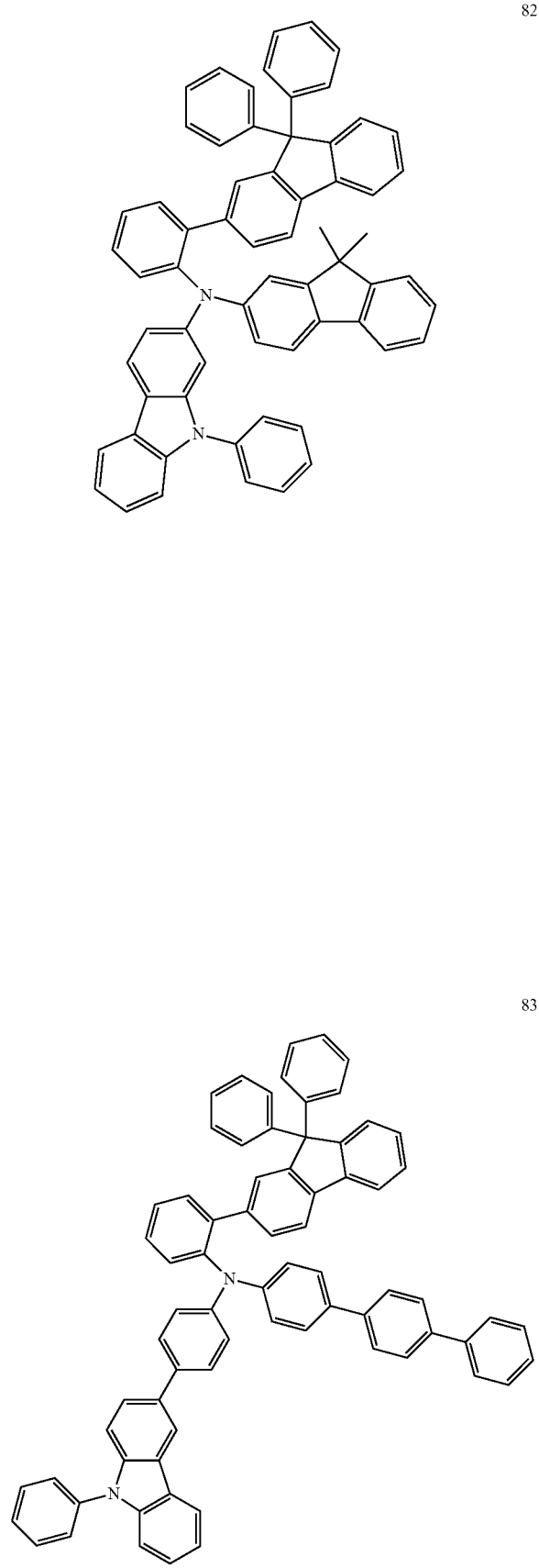
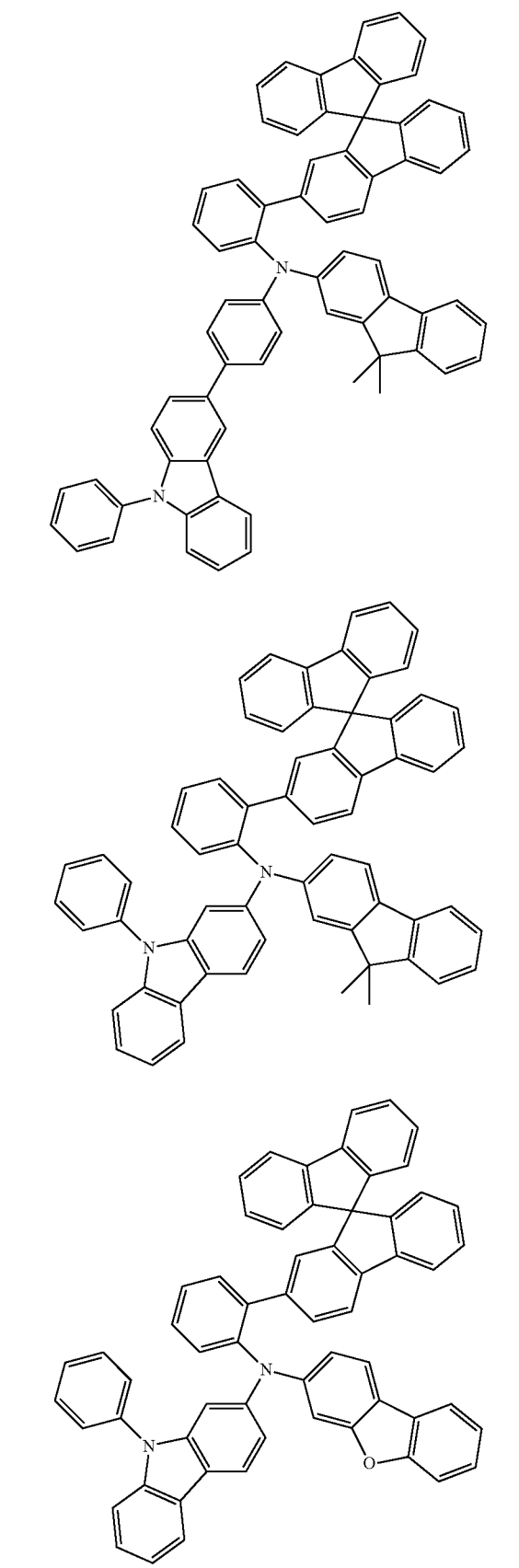

87
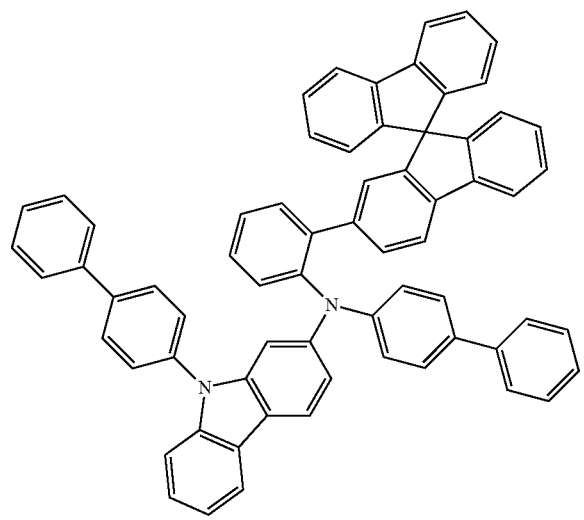
88
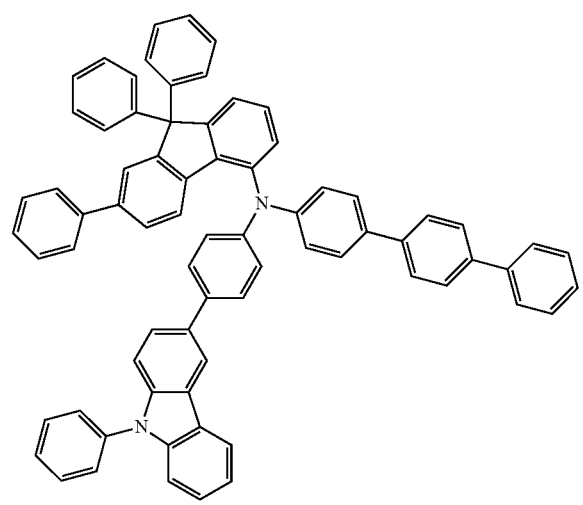
89
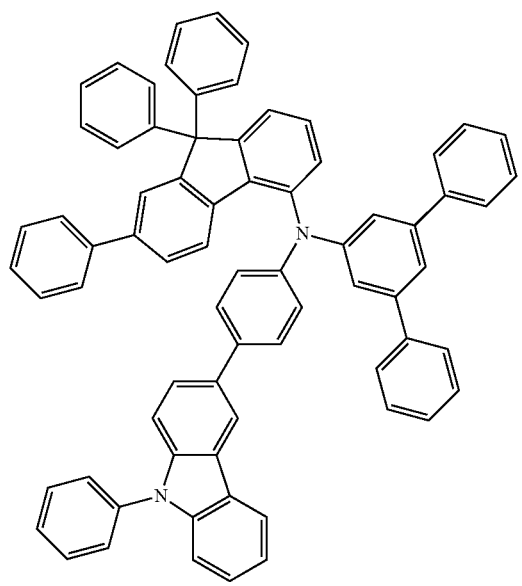
90
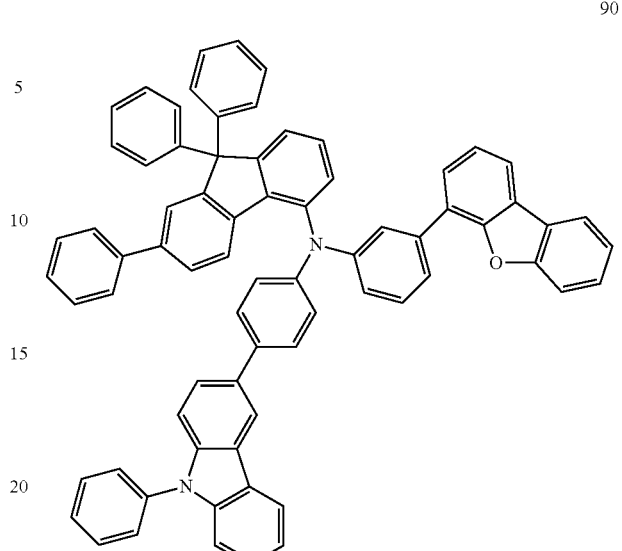
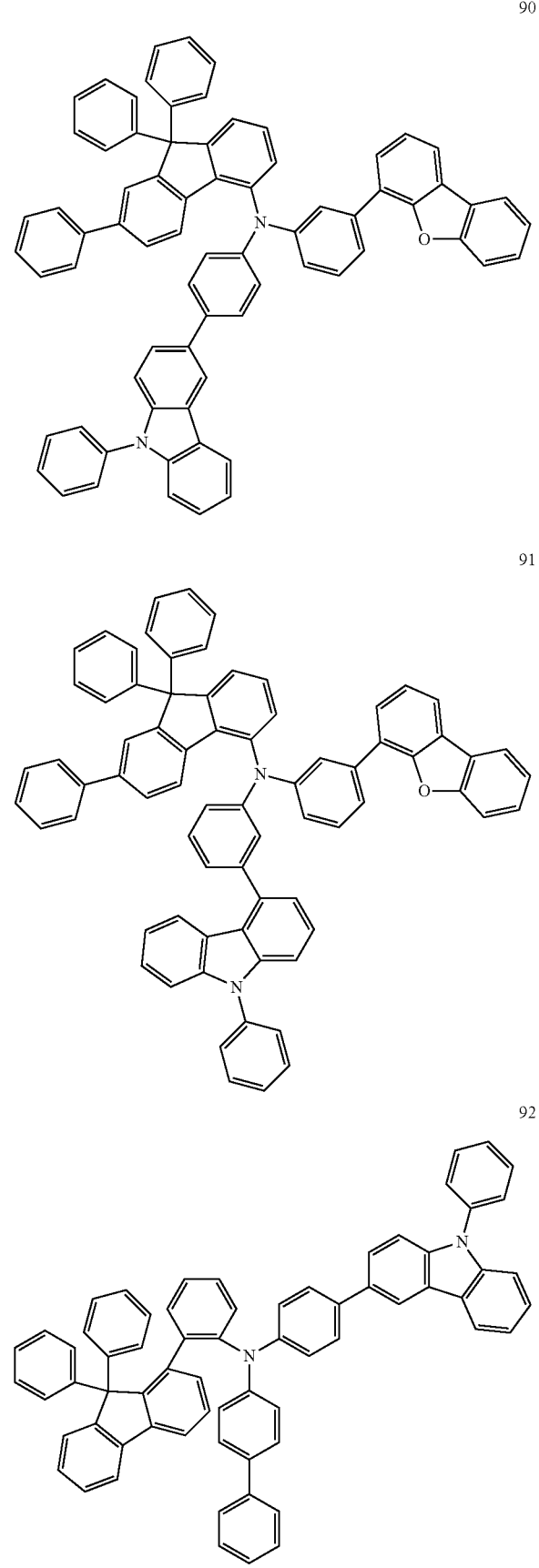

131
-continued
93
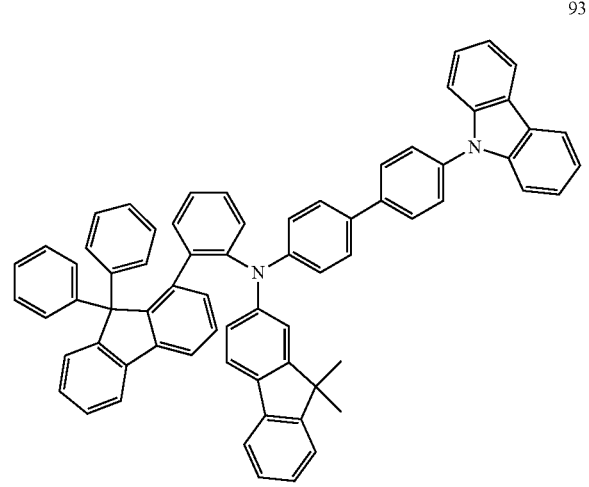
94
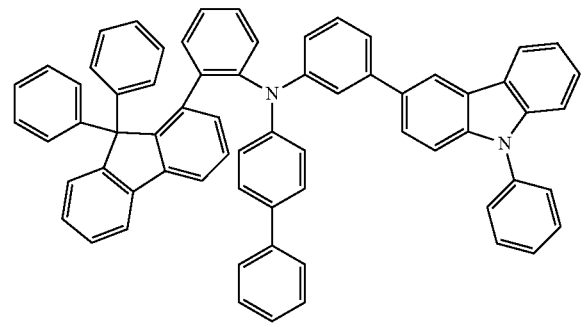
95
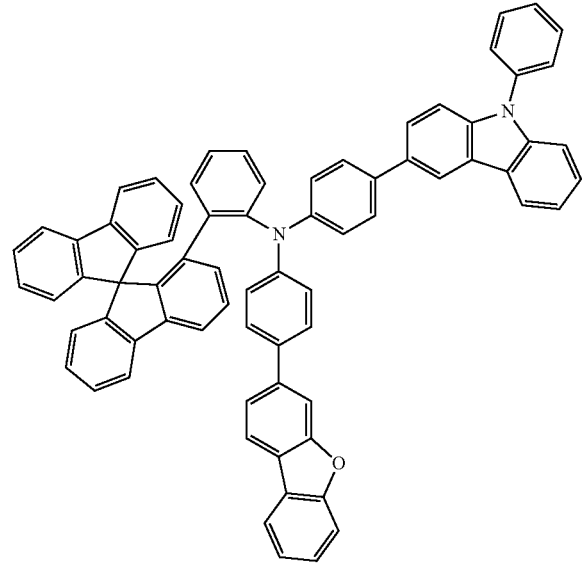
132
-continued
96
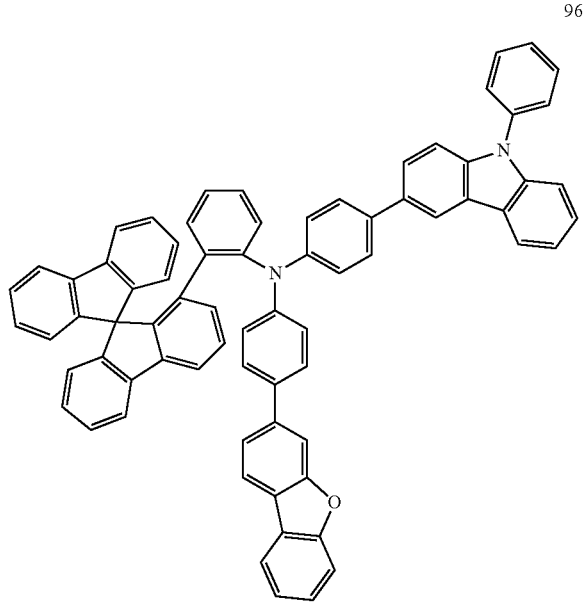
97
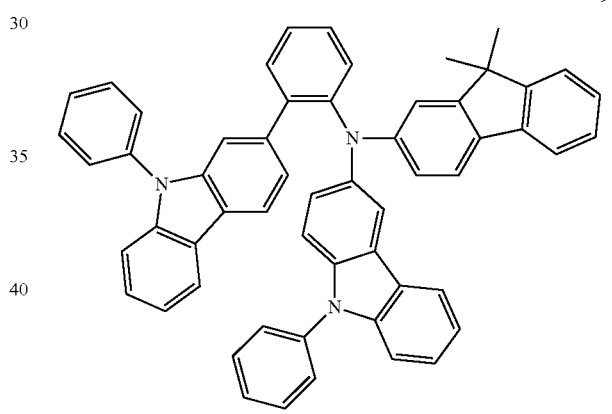
98
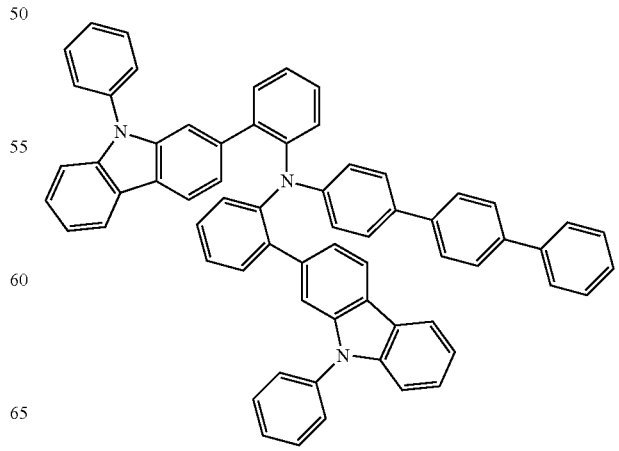

99
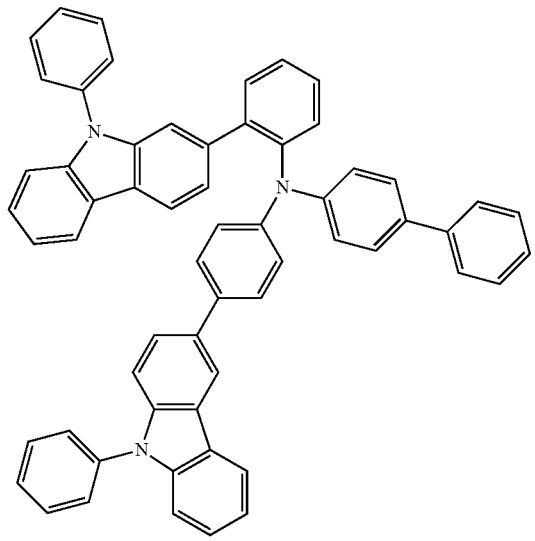
100
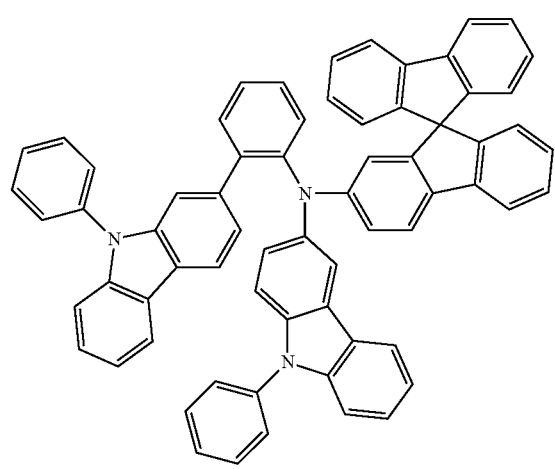
101
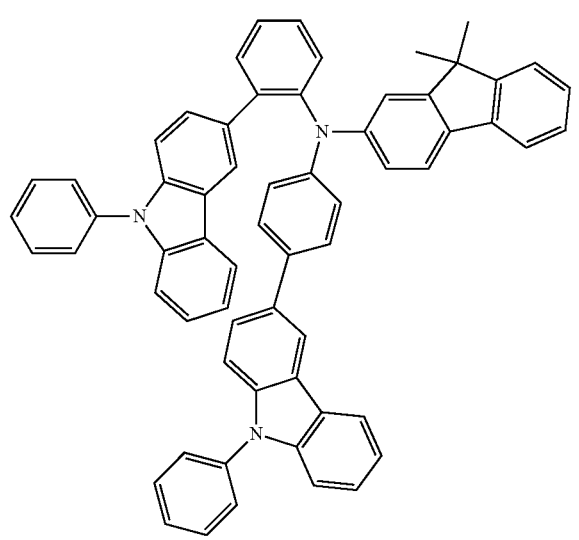
102
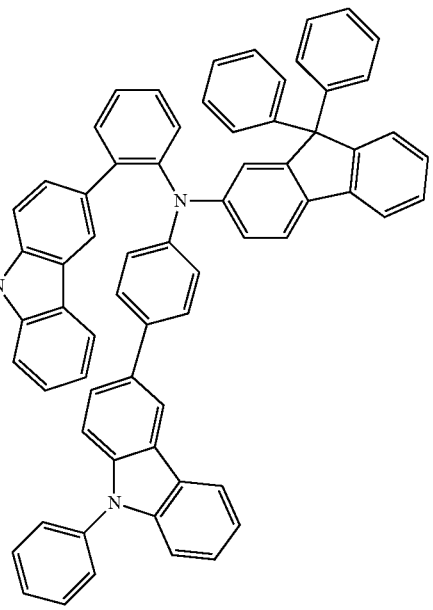
103
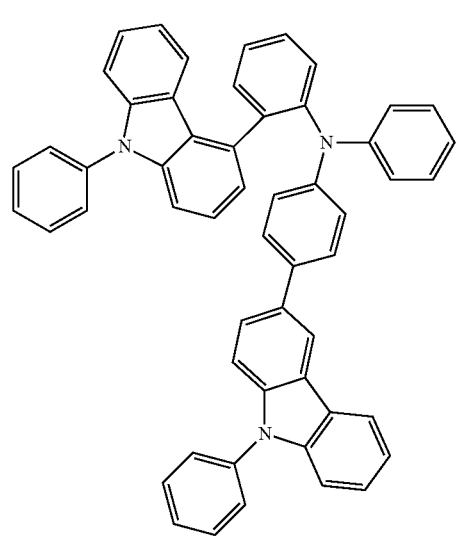
104

135
-continued
105
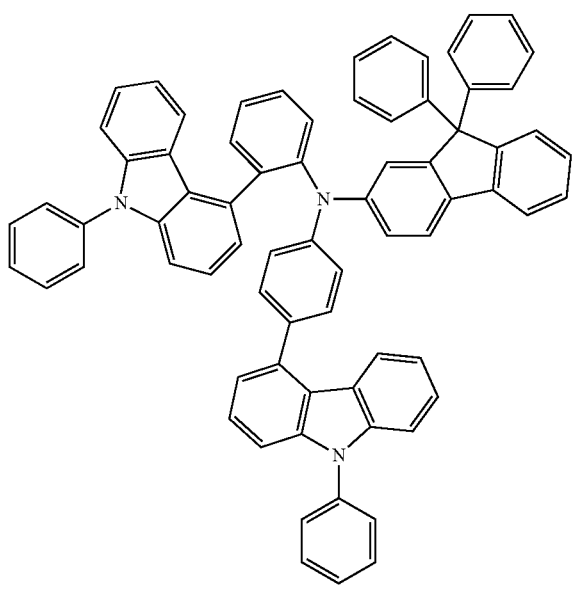
106
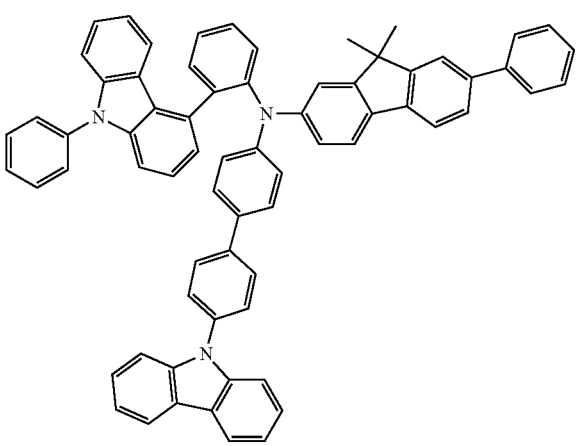
107
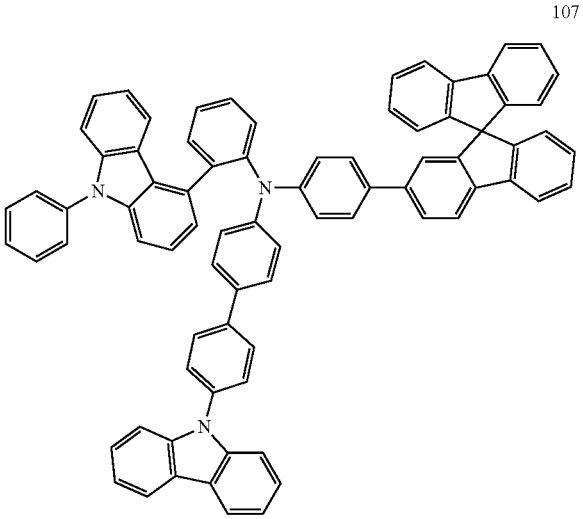
136
-continued
108
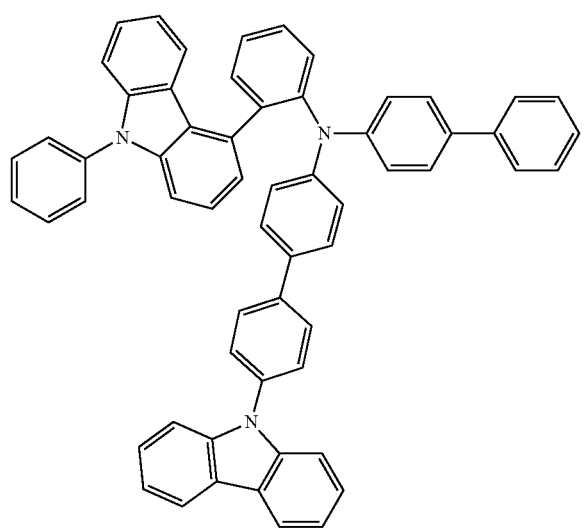
109
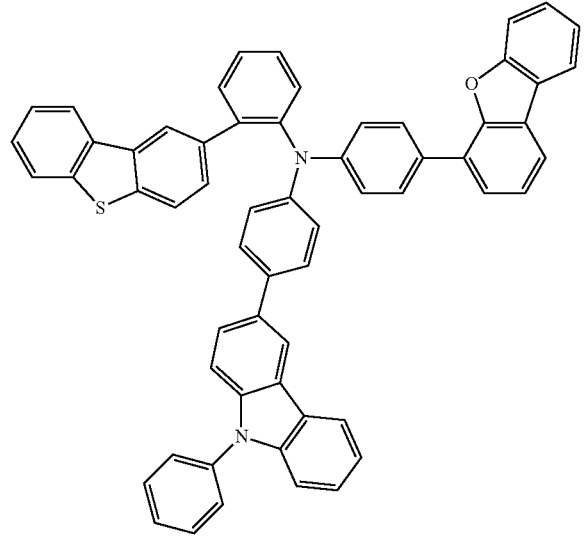
110
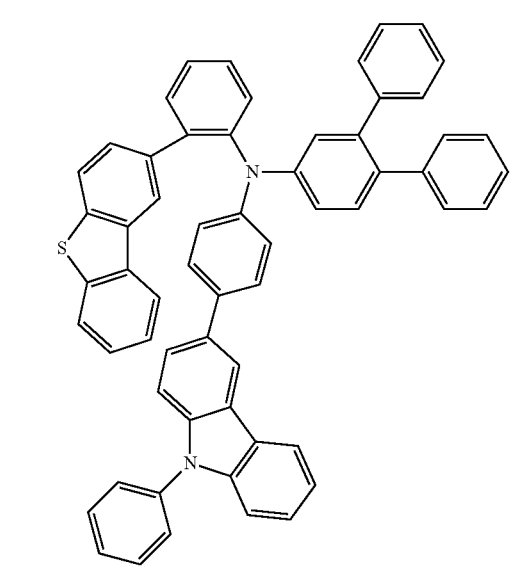

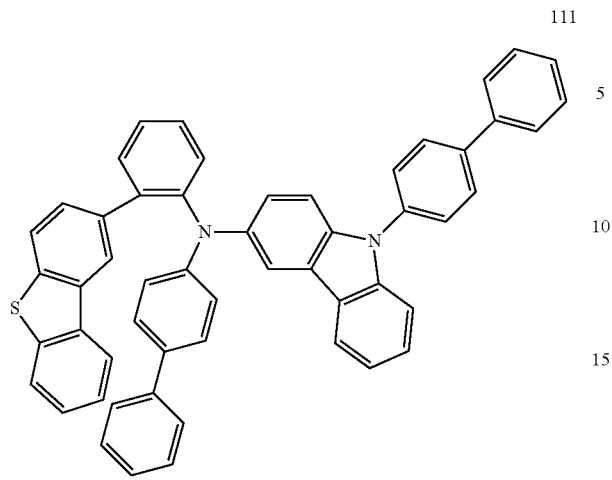
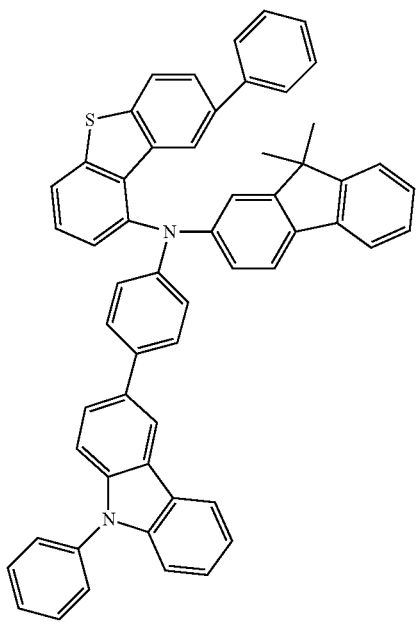
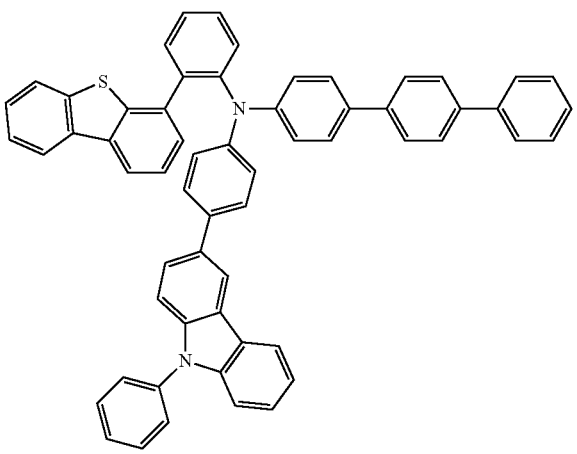

-continued
116
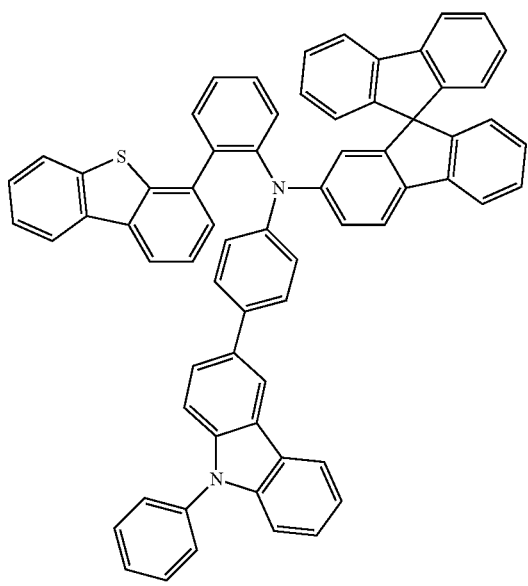
117
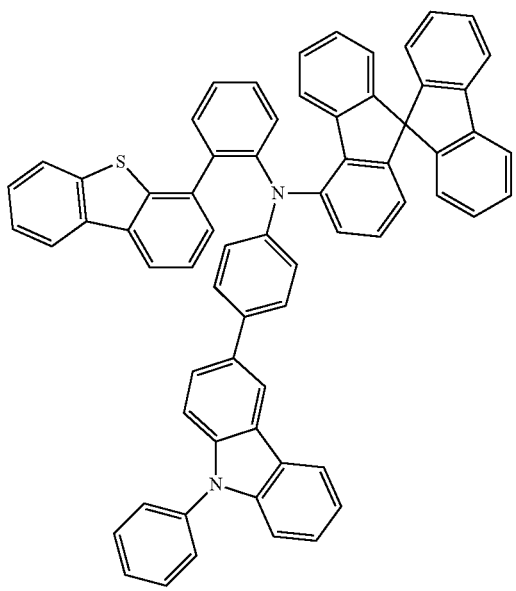
-continued
118
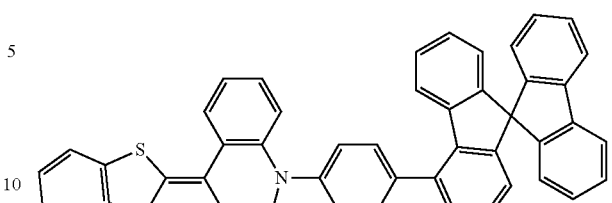
119
120
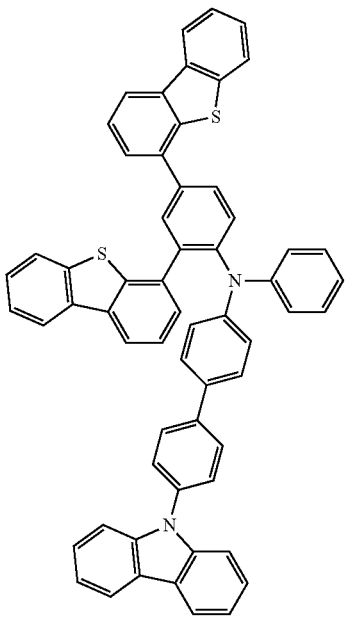

121
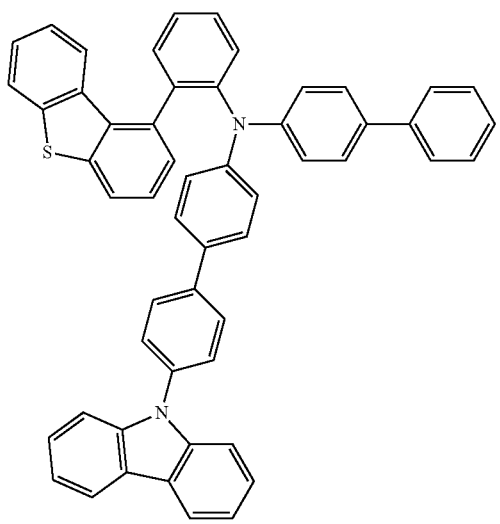
122
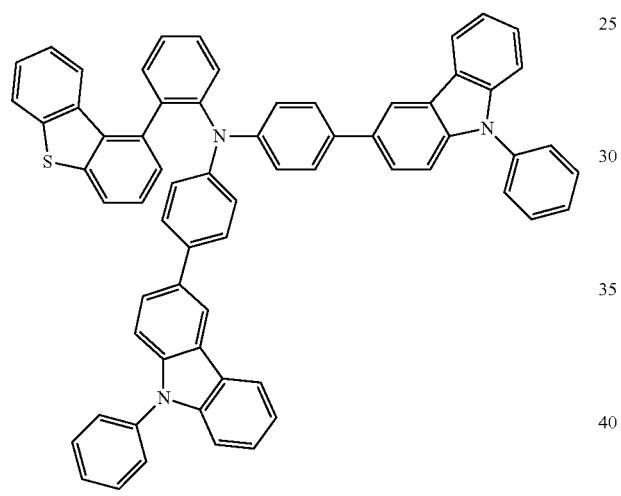
123
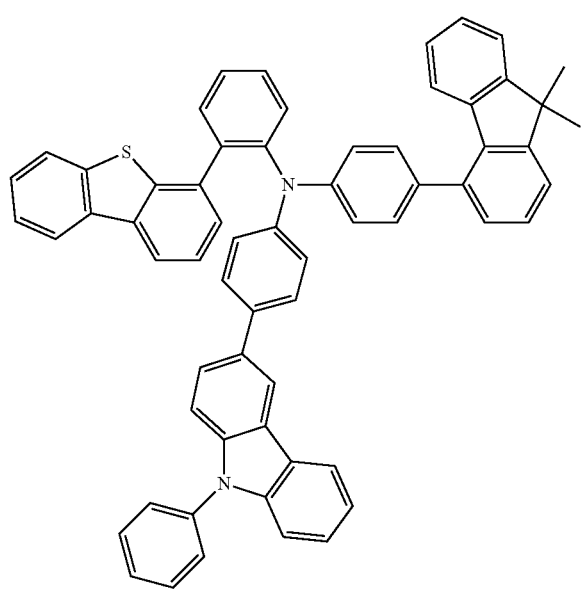
124
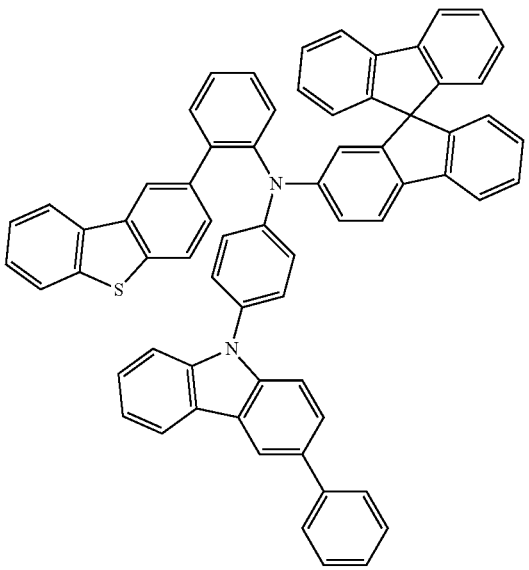
125
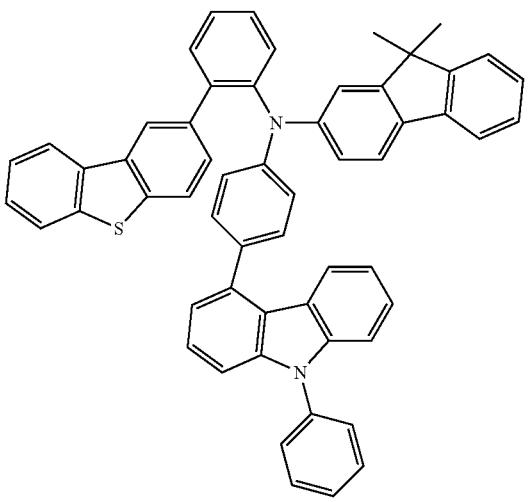
126
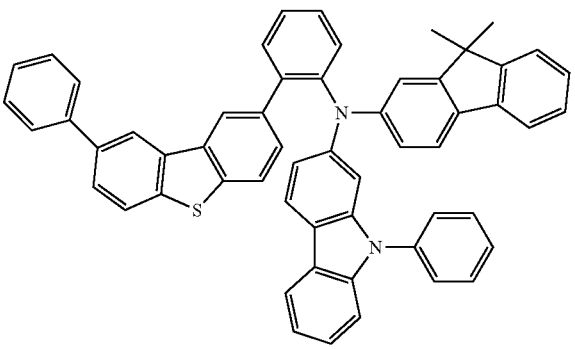

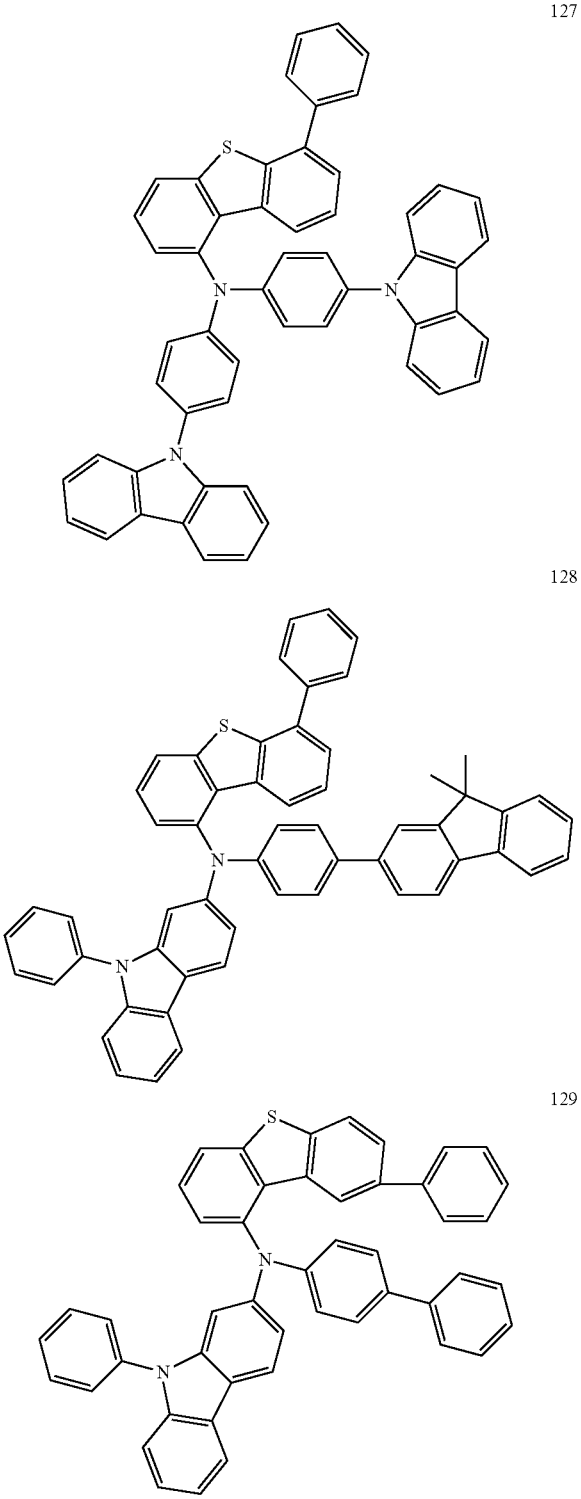

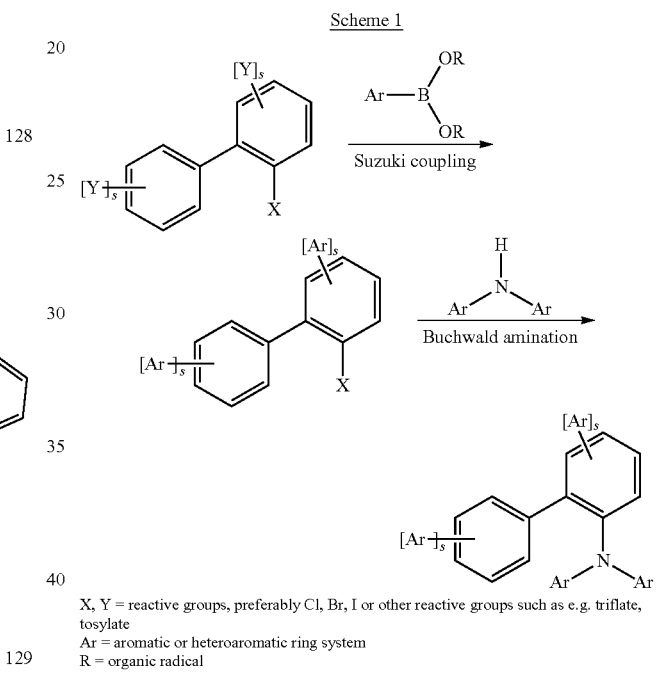

X, Y = reactive groups, preferably Cl, Br, I or other reactive groups such as e.g. triflate, tosylate
Ar = aromatic or heteroaromatic ring system
R = organic radical The compounds of formula (I) may be prepared using known reactions of organic chemistry, more particularly using metal-catalysed coupling reactions such as Suzuki coupling and Buchwald coupling.

A preferred process for preparing the compounds of formula (I) is elucidated in more detail below (Scheme 1). The skilled person is able to modify and adapt this process, where necessary, within the bounds of his or her general knowledge concerning organic synthetic chemistry.

According to scheme 1, in a first step a biphenyl derivative substituted by two reactive groups X and Y, the X group being in the ortho-position to the bond between the two phenyl groups, is reacted in a Suzuki reaction with an aromatic or heteroaromatic ring system Ar that is substituted by a boronic acid group. In this reaction, the ring system Ar is introduced at the position of the reactive Y group. In a second step, the intermediate obtained is reacted with an amine compound of the formula HNAr$_2$ in a Buchwald coupling reaction. In this reaction, the —NAr$_2$ group is introduced in the position of the reactive X group, and so is in the ortho-position to the bond between the two phenyl groups.

The resulting compound may optionally be modified further.

A subject of the present application is therefore a process for preparing a compound of the formula (I), characterized in that in a first step i) a biphenyl derivative substituted by reactive groups X and Y, where group X is present in the ortho-position to the bond between the two phenyl groups, is reacted with an aromatic or heteroaromatic ring system that is substituted by a boronic acid group, so that the aromatic or heteroaromatic ring system is introduced in the position of the Y group, and in that in a second step ii) the intermediate obtained in step i) is reacted with a compound of the formula HNAr$_2$, where Ar is selected from aromatic ring systems and heteroaromatic ring systems, and in this reaction the —NAr$_2$ group is introduced in the position of the X group.

The reaction of step i) is preferably a Suzuki coupling reaction. The reaction of step ii) is preferably a Buchwald coupling reaction.

The intermediate formed in step i) corresponds here preferably to a formula (I-Int-1)

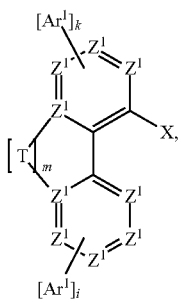
Formula (I-Int-1)

where the variables that occur are defined as above and where X is a reactive group, preferably Cl, Br, I or a triflate or tosylate group, more preferably Cl or Br.

The compound of the formula HNAr$_2$ which is used in step ii) corresponds preferably here to a formula (I-Int-2)

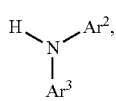
Formula (I-Int-2)

where the variables that occur are as defined above.

The above-described compounds of the formula (I), especially compounds substituted by reactive leaving groups, such as bromine, iodine, chlorine, boronic acid or boronic esters, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$ or $R^4$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are selected from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

More preferable is an organic electroluminescent device (OLED) comprising anode, cathode and at least one emitting layer, characterized in that at least one organic layer, which may be an emitting layer, a hole-transporting layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present here in a hole transport layer, hole injection layer, electron blocker layer, emitting layer, hole-blocking layer and/or electron-transporting layer, more preferably in an emitting layer as matrix material, in a hole blocker layer and/or in an electron transport layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer, an emitting layer, a hole blocker layer and/or an electron transport layer. More preferably, it is in this case present in an electron blocker layer or in an emitting layer in combination with a phosphorescent emitting compound.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in the following table:

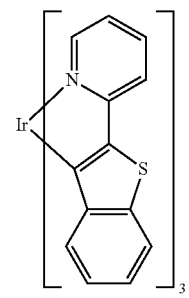

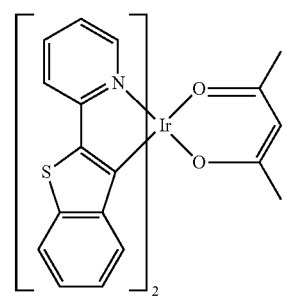

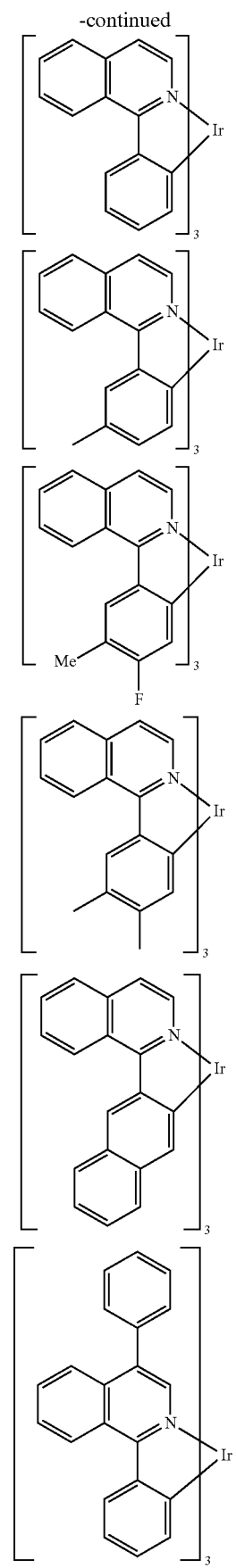
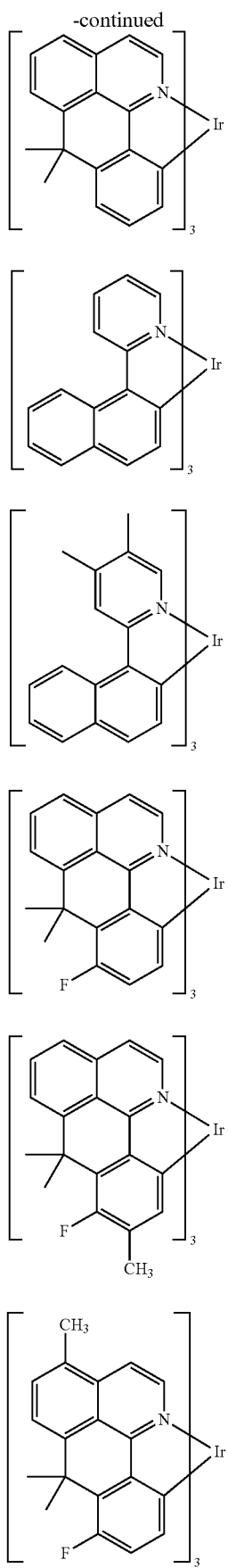

151
-continued
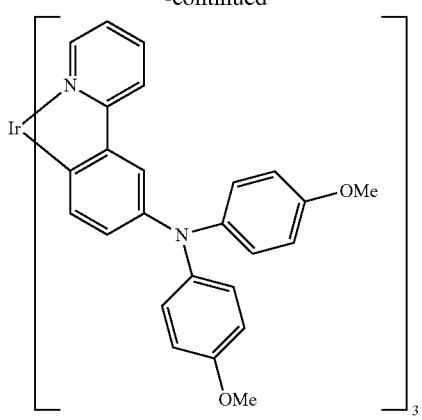
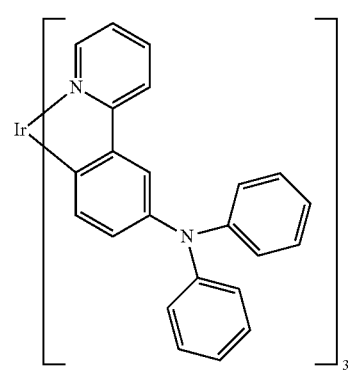
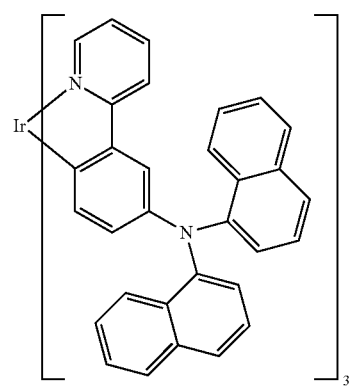
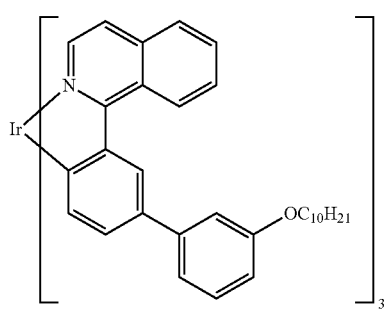
152
-continued
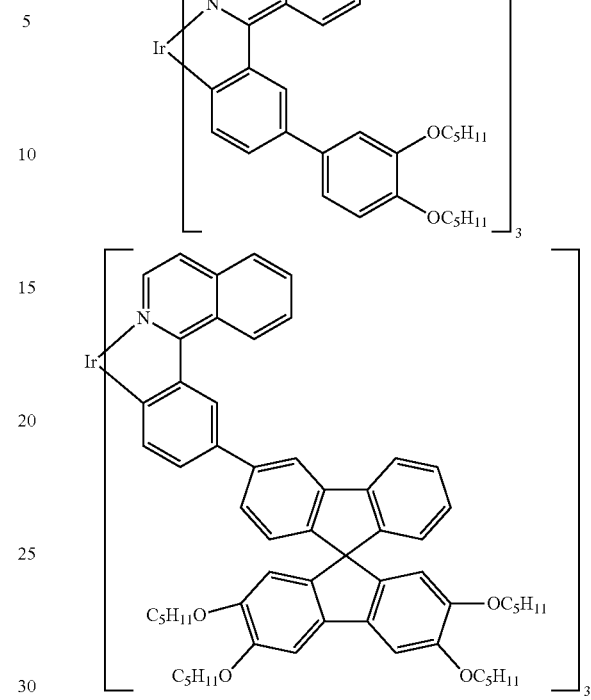
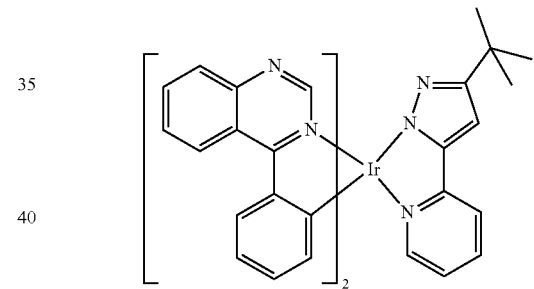
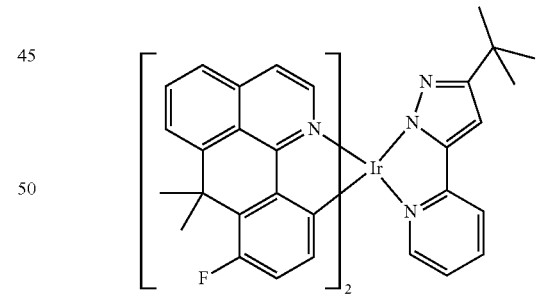
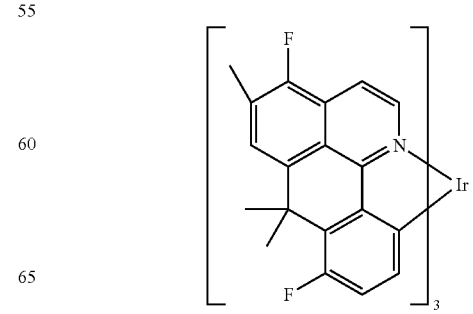

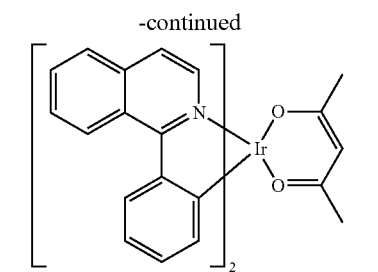
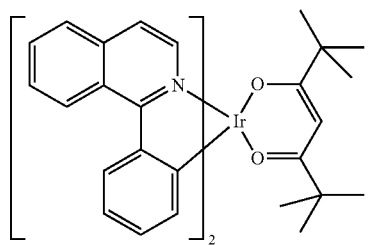
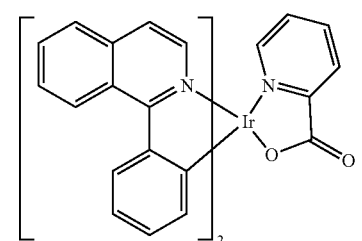
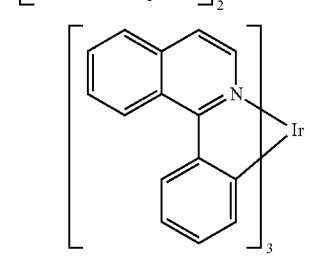
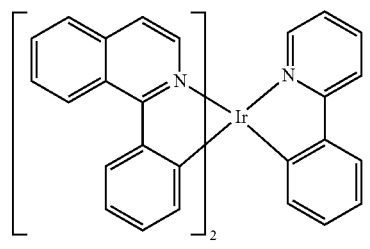
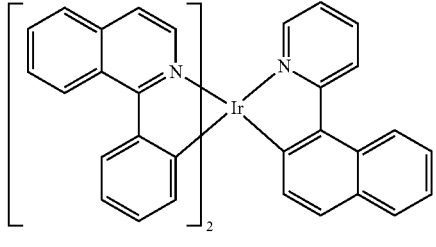
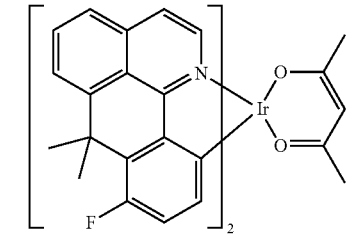
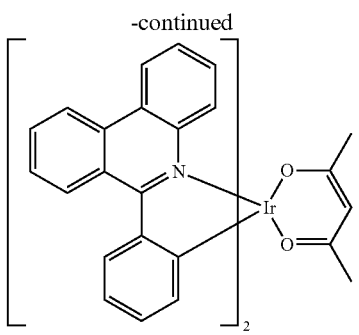
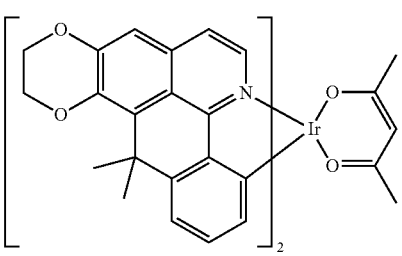
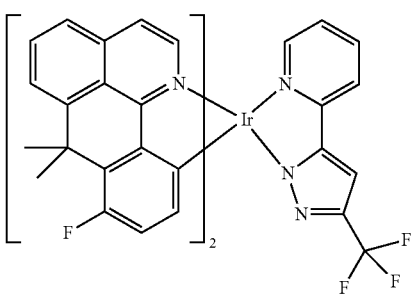
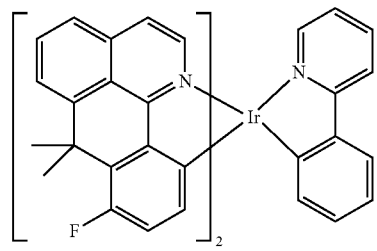
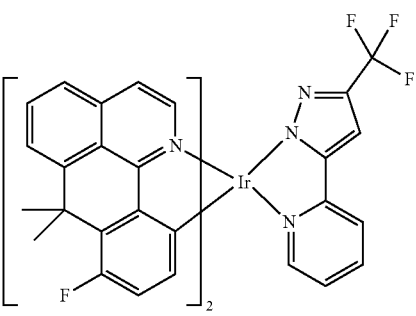

155
-continued
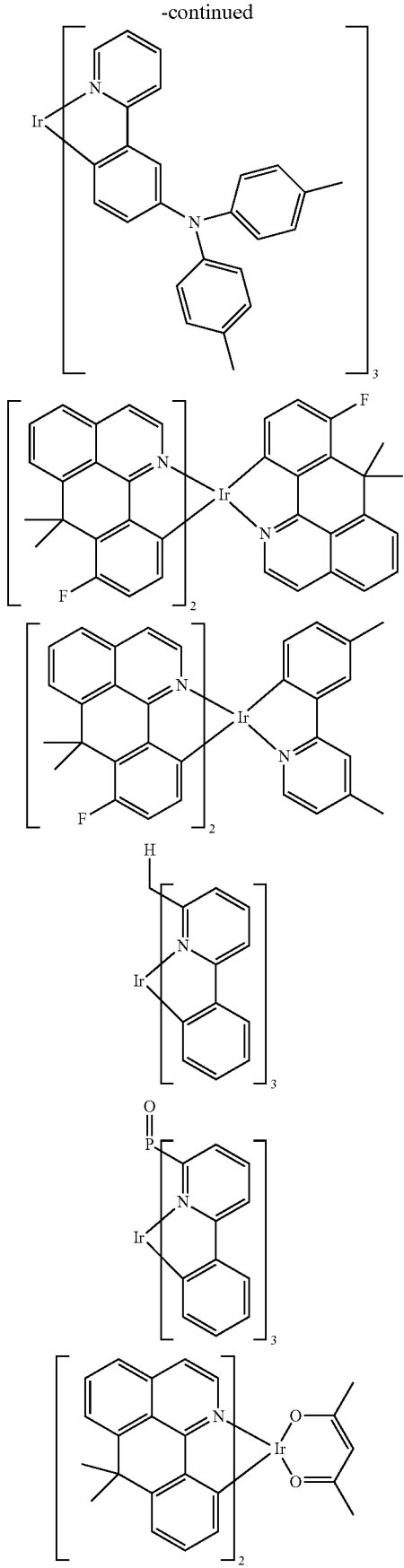
156
-continued
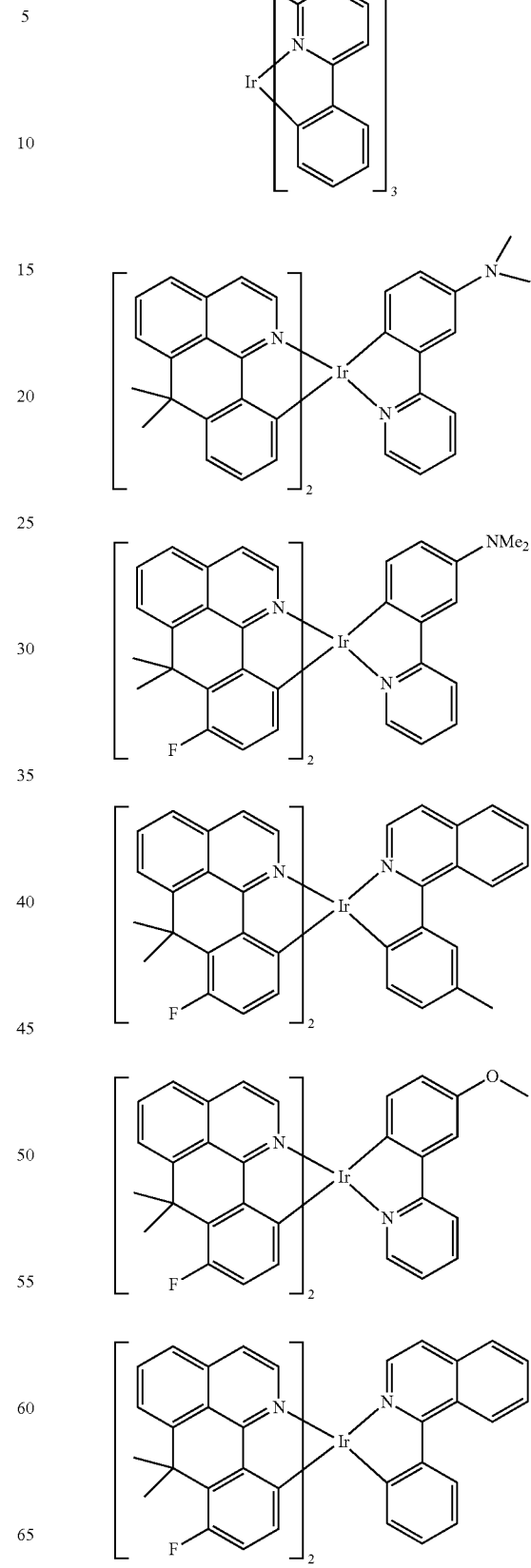

157
-continued
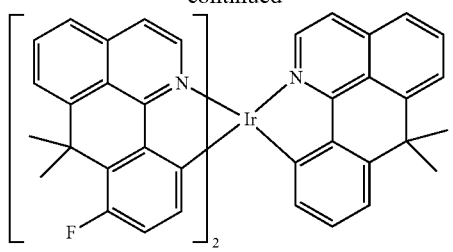
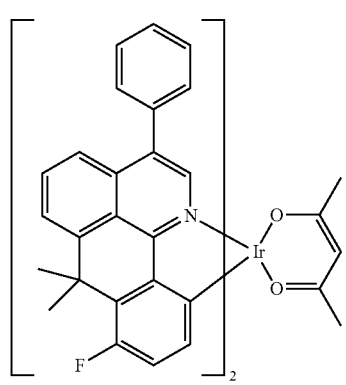
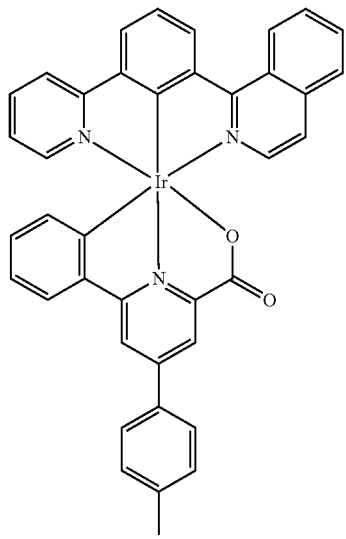
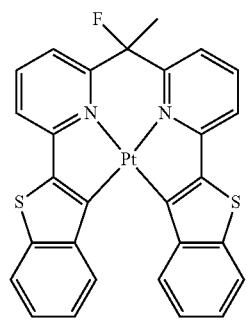
158
-continued
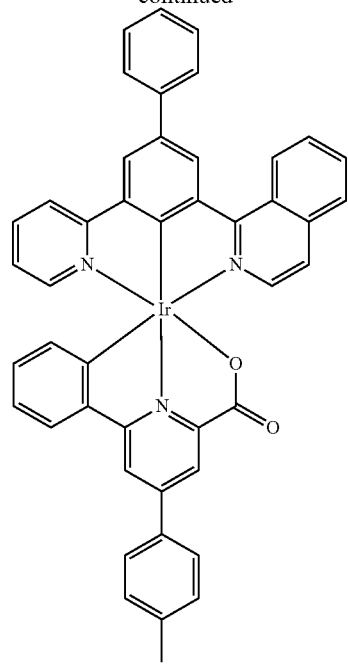
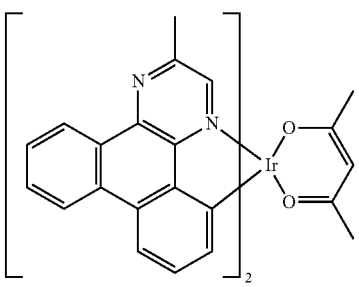
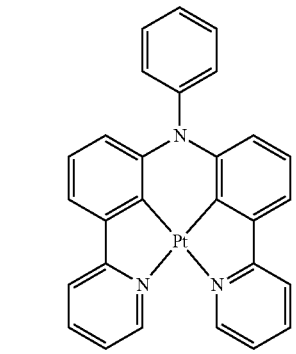
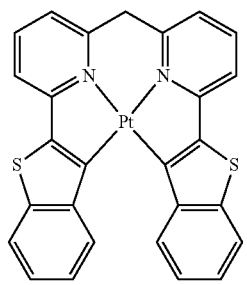

159
-continued
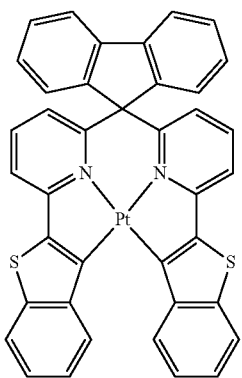
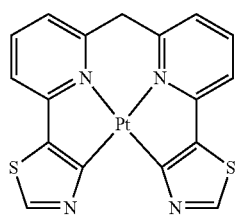
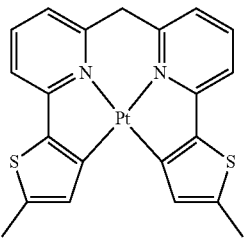
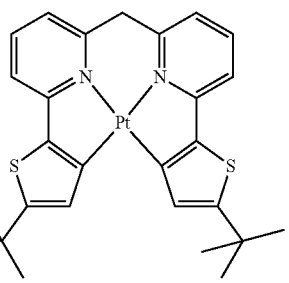
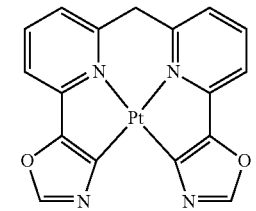
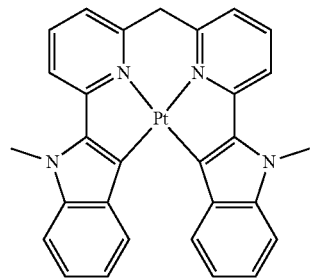
160
-continued
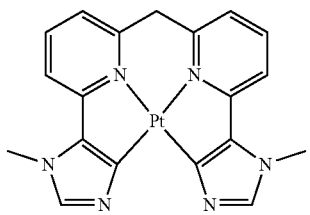
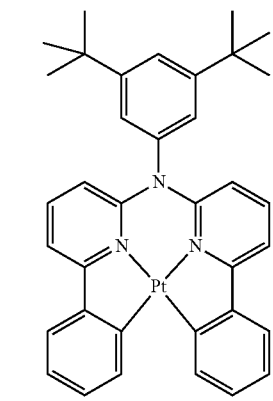
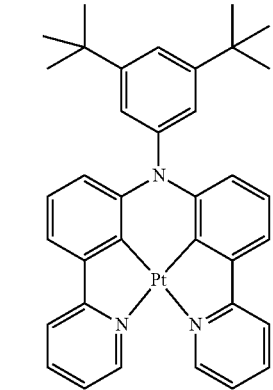
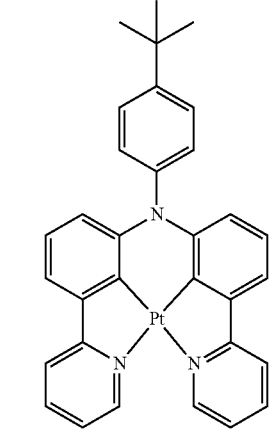

161
-continued
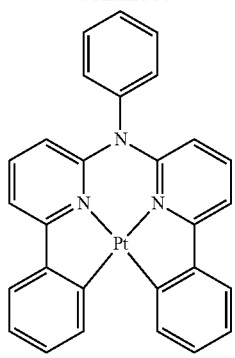
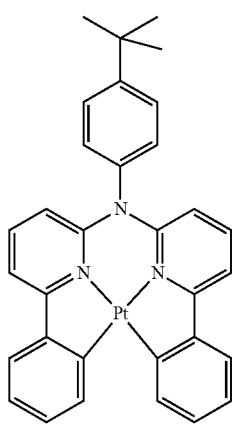
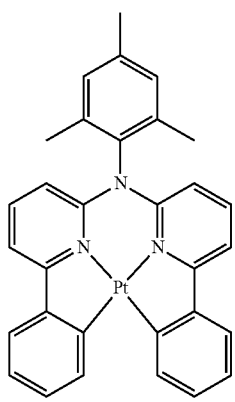
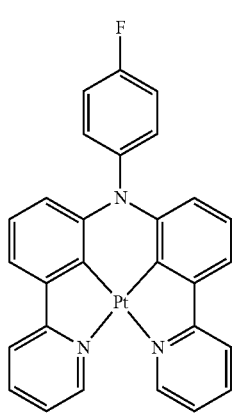
162
-continued
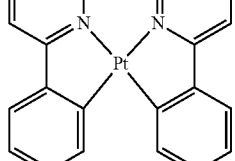
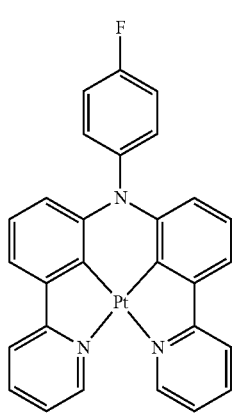
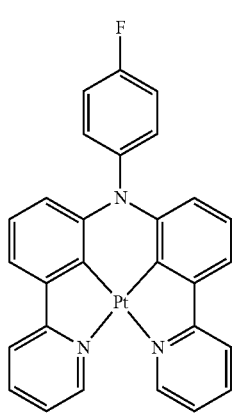
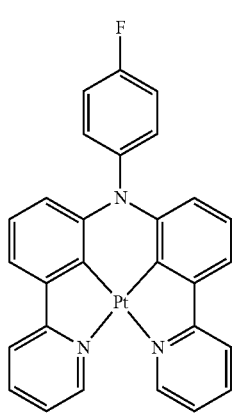

163
-continued
164
-continued
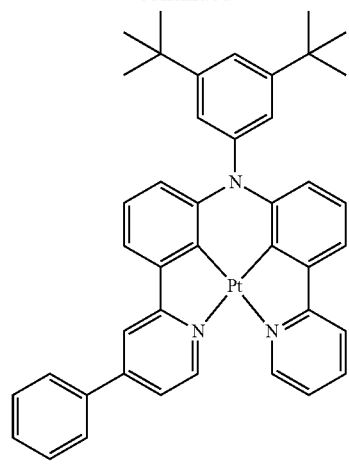
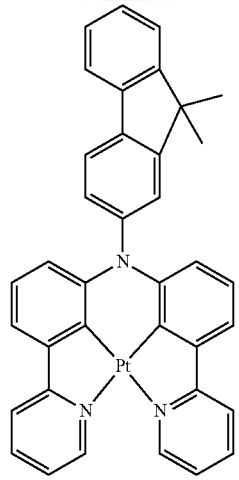
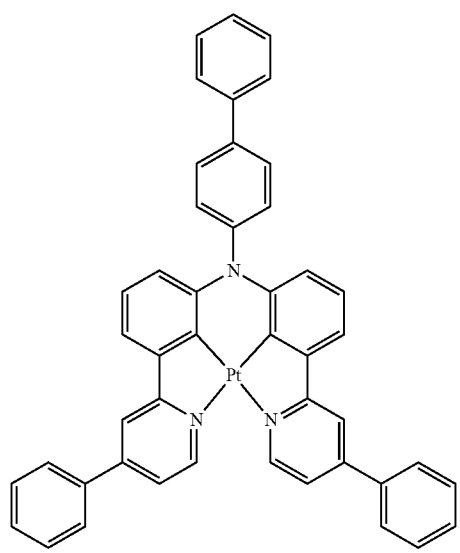
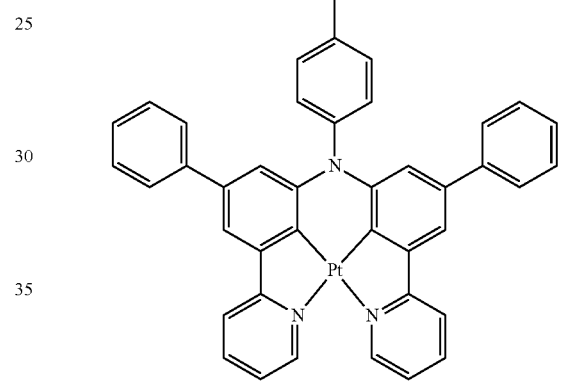
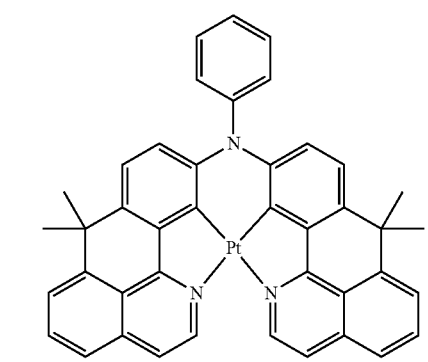
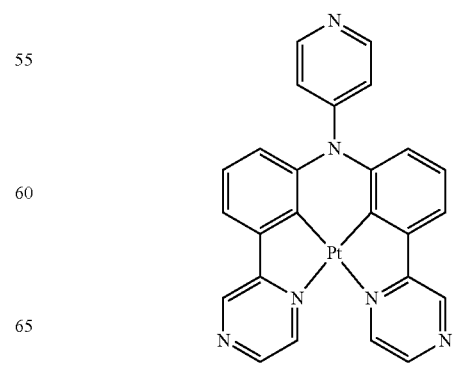

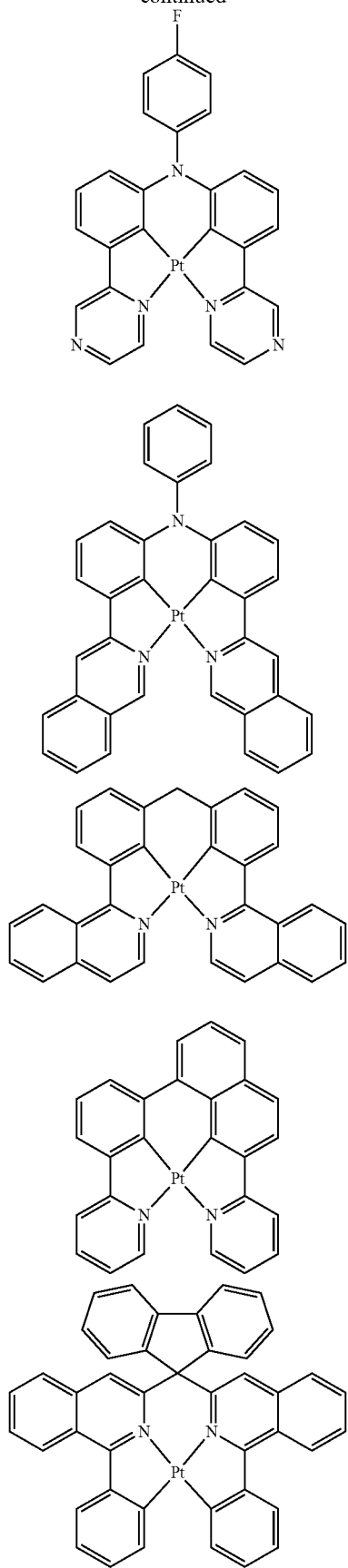
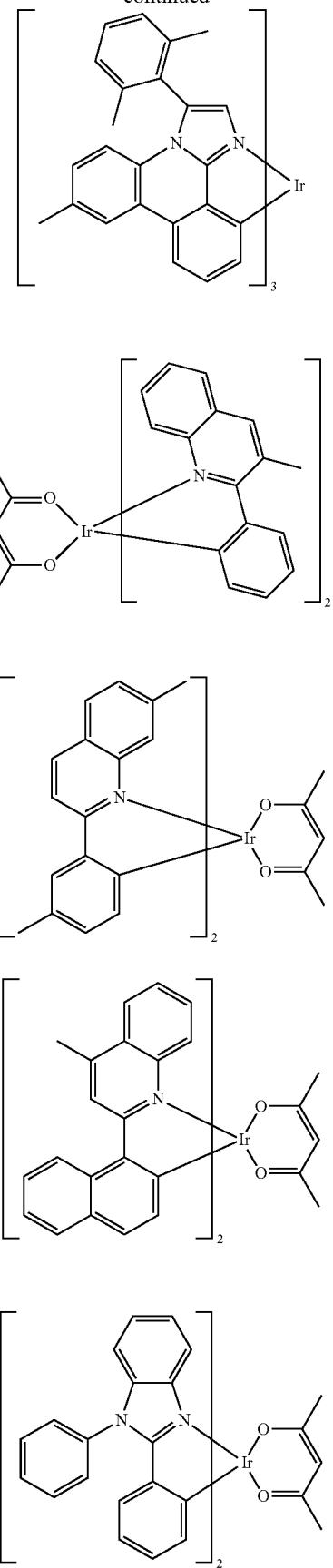

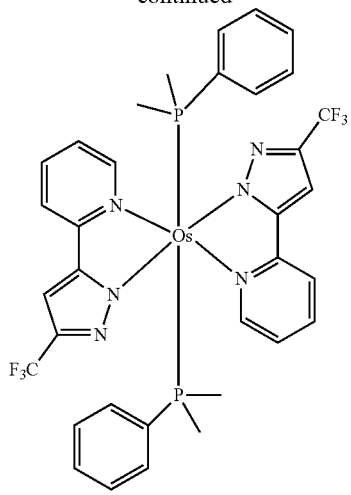
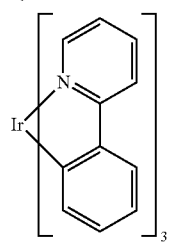
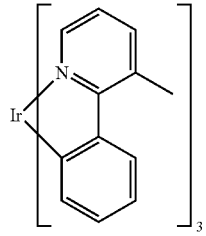
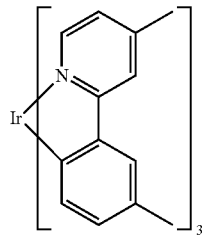
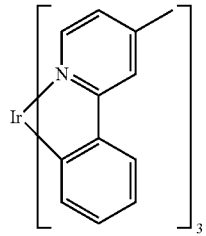
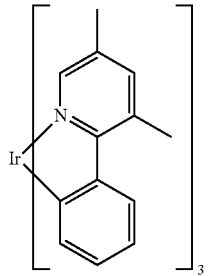
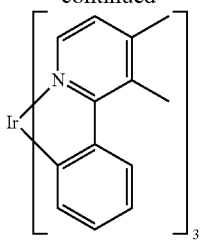
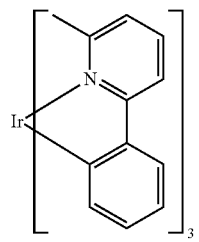
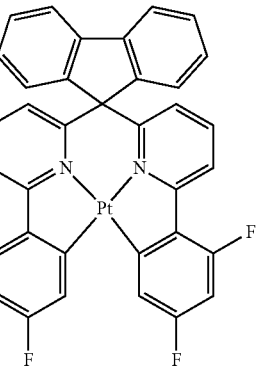
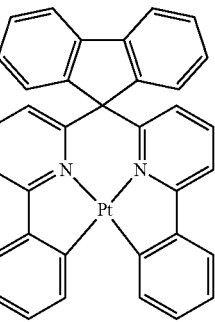
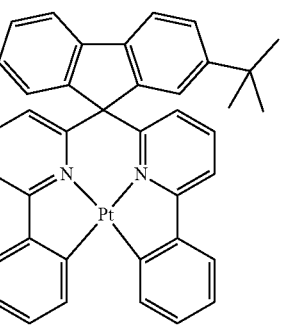

169
-continued
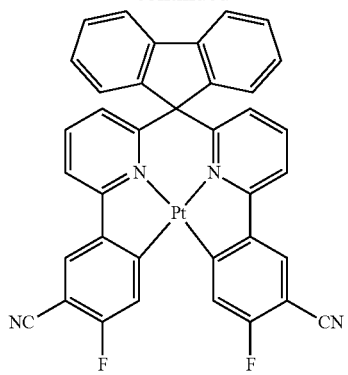
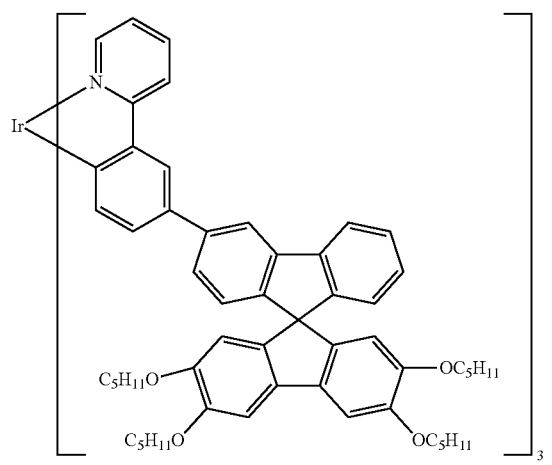
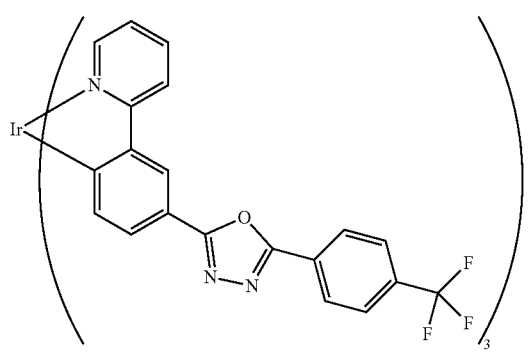
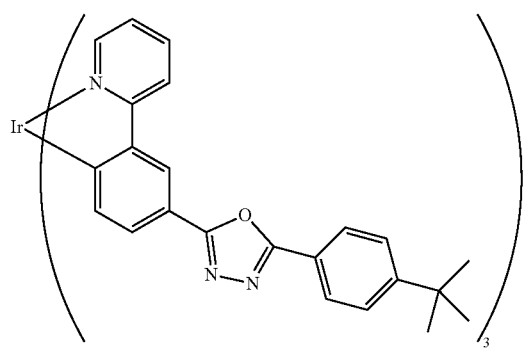
170
-continued
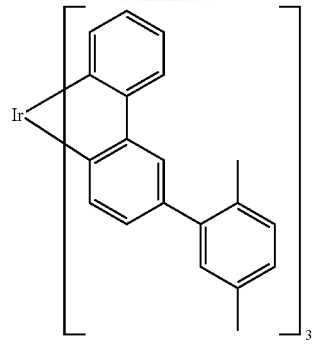
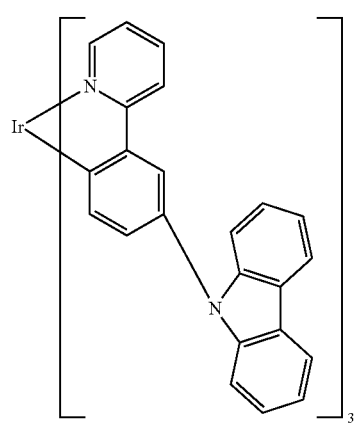
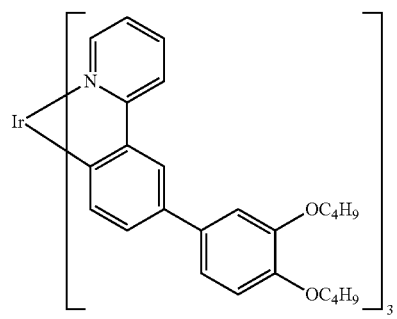
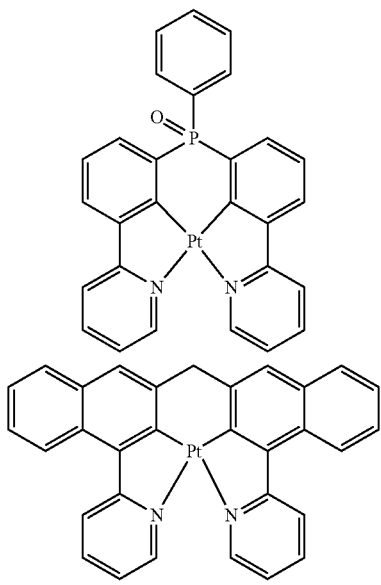

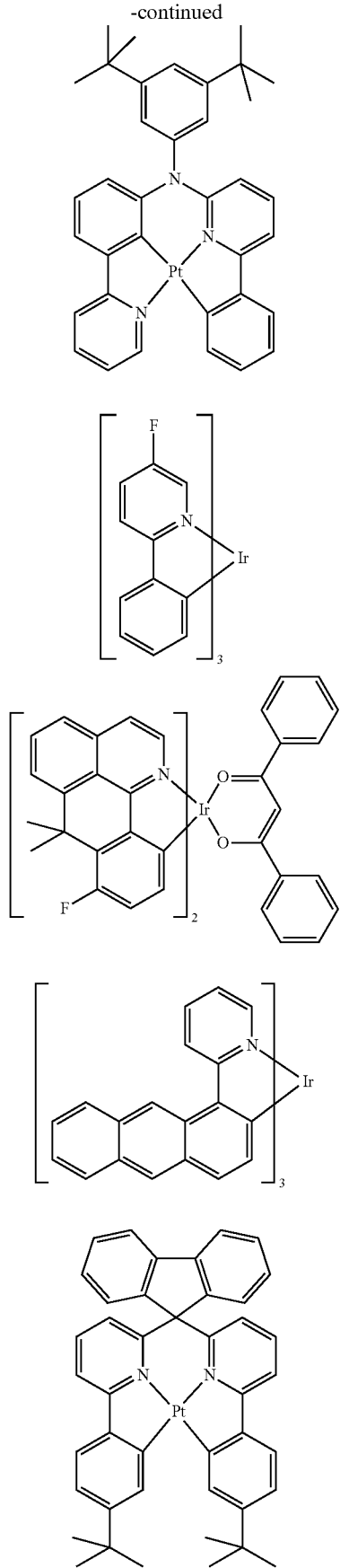

173
-continued
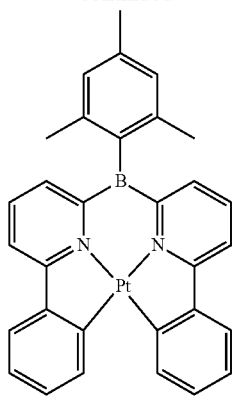
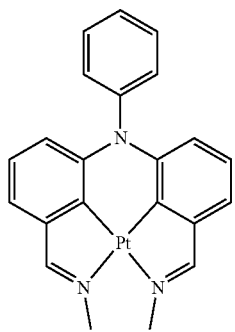
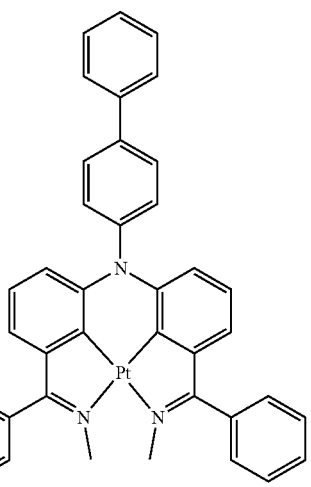
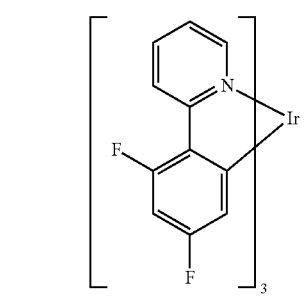
174
-continued
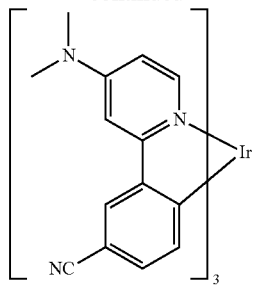
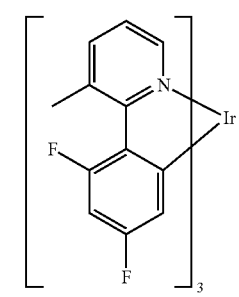
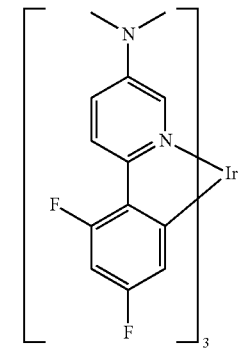
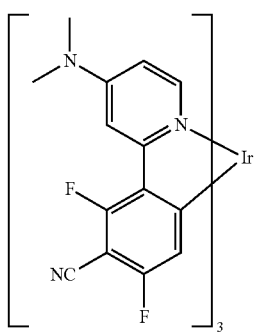
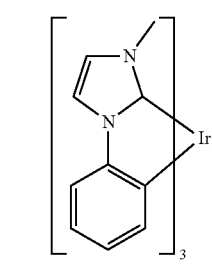

-continued
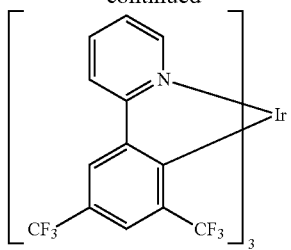
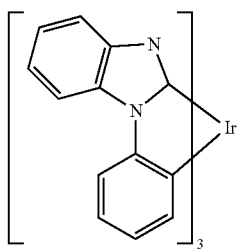
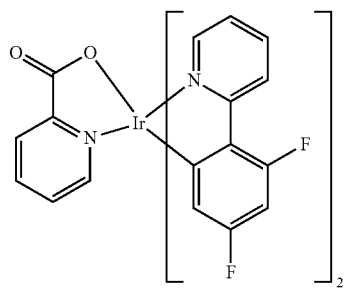
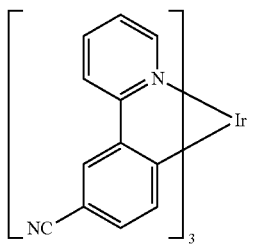
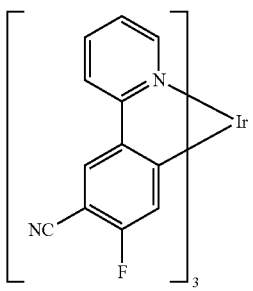
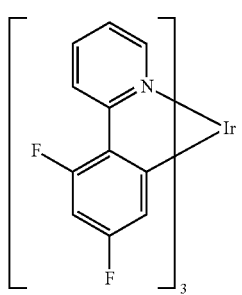
-continued
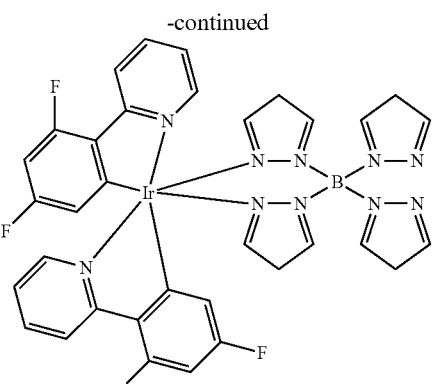
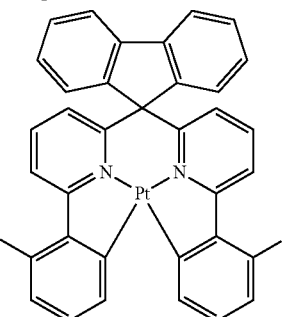
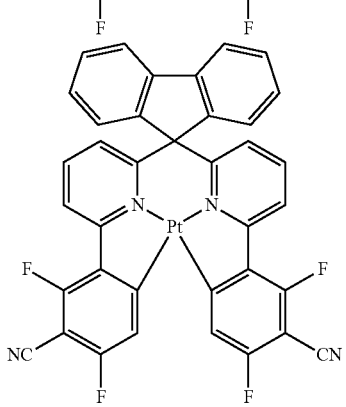
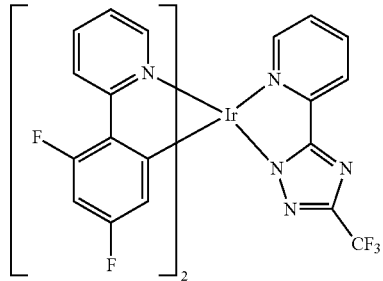
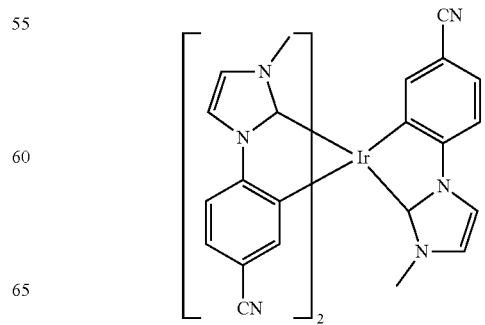

177
-continued
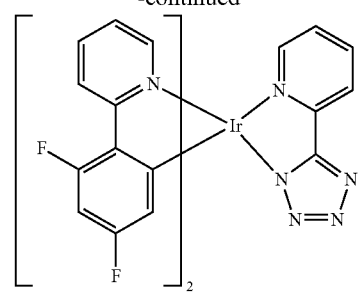
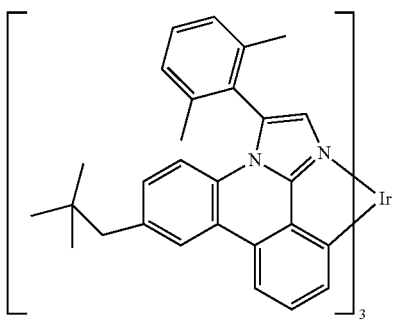
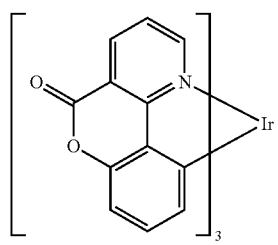
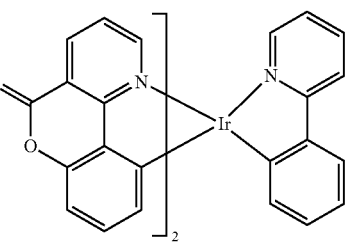
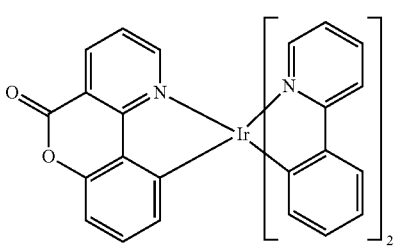
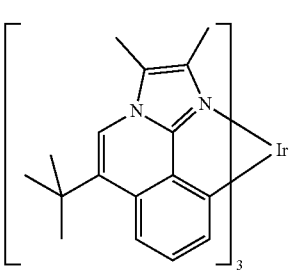
178
-continued
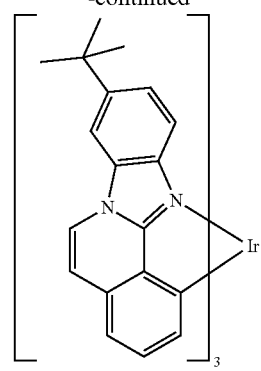
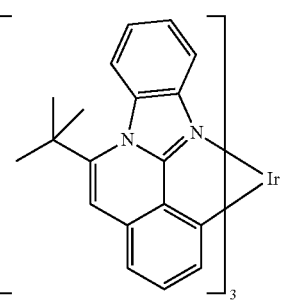
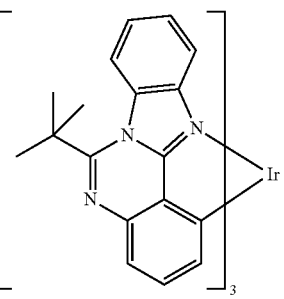
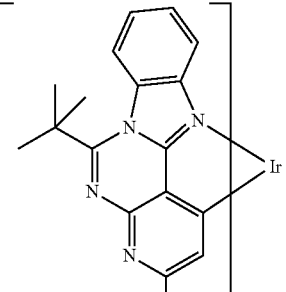
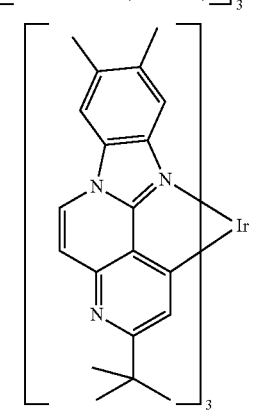

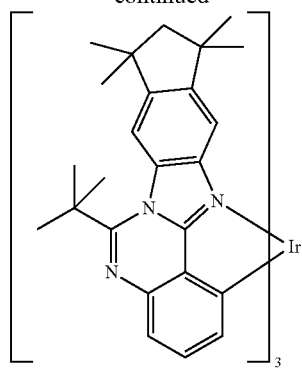
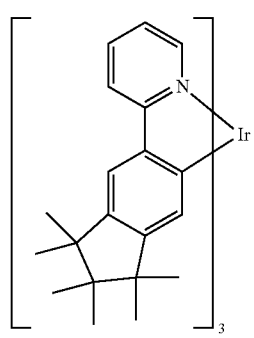
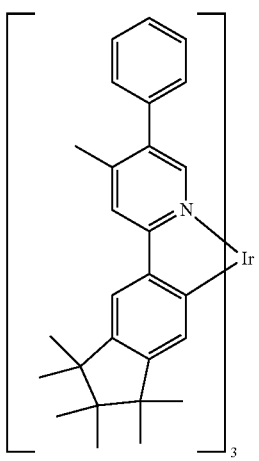
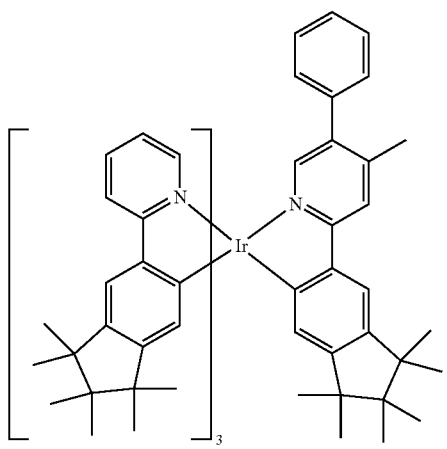
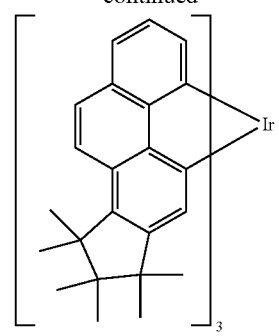
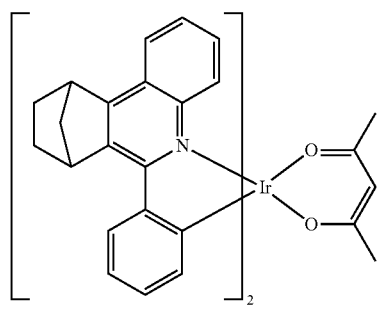
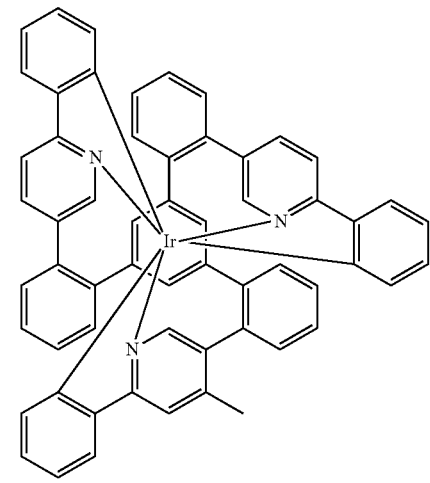
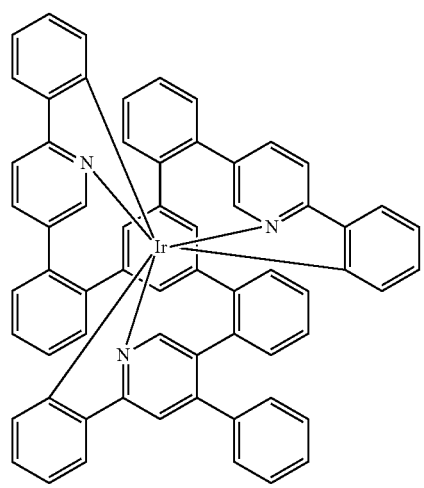

181
-continued

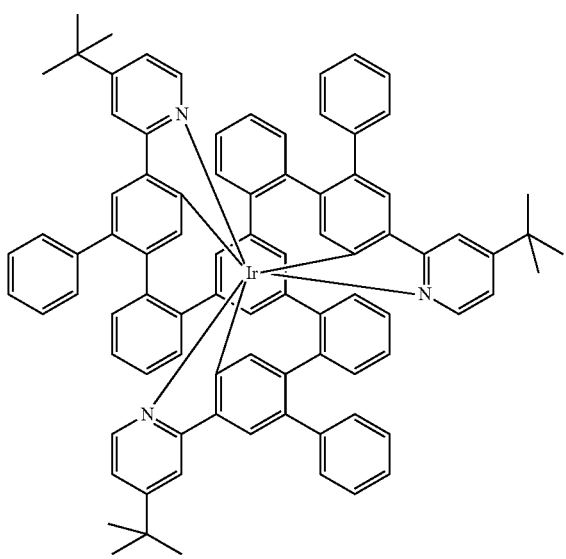

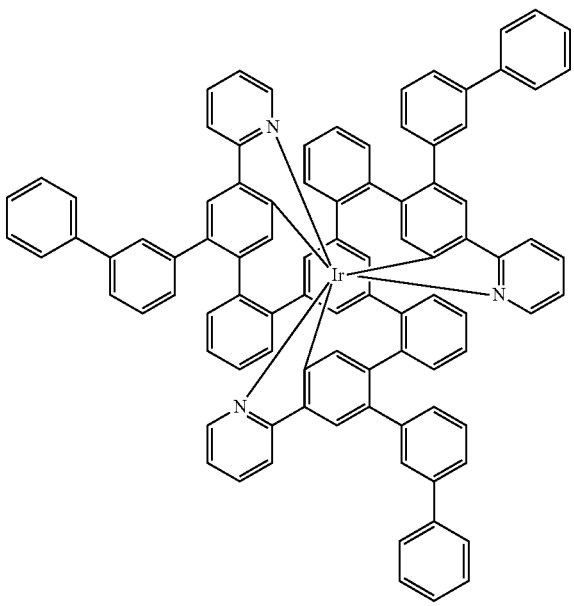

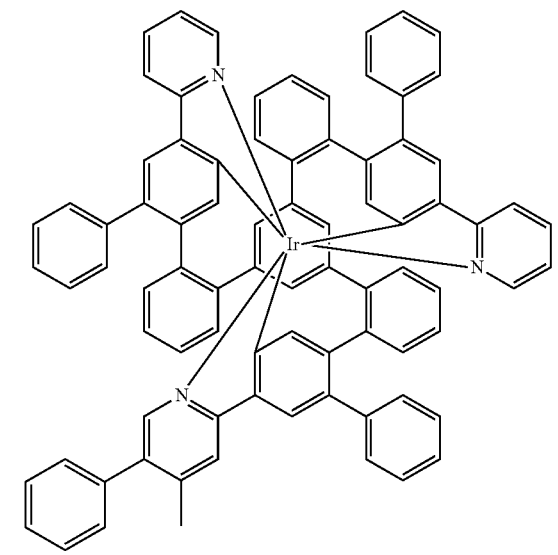

182
-continued

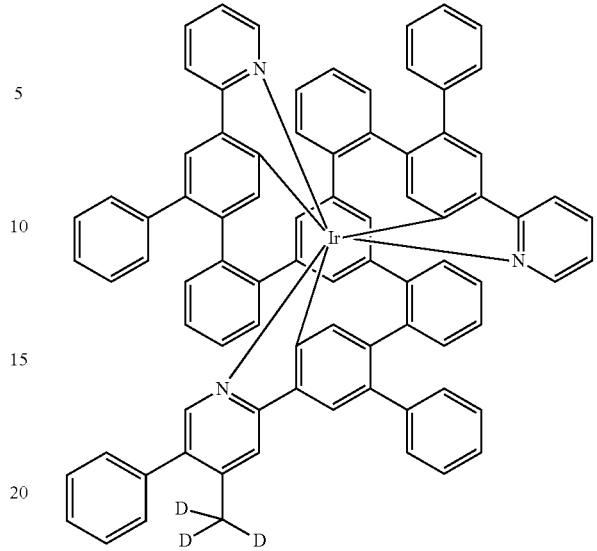

In a preferred embodiment of the invention, the compounds of formula (I) are used as hole-transporting material. The compounds are then preferably in a hole-transporting layer. Preferred embodiments of hole-transporting layers are hole transport layers, electron blocker layers and hole injection layers. With particular preference there is at least one compound of the formula (I) present in the electron blocker layer of the device.

A hole transport layer according to the present application is a layer having a hole-transporting function between the anode and emitting layer. More particularly, it is a hole-transporting layer which is not a hole injection layer and not an electron blocker layer.

Hole injection layers and electron blocker layers are understood in the context of the present application to be specific embodiments of hole-transporting layers. A hole injection layer, in the case of a plurality of hole-transporting layers between the anode and emitting layer, is a hole-transporting layer which directly adjoins the anode or is separated therefrom only by a single coating of the anode. An electron blocker layer, in the case of a plurality of hole-transporting layers between the anode and emitting layer, is that hole-transporting layer which directly adjoins the emitting layer on the anode side. Preferably, the OLED of the invention comprises two, three or four hole-transporting layers between the anode and emitting layer, at least one of which preferably contains a compound of formula (I), and more preferably exactly one or two contain a compound of formula (I).

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds.

In a preferred embodiment, a hole-transporting layer comprising the compound of the formula (I) additionally comprises one or more further hole-transporting compounds. These further hole-transporting compounds are preferably selected from triarylamine compounds, more preferably from mono-triarylamine compounds. With very particular preference they are selected from the preferred embodiments of hole transport materials that are indicated later on below. In the preferred embodiment described, the compound of the formula (I) and the one or more further hole-transporting compounds are preferably each present in a proportion of at least 20%, more preferably each in a proportion of at least 30%.

In a preferred embodiment, a hole-transporting layer comprising the compound of the formula (I) additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred as p-dopants are quinodimethane compounds, azaindenofluorenediones, azaphenalenes, azatriphenylenes, $I_2$, metal halides, preferably transition metal halides, metal oxides, preferably metal oxides comprising at least one transition metal or a metal from main group 3, and transition metal complexes, preferably complexes of Cu, Co, Ni, Pd and Pt with ligands containing at least one oxygen atom as binding site. Preference is further given to transition metal oxides as dopants, preferably oxides of rhenium, molybdenum and tungsten, more preferably $Re_2O_7$, $MoO_3$, $WO_3$ and $ReO_3$. Still further preference is given to complexes of bismuth in the (III) oxidation state, more particularly bismuth(III) complexes with electron-deficient ligands, more particularly carboxylate ligands.

The p-dopants are preferably in substantially homogeneous distribution in the p-doped layers. This can be achieved, for example, by coevaporation of the p-dopant and the hole transport material matrix.

Preferred p-dopants are especially the following compounds:

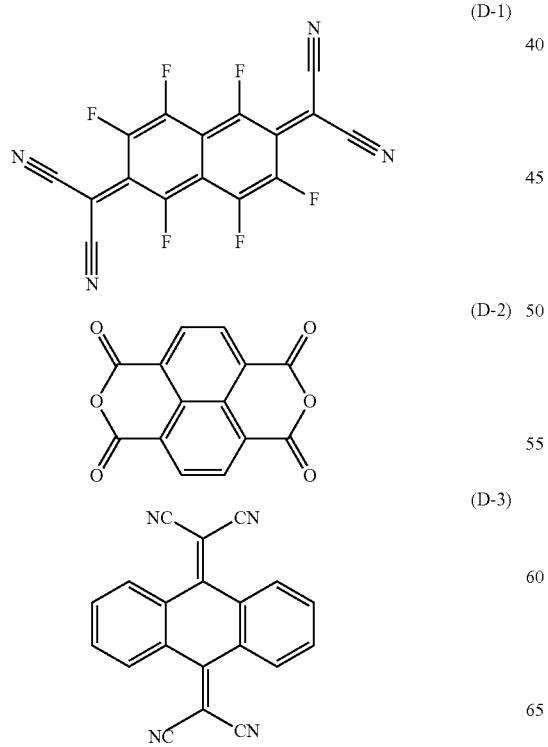

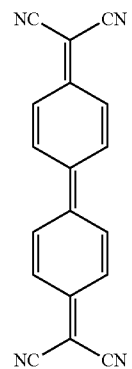

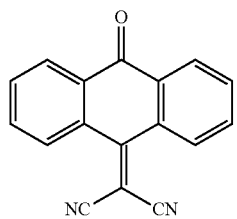

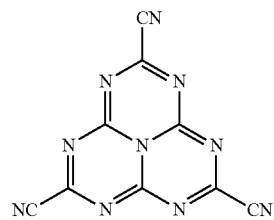

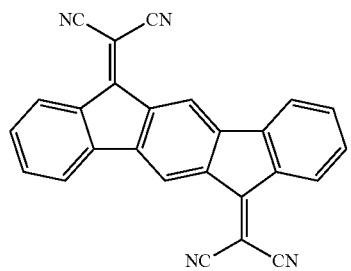

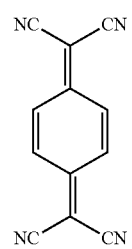

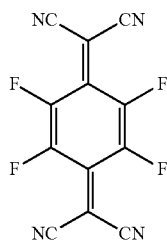

(D-10)
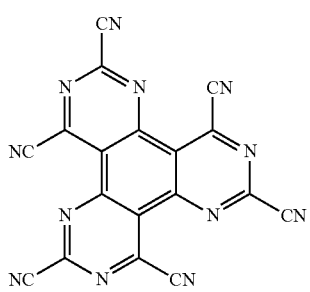

(D-11)
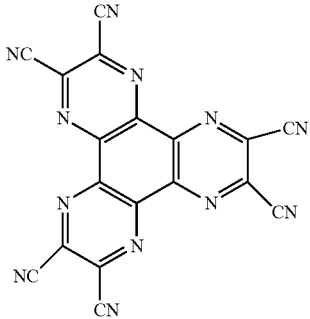

(D-12)
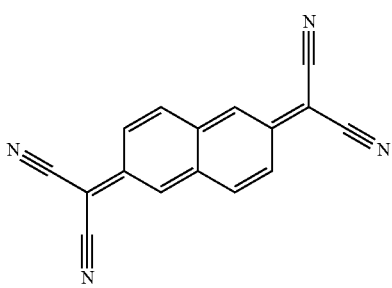

(D-13)
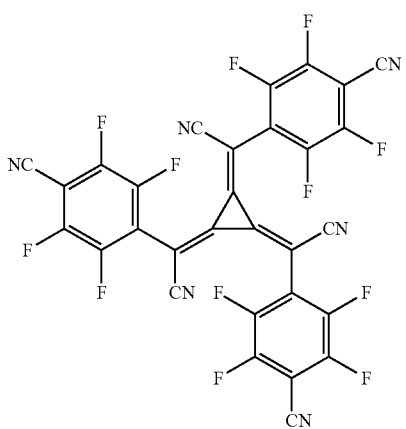

In a further preferred embodiment of the invention, the compound of formula (I) is used as hole transport material in combination with a hexaazatriphenylene derivative as described in US 2007/0092755 in an OLED. Particular preference is given here to using the hexaazatriphenylene derivative in a separate layer.

In a preferred embodiment of the present invention, the compound of the formula (I) is used in an emitting layer as matrix material in combination with one or more emitting compounds, preferably phosphorescent emitting compounds.

The proportion of the matrix material in the emitting layer in this case is between 50.0% and 99.9% by volume, preferably between 80.0% and 99.5% by volume, and more preferably between 85.0% and 97.0% by volume.

Correspondingly, the proportion of the emitting compound is between 0.1% and 50.0% by volume, preferably between 0.5% and 20.0% by volume, and more preferably between 3.0% and 15.0% by volume.

An emitting layer of an organic electroluminescent device may also contain systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems, preferably for phosphorescent emitters. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. Correspondingly, when the compound of the formula (I) is used as matrix material for a phosphorescent emitter in the emitting layer of an OLED, a second matrix compound having electron-transporting properties is present in the emitting layer. The two different matrix materials may be present in a ratio of 1:50 to 1:1, preferably 1:20 to 1:1, more preferably 1:10 to 1:1 and most preferably 1:4 to 1:1. More specific details relating to mixed matrix systems are given inter alia in the application WO 2010/108579, the corresponding technical teaching of which is incorporated by reference in this connection.

The desired electron-transporting and hole-transporting properties of the mixed matrix components may, however, also be combined mainly or entirely in a single mixed matrix component, in which case the further mixed matrix component(s) fulfil(s) other functions.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the inventive compounds as matrix components of a mixed matrix system are selected from the preferred matrix materials specified below for phosphorescent emitting compounds, and among these especially from those having electron-transporting properties.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in the as yet unpublished application EP 15182993.4, the phenoxazines disclosed in the as yet unpublished applications EP 15181178.3 and EP 15181177.5, and the fluorene derivatives bonded to furan units or to thiophene units that are disclosed in WO 2016/150544.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in the as yet unpublished application EP 15180777.3, and the phenanthrylanthracenes disclosed in the as yet unpublished application EP 15182962.9.

Preferred matrix materials for phosphorescent emitting compounds are, as well as the compounds of the formula (I), aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Preferably, the inventive OLED comprises two or more different hole-transporting layers. The compound of the formula (I) may be used here in one or in more of or in all the hole-transporting layers. In a preferred embodiment, the compound of the formula (I) is used in exactly one or exactly two hole-transporting layers, and other compounds, preferably aromatic amine compounds, are used in the further hole-transporting layers present. Further compounds which are used alongside the compounds of the formula (I), preferably in hole-transporting layers of the OLEDs of the invention, are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051 and the as yet unpublished applications PCT/EP2015/002475 and PCT/EP2016/000084, phenanthrenediarylamines, for example according to WO 2015/131976, spirotribenzotropolones, for example according to the as yet unpublished application PCT/EP2015/002225, spirobifluorenes with meta-phenyldiamine groups, for example according to the as yet unpublished application PCT/EP2015/002112, spirobisacridines, for example according to WO 2015/158411, xanthenediarylamines, for example according to WO 2014/072017, and 9,10-dihydroanthracene spiro compounds with diarylamino groups according to WO 2015/086108.

Materials used for the electron transport layer may be any materials as used according to the prior art as electron transport materials in the electron transport layer. Especially suitable are aluminium complexes, for example Alq$_3$, zirconium complexes, for example Zrq$_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, Li$_2$O, BaF$_2$, MgO, NaF, CsF, Cs$_2$CO$_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiO$_x$, Al/PtO$_x$) may also be preferred. For some applications, at least one of the electrodes has to be transparent or partly transparent in order to enable either the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects of water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar.

In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

EXAMPLES

A) Synthesis Examples

Synthesis of the compound biphenyl-4-yl(9-phenyl-9H-carbazol-2-yl)-[1,1';3',1'']terphenyl-2-yl-amine (1-1) and of the Compounds (1-2) to (1-22)

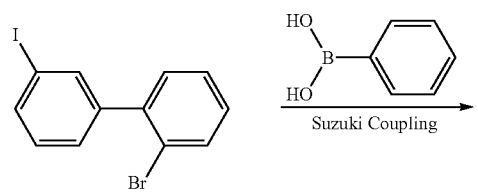

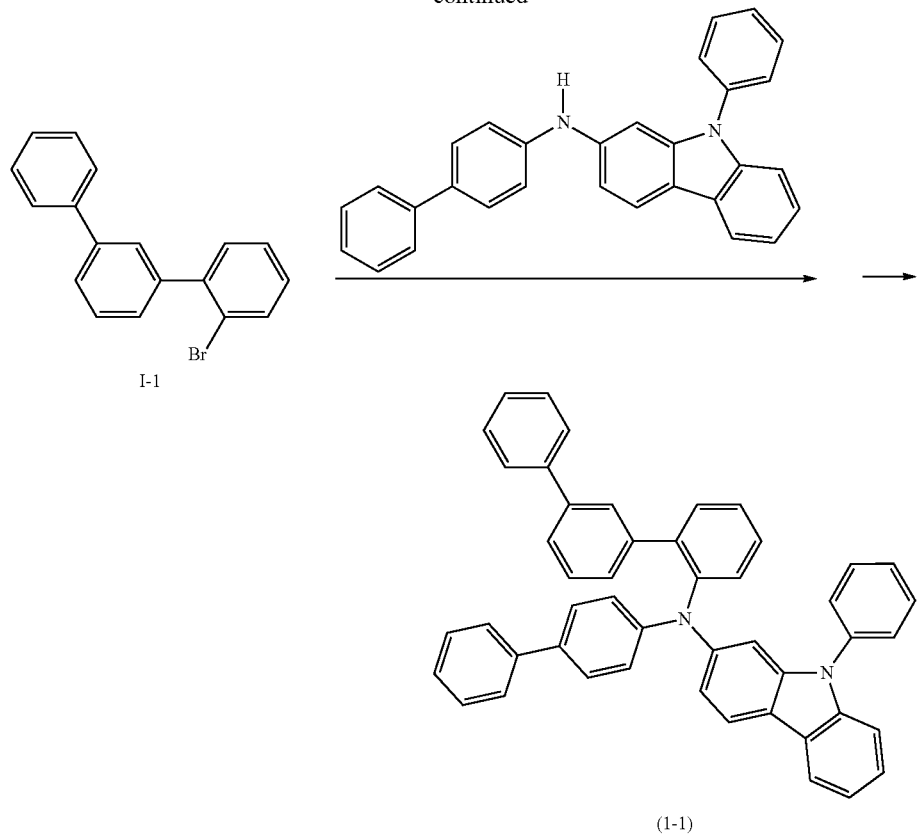

Synthesis of Intermediate I-1: 2-Bromo-[1,1';3',1"]-terphenyl 14.3 g (117 mmol) of phenylboronic acid, 40 g (111.4 mmol) of 2-bromo-3'-iodo-biphenyl and 84 ml of an aqueous 2 M K$_2$CO$_3$ solution (168 mmol) are suspended in 400 ml of toluene. To this suspension are added 1.2 g (1.2 mmol) of tetrakis(triphenyl)phosphinepalladium(0). The reaction mixture is heated under reflux for 16 h. After cooling, the organic phase is removed, filtered through silica gel, washed three times with 150 ml of water and then concentrated to dryness. After the crude product has been filtered through silica gel with heptane/ethyl acetate, 29 g (85%) of 2-bromo-[1,1';3',1"]-terphenyl are obtained.

The following compounds are prepared in an analogous manner:

-continued
| | Reactant 1 | Reactant 2 | Product |
|---|---|---|---|
| I-4 | 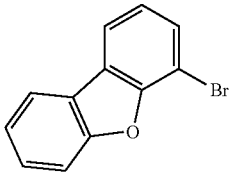 [SMILES: Brc1cccc2c1oc1ccccc12] | 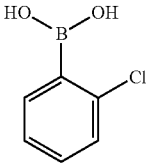 | 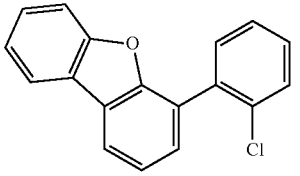 [SMILES: Clc1ccccc1-c1cccc2c1oc1ccccc12] |
| I-5 | 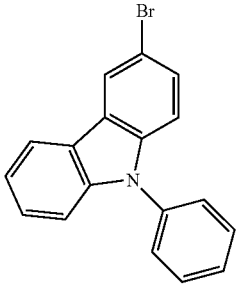 [SMILES: Brc1ccc2c(c1)c1ccccc1n2-c1ccccc1] | 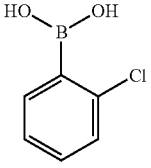 | 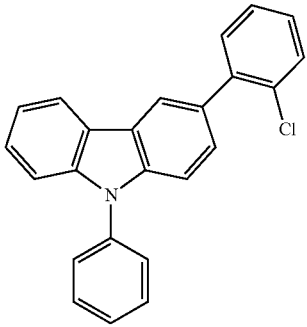 [SMILES: Clc1ccccc1-c1ccc2c(c1)c1ccccc1n2-c1ccccc1] |
| I-6 | 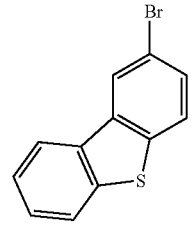 [SMILES: Brc1ccc2sc3ccccc3c2c1] | 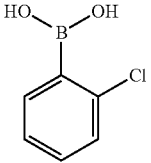 | 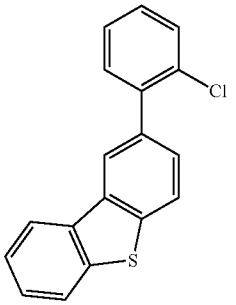 [SMILES: Clc1ccccc1-c1ccc2sc3ccccc3c2c1] |
| I-7 | 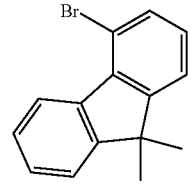 [SMILES: CC1(C)c2ccccc2-c2c(Br)cccc21] | 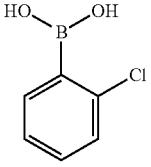 | 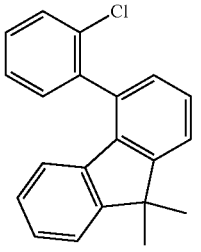 [SMILES: CC1(C)c2ccccc2-c2c(-c3ccccc3Cl)cccc21] |
| I-8 | 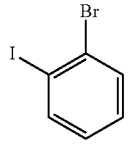 | 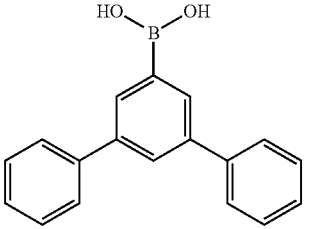 [SMILES: OB(O)c1cc(-c2ccccc2)cc(-c2ccccc2)c1] | 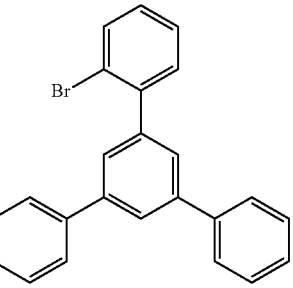 |

-continued
| Reactant 1 | Reactant 2 | Product |
|---|---|---|
| I-9 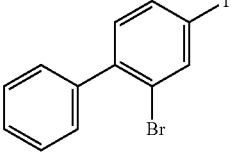 | 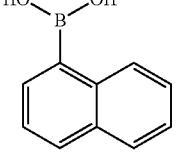 | 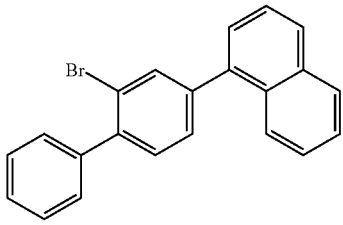 [SMILES: Brc1cc(-c2cccc3ccccc23)ccc1-c1ccccc1] |
| I-10 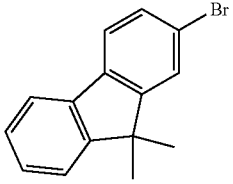 [SMILES: CC1(C)c2ccccc2-c2ccc(Br)cc21] | 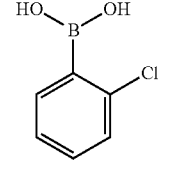 | 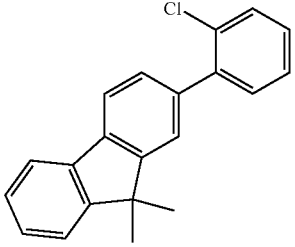 [SMILES: CC1(C)c2ccccc2-c2ccc(-c3ccccc3Cl)cc21] |
| I-11 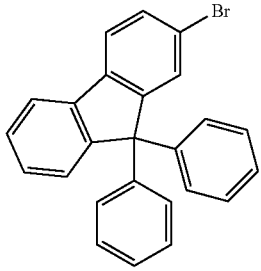 [SMILES: Brc1ccc2c(c1)C(c1ccccc1)(c1ccccc1)c1ccccc1-2] | 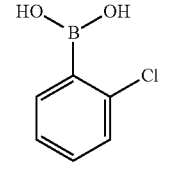 | 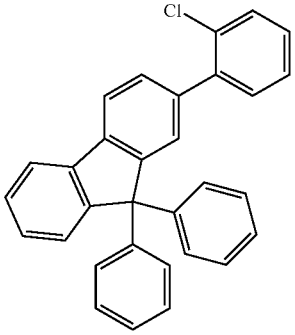 [SMILES: Clc1ccccc1-c1ccc2c(c1)C(c1ccccc1)(c1ccccc1)c1ccccc1-2] |
| I-12 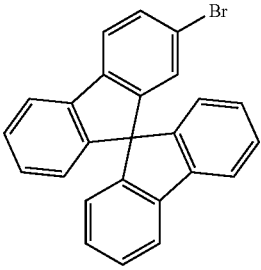 [SMILES: Brc1ccc2c(c1)C1(c3ccccc3-c3ccccc31)c1ccccc1-2] | 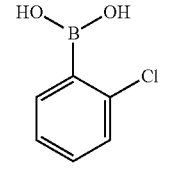 | 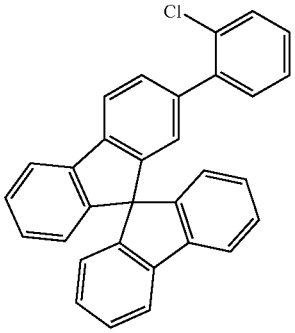 [SMILES: Clc1ccccc1-c1ccc2c(c1)C1(c3ccccc3-c3ccccc31)c1ccccc1-2] |

Synthesis of Intermediate I-13:
5-chloro-9,9-dimethyl-2-phenylfluorene

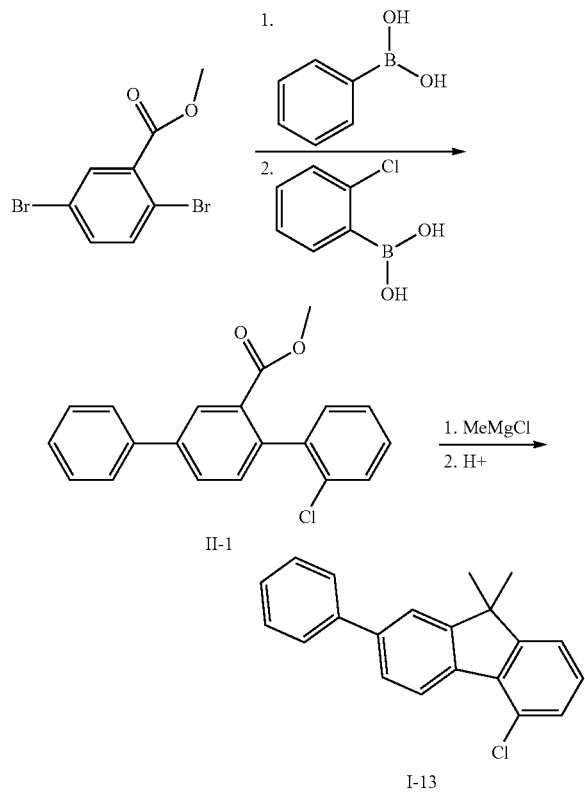

I-13

Intermediate II-1

8.3 g of phenylboronic acid (68 mmol) and 20 g of dibromocarboxylic ester derivative (68 mmol) are suspended in 400 ml of toluene, 160 ml of ethanol and 80 ml of water. 14.4 g of sodium carbonate are added thereto. The solution is degassed and saturated with $N_2$. Thereafter, 0.79 g (0.68 mmol) of $Pd(Ph_3P)_4$ is added. The reaction mixture is heated (80° C.) under a protective atmosphere for 4 h. The mixture is subsequently partitioned between toluene and water, and the organic phase is washed three times with water and dried over $Na_2SO_4$ and concentrated by rotary evaporation. After the crude product has been filtered through silica gel with heptane/ethyl acetate, the remaining residue is recrystallized from EtOH.

The yield is 11.0 g (55% of theory). 5.9 g of 2-chlorophenylboronic acid (38 mmol) and 11 g of the bromine derivative (38 mmol) are suspended in 200 ml of toluene and 70 ml of water. 7.2 g of sodium carbonate (67.6 mmol) are added thereto. The solution is degassed and saturated with $N_2$. Thereafter, 140 mg (0.15 mmol) of $Pd_2(dba)_3$ and 250 mg of SPhos (0.3 mmol) are added. The reaction mixture is heated to boiling under a protective atmosphere for 12 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from EtOH. The yield is 10.4 g (85% of theory).

The following compounds are prepared in an analogous manner:

| | Reactant 1 | Boronic acid 1 | Boronic acid 2 | Product |
|---|---|---|---|---|
| II-2 | ![structure] | ![structure] | ![structure] | ![structure] |
| II-3 | ![structure] | ![structure] | ![structure] | ![structure] |

| Reactant 1 | Boronic acid 1 | Boronic acid 2 | Product |
|---|---|---|---|
| ii-4 | | | |

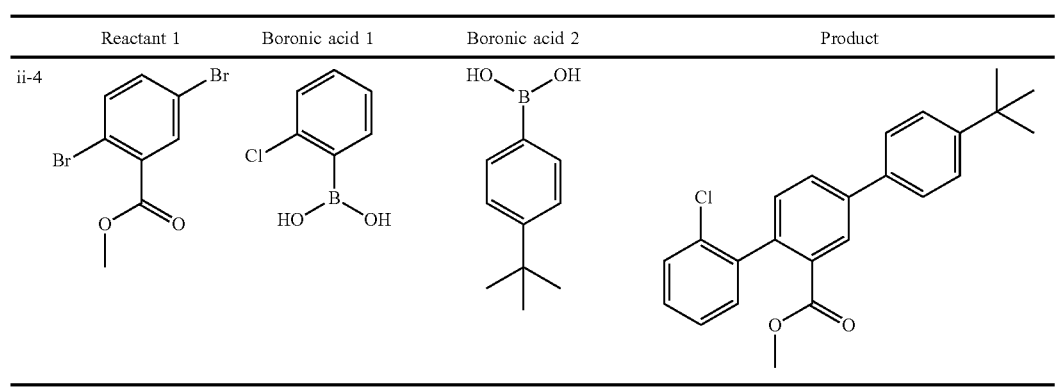

Intermediate 1-13

10.4 g (32.2 mmol) of intermediate II-1 are dissolved in a baked-out flask in 100 ml of dried THF. The solution is saturated with $N_2$. The clear solution is cooled down to −5° C. and then 32.2 ml (96.7 mmol) of a 3M methylmagnesium chloride solution are added. The reaction mixture is gradually warmed to room temperature and then quenched with ammonium chloride. The mixture is subsequently partitioned between ethyl acetate and water, and the organic phase is washed three times with water, dried over $Na_2SO_4$ and concentrated by rotary evaporation. The solution that has been concentrated by rotary evaporation is dissolved in toluene, and 8 g of Amberlyst 15 are added. The mixture is heated to 110° C. and kept at this temperature for 4 h. During this time, a white solid precipitates out. The mixture is then cooled to room temperature, and the precipitated solid is filtered off with suction and washed with heptane. The residue is dried at 40° C. under reduced pressure. After the crude product has been filtered through silica gel with heptane:ethyl acetate, 1:1, 9.3 g (90% of theory) of the product are obtained.

The following compounds are prepared in an analogous manner:

| Reactant 1 | Reactant 2 | Product |
|---|---|---|
| I-13 | MeMgCl | |
| I-14 | PhLi | |

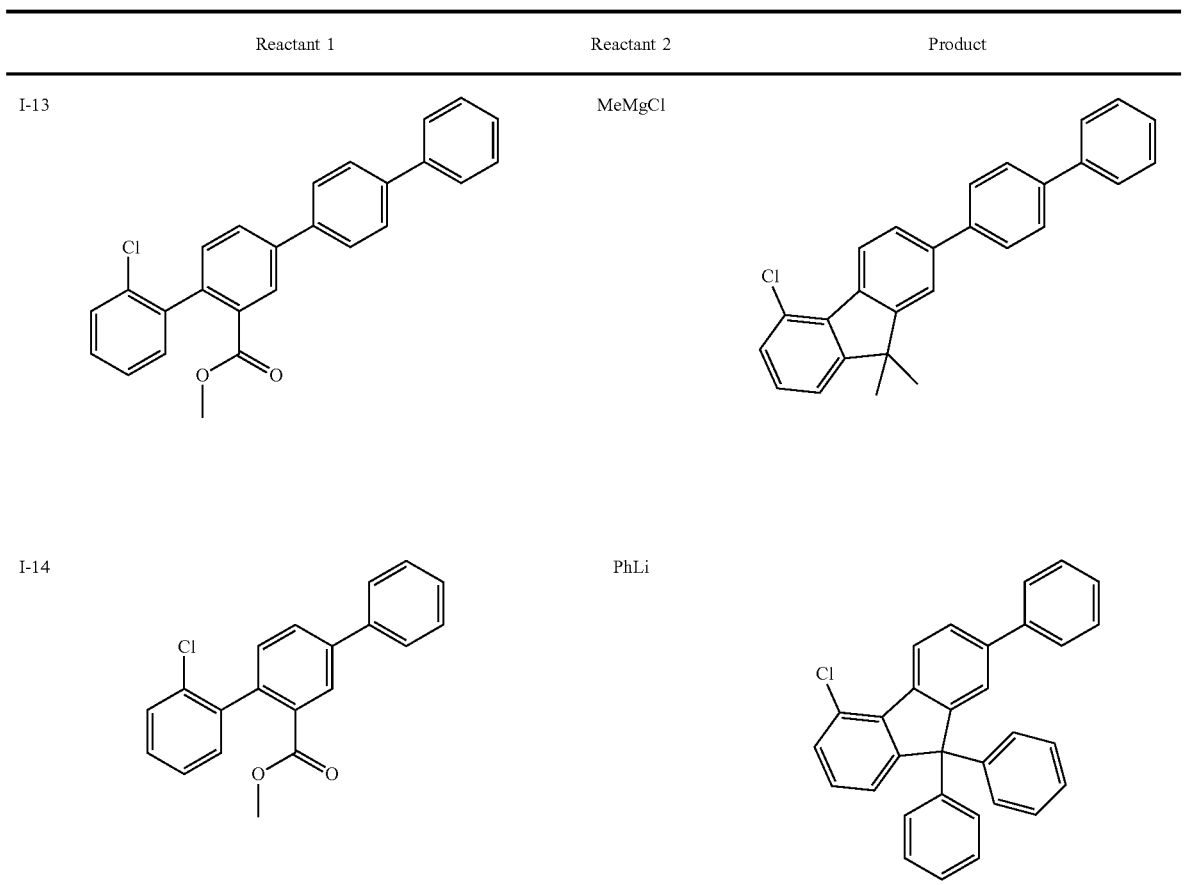

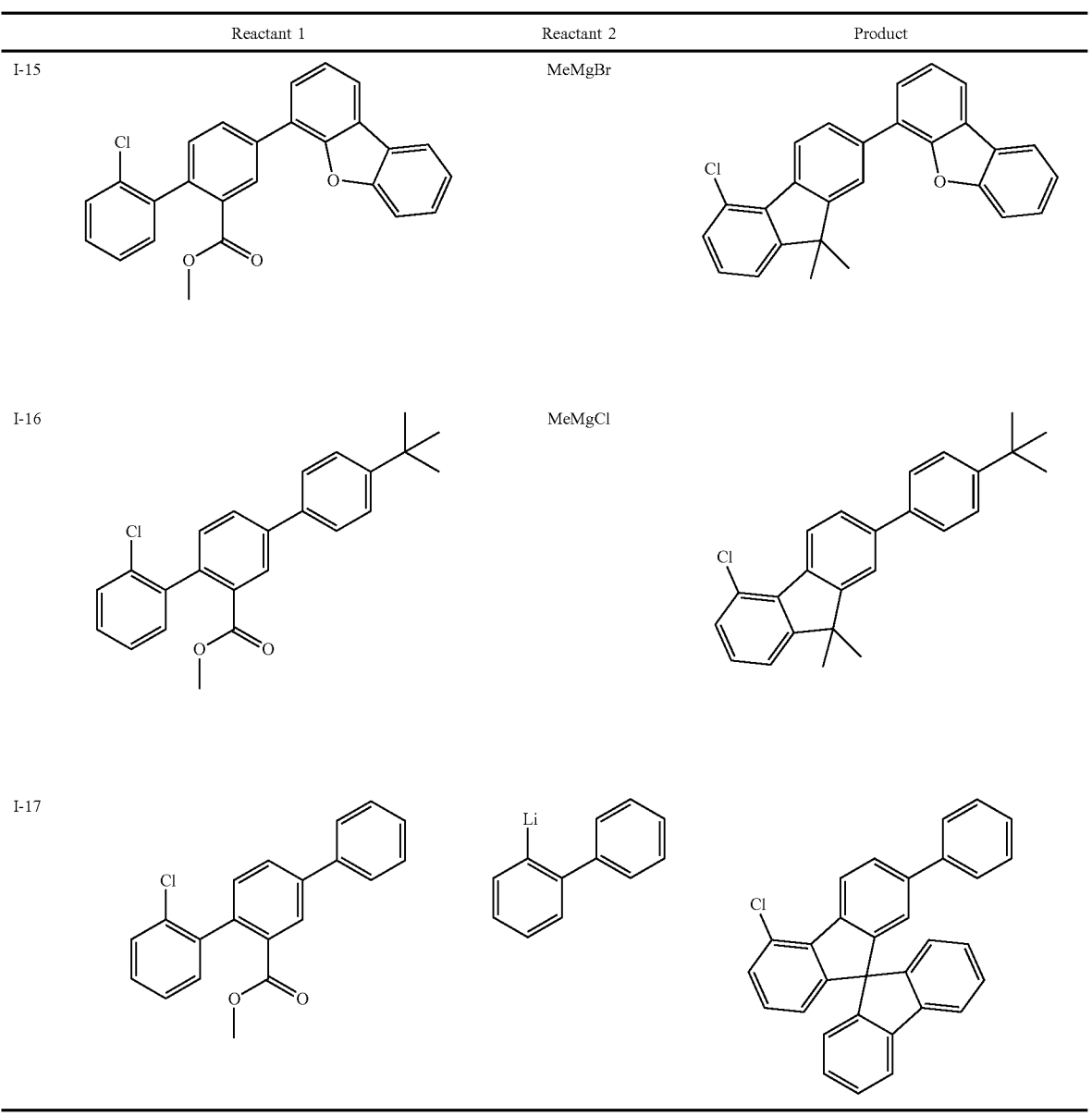

Synthesis of biphenyl-4-yl(9-phenyl-9H-carbazol-2-yl)-[1,1';3',1"]terphenyl-2-yl-amine) (compound 1-1) and also of Compounds (1-2) to (1-14)

16.2 g of biphenyl-4-yl(9-phenyl-9H-carbazol-2-yl) amine (48.5 mmol) and 15 g of 2-bromo-[1,1';3',1"]-terphenyl (48.5 mmol) are dissolved in 300 ml of toluene. The solution is degassed and saturated with $N_2$. Thereafter, 1.94 ml (1.94 mmol) of a 1 M tri-tert-butylphosphine solution and 0.89 g (0.97 mmol) of $Pd_2(dba)_3$ are added thereto. Subsequently, 7.0 g of sodium tert-butoxide (72.8 mmol) are added. The reaction mixture is heated to boiling under a protective atmosphere for 5 h. The mixture is subsequently partitioned between toluene and water, and the organic phase is washed three times with water, dried over $Na_2SO_4$ and concentrated by rotary evaporation. After the crude product has been filtered through silica gel with toluene, the remaining residue is recrystallized from heptane/toluene. The residue of 22.3 g (72% of theory) is finally sublimed under high vacuum.

The following compounds are prepared in an analogous manner:

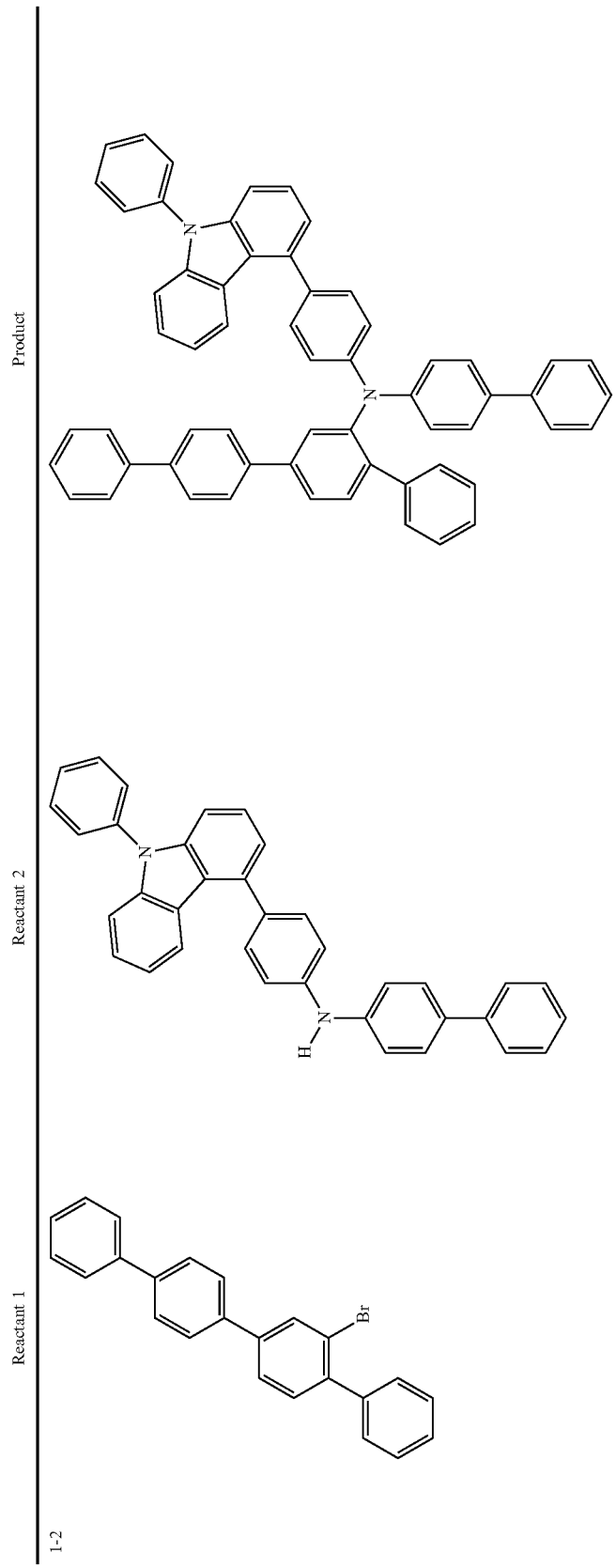

| | Reactant 1 | Reactant 2 | Product |
|---|---|---|---|
| 1-3 | 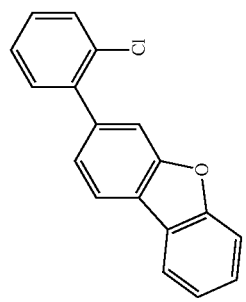 | 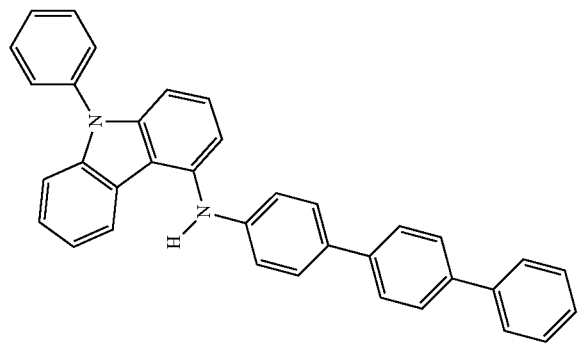 | 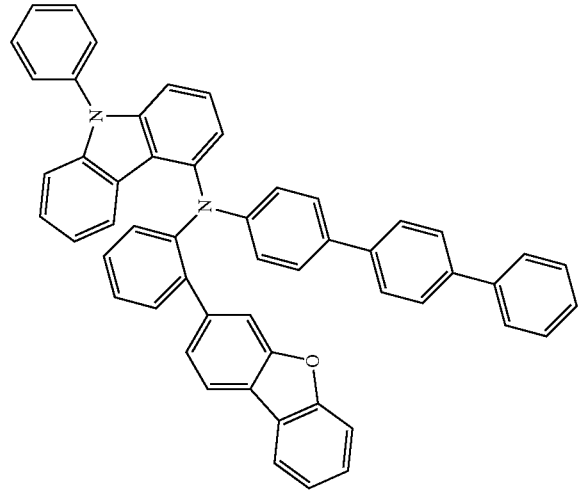 |
| 1-4 | 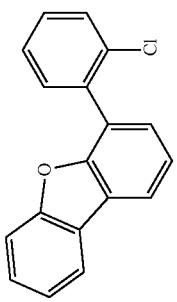 | 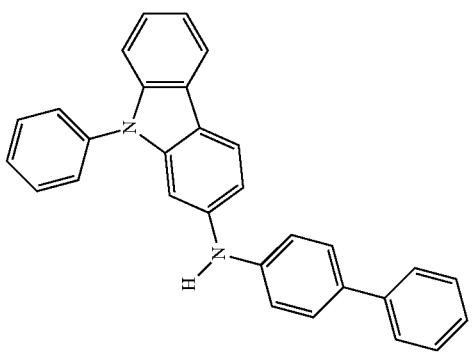 | 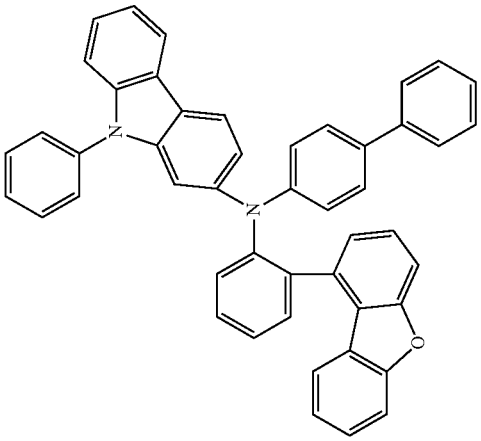 |

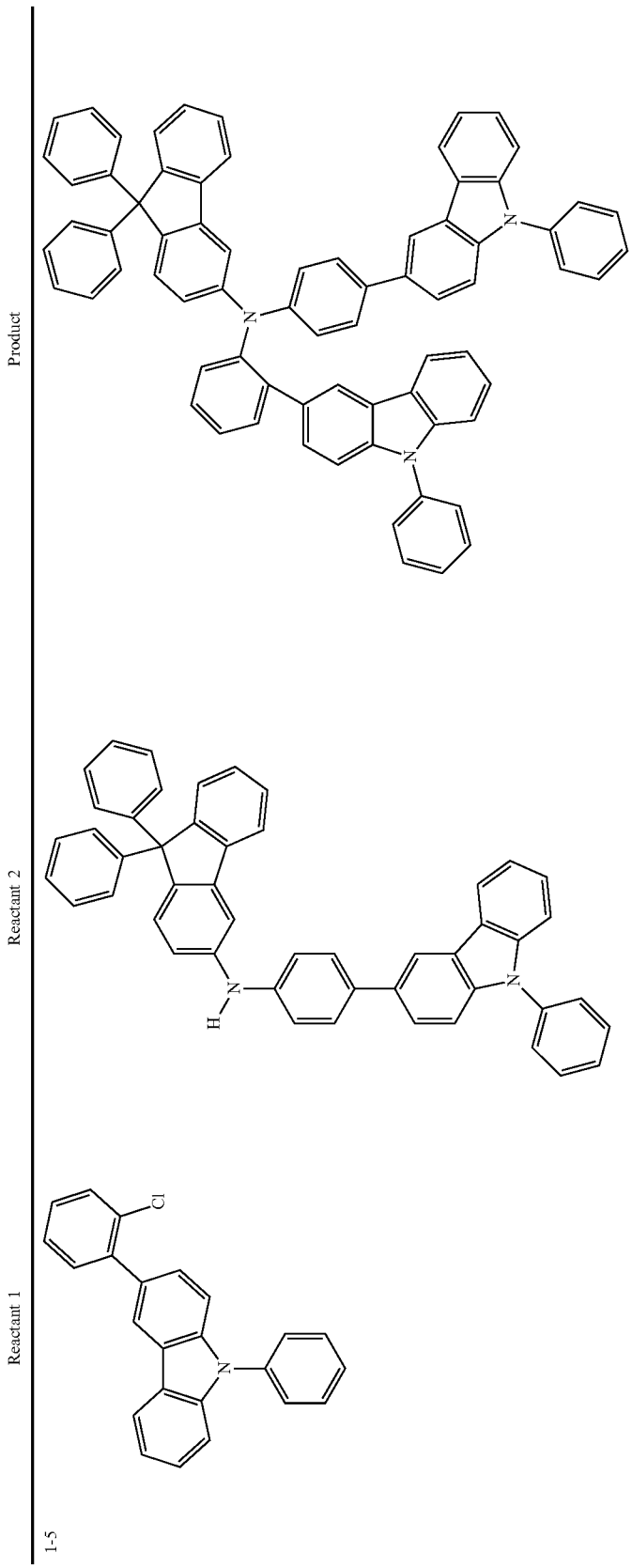

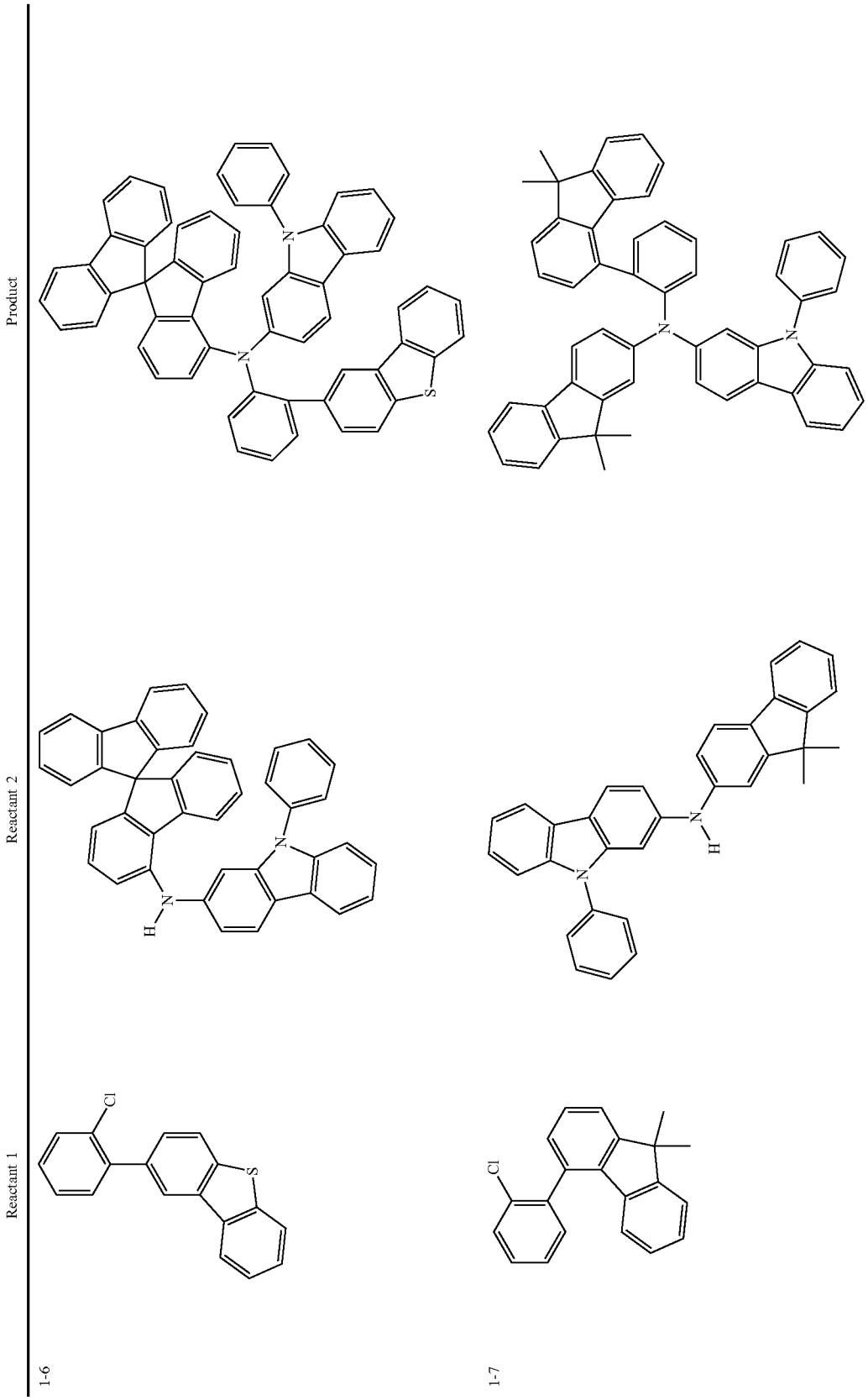

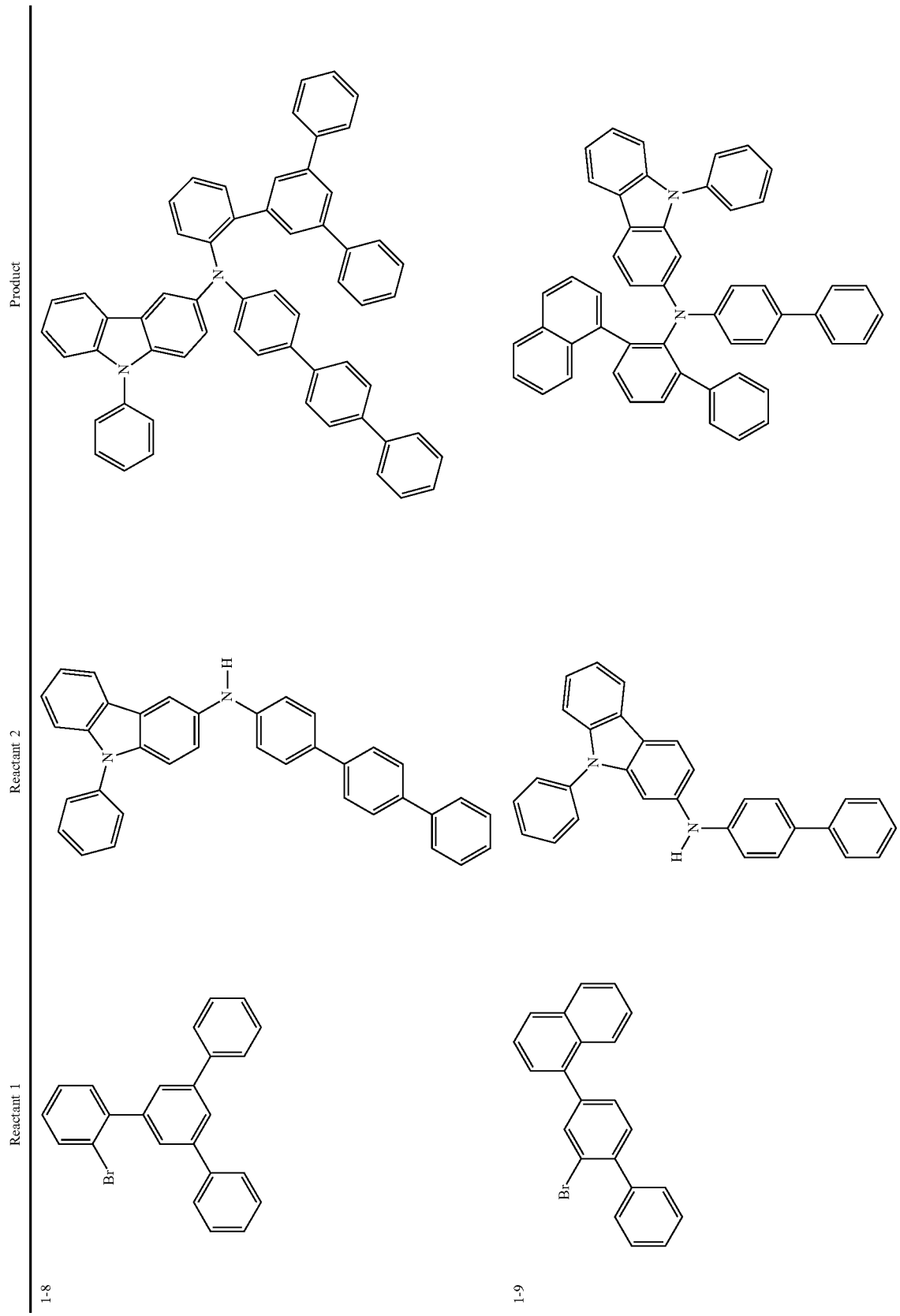

| | Reactant 1 | Reactant 2 | Product |
|---|---|---|---|
| 1-10 | 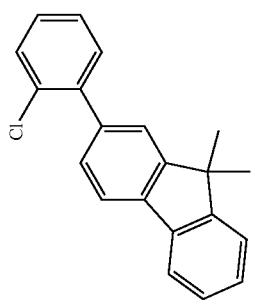 | 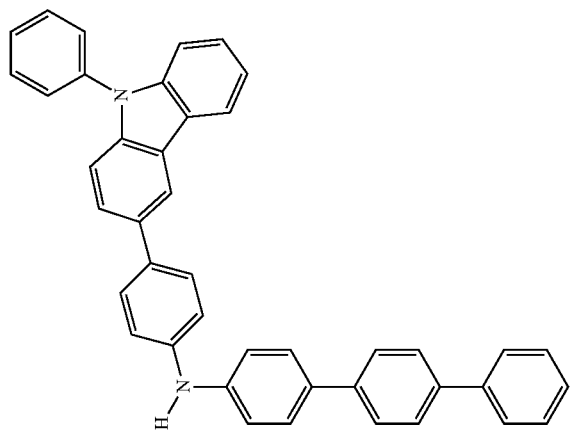 | 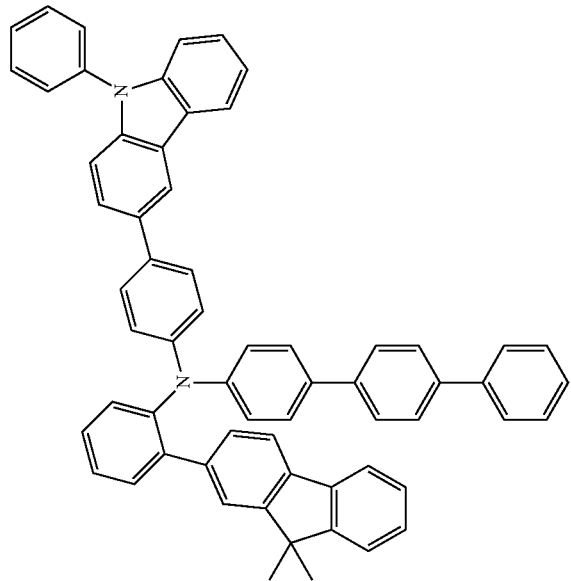 |
| 1-11 | 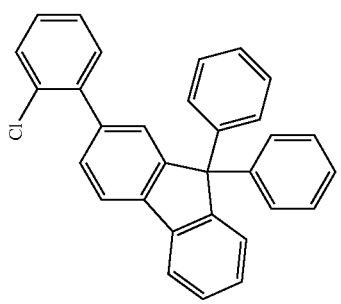 | 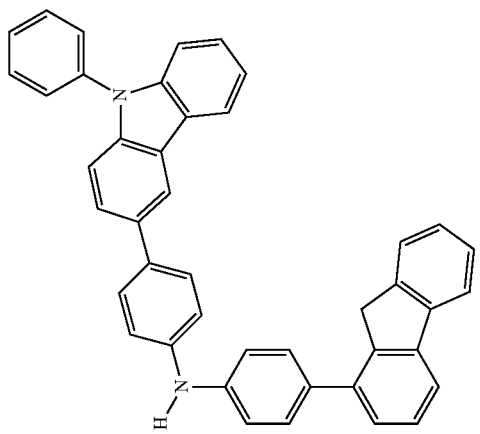 | 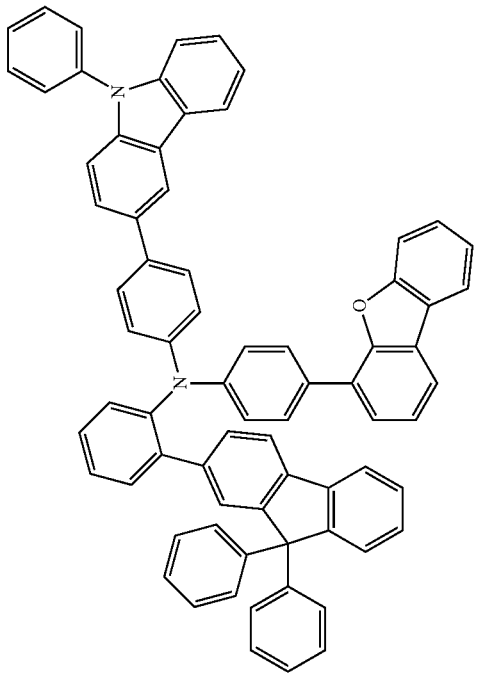 |

-continued
| | Reactant 1 | Reactant 2 | Product |
|---|---|---|---|
| 1-12 | 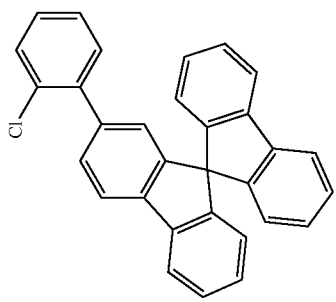 | 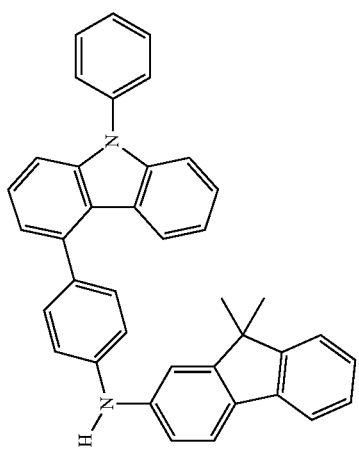 | 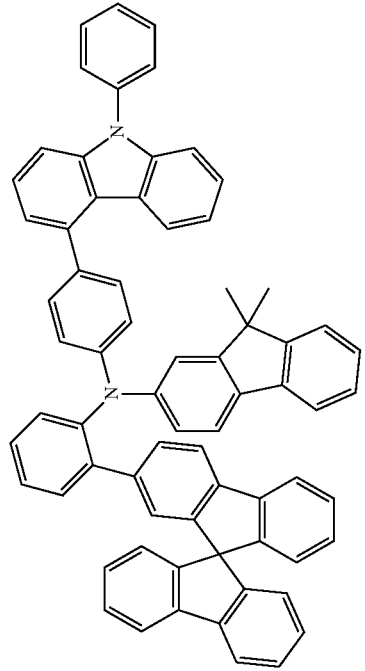 |
| 1-13 | 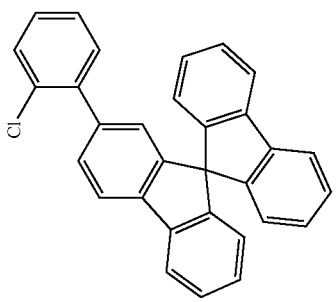 | 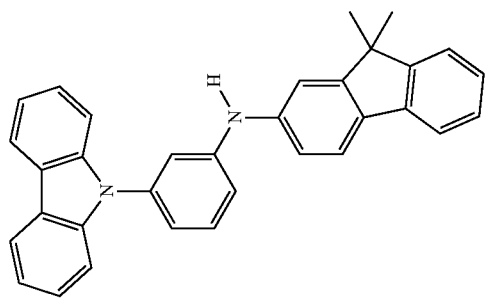 | 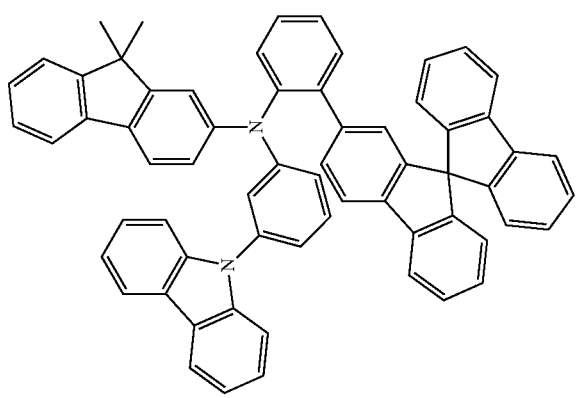 |

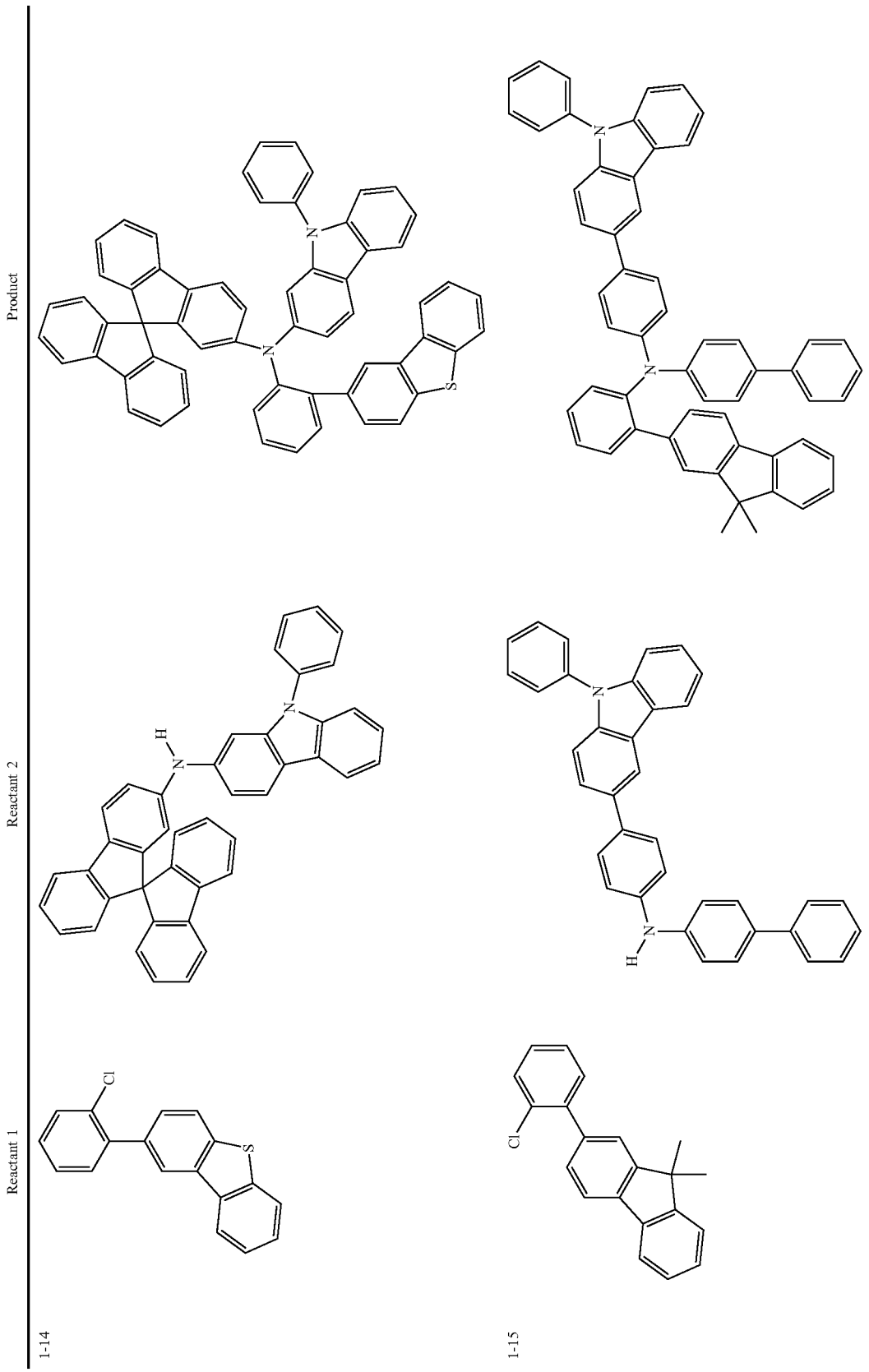

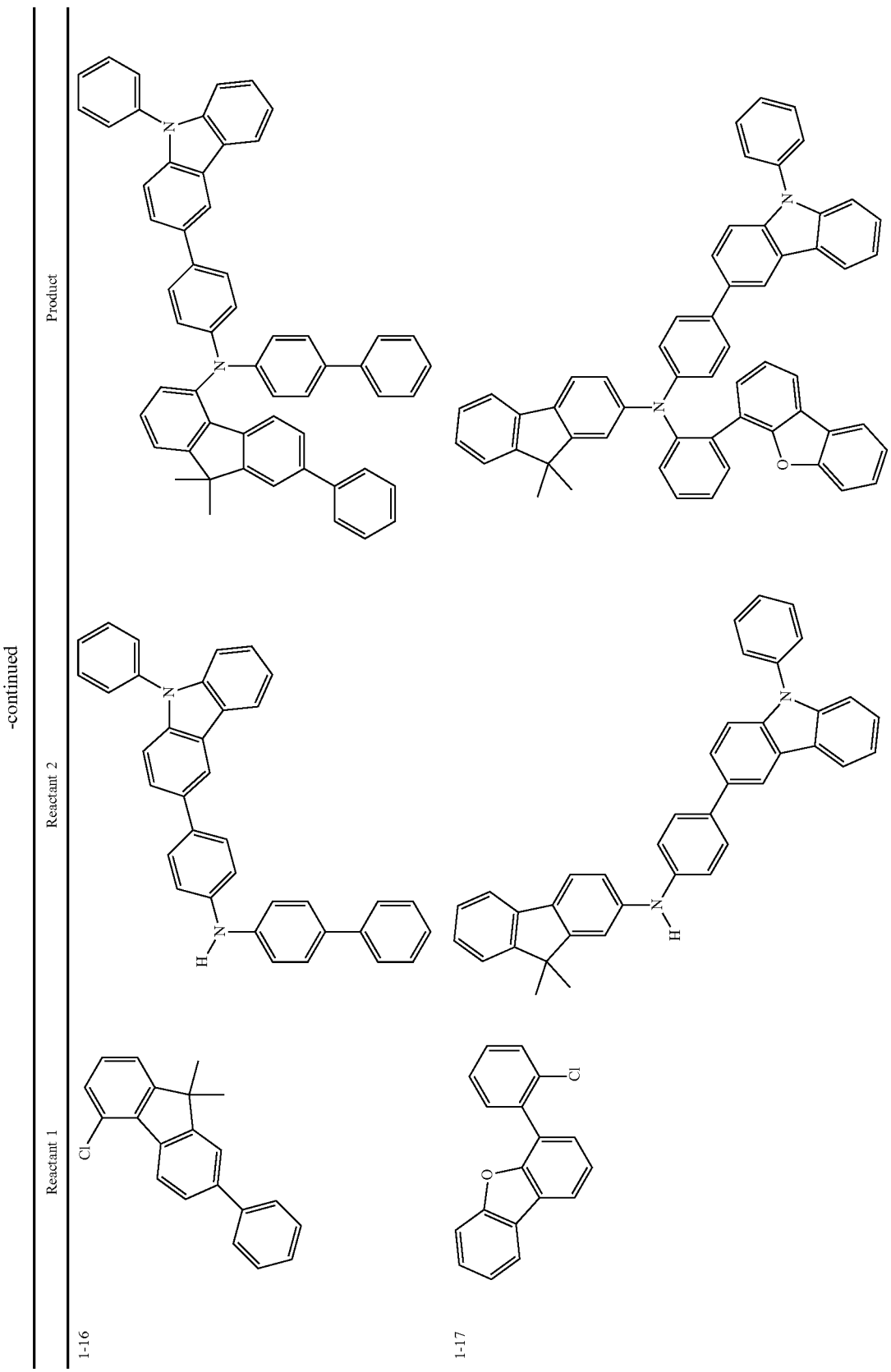

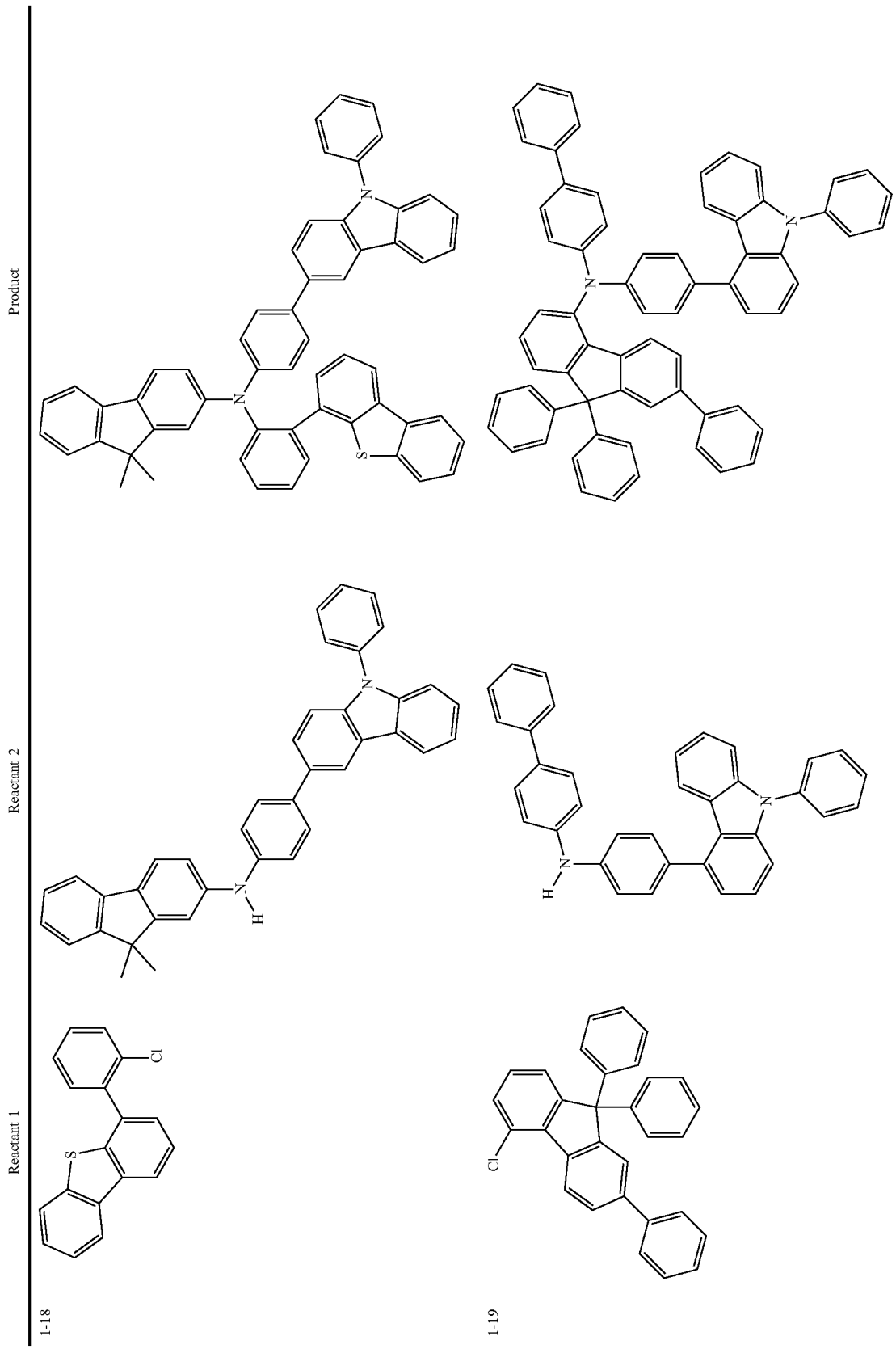

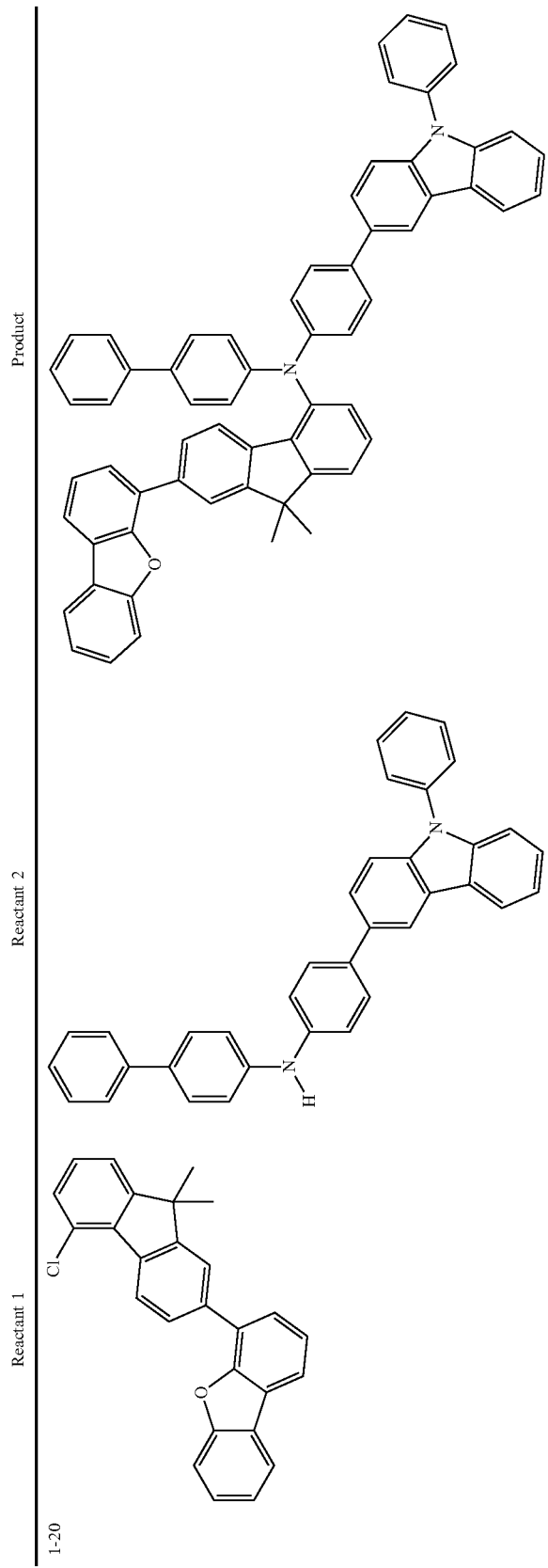

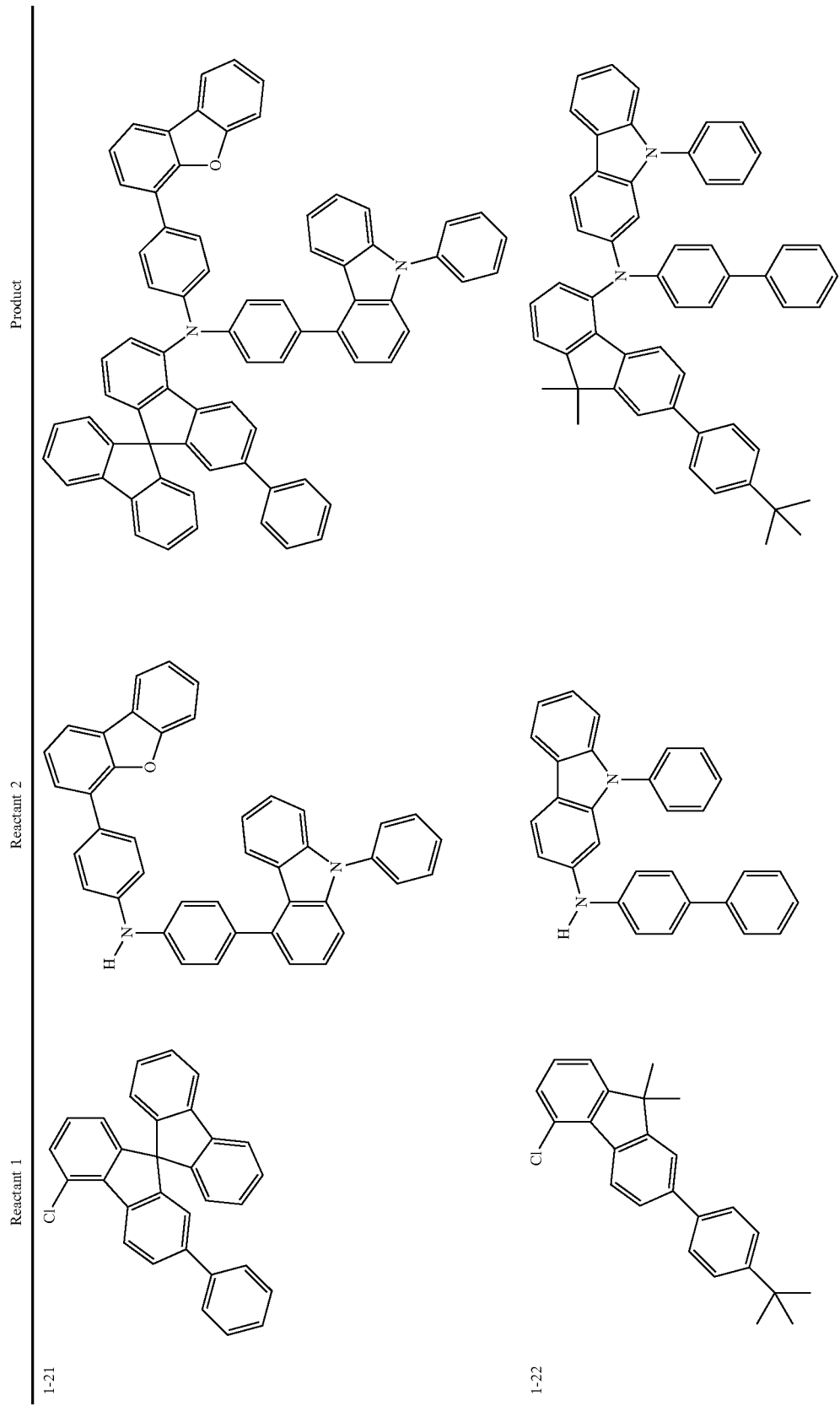

B) Device Examples

Example OLEDs are produced according to the following general method:

The substrates used are glass plaques coated with a 50 nm-thick layer of structured ITO (indium tin oxide). The following layer structure is applied thereto: hole injection layer (HIL)/hole transport layer (HTL)/electron blocker layer (EBL)/emission layer (EML)/electron transport layer (ETL)/electron injection layer (EIL)/cathode. The cathode consists of an aluminium layer of thickness 100 nm. The materials that are used in the corresponding layers of the example OLEDs are specified in Table 1, and the chemical structures of these materials are listed in Table 3.

The materials are applied by means of thermal gas phase deposition in a vacuum chamber. The emission layer here always consists of two matrix materials (hosts) and an emitting dopant (emitter) which is added to the matrix materials in a particular proportion by volume by co-evaporation. The percentages after the materials should therefore be understood as percent by volume. The same applies to layers other than the emitting layer. These may likewise correspondingly contain two or more materials.

The OLEDs are characterized in a standard manner. For this purpose, the electroluminescence spectra and the external quantum efficiency (EQE, measured in %), as a function of luminance, calculated from current flow-voltage-luminance characteristics (IUL characteristics), are determined. This is done assuming Lambertian emission characteristics. In addition, the operating voltage is determined (U, in V).

EQE @ 1000 cd/m$^2$ is the external quantum efficiency at an operating luminous density of 1000 cd/m$^2$. EQE @ 10 mA/cm$^2$ is the external quantum efficiency at a current density of 10 mA/cm$^2$.

Use of the Compounds in the EBL of Green-Phosphorescing OLEDs

OLED examples C1 to I12 have the layer structure shown in table 1a, with the EBL containing in each case one of the compounds 1-1, 1-2, 1-3, 1-4, 1-6, 1-7, 1-10, 1-14, 1-15, 1-16, 1-17 and 1-18 of the invention.

In all cases, the OLEDs of the invention achieve good results with regard to operating voltage and EQE (Table 2a). Furthermore, the OLEDs of the invention have a good lifetime.

With compounds containing N-bonded carbazol as well, such as the compound 1-13 for example, it is possible to obtain OLEDs having comparable power data as shown in Table 2a.

TABLE 1a

| Structure of the OLEDs | | | | | | |
|---|---|---|---|---|---|---|
| Ex. | HIL | HTL | EBL | EML | HBL | ETL | EIL |
| C1 | HTM:F4TCNQ(5%) 20 nm | HTM 215 nm | HTMC1 10 nm | H1(59%):H2(29%):TEG(12%) 30 nm | ETM 10 nm | ETM:LiQ(50%) 30 nm | LiQ 1 nm |
| I1 | HTM:F4TCNQ(5%) 20 nm | HTM 215 nm | 1-1 10 nm | H1(59%):H2(29%):TEG(12%) 30 nm | ETM 10 nm | ETM:LiQ(50%) 30 nm | LiQ 1 nm |
| I2 | HTM:F4TCNQ(5%) 20 nm | HTM 215 nm | 1-2 10 nm | H1(59%):H2(29%):TEG(12%) 30 nm | ETM 10 nm | ETM:LiQ(50%) 30 nm | LiQ 1 nm |
| I3 | HTM:F4TCNQ(5%) 20 nm | HTM 215 nm | 1-3 10 nm | H1(59%):H2(29%):TEG(12%) 30 nm | ETM 10 nm | ETM:LiQ(50%) 30 nm | LiQ 1 nm |
| I4 | HTM:F4TCNQ(5%) 20 nm | HTM 215 nm | 1-4 10 nm | H1(59%):H2(29%):TEG(12%) 30 nm | ETM 10 nm | ETM:LiQ(50%) 30 nm | LiQ 1 nm |
| I5 | HTM:F4TCNQ(5%) 20 nm | HTM 215 nm | 1-6 10 nm | H1(59%):H2(29%):TEG(12%) 30 nm | ETM 10 nm | ETM:LiQ(50%) 30 nm | LiQ 1 nm |
| I6 | HTM:F4TCNQ(5%) 20 nm | HTM 215 nm | 1-7 10 nm | H1(59%):H2(29%):TEG(12%) 30 nm | ETM 10 nm | ETM:LiQ(50%) 30 nm | LiQ 1 nm |
| I7 | HTM:F4TCNQ(5%) 20 nm | HTM 215 nm | 1-10 10 nm | H1(59%):H2(29%):TEG(12%) 30 nm | ETM 10 nm | ETM:LiQ(50%) 30 nm | LiQ 1 nm |
| I8 | HTM:F4TCNQ(5%) 20 nm | HTM 215 nm | 1-14 10 nm | H1(59%):H2(29%):TEG(12%) 30 nm | ETM 10 nm | ETM:LiQ(50%) 30 nm | LiQ 1 nm |
| I9 | HTM:F4TCNQ(5%) 20 nm | HTM 215 nm | 1-15 10 nm | H1(59%):H2(29%):TEG(12%) 30 nm | ETM 10 nm | ETM:LiQ(50%) 30 nm | LiQ 1 nm |
| I10 | HTM:F4TCNQ(5%) 20 nm | HTM 215 nm | 1-16 10 nm | H1(59%):H2(29%):TEG(12%) 30 nm | ETM 10 nm | ETM:LiQ(50%) 30 nm | LiQ 1 nm |
| I11 | HTM:F4TCNQ(5%) 20 nm | HTM 215 nm | 1-17 10 nm | H1(59%):H2(29%):TEG(12%) 30 nm | ETM 10 nm | ETM:LiQ(50%) 30 nm | LiQ 1 nm |
| I12 | HTM:F4TCNQ(5%) 20 nm | HTM 215 nm | 1-18 10 nm | H1(59%):H2(29%):TEG(12%) 30 nm | ETM 10 nm | ETM:LiQ(50%) 30 nm | LiQ 1 nm |

TABLE 2a

| Data of the OLEDs | | |
|---|---|---|
| Example | U @ 1000 cd/m$^2$ [V] | EQE @ 1000 cd/m$^2$ % |
| C1 | 3.3 | 15.2 |
| I1 | 3.0 | 17.2 |
| I2 | 3.1 | 19.1 |
| I3 | 3.1 | 17.4 |
| I4 | 3.0 | 17.1 |
| I5 | 3.4 | 16.6 |
| I6 | 3.0 | 17.1 |
| I7 | 3.2 | 18.8 |
| I8 | 3.2 | 16.3 |
| I9 | 3.1 | 17.9 |
| I10 | 3.2 | 18.5 |
| I11 | 2.9 | 17.3 |
| I12 | 2.9 | 17.4 |

Use of the Compounds in the HIL and HTL of Blue-Fluorescing OLEDs

OLED examples I13 to I15 have the layer structure shown in Table 1 b, with the hole-transporting layers HIL and HTL each containing one of the compounds 1-15, 1-17 and 1-18 of the invention.

In all cases, the OLEDs of the invention achieve good results with regard to operating voltage and EQE (Table 2b). Furthermore, the OLEDs of the invention have a good lifetime.

TABLE 1b

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| I13 | 1-15: F4TCNQ (5%) 20 nm | 1-15 180 nm | EBL 10 nm | H:SEB(5%) 20 nm | ETM:LiQ(50%) 30 nm | LiQ 1 nm |
| I14 | 1-17: F4TCNQ (5%) 20 nm | 1-17 180 nm | EBL 10 nm | H:SEB(5%) 20 nm | ETM:LiQ(50%) 30 nm | LiQ 1 nm |
| I15 | 1-18: F4TCNQ (5%) 20 nm | 1-18 180 nm | EBL 10 nm | H:SEB(5%) 20 nm | ETM:LiQ(50%) 30 nm | LiQ 1 nm |

TABLE 2b

Data of the OLEDs

| | U @ 10 mA/cm$^2$ [V] | EQE @ 10 mA/cm$^2$ [%] |
|---|---|---|
| I13 | 4.8 | 9.0 |
| I14 | 4.5 | 8.1 |
| I15 | 4.4 | 8.5 |

Use of the Compounds in the EBL of Blue-Fluorescing OLEDs

OLED examples 116 and 117 have the layer structure shown in Table 1c, with the EBL containing in each case one of the compounds 1-15 and 1-16 of the invention.

In all cases, the OLEDs of the invention achieve good results with regard to operating voltage and EQE (Table 2c). Furthermore, the OLEDs of the invention have a good lifetime.

TABLE 1c

| Ex. | HIL Thickness/nm | HTL Thickness/nm | EBL Thickness/nm | EML Thickness/nm | ETL Thickness/nm | EIL Thickness/nm |
|---|---|---|---|---|---|---|
| I-16 | HTM: F4TCNQ (5%) 20 nm | HTM 180 nm | 1-15 10 nm | H:SEB(5%) 20 nm | ETM:LiQ(50%) 30 nm | LiQ 1 nm |
| I-17 | HTM: F4TCNQ (5%) 20 nm | HTM 180 nm | 1-16 10 nm | H:SEB(5%) 20 nm | ETM:LiQ(50%) 30 nm | LiQ 1 nm |

TABLE 2c

Data of the OLEDs

| | U @ 10 mA/cm$^2$ [V] | EQE @ 10 mA/cm$^2$ [%] |
|---|---|---|
| I-16 | 3.8 | 8.5 |
| I-17 | 3.8 | 9.3 |

TABLE 3

Structures of the materials

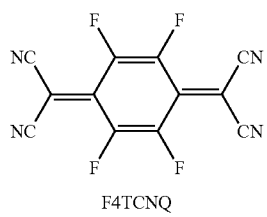

F4TCNQ

TABLE 3-continued
Structures of the materials
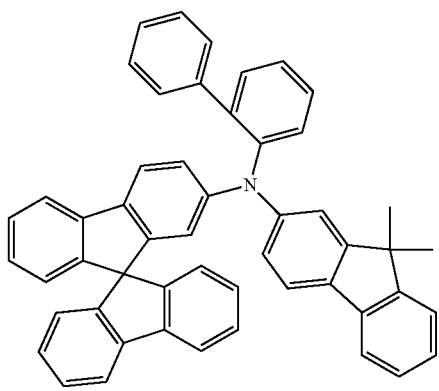
HTM
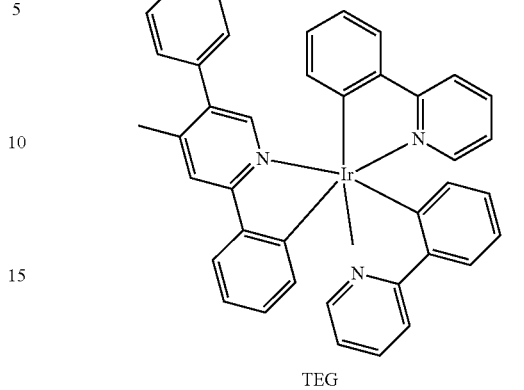
TEG facial
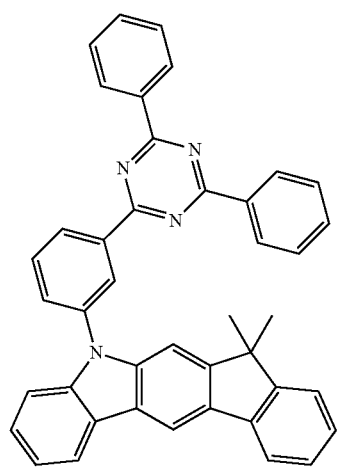
H1
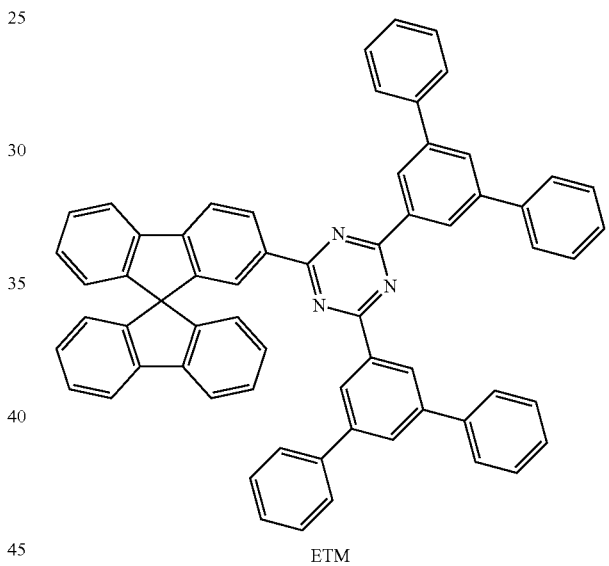
ETM
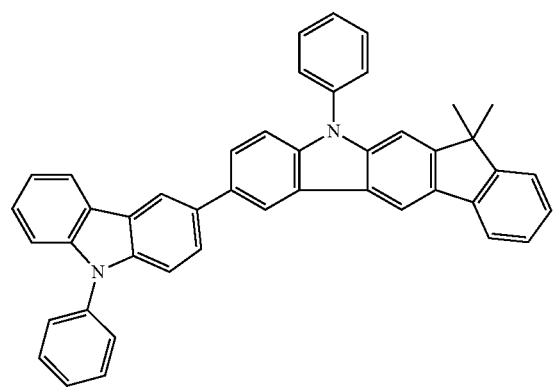
H2
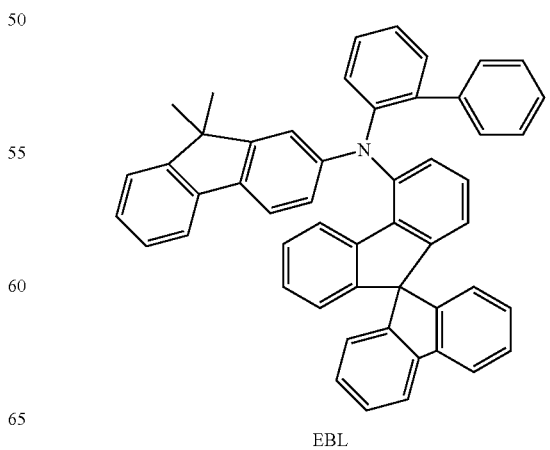
EBL TABLE 3-continued
Structures of the materials
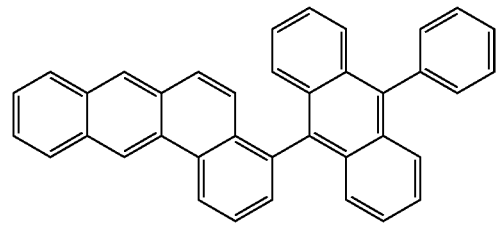
H
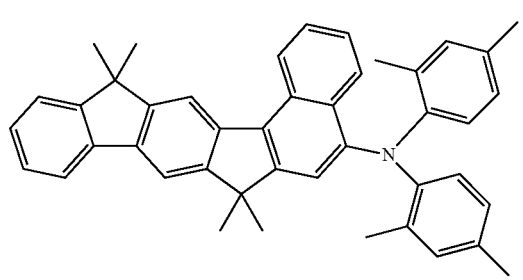
SEB
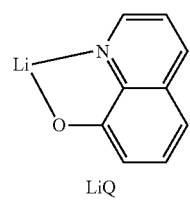
LiQ
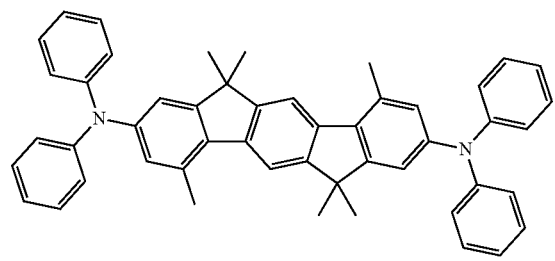
HTMV1
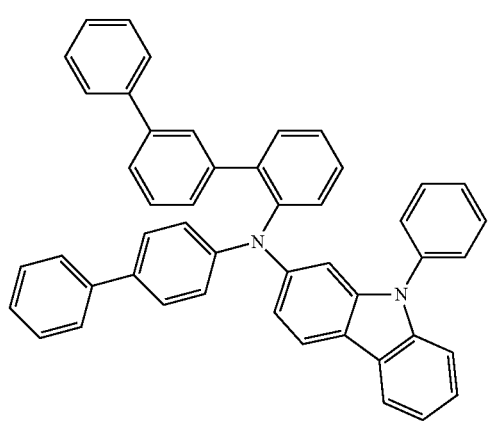
1-1
TABLE 3-continued
Structures of the materials
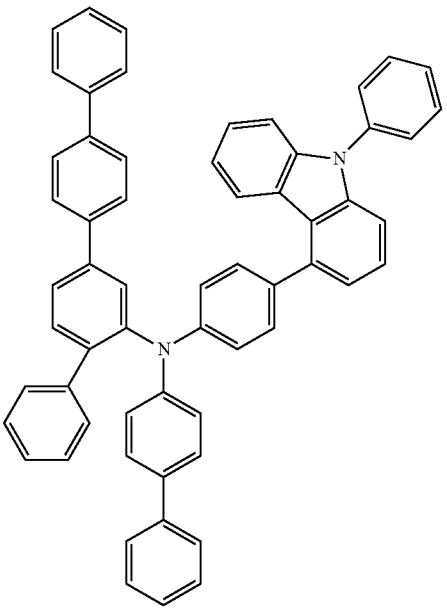 [SMILES: c1ccc(-c2ccc(-c3ccc(-c4ccccc4)c(N(c4ccc(-c5ccccc5)cc4)c4ccc(-c5cccc6c5c5ccccc5n6-c5ccccc5)cc4)c3)cc2)cc1]
1-2
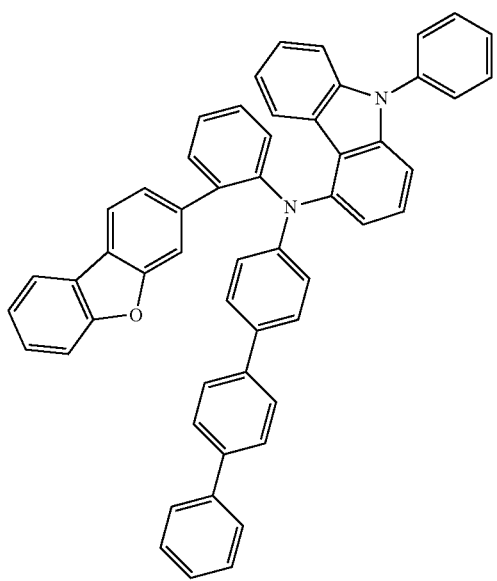 [SMILES: c1ccc(-c2ccc(-c3ccc(N(c4ccccc4-c4ccc5c(c4)oc4ccccc45)c4cccc5c4c4ccccc4n5-c4ccccc4)cc3)cc2)cc1]
1-3

TABLE 3-continued
Structures of the materials
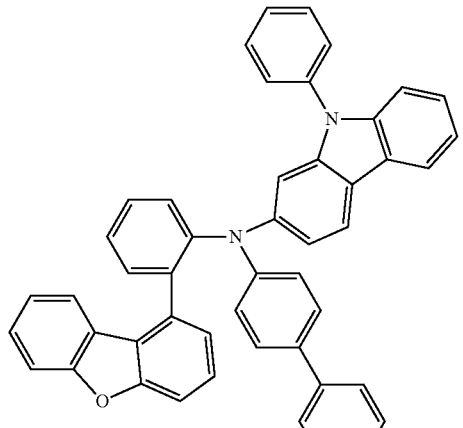
1-4
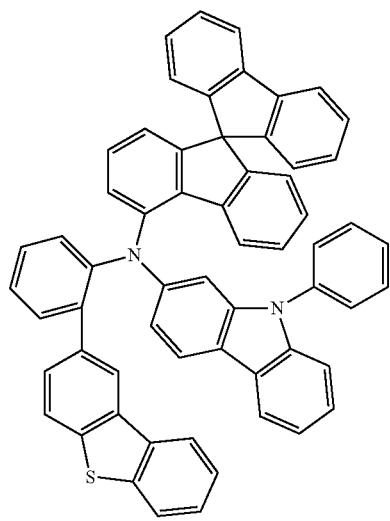 [SMILES: c1ccc(-n2c3ccccc3c3ccc(N(c4ccccc4-c4ccc5sc6ccccc6c5c4)c4cccc5c4-c4ccccc4C54c5ccccc5-c5ccccc54)cc32)cc1]
1-6
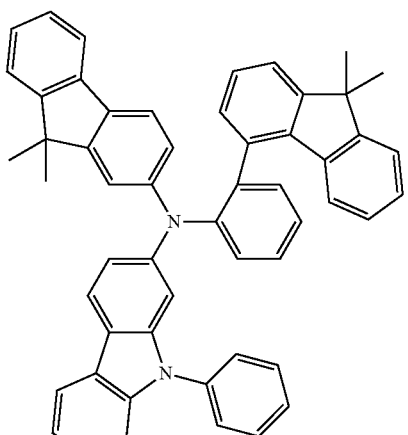
1-7
TABLE 3-continued
Structures of the materials
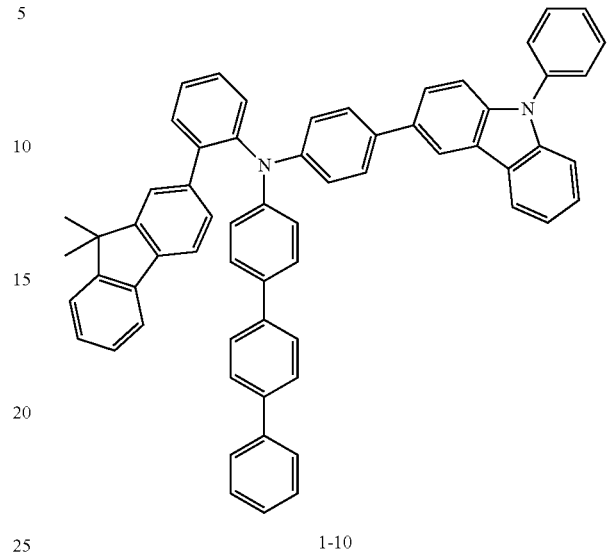
1-10
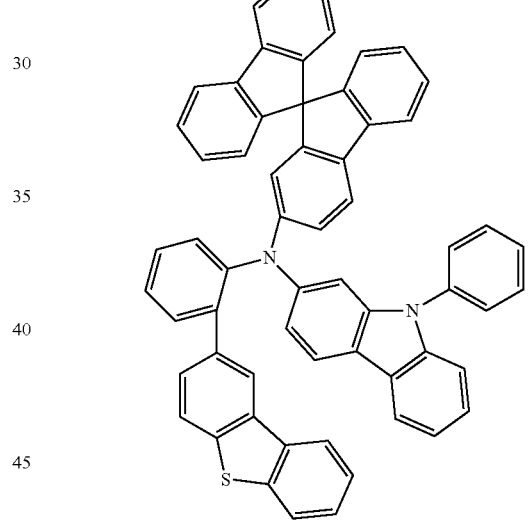
1-14
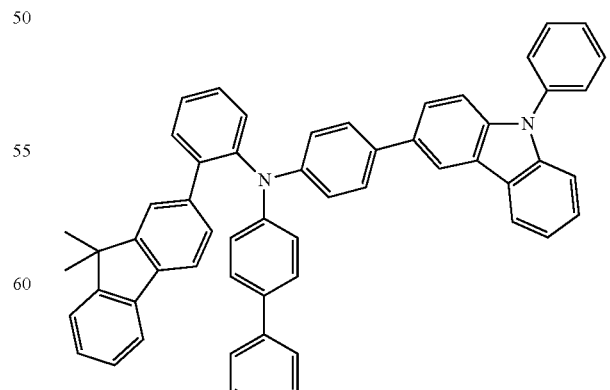
1-15

TABLE 3-continued

Structures of the materials

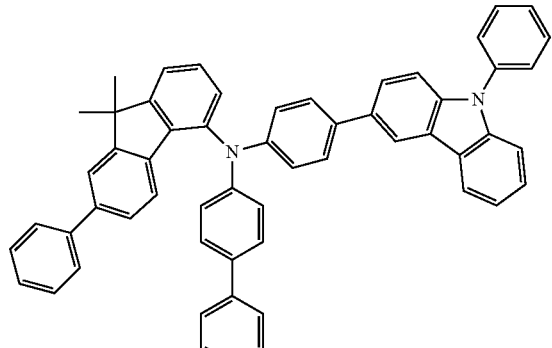

1-16

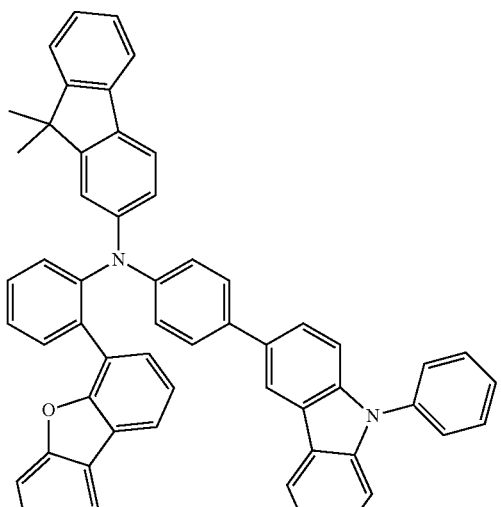

1-17

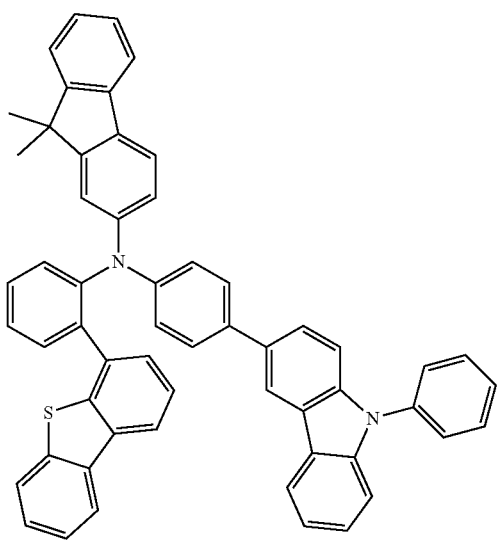 [SMILES: CC1(C)c2ccccc2-c2ccc(N(c3ccc(-c4ccc5c(c4)c4ccccc4n5-c4ccccc4)cc3)c3ccccc3-c3cccc4c3sc3ccccc34)cc21]

1-18

The invention claimed is:

1. A compound of formula (1)

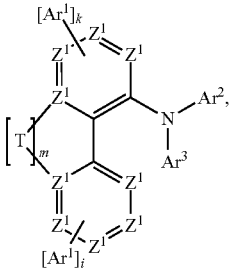

Formula (I)

where the variables that occur are as follows:
$Z^1$ is the same or different at each instance and is selected from $CR^1$ and N, where $Z^1$ is C when an $Ar^1$ or T group is bonded thereto;
$Ar^1$ is the same or different at each instance and is an aromatic ring system which has 6 to 30 aromatic ring atoms and may be substituted by one or more $R^2$ radicals;
$Ar^2$ corresponds to a formula (A) or (B)

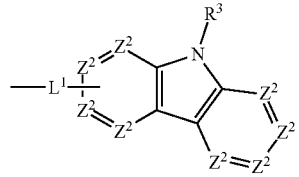

Formula (A)

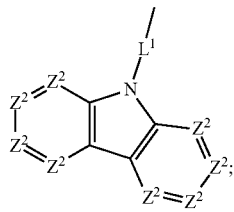

Formula (B)

$Z^2$ is the same or different at each instance and is $C^3$ or N, where $Z^2$ is C when an $L^1$ group is bonded thereto;
$L^1$ is selected from benzene, biphenyl and terphenyl, each of which may be substituted by one or more $R^3$ radicals;
$Ar^3$ a corresponds to a formula (A) or a formula (B) or is an aromatic ring system which has 6 to 30 aromatic ring atoms and may be substituted by one or more $R^4$ radicals, or a heteroaromatic ring system which has 5 to 30 aromatic ring atoms and may be substituted by one or more $R^4$ radicals;
T is selected from $C(R^1)_2$, $Si(R^1)_2$, $NR^1$, O and S;
$R^1$ are the same or different at each instance and are selected from H, D, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —$R^5C$=$CR^5$—, —C≡C—, $Si(R^5)_2$, C=O, C=$NR^5$, —C(=O)O—, —C(=O)$NR^5$-, $NR^5$, P(=O)($R^5$), —O—, —S—, SO or $SO_2$;

$R^2$, $R^3$, $R^4$ are the same or different at each instance and are selected from H, D, F, C(=O)$R^5$, CN, $Si(R^5)_3$, $N(R^5)_2$, P(=O)$(R^5)_2$, $OR^5$, S(=O)$R^5$, S(=O)$_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —$R^5C$=$CR^5$—, —C≡C—, $Si(R^5)_2$, C=O, C=$NR^5$, —C(=O)O—, —C(=O)$NR^5$-, $NR^5$, P(=O)($R^5$), —O—, —S—, SO or $SO^2$;

$R^5$ is the same or different at each instance and is selected from H, D, F, C(=O)$R^6$, CN, $Si(R^6)_3$, $N(R^6)_2$, P(=O)$(R^6)_2$, $OR^6$, S(=O)$R^6$, S(=O)$_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by —$R^6C$=$CR^6$—, —C≡C—, $Si(R^6)_2$, C=O, C=$NR^6$, —C(=O)O—, —C(=O)$NR^6$-, $NR^6$, P(=O)($R^6$), —O—, —S—, SO or $SO_2$;

$R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

m is 0 or 1;
i is 0, 1, 2, 3, 4 or 5;
k is 0, 1, 2, 3 or 4;
where the sum of k and i is at least 1; and
where $Ar^1$ groups may each be connected via a divalent group Y with the six-membered ring to which they are bonded, where
Y is the same or different at each instance and is selected from $C(R^1)_2$, $Si(R^1)_2$, $NR^1$, O and S.

2. The compound according to claim 1, wherein $Z^1$ is C when an $AR^1$ or T group is bonded thereto, and in that $Z^2$ is $CR^3$, where $Z^2$ is C when an $L^1$ group is bonded thereto.

3. The compound according to claim 1, wherein $AR^1$ is the same or different at each instance and is selected from phenyl, biphenyl, terphenyl, quaterphenyl, naphthyl, anthracenyl, fluorenyl, indenofluorenyl and phenanthrenyl, where the groups mentioned may each be substituted by one or more $R^2$ radicals.

4. The compound according to claim 1, wherein there are at most two $AR^1$ groups in the compound.

5. The compound according to claim 1, wherein there is at most one $Ar^1$ group in the compound, this $Ar^1$ group being a phenyl group which may be substituted by one or more $R^2$ radicals, and this group $AR^1$ being connected via a group Y to the six-membered ring to which it is bonded, where the $AR^1$ group, the Y bridge and the six-membered ring to which the Y bridge and the $AR^1$ group bond form a five-membered ring which is inserted between the six-membered ring and the $Ar^1$ group and which with the six-membered ring and the $AR^1$ group form a fused unit.

6. The compound according to claim 5, wherein the fused unit is selected from fluorene, spirobifluorene, carbazole, dibenzofuran and dibenzothiophene, each of which may be substituted by $R^1$ and $R^2$.

7. The compound according to claim 1, wherein $Ar^2$ is selected from groups of the following formulae

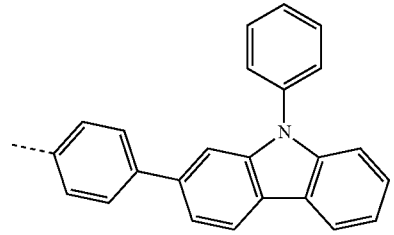

Ar²-5

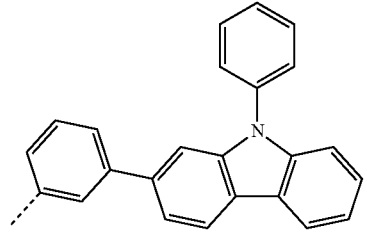

Ar²-6

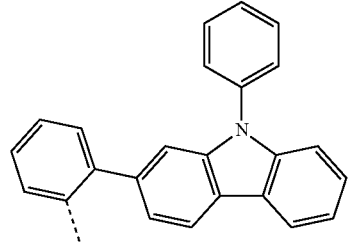

Ar²-7

Ar²-8
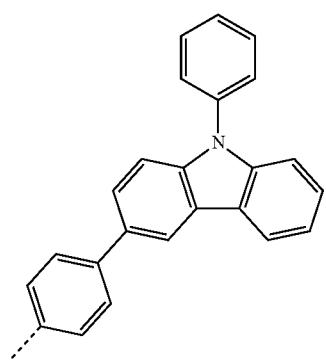
Ar²-9
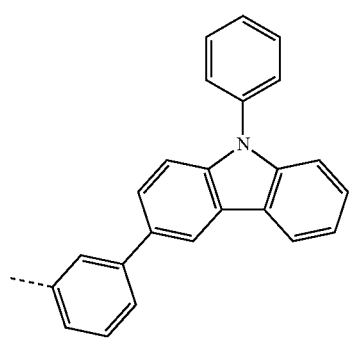
Ar²-10
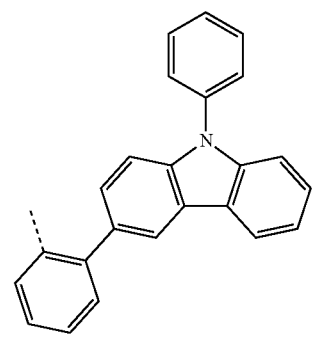
Ar²-11
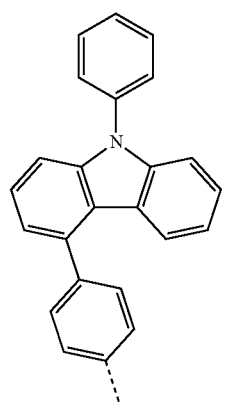
Ar²-12
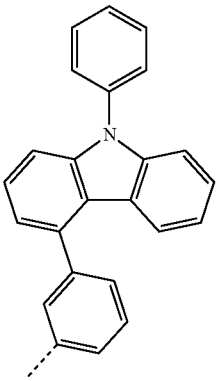
Ar²-13
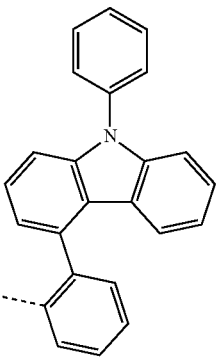
Ar²-14
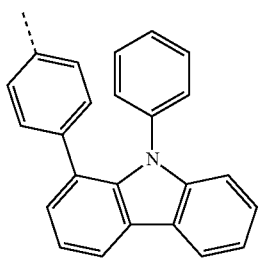
Ar²-15
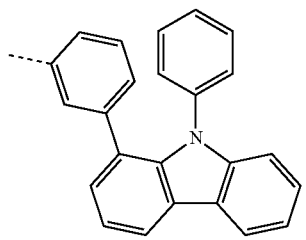
Ar²-16
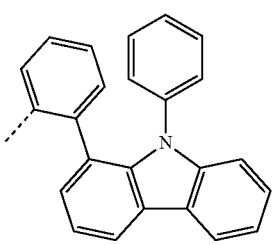

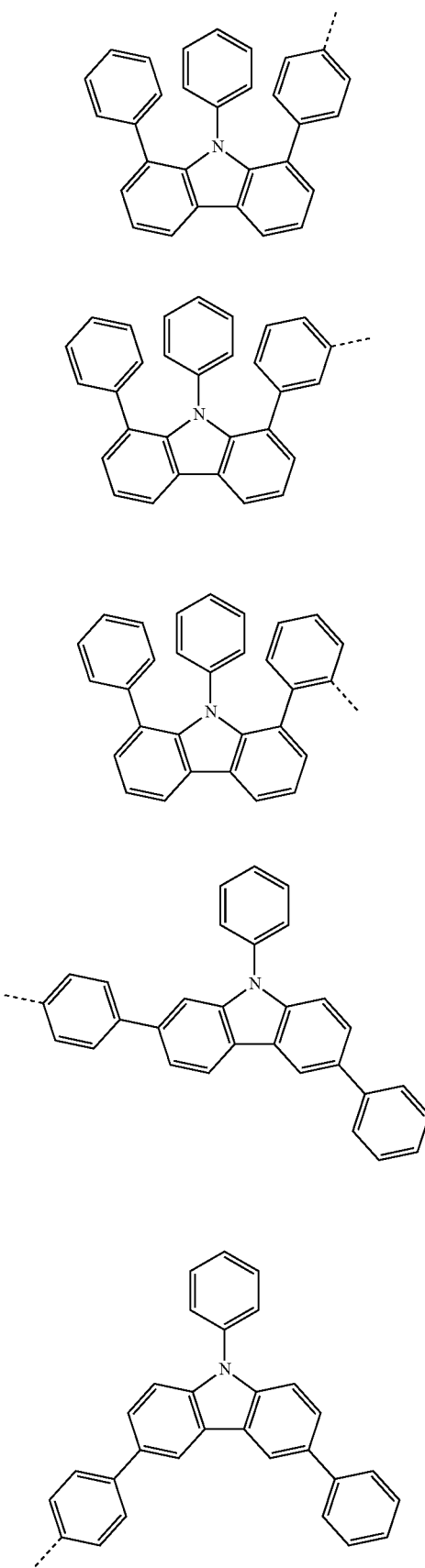
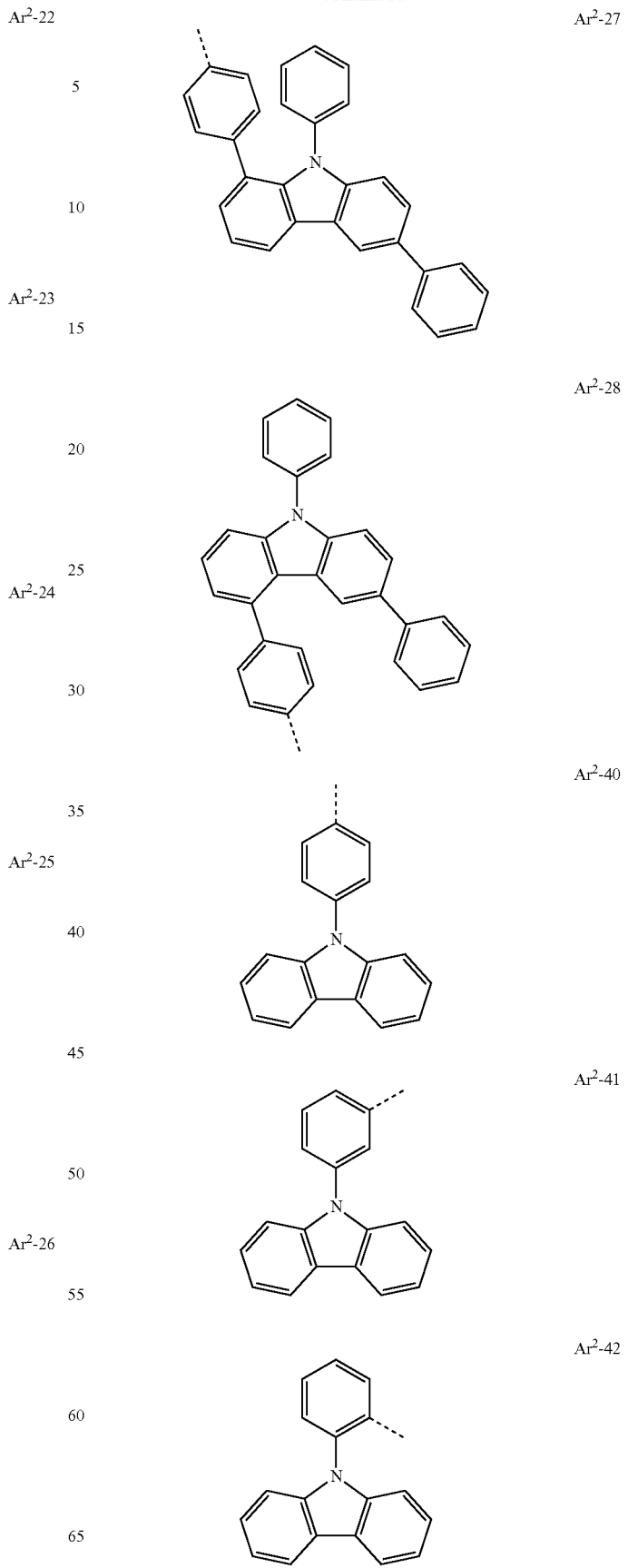

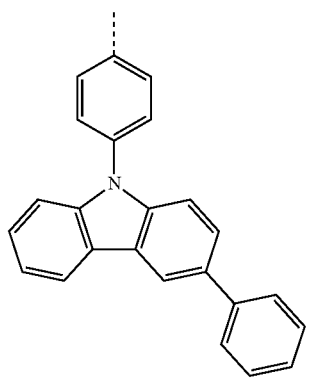 Ar²-43
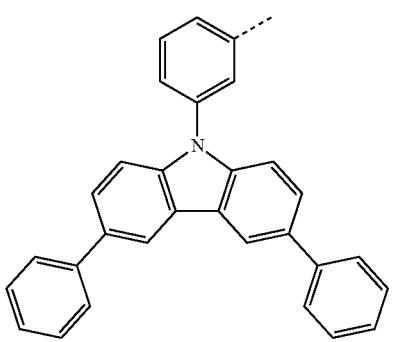 Ar²-47
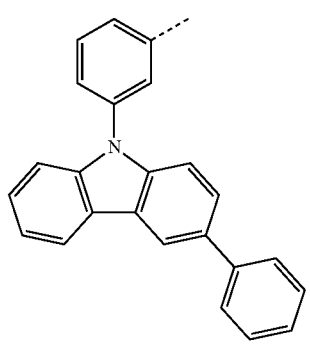 Ar²-44
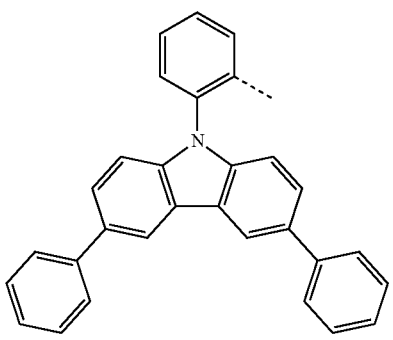 Ar²-48
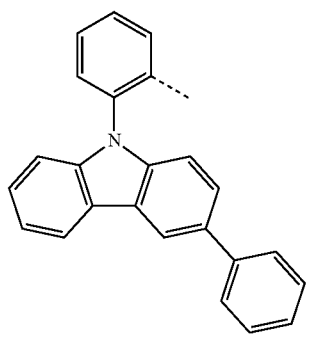 Ar²-45
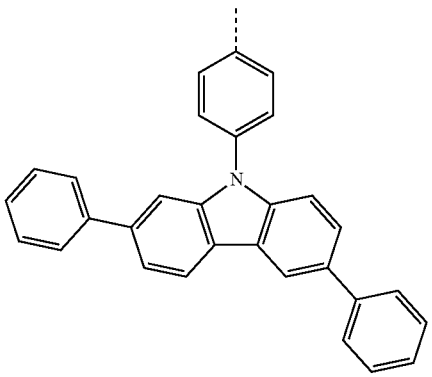 Ar²-49
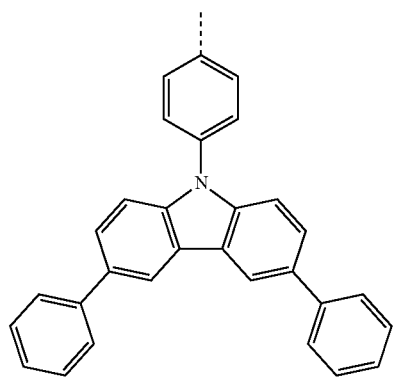 Ar²-46
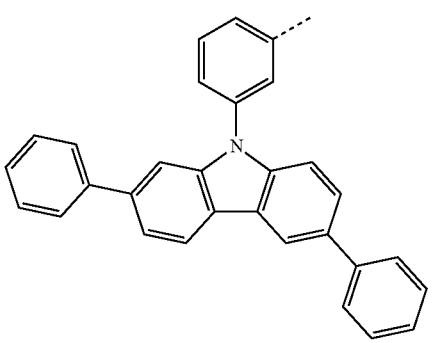 Ar²-50

-continued
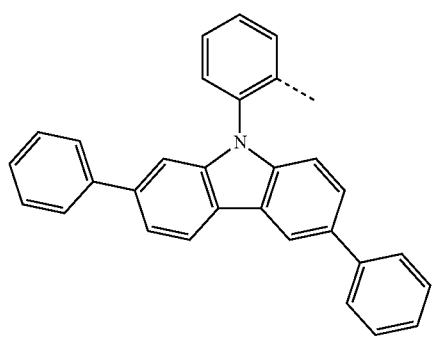
Ar²-51
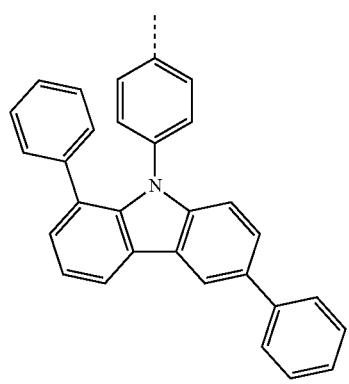
Ar²-52
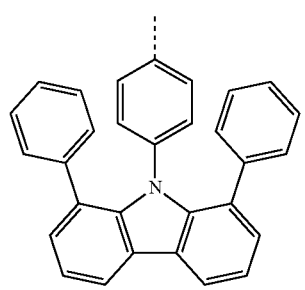
Ar²-53
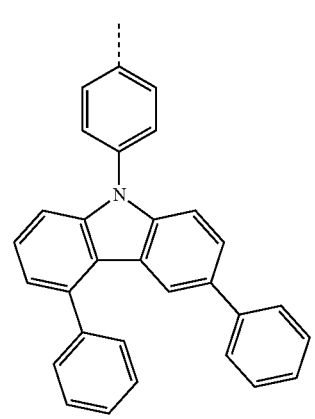
Ar²-54
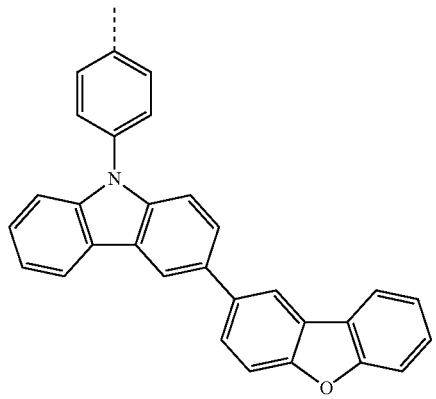
Ar²-55
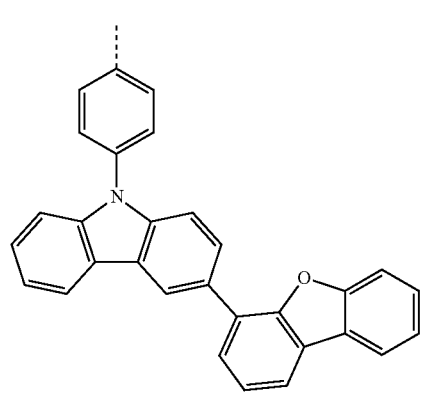
Ar²-56
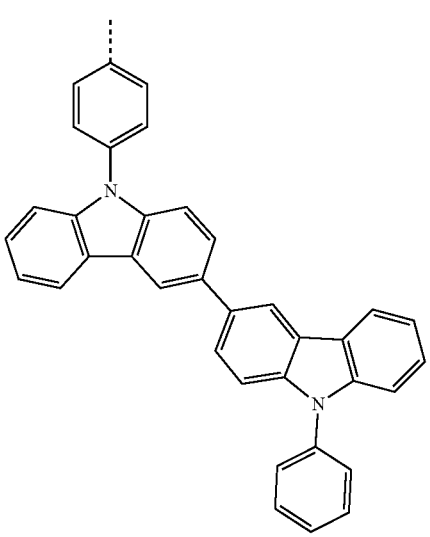
Ar²-57

-continued
Ar²-58
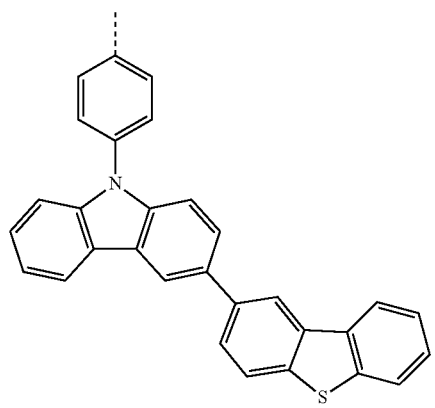
Ar²-59
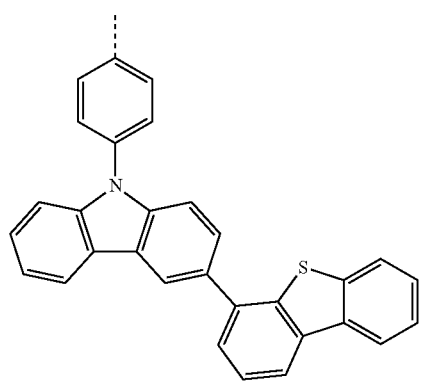
Ar²-60
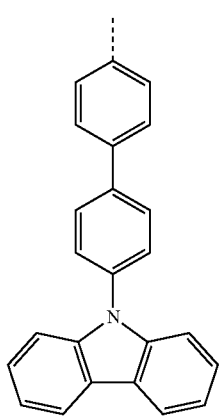
Ar²-61
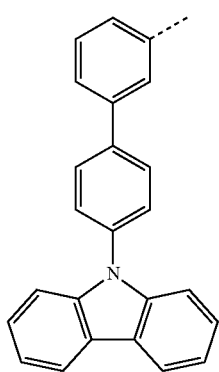
-continued
Ar²-62
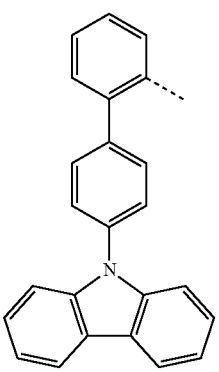
Ar²-63
Ar²-64
Ar²-65
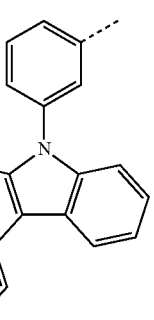

-continued

Ar²-66
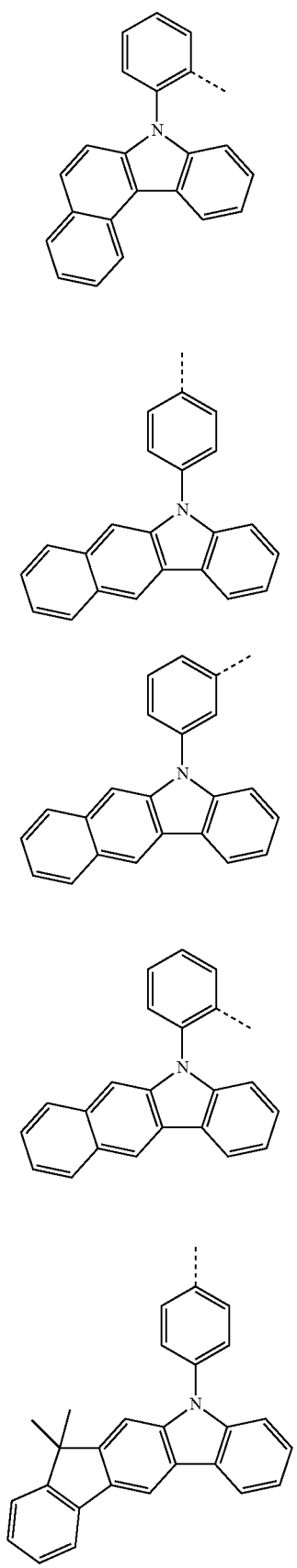

Ar²-67

Ar²-68

Ar²-69

Ar²-70

-continued

Ar²-71
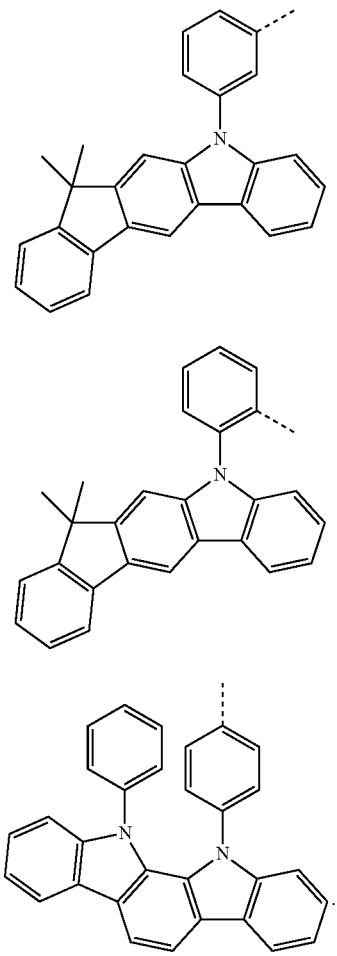

Ar²-72

Ar²-76

8. The compound according to claim 1, wherein Ar³ a is phenyl, biphenyl, terphenyl, fluorenyl, fluorenyl-phenyl, naphthyl, naphthyl-phenyl, spirobifluorenyl, spirobifluorenyl-phenyl, pyridyl, pyrimidyl, triazinyl, dibenzofuranyl, dibenzofuranyl-phenyl, benzofused dibenzofuranyl, dibenzothiophenyl, dibenzothiophenyl-phenyl, benzofused dibenzothiophenyl, carbazolyl, carbazolyl-phenyl or benzofused carbazolyl, or combinations of two, three or four of these groups, where the groups mentioned may each be substituted by one or more $R^4$ radicals.

9. The compound according to claim 1, wherein $R^1$ are the same or different at each instance and are selected from H, D, CN, $Si(R^5)_3$, $N(R^5)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned may each be substituted by one or more $R^5$ radicals; and where one or more $CH_2$ groups in the alkyl groups mentioned may be replaced by —C≡C—, —$R^5$C=C$R^5$-, $Si(R^5)_2$, C=O, C=N$R^5$, —N$R^5$-, —O—, —S—, —C(=O)O— or —C(=O)N$R^5$-, and $R^2$, $R^3$ and $R^4$ are the same or different at each instance and are selected from H, D, F, CN, $Si(R^5)_3$, $N(R^5)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms;

where the alkyl groups mentioned, the aromatic ring systems mentioned and the heteroaromatic ring systems mentioned may each be substituted by one or more $R^5$ radicals, and where one or more $CH_2$ groups in the alkyl groups mentioned may be —C≡C—, —$R^5$C=C$R^5$—, Si($R^5$)$_2$, C=O, C=N$R^5$, —N$R^5$—, —O—, —S—, —C(=O)O— or —C(=O)N$R^5$—.

10. The compound according to claim 1, wherein the compound corresponds to one of the formulae (I-1-1), (I-1-3) (I-2-1), or (I-2-3)

Formula (I-1-1)

Formula (I-1-3)

Formula (I-2-1)

Formula (I-2-3)

where for formulae (I-1-1) to (I-1-3) the following applies:
i is 0 or 1,
k is 0 or 1,
the sum of k and i is 1 or 2,
the free positions on the benzene rings may each be substituted by an $R^1$ radical, and
there is no divalent group Y, and
where for formulae (I-2-1) to (I-2-3) the following applies:
Y is selected from C($R^1$)$_2$, Si($R^1$)$_2$, N$R^1$, O and S; and
the free positions on the benzene rings may each be substituted by an $R^1$ radical.

11. Process for preparing a compound according to claim 1, wherein in a first step i) a biphenyl derivative substituted by reactive groups X and Y, where group X is present in the ortho-position to the bond between the two phenyl groups, is reacted with an aromatic or heteroaromatic ring system, which is substituted by a boronic acid group, so that the aromatic or heteroaromatic ring system is introduced in the position of the Y group, and in that in a second step ii) the intermediate obtained in step i) is reacted with a compound of the formula HNAr$^2$, where Ar is selected from aromatic ring systems and heteroaromatic ring systems, and in this reaction the —NAr$_2$ group is introduced in the position of the X group.

12. An oligomer, polymer or dendrimer containing one or more compounds according to claim 1, wherein the bond(s) to the polymer, oligomer or dendrimer may be localized at any desired positions substituted by $R^1$, $R^2$, $R^3$ or $R^4$ in formula (I).

13. A formulation comprising at least one compound according to claim 1 And at least one solvent.

14. An electronic device comprising at least one compound according to claim 1.

15. The electronic device according to claim 14, wherein the device is an organic electroluminescent device comprising anode, cathode and at least one emitting layer, where at least one organic layer of the device, which may be an emitting layer or a hole-transporting layer, that contains the at least one compound.

16. The device according to claim 15, wherein the organic electroluminescent device comprises at least one electron blocker layer which comprises at least one compound of the formula (I).

17. The compound according to claim 1, wherein a sub-unit of formula (I) is one of the formula (I-A)

Formula (I-A)
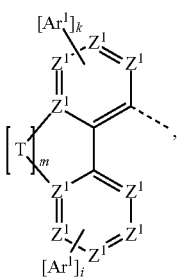
where the dashed line represents the bond to the —N(Ar²)(Ar³) substituent group, and where formula (I-A) is selected one of from the following structures:
Formel (I-A-1)
Formel (I-A-2)
Formel (I-A-8)
Formel (I-A-9)
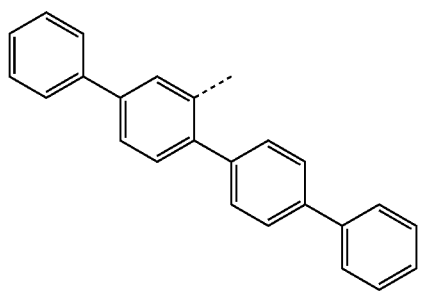
-continued
Formel (I-A-10)
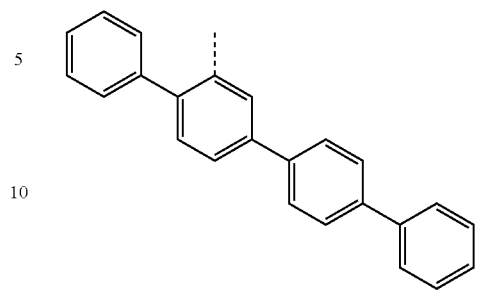
Formel (I-A-16)
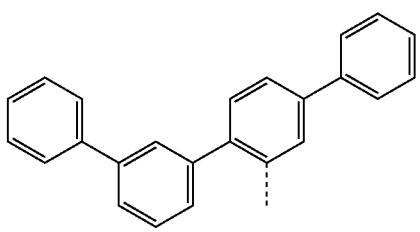
Formel (I-A-17)
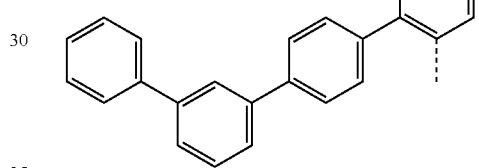
Formel (I-A-19)
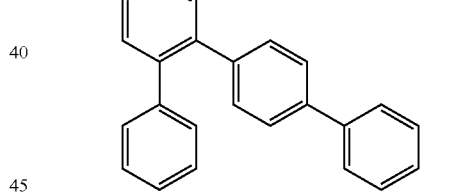
Formel (I-A-21)
Formel (I-A-22)
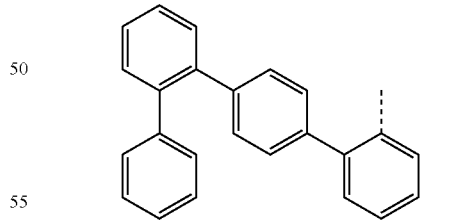

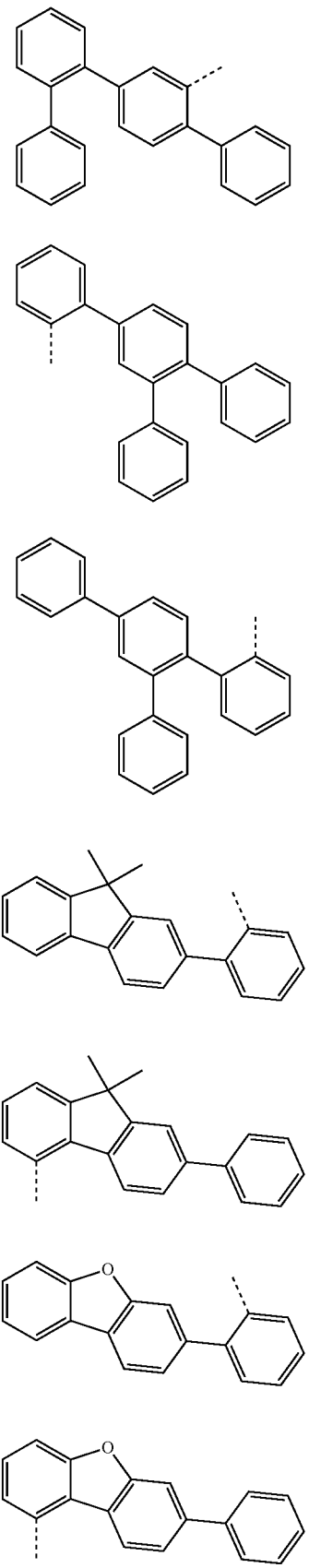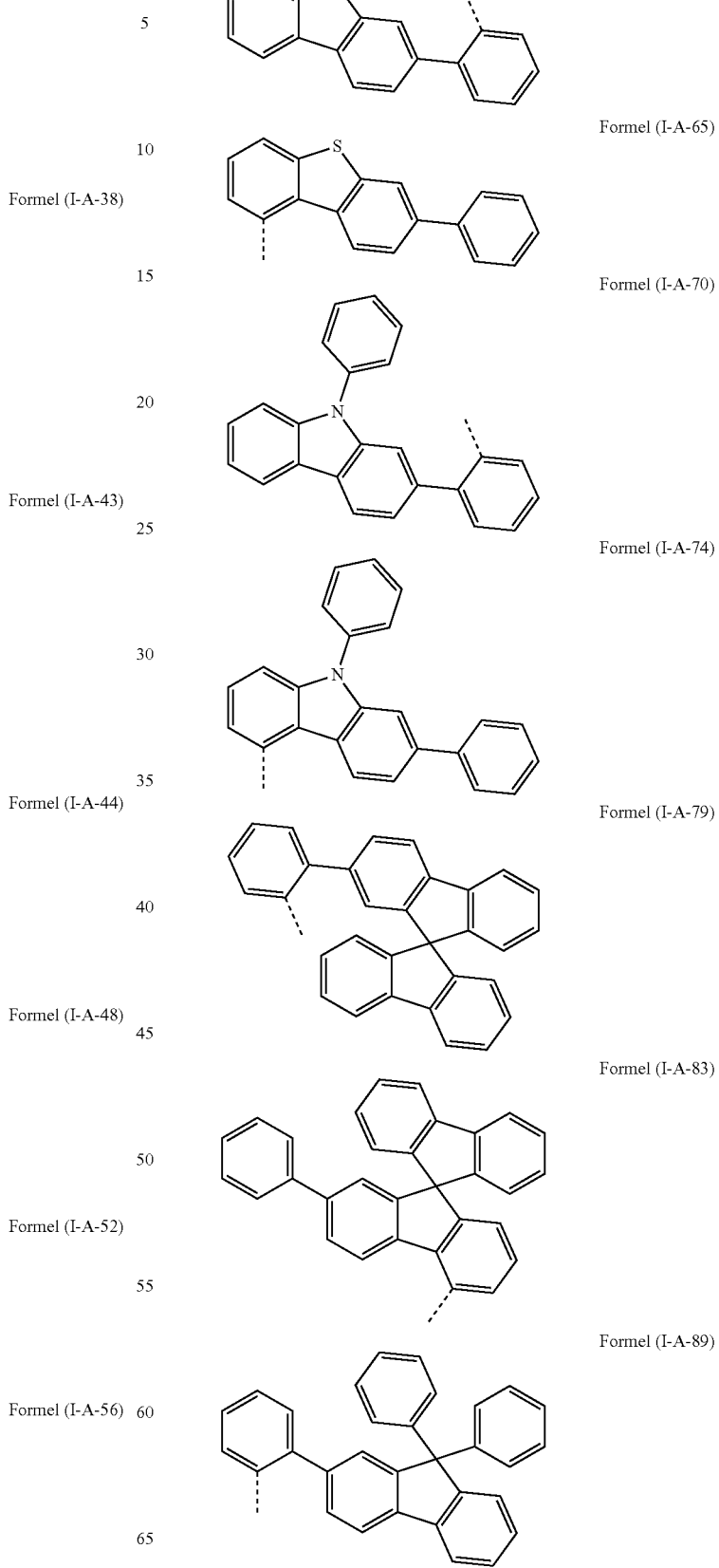

Formel (I-A-92)
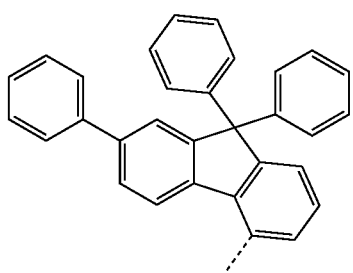
Formel (I-A-97)
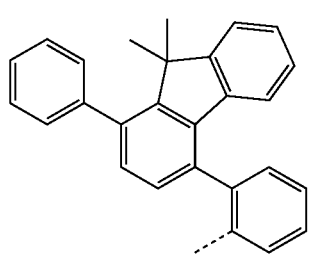
Formel (I-A-98)
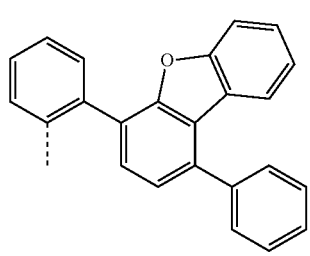
Formel (I-A-99)
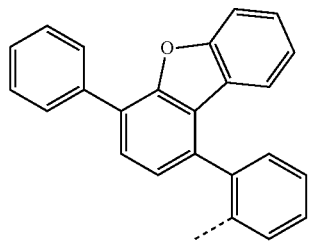
Formel (I-A-100)
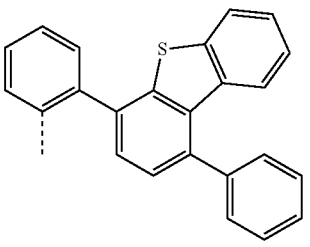
Formel (I-A-101)
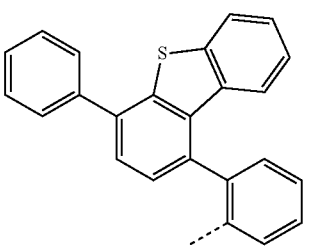
Formel (I-A-102)
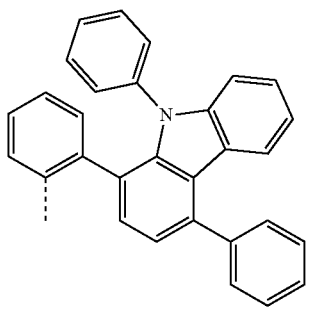
Formel (I-A-103)
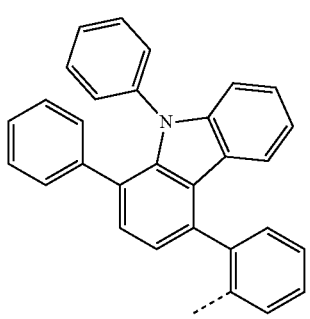
Formel (I-A-104)
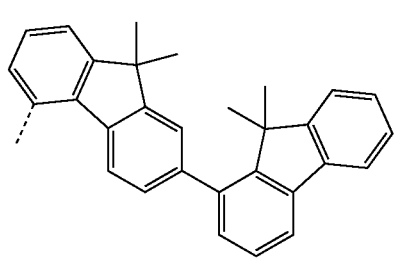
Formel (I-A-105)
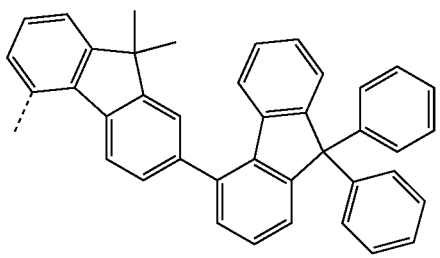
Formel (I-A-106)
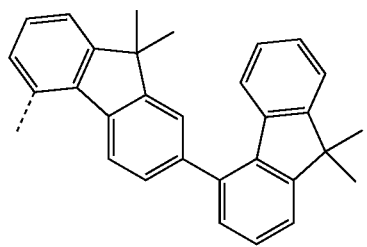

-continued

Formel (I-A-107)
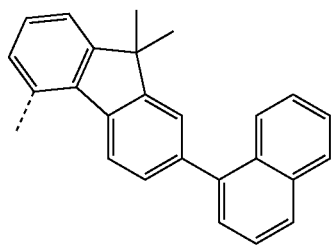

Formel (I-A-108)
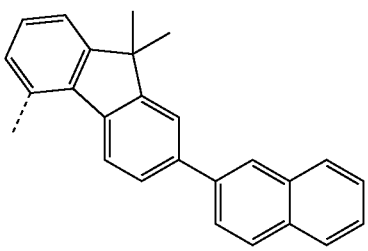

Formel (I-A-110)
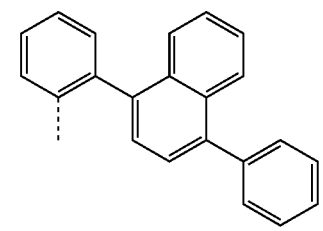

Formel (I-A-117)
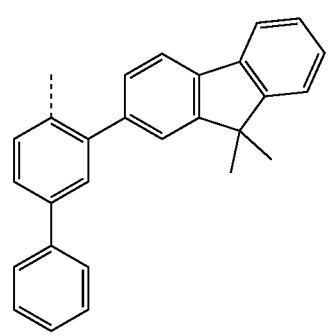

Formel (I-A-120)
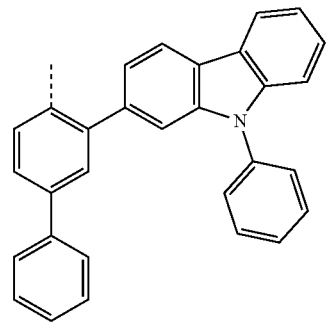

Formel (I-A-123)
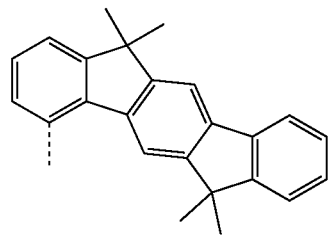

-continued

Formel (I-A-124)
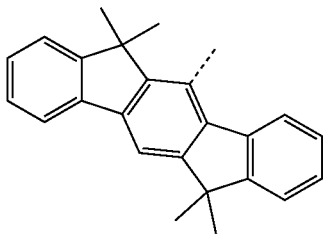

Formel (I-A-125)
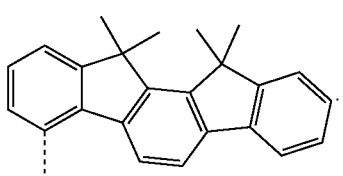

18. A compound of formula (1)

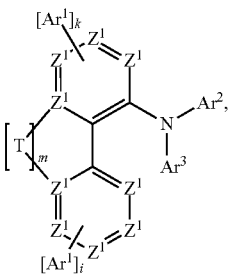

Formula (I)

where the variables that occur are as follows:

$Z^1$ is the same or different at each instance and is selected from $CR^1$ and N, where $Z^1$ is C when an $Ar^1$ or T group is bonded thereto;

$Ar^1$ is the same or different at each instance and is an aromatic ring system which has 6 to 30 aromatic ring atoms and may be substituted by one or more $R^2$ radicals;

$Z^2$ is the same or different at each instance and is $CR^3$ or N, where $Z^2$ is C when an $L^1$ group is bonded thereto, $L^1$ is an aromatic ring system which has 6 to 30 aromatic ring atoms and may be substituted by one or more $R^3$ radicals, or a heteroaromatic ring system which has 5 to 30 aromatic ring atoms and may be substituted by one of more $R^3$ radicals;

$Ar^3$ corresponds to a formula (A) or a formula (B) or is an aromatic ring system which has 6 to 30 aromatic ring atoms and may be substituted by one or more $R^4$ radicals, or a heteroaromatic ring system which has 5 to 30 aromatic ring atoms and may be substituted by one or more $R^4$ radicals;

T is selected from $C(R^1)_2$, $Si(R^1)_2$, $NR^1$, O and S;

$R^1$, $R^2$, $R^3$, $R^4$ are the same or different at each instance and are selected from H, D, F, C(=O) $R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic dug atoms; where two or more $R^1R^2$ or $R^3R^4$ or radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by $R^5C$=$CR^5$-, —C≡C—, $Si(R^5)_2$, C=O, C=$NR^5$, —C(=O)O—, —C(=O)$NR^5$-, $NR^5$, P(=O)($R^5$), —O—, —S—, SO or $SO_2$;

$R^5$ is the same different at each instance and is selected from, H, D, F, C(=O)$R^6$, CN, $Si(R^6)_3$, $N(R^6)_2$, P(=O)($R^6$)$_2$, $OR^6$, S(=O)$R^6$, S(=O)$_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms, where two of more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals, and where one or more $CH_2$ groups in the alkyl, alkoxy, alkenyl and alkynyl groups mentioned may be replaced by —$R^6C$=$CR^6$-, —C≡C—, $Si(R^6)_2$, C=O, C=$NR^6$, —C(=O)O—, —C(=O)$NR^6$-, $NR^6$-, P(=O)($R^6$), —O—, —S—, SO or $SO_2$, $R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

m is 0 or 1;

i is 0, 1, 2, 3, 4 Or 5;

k is 0, 1, 2, 3 Or 4;

where the sum of k and i is at least 1; and where $AR^1$ groups may each be connected via a divalent group Y with the six-membered ring to which they are bonded, where Y is the same or different at each instance and is selected from $C(R^1)_2$, $Si(R^1)_2$, $NR^1$, O and S, wherein there is at most One $Ar^1$ group in the compound, this $AR^1$ group being a phenyl group which may be substituted by one or more $R^2$ radicals, and this group $Ar^1$ being connected via a group Y to the six-membered ring to which it is bonded, where the $Ar^1$ group, the Y bridge and the six-membered ring to which the Y bridge and the $Ar^1$ group bond form a five-membered ring which is inserted between the six-membered ring and the $Ar^1$ group and which with the six-membered ring and the $AR^1$ group form a fused unit, and where $Ar^2$ is selected from groups of the following formulae

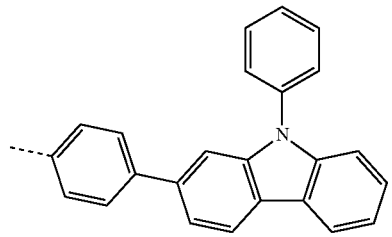
Ar²-5

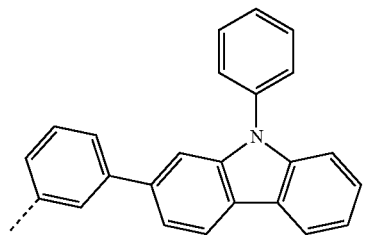
Ar²-6

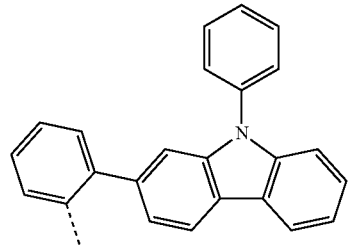
Ar²-7

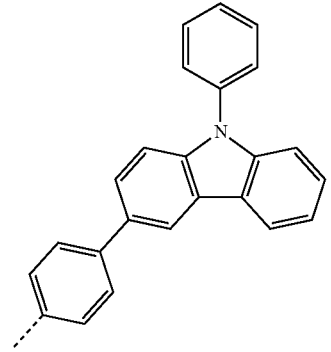
Ar²-8

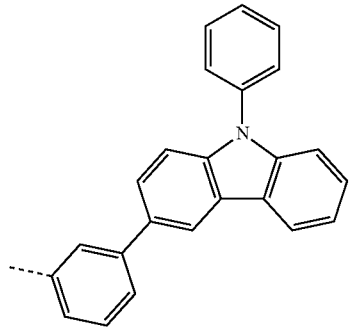
Ar²-9

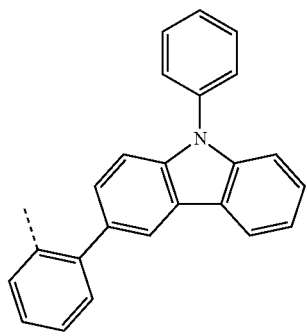
Ar²-10
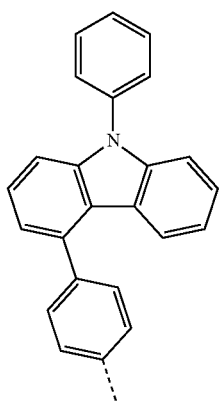
Ar²-11
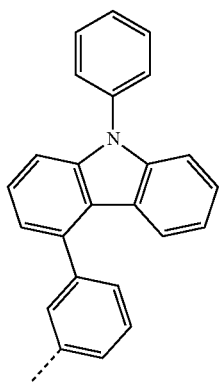
Ar²-12
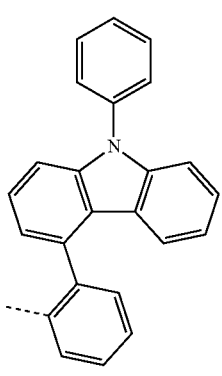
Ar²-13
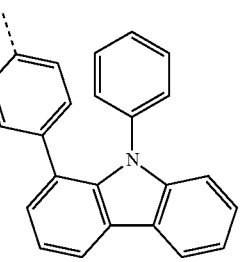
Ar²-14
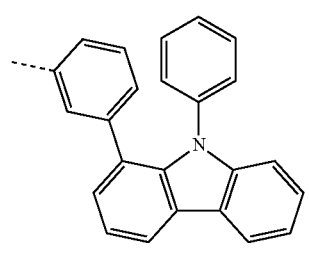
Ar²-15
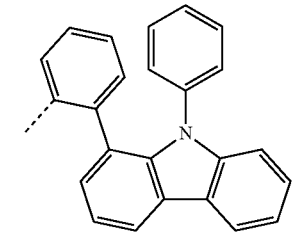
Ar²-16
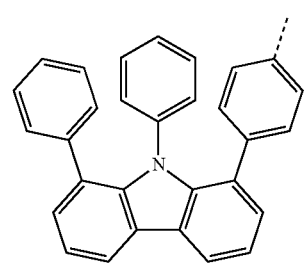
Ar²-22
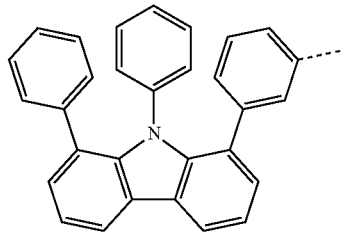
Ar²-23
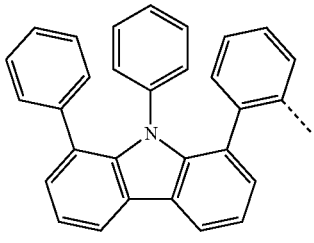
Ar²-24

| | |
|---|---|
| 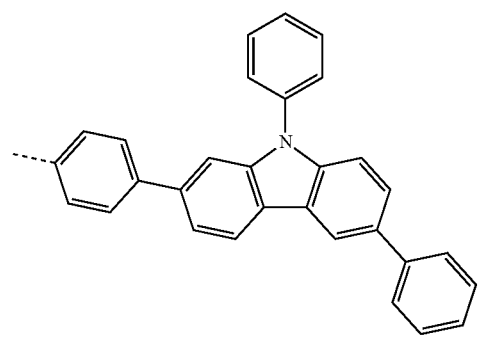 Ar²-25 | 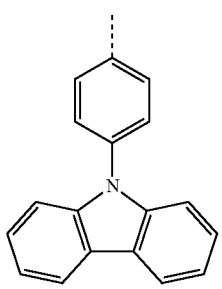 Ar²-40 |
| 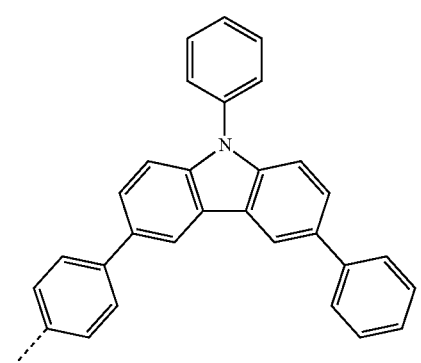 Ar²-26 | 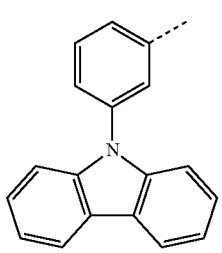 Ar²-41 |
| 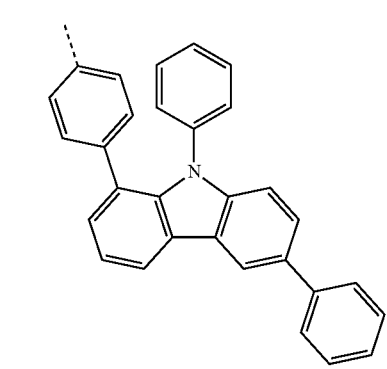 Ar²-27 | 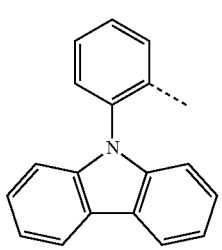 Ar²-42 |
| 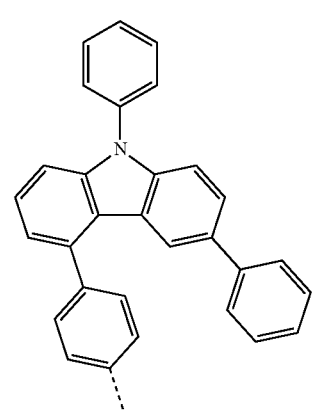 Ar²-28 | 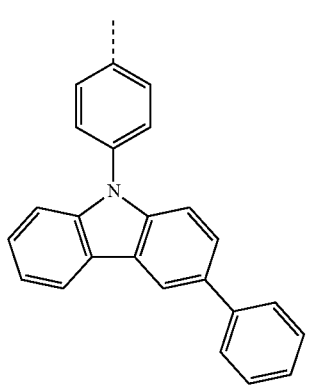 Ar²-43 |
| | 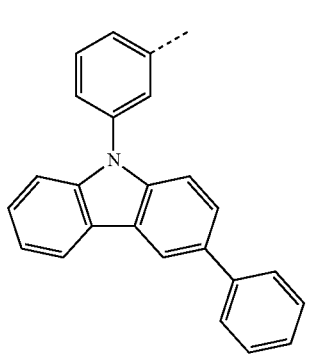 Ar²-44 |

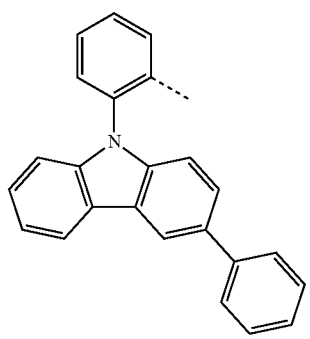
Ar²-45
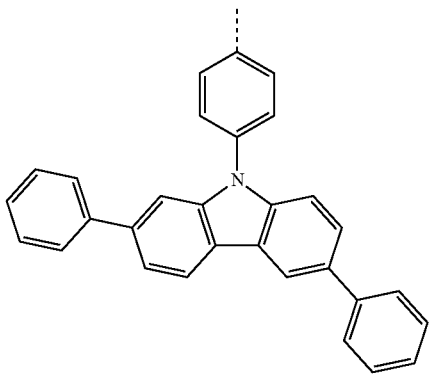
Ar²-49
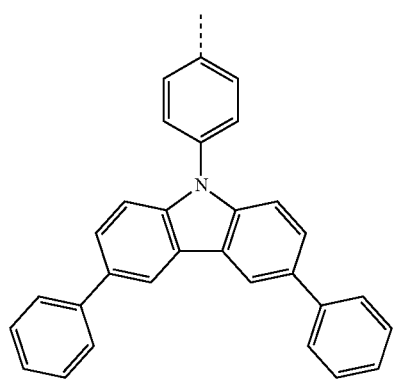
Ar²-46
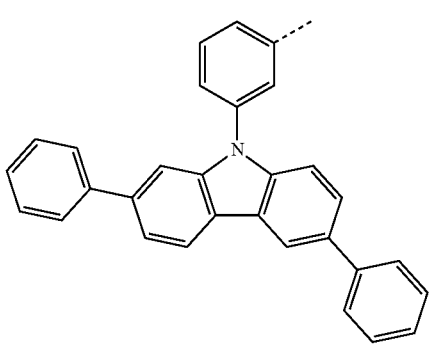
Ar²-50
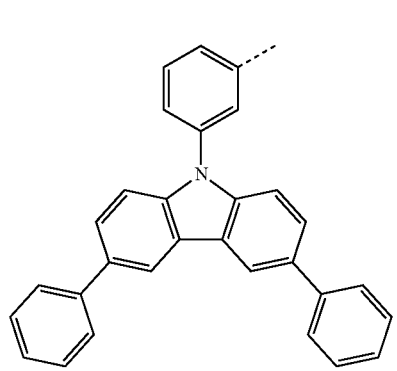
Ar²-47
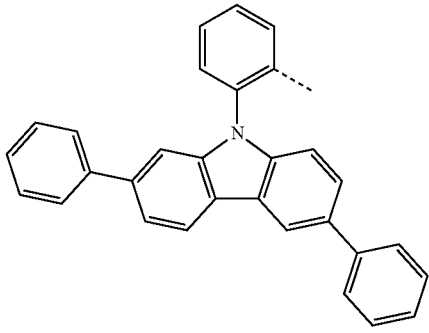
Ar²-51
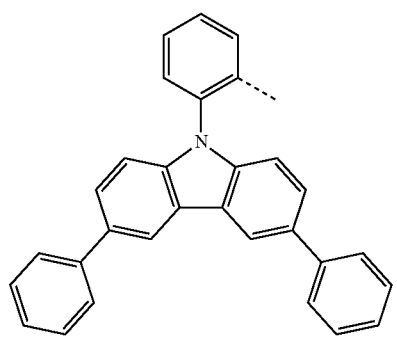
Ar²-48
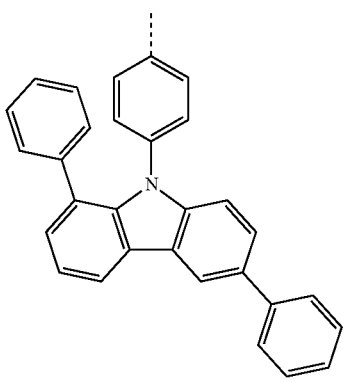
Ar²-52

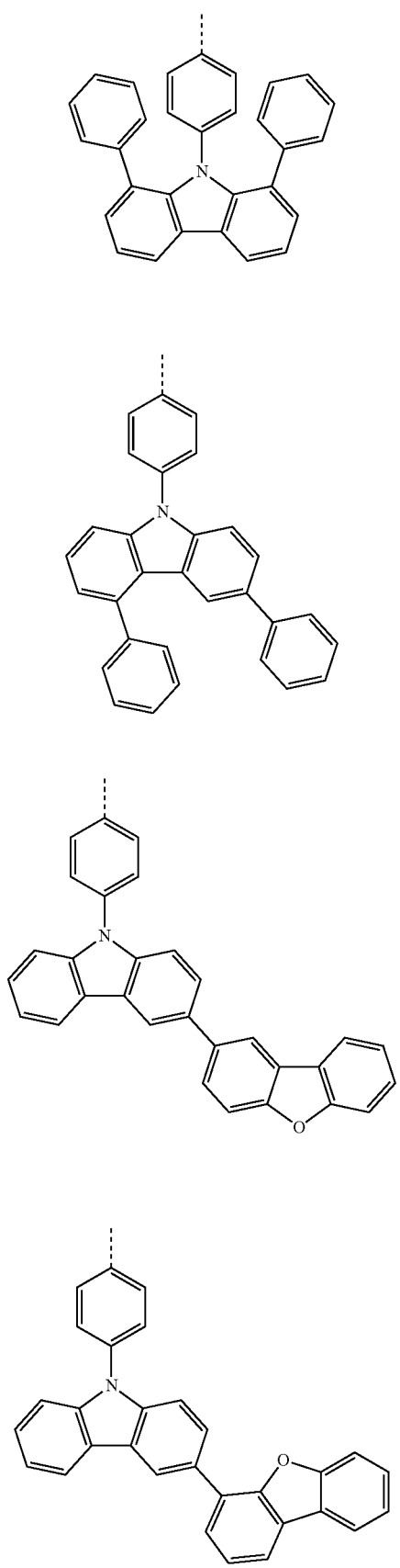
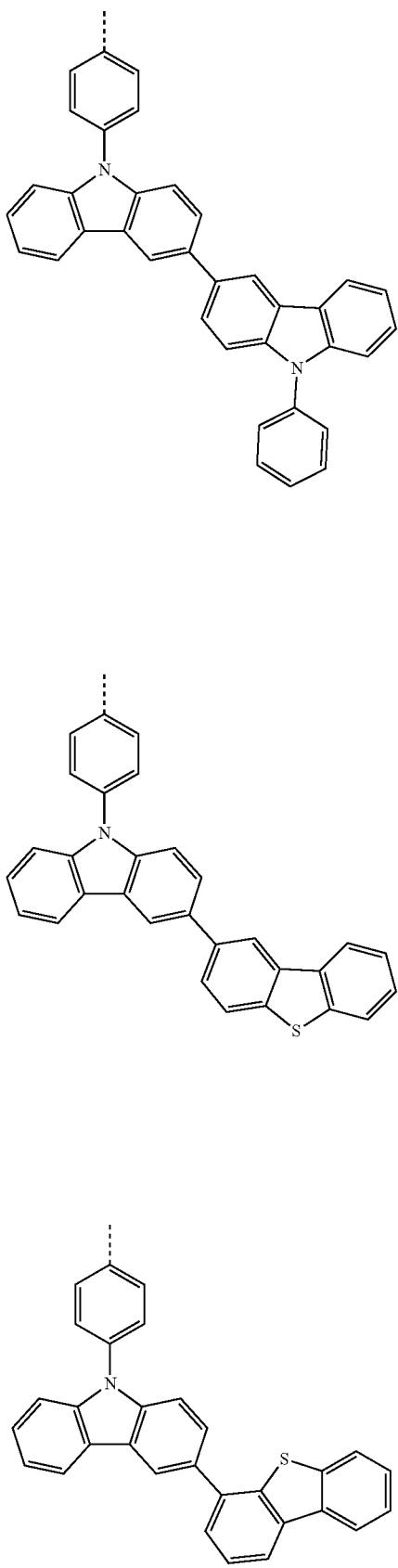

Ar²-60 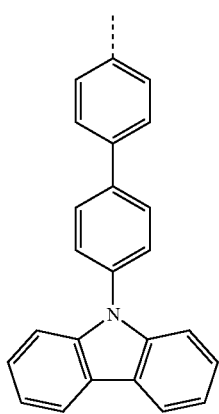
Ar²-61 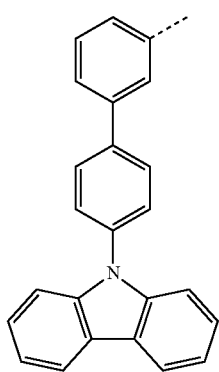
Ar²-62 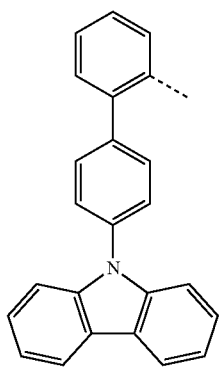
Ar²-63 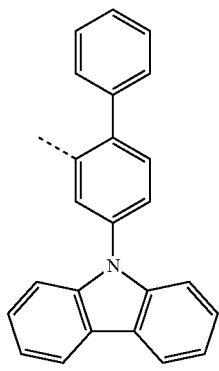
Ar²-64 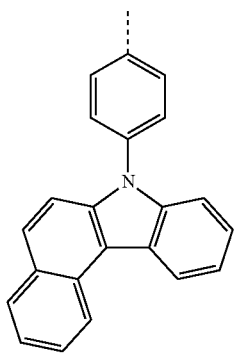
Ar²-65 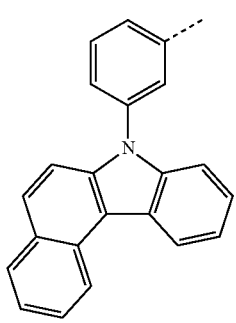
Ar²-66 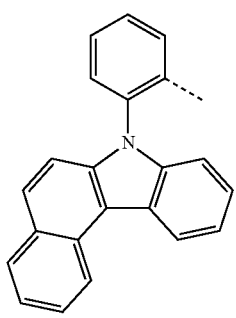
Ar²-67 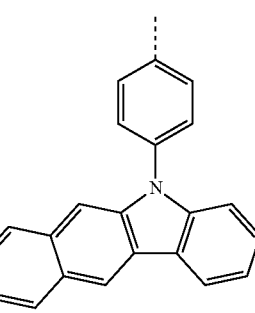
Ar²-68 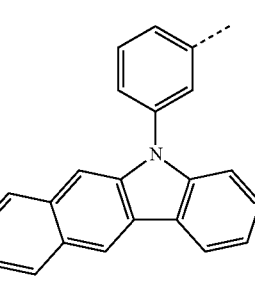

-continued

Ar²-69
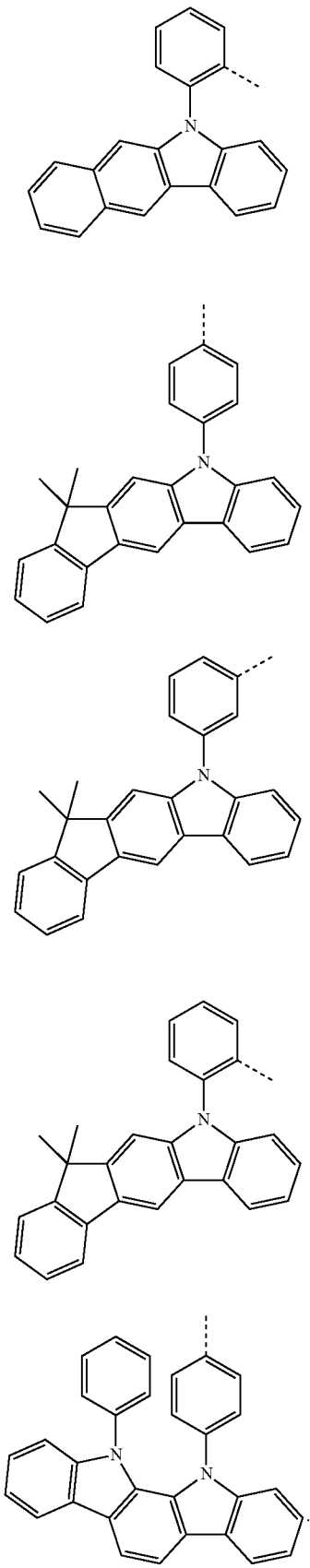
Ar²-70

Ar²-71

Ar²-72

Ar²-76

19. A compound of formula (1)

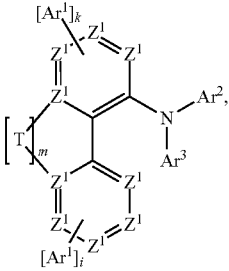

Formula (I)

where the variables that occur are as follows:
$Z^1$ is the same or different at each instance and is selected from $CR^1$ and N, where $Z^1$ is C when an $AR^1$ or T group is bonded thereto;
$AR^1$ is the same or different at each instance and is an aromatic ring system which has 6 to 30 aromatic ring atoms and may be substituted by one or more $R^2$ radicals;
$Z^2$ is the same or different at each instance and is $CR^3$ or N, where $Z^2$ is C when an $L^1$ group is bonded thereto;
$L^1$ is an aromatic ring system which has 6 to 30 aromatic ring atoms and may be substituted by one or more $R^3$ radicals, or a heteroaromatic ring system which has 5 to 30 aromatic ring atoms and may be substituted by one or more $R^3$ radicals;
$Ar^3$ a corresponds to a formula (A) or a formula (B) or is an aromatic ring system which has 6 to 30 aromatic ring atoms and may be substituted by one or more $R^4$ radicals, or a heteroaromatic ring system which has 5 to 30 aromatic ring atoms and may be substituted by one or more $R^4$ radicals;
T is selected from $C(R^1)_2$, $Si(R^1)_2$, $NR^1$, O and S;
$R^1$, $R^2$, $R^3$, $R^4$ are the same or different at each instance and are selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms;
where two or more $R^1$ or $R^2$ or $R^3$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^5$ radicals; and where one or more $CH_2$ groups in the alkyl, alkoxy, alkenyl and alkynyl groups mentioned may be replaced by —$R^5C=CR^5$—, —C≡C—, $Si(R^5)_2$, C=O, C=$NR^5$, —C(=O)O—, —C(=O)$NR^5$-, $NR^5$, $P(=O)(R^5)$, —O—, —S—, SO or $SO_2$;
$R^5$ is the same or different at each instance and is selected from H, D, F, $C(=O)R^6$, CN, $Si(R^6)_3$, $N(R^6)_2$, $P(=O)(R^6)_2$, $OR^6$, $S(=O)R^6$, $S(=O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by —$R^6C$=$CR^6$-, C≡C—, $Si(R^6)_2$, C=O, C=$NR^6$, —C(=O)O—, —C(=O)$NR^6$-, $NR^6$, P(=O)($R^6$), —O—, —S—, SO or $SO^2$;

$R^6$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^6$ radicals may be joined to one another and may form a ring; and where the alkyl, alkoxy, alkenyl and alkynyl groups, aromatic ring systems and heteroaromatic ring systems mentioned may be substituted by F or CN;

m is 0 or 1;
i is 0, 1, 2, 3, 4 or 5;
k is 0, 1, 2, 3 or 4;
where the sum of k and i is at least 1; and
where $AR^1$ groups may each be connected via a divalent group Y with the six-membered ring to which they are bonded, where
Y is the same or different at each instance and is selected from $C(R^1)_2$, $Si(R^1)_2$, $NR^1$, O and S,
wherein there is at most one $AR^1$ group in the compound, this $AR^1$ group being a phenyl group which may be substituted by one or more $R^2$ radicals, and this group $AR^1$ being connected via a group Y to the six-membered ring to which it is bonded, where the $AR^1$ group, the Y bridge and the six-membered ring to which the Y bridge and the $AR^1$ group bond form a five-membered ring which is inserted between the six-membered ring and the $Ar^1$ group and which with the six-membered ring and the $AR^1$ group form a fused unit,
wherein the fused unit is selected from fluorene, spirobifluorene, carbazole, dibenzofuran and dibenzothiophene, each of which may be substituted by $R^1$ and $R^2$, and
wherein $Ar^2$ is selected from groups of the following formulae Ar²-5

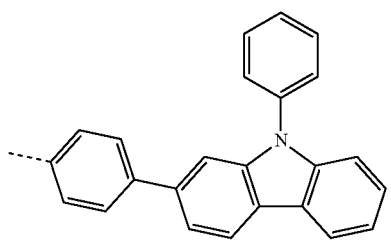

Ar²-6

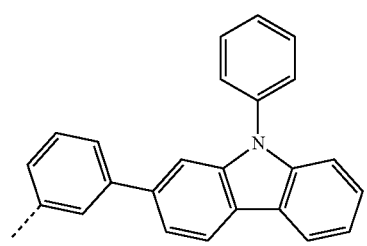

-continued

Ar²-7

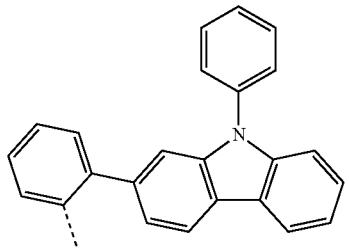

Ar²-8

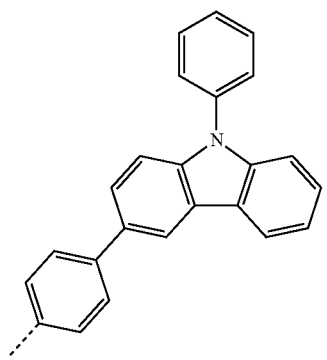

Ar²-9

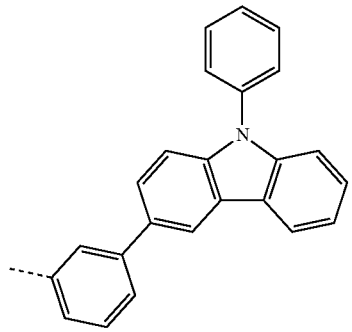

Ar²-10

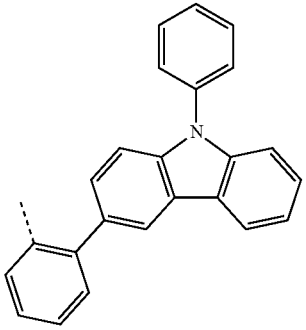

Ar²-11
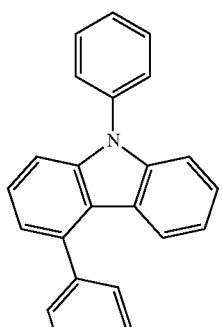
Ar²-12
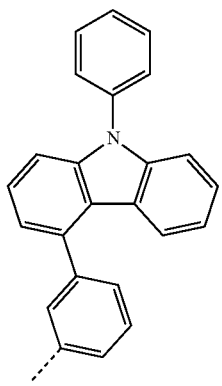
Ar²-13
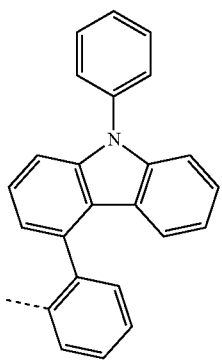
Ar²-14
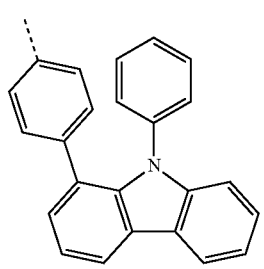
Ar²-15
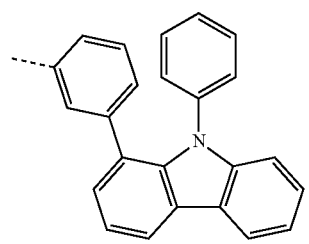
Ar²-16
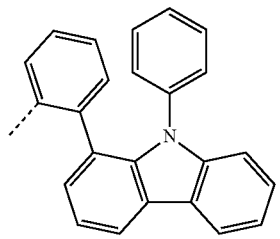
Ar²-22
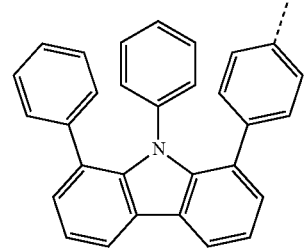
Ar²-23
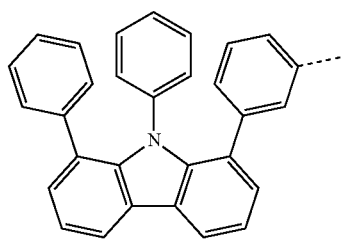
Ar²-24
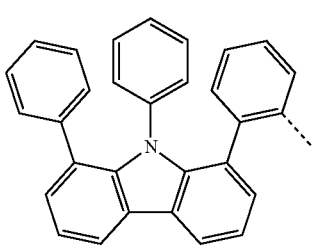
Ar²-25
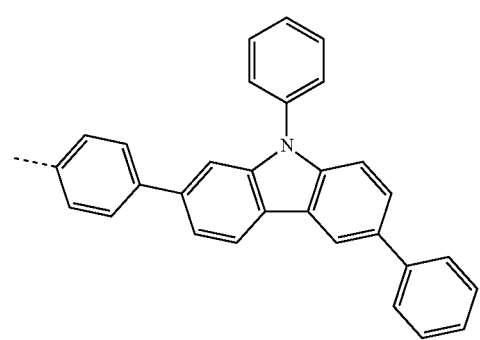

-continued
Ar²-26
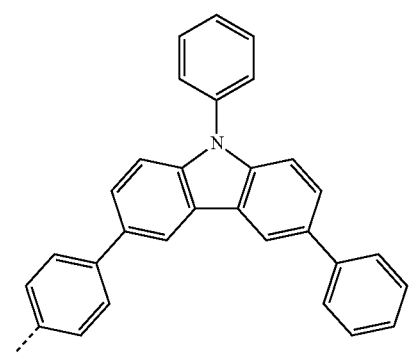
Ar²-27
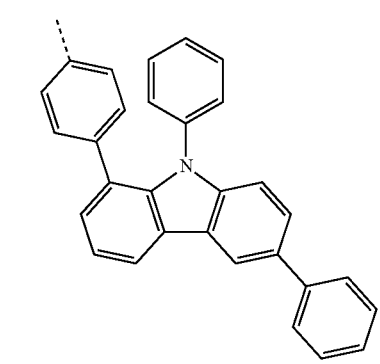
Ar²-28
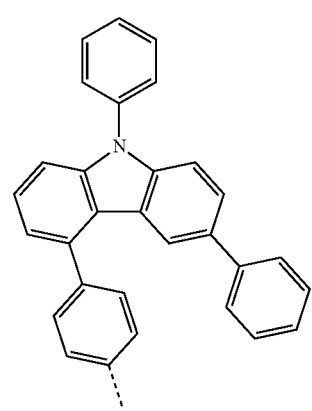
Ar²-40
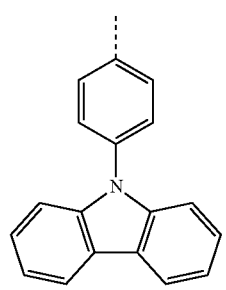
-continued
Ar²-41
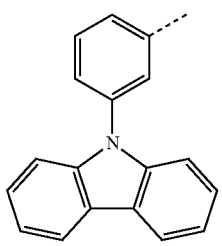
Ar²-42
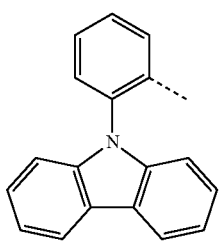
Ar²-43
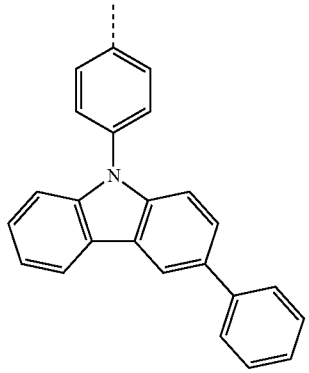
Ar²-44
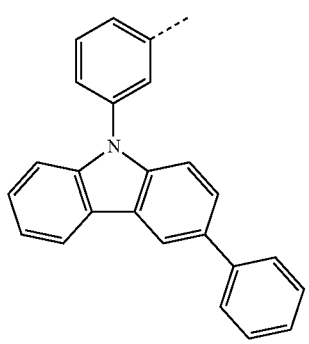
Ar²-45
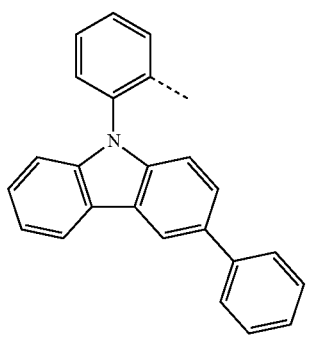

-continued
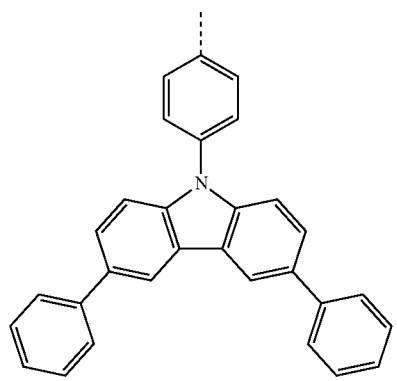
Ar²-46
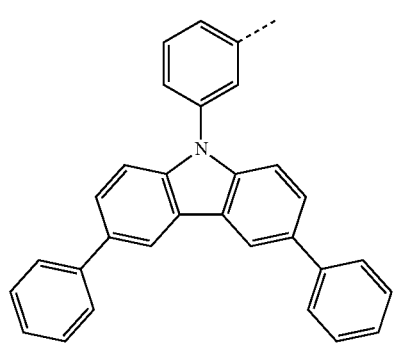
Ar²-47
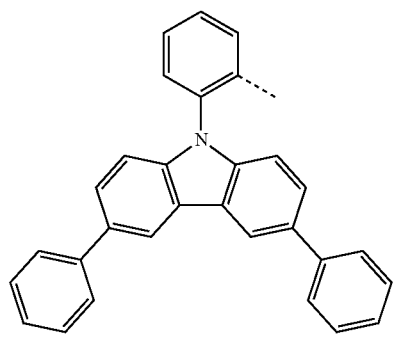
Ar²-48
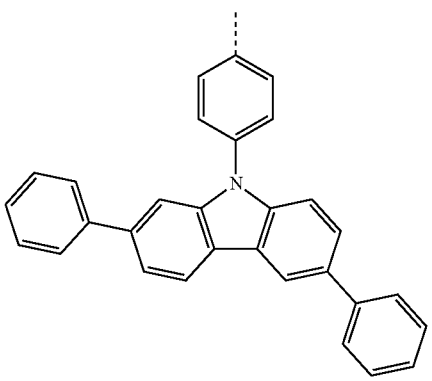
Ar²-49
-continued
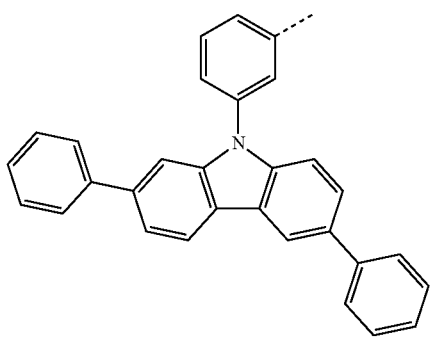
Ar²-50
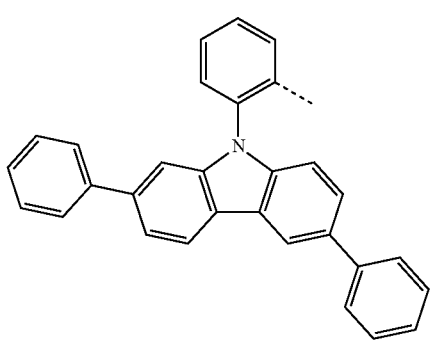
Ar²-51
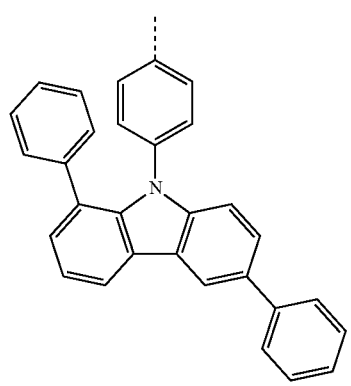
Ar²-52
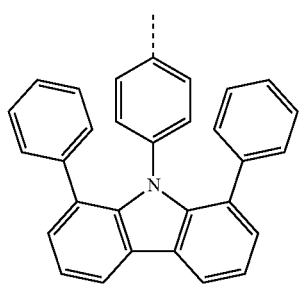
Ar²-53

-continued
Ar²-54
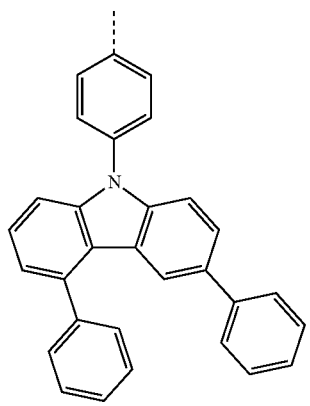
Ar²-55
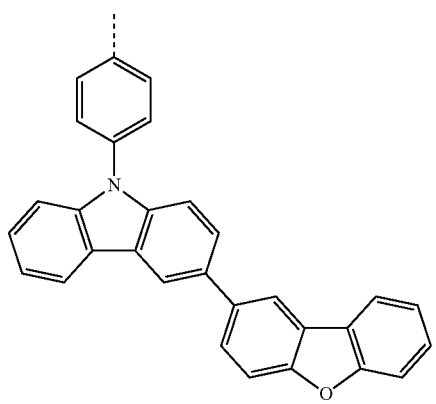
Ar²-56
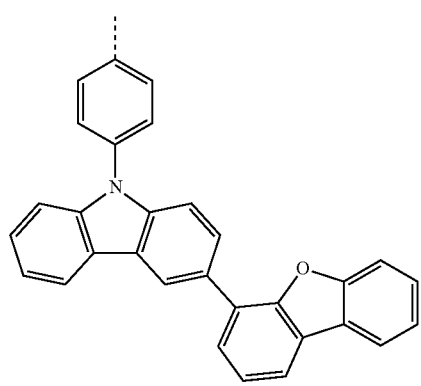
Ar²-57
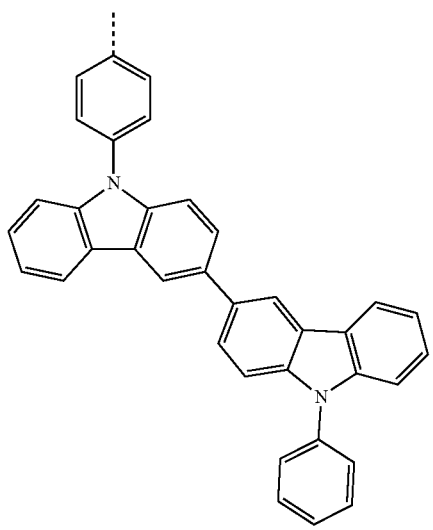
Ar²-58
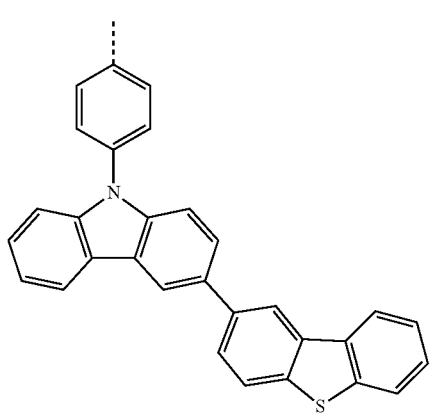
Ar²-59
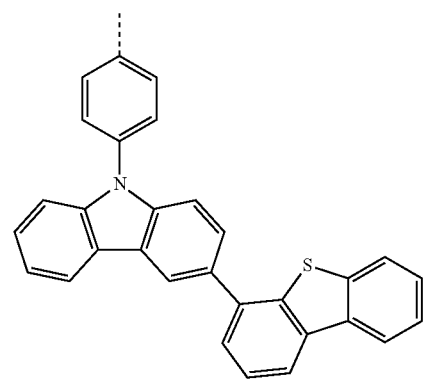

-continued
Ar²-60
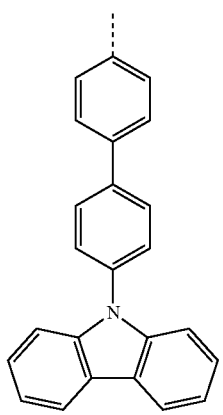
Ar²-61
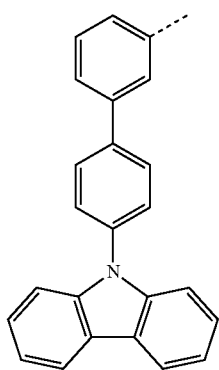
Ar²-62
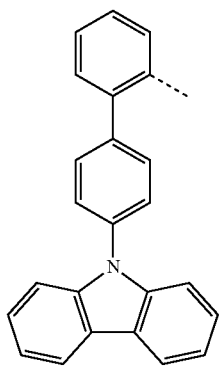
Ar²-63
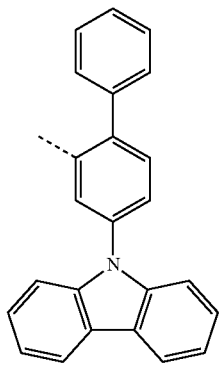
-continued
Ar²-64
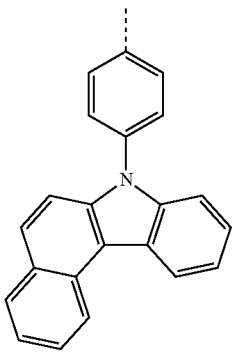
Ar²-65
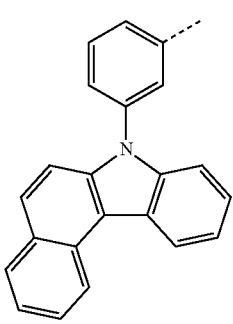
Ar²-66
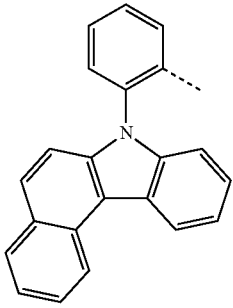
Ar²-67
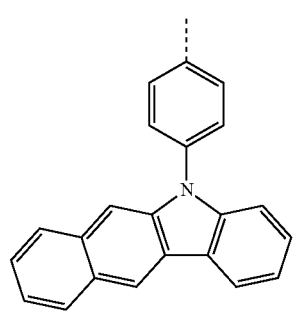
Ar²-68
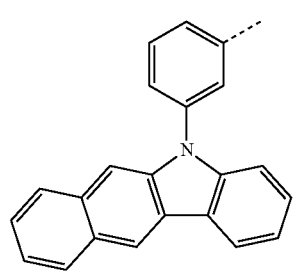

-continued
Ar²-69
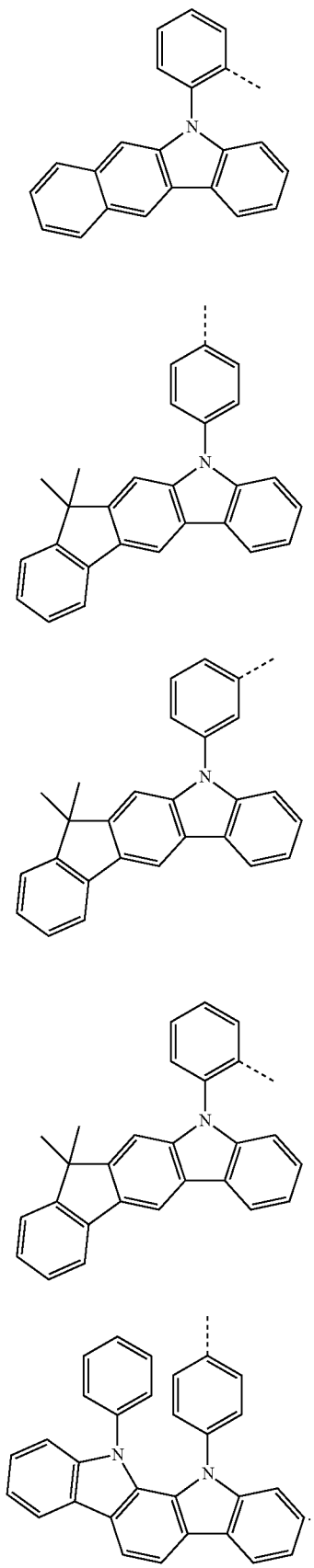
Ar²-70
Ar²-71
Ar²-72
Ar²-76
20. A compound of formula (1)
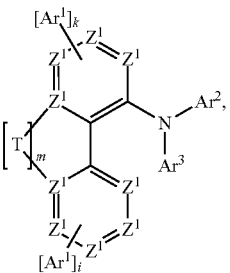
Formula (I)
wherein a sub-unit of formula (1) is one of the formula (I-A)
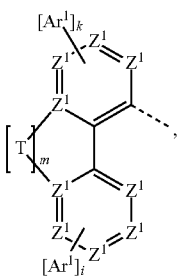
Formula (I-A)
where the dashed line represents the bond to the —N(Ar²)(Ar³) substituent group, and where formula (I-A) is selected one of from the following structures:
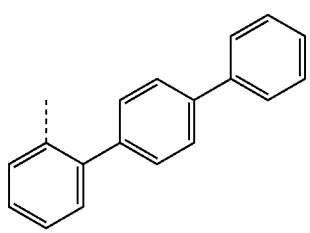
Formel (I-A-1)
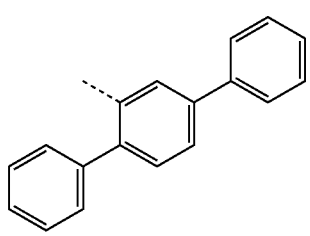
Formel (I-A-2)
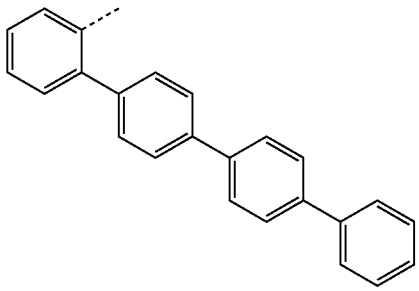
Formel (I-A-8)

Formel (I-A-9)
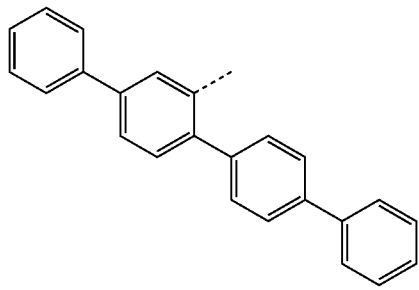
Formel (I-A-10)
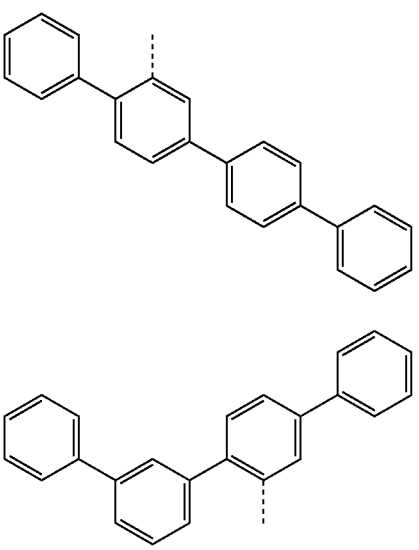
Formel (I-A-16)
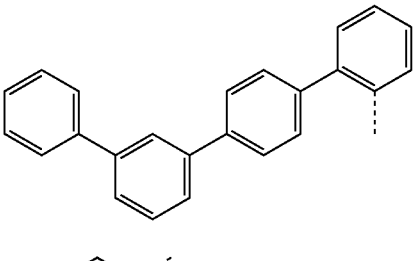
Formel (I-A-17)
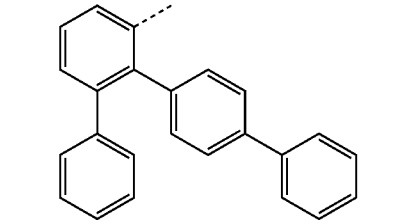
Formel (I-A-19)
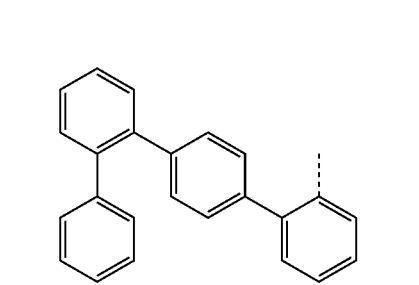
Formel (I-A-21)
Formel (I-A-22)
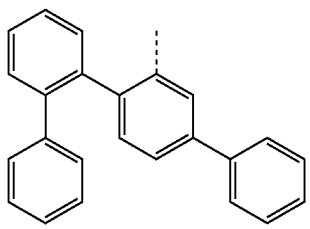
Formel (I-A-23)
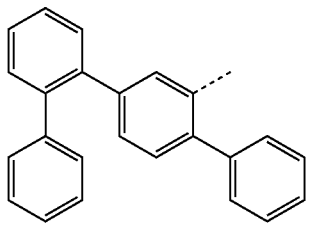
Formel (I-A-38)
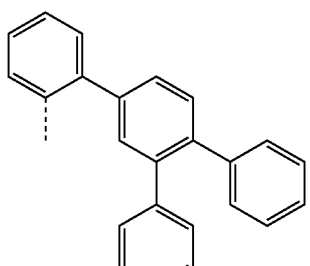
Formel (I-A-43)
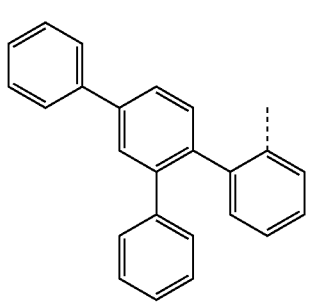
Formel (I-A-44)
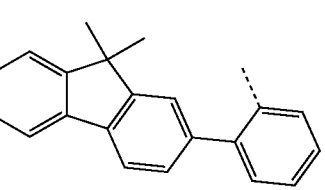
Formel (I-A-48)
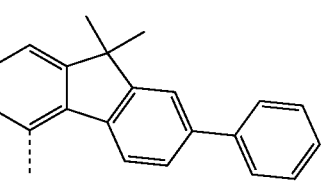
Formel (I-A-52)
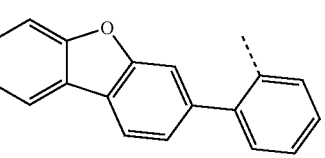

293
-continued
Formel (I-A-56)
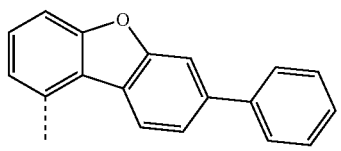
Formel (I-A-61)
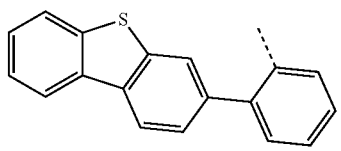
Formel (I-A-65)
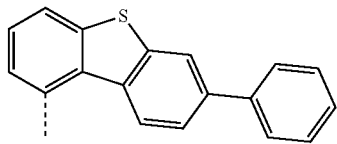
Formel (I-A-70)
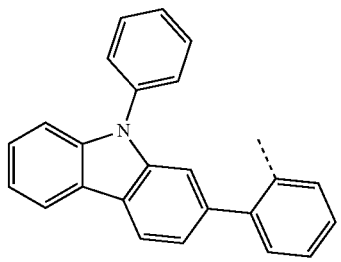
Formel (I-A-74)
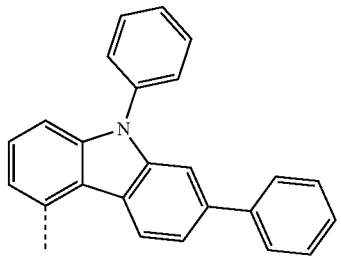
Formel (I-A-79)
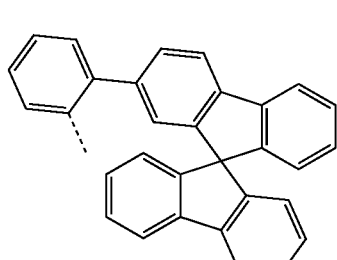
Formel (I-A-83)
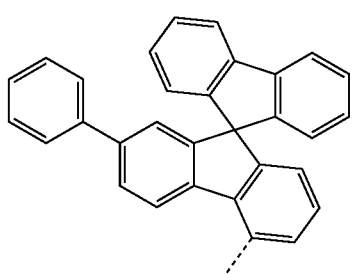
294
-continued
Formel (I-A-89)
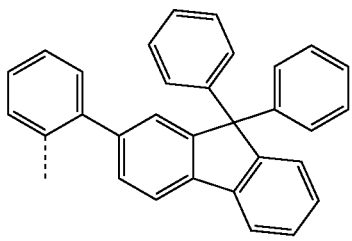
Formel (I-A-92)
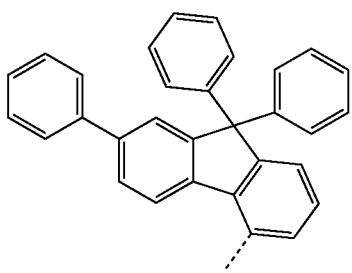
Formel (I-A-97)
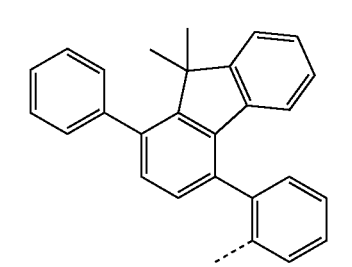
Formel (I-A-98)
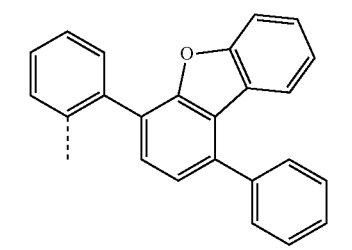
Formel (I-A-99)
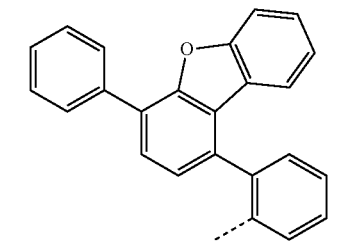
Formel (I-A-100)
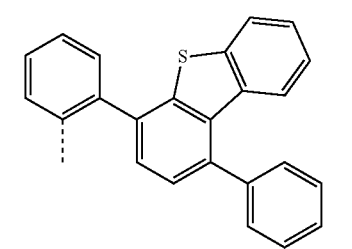

Formel (I-A-101)
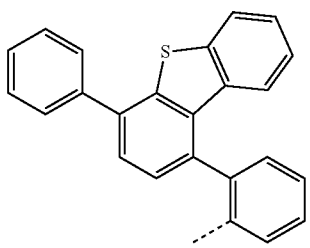
Formel (I-A-102)
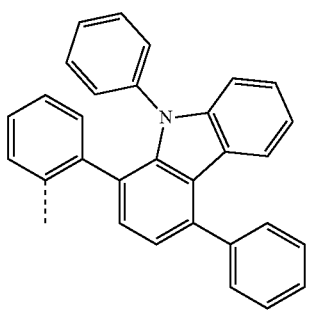
Formel (I-A-103)
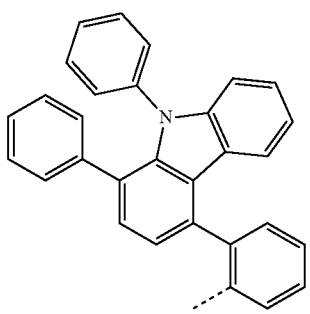
Formel (I-A-104)
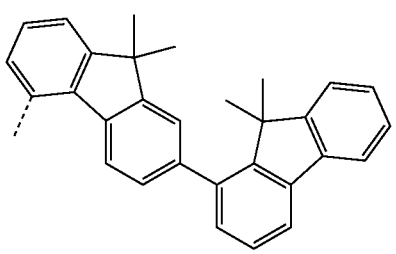
Formel (I-A-105)
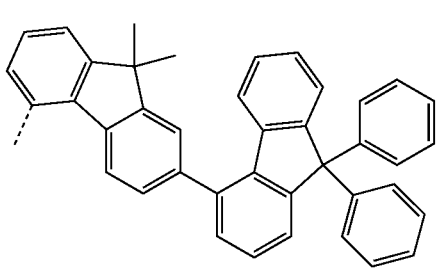
Formel (I-A-106)
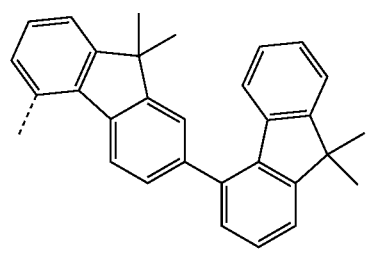
Formel (I-A-107)
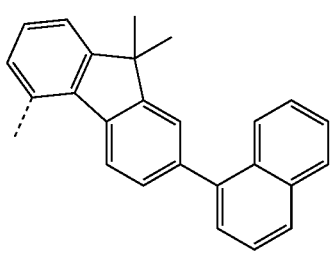
Formel (I-A-108)
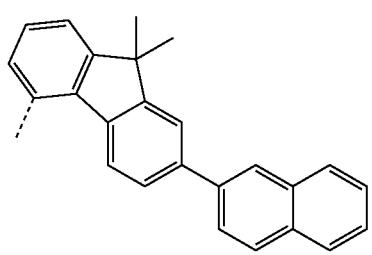
Formel (I-A-110)
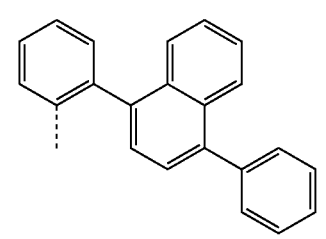
Formel (I-A-117)
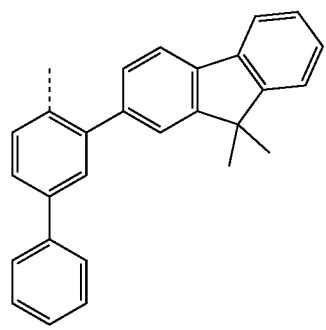
Formel (I-A-120)
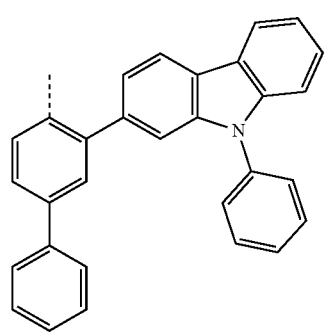

-continued

Formel (I-A-123)

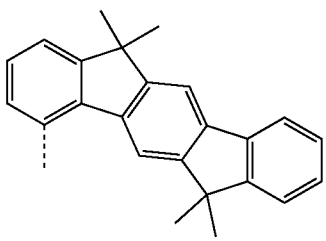

Formel (I-A-124)

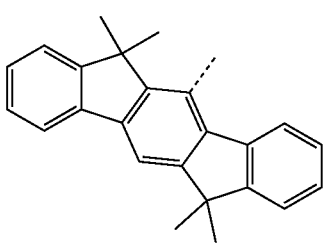

Formel (I-A-125)

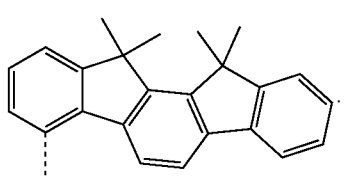

where the variables that occur are as follows:
Ar² corresponds to a formula (A) or (B)

Formula (A)

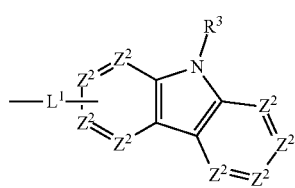

Formula (B)

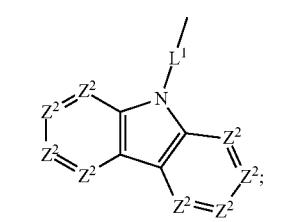

Z² is the same or different at each instance and is CR³ or N, where Z² is C when an L¹ group is bonded thereto;
L¹ is selected from benzene, biphenyl and terphenyl, each of which may be substituted by one or more R³ radicals;
Ar³ corresponds to a formula (A) or a formula (B) or is an aromatic ring, system which has 6 to 30 aromatic ring atoms and may be substituted by one or more R⁴ radicals, or a heteroaromatic ring system which has 5 to 30 aromatic ring atoms and may be substituted by one or more R⁴ radicals;
T is selected from C(R¹)₂, Si(R¹)₂, NR¹, O and S;
R¹ are the same or different at each instance and are selected from H, D, C(=O)R⁵, CN, Si(R⁵)₃, N(R⁵)₂, P(=O)(R⁵)₂, OR⁵, S(=O)R⁵, S(=O)₂R⁵, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic atom, and heteroaromatic ring systems having 5 to 40 aromatic ring atoms; where two or more R¹ or R² or R³ or R⁴ radicals may be joined to one another and may form a ring; where the alkyl, alkoxy, alkenyl and alkynyl groups mentioned and the aromatic ring systems and heteroaromatic ring systems mentioned may each be substituted by one or more R⁵ radicals; and where one or more CH₂ groups in the alkyl, alkoxy and alkynyl groups mentioned may be replaced by —R⁵C=CR⁵—, —C≡C—, Si(R⁵)₂, C=O, C=NR⁵, —C(=O)O—, —C(=O)NR⁵—, NR⁵, P(=O)(R⁵), —O—, —S—, SO or SO₂:
R², R³, R⁴ are the same or different at each instance and are selected from H, D, F, C(=O)R⁵, CN, Si(R⁵)₃, N(R⁵)₂, P(=O)(R⁵)₂, OR⁵, S(=O)R⁵, S(=O)₂R⁵, straight-chain alkyl or alkoxy groups having 1 to 20 carbon atoms, branched or cyclic alkyl alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 0.40 aromatic ring atoms; where two or more R¹ or R² or R⁴ radicals may be joined to one another and may form a ring; where the alkyl, alkoxy, alkoxy, and alkenyl groups mentioned and the aromatic ring systems and heteroaromatic ring systems mentioned may each be substituted by one or more R⁵ radicals; and where one or more CH₂ groups in the alkyl, alkoxy, alkenyl and alkynyl groups mentioned may be replaced by —R⁵C=CR⁵—, —C≡C—, Si(R⁵)₂, C=O, C=NR⁵, —C(=O)O—, —C(=O)NR⁵-, NR⁵, P(=O)(R⁵), —O—, —S—, SO or SO₂:
R⁵ is the same or different at each instance and is selected from H, D, F, C(=O)R⁶, CN, Si(R⁶)₃, N(R⁶)₂, P(=O)(R⁶)₂, OR⁶, S(=O)R⁶, S(=O)₂R⁶, straight-chain alkyl or alkoxy groups having to 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R⁵ radicals may be joined to one another and may form a ring; where the alkyl, alkoxy, alkenyl and alkynyl groups mentioned and the aromatic ring systems and heteroaromatic ring systems mentioned may each be substitute by one or more R⁶ radicals; and where one or more CH₂ groups in the alkyl, alkoxy, alkenyl and alkynyl groups mentioned may be replaced by —R⁶C=CR⁶—, —C≡C—, Si(R⁶)₂, C=O, C=NR⁶, —C(=O)O—, —C(=O)NR⁶-, NR⁶, P(=O)(R⁶), —O—, —S—, SO or SO₂;
R⁶ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic dog atoms and heteroaromatic ring systems having 5 to 40 aromatic ring atoms, where two or more R⁶ radicals may be joined to one another and m form a ring, and where the alkyl, alkoxy, alkenyl and alkynyl groups, aromatic ring systems and heteroaromatic ring systems mentioned may be substituted by F or CN,
m is 0 or 1;
is 0, 1, 2, 3, 4 or 5;
k is 0,1,2,3 or 4;
where the sum of k and i is at least 1.

\* \* \* \* \*